(12) United States Patent
Grant et al.

(10) Patent No.: US 7,183,281 B2
(45) Date of Patent: *Feb. 27, 2007

(54) SULFONYLQUINOXALONE DERIVATIVES AND RELATED COMPOUNDS AS BRADYKININ ANTAGONISTS

(75) Inventors: Francine S. Grant, Mercer Island, WA (US); Sarah Bartulis, Oakland, CA (US); Louis Brogley, Santa Cruz, CA (US); Michael S. Dappen, Redwood City, CA (US); Ramesh Kasar, San Bruno, CA (US); Mohammed A. Khan, Morgan Hill, CA (US); Martin Neitzel, Concord, CA (US); Michael A. Pleiss, Sunnyvale, CA (US); Eugene D. Thorsett, Kirkland, WA (US); John Tucker, San Mateo, CA (US); Michael Ye, Palo Alto, CA (US); Jon E. Hawkinson, Palo Alto, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 16 days.

This patent is subject to a terminal disclaimer.

(21) Appl. No.: 10/429,917

(22) Filed: May 2, 2003

(65) Prior Publication Data

US 2004/0147520 A1    Jul. 29, 2004

Related U.S. Application Data

(60) Provisional application No. 60/378,206, filed on May 3, 2002.

(51) Int. Cl.
| | |
|---|---|
| *A01N 43/58* | (2006.01) |
| *A01N 43/60* | (2006.01) |
| *A61K 31/50* | (2006.01) |
| *A61K 31/495* | (2006.01) |
| *C07D 413/00* | (2006.01) |

(52) U.S. Cl. .................. 514/249; 544/119; 544/353; 544/354

(58) Field of Classification Search ............... 544/119, 544/353, 354
See application file for complete search history.

(56) References Cited

U.S. PATENT DOCUMENTS

| | | | |
|---|---|---|---|
| 3,635,971 A | 1/1972 | Yellin, et al | 260/250 |
| 3,654,275 A | 4/1972 | McManus | 260/250 |
| 5,968,951 A | 10/1999 | Dodey et al. | |
| 6,211,196 B1 | 4/2001 | Heitsch et al. | 514/311 |
| 6,369,057 B1 | 4/2002 | Billhardt et al. | 514/234.8 |

FOREIGN PATENT DOCUMENTS

| | | |
|---|---|---|
| DE | 43 41 663 A1 | 12/1993 |
| EP | 0 622 361 A1 | 11/1994 |
| EP | 1 188 755 A1 | 3/2002 |
| WO | 03/007958 A1 | 1/2003 |

OTHER PUBLICATIONS

Couture et al, "Kinin receptors in pain and inflammation" European Journal of Pharmacology, vol. 429, pp. 161-176 (2001).*
Ozturk, "Kinin Receptors and Their Antagonists as Novel Therapeutic Agents" Current Pharmaceutical Design, vol. 7, pp. 135-161 (2001).*
Howl and Payne, "Bradykinin receptors as a therapeutic target" Expert Opinion on Therapeutic Targets, vol. 7(2), pp. 277-2 (2003).*
Scoffone et al, Gazzetta Chimica Italiana, vol. 87, pp. 354-365 (1957).*
Romanenko et al, "Condensed and bound quinoxalines. IV. New pathway to acrylamides of (1,2-dihydro-2-oxo-3-quinoxalinyl acetic acid" Khimiya Geterotsiklicheskikh Soedinenii, vol. 2, pp. 264-266 (1973). ENGLISH TRANSLATION*
S.B. Wagh, et al., "Reactions of Cyclic, Anhydrides: Part VII—Reductive Cyclisation of 2-Nitromaleanilates & 2-Nitrofurmaranitates, a New Synthesis of 2-Oxo-1,2,3,4-tetrahydroquinoxalines", Indian Journal of Chemistry, Section B: Organic, Incl. Medicinal, Publications and Informations Diectorate, New Delhi, IN, V21B, No. 12, 12-82, pp. 1071-1073.
Scoffone E. et al., "Indagini Sulla Struttura Delle Proteine", Gazzetta Chimica Italiana, Societa Chimica Italiana, Rome, IT, V87, 1957, pp. 354-365.
Menke, et al., "Expression Cloning of a Human $B_1$ Bradykinin Receptor", J. Biol. Chem., 269(34):21583-21586 (1994).
Hess, et al., "Cloning and Pharmacological Characterization of a Human Bradykinin (BK-2) Receptor", Biochem Biophys. Res. Commun., 184:260-268 (1992).
Ammons, et al., "Effects of Intracardiac Bradykinin on $T_2$-$T_5$ Medial Spinothalamic Cells", The American Physiological Society, 0363-6119, R147-R152 (1985).
Costello, et al., "Suppression of Carageenan-Induced Hyperalgesia, Hyperthermia and Edema by a Bradykinin Antagonist", European Journal of Pharmacology, 171:259-263 (1989).
Laneuville, et al., "Bradykinin Analogue Blocks Bradykinin-induced Inhibition of a Spinal Nociceptive Reflex in the Rat", European Journal of Pharmacology, 137:281-285 (1987).
Steranka, et al., "Antinociceptive Effects of Bradykinin Antagonists", European Journal of Pharmacology, 136:261-262 (1987).

(Continued)

Primary Examiner—James O. Wilson
Assistant Examiner—Zachary C. Tucker
(74) Attorney, Agent, or Firm—Foley & Lardner LLP

(57) ABSTRACT

Disclosed are sulfonylquinoxalone derivatives of the general formula:

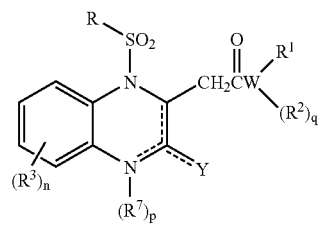

These compounds are useful as bradykinin antagonists.

8 Claims, No Drawings

OTHER PUBLICATIONS

Steranka, et al., "Bradykinin as a Pain Mediator: Receptors are Localized to Sensory Neurons, and Antagonists have Analgesic Actions", Neurobiology, 85:3245-3249 (1988).

Whalley, et al., "The Effect of Kinin Agonists and Antagonists on the Pain Response of the Human Blister Base", Naunyn Schmiederberg's Arch. Pharmacol., 336:652-655 (1987).

Back, et al., "Determination of Components of the Kallikrein-Kinin System in the Cerebrospinal Fluid of Patients with Various Diseases", Res. Clin. Stud. Headaches, 3:219-226 (1972).

Ness, et al., "Visceral Pain: a Review of Experimental Studies", Pain, 41:167-234 (1990).

Aasen, et al., "Plasma Kallikrein Activity and Prekallikrein Levels during Endotoxin Shock in Dogs", Eur. Surg. Res., 10:50-62(1978).

Aasen, et al., "Plasma Kallikrein-Kinin System in Septicemia", Arch. Surg., 118:343-346 (1983).

Katori, et al., "Evidence for the Involvement of a Plasma Kallikrein-Kinin System in the Immediate Hypotension Produced by Endotoxin in Anaesthetized Rats", Br. J. Pharmacol., 98:1383-1391 (1989).

Marceau, et al., "Pharmacology of Kinins: Their Relevance to Tissue Injury and Inflammation", Gen. Pharmacol., 14:209-229 (1983).

Weipert, et al., "Attenuation of arterial blood pressure fall endotoxin shock in the rat using the competitive bradykinin antagonist Lys-Lys-[Hyp$^2$, Thi$^{5,8}$, DPhe$^7$]-BK (B4148)", Brit J. Pharm., 94:282-284 (1988).

Haberland, "The Role of Kininogenases, Kinin Formation and Kininogenase Inhibition in Post Traumatic Shock and Related Conditions", Klinische Woochen-Schrift, 56:325-331 (1978).

Ellis, et al., "Inhibition of Bradykinin-and Kallikrein-Induced Cerebral Arteriolar Dilation by Specific Bradykinin Antagonist", Stroke, 18:792-795 (1987).

Kamitani, et al., "Evidence for a Possible Role of the Brain Kallikrein-Kinin System in the Modulation of the Cerebral Circulation", Circ. Res., 57:545-552 (1985).

Barnes, "Inflammatory Mediator Receptors and Asthma", Am. Rev. Respir. Dis., 135:S26-S31 (1987).

Burch, et al., "Bradykinin Receptor Antagonists", Med Res. Reviews., 10::237-269 (1990).

Fuller, et al., "Bradykinin-induced Bronchoconstriction in Humans", Am. Rev. Respir. Dis., 135:176-180 (1987).

Jin, et al., "Inhibition of Bradykinin-Induced Bronchoconstriction in the Guinea-Pig by a Synthetic B$_2$ Receptor Antagonist", Br. J. Pharmacol., 97:598-602 (1989).

Polosa, et al., "Contribution of Histamine and Prostanoids to Bronchoconstriction Provoked by Inhaled Bradykinin in Atopic Asthma", Allergy, 45:174-182 (1990).

Baumgarten, et al., "Concentrations of Glandular Kallikrein in Human Nasal Secretions Increase During Experimentally Induced Allergic Rhinitis", J. Immunology, 137:1323-1328 (1986).

Proud, et al., "Nasal Provocation with Bradykinin Induces Symptoms of Rhinitis and a Sore Throat", Am. Rev. Respir Dis., 137:613-616 (1988).

Seabrook, et al., "Expression of B$_1$ and B$_2$ Bradykinin Receptor mRNA and Their Functional Roles in Sympathetic Ganglia and Sensory Dorsal Root Ganglia Neurons from Wild-type and B$_2$ Receptor Knockout Mice", Neuropharmacology, 36(7):1009-17 (1997).

Romanenko et al. "Condensed and bound quinoxalines. IV. New pathway to acrylamides of (1,2-dihydro-2-oxo-3-quinoxalinyl) acetic acid" *Khimiya Geterotsiklicheskikh Soedinenii*, vol. 2, pp. 264-266 (1973).

De la Losa et al., Bulletin de la Societe Chimique de France, pp. 1621-1625 (1960).

Cunningham and Day, Journal of Organic Chemistry, vol. 38(6), pp. 1225-1227 (1973).

* cited by examiner

SULFONYLQUINOXALONE DERIVATIVES AND RELATED COMPOUNDS AS BRADYKININ ANTAGONISTS

BACKGROUND OF THE INVENTION

This application under 35 U.S.C. § 119(e) claims the benefit of U.S. Provisional Application No. 60/378,206, filed May 3, 2002, which is hereby incorporated by reference in its entirety.

FIELD OF THE INVENTION

This invention is directed to certain 1,2,3,4-tetrahydro-sulfonylquinoxalone acetamide derivatives and related compounds. These compounds are useful as bradykinin antagonists to relieve adverse symptoms, associated with bradykinin including pain, inflammation, bronchoconstriction, cerebral edema, etc.

REFERENCES

The following literature and patent publications are cited in this application as superscript numbers.

[1] J. G. Menke, et al., *J. Biol. Chem.*, 269(34):21583–21586 (1994)
[2] J. F. Hess, *Biochem. Human $B_2$ Receptor, Biophys. Res. Commun.*, 184:260–268 (1992)
[3] Burch, et al., "Bradykinin Receptor Antagonists", *J. Med. Chem.*, 30:237–269 (1990).
[4] Clark, W. G. "Kinns and the Peripheral Central Nervous Systems", Handbook of Experimental Pharmacology, Vol. XXV: Bradykinin, Kallidin, and Kallikrein. Erdo, E. G. (Ed.), 311–322 (1979).
[5] Ammons, W. S., et al., "Effects of Intracardiac Bradykinin on $T_2$-$T_5$ Medial Spinothalamic Cells", *Amer. J. Phys.*, 249:147–152 (1985).
[6] Costello, A. H. et al., "Suppression of Carageenan-Induced Hyperalgesia, Hyperthermia and Edema by a Bradykinin Antagonist", *European Journal of Pharmacology*, 171: 259–263 (1989).
[7] Laneuville, et al., "Bradykinin Analog Blocks Bradykinin-induced Inhibition of a Spinal Nociceptive Reflex in the Rat", *European Journal of Pharmacology*, 137:281–285 (1987).
[8] Steranka, et al., "Antinociceptive Effects of Bradykinin Antagonists", *European Journal of Pharmacology*, 136: 261–262 (1987).
[9] Steranka, et al., "Bradykinin as a Pain Mediator: Receptors are Localized to Sensory Neurons, and Antagonists have Analgesic Actions", *Neurobiology*, 85:3245–3249 (1987).
[10] Whalley, et al., in *Naunyn Schmiederberg's Arch. Pharmacol.*, 336:652–655 (1987).
[11] Back, et al., "Determination of Components of the Kallikrein-Kinin System in the Cerebrospinal Fluid of Patients with Various Diseases", *Res. Clin. Stud. Headaches*, 3:219–226 (1972).
[12] Ness, et al., "Visceral pain: a Review of Experimental Studies", *Pain*, 41:167–234 (1990).
[13] Aasen, et al., "Plasma kallikrein Activity and Prekallikrein Levels during Endotoxin Shock in Dogs", *Eur. Surg.*, 10:50–62 (1977).
[14] Aasen, et al., "Plasma Kallikrein-Kinin System in Septicemia", *Arch. Surg.*, 118:343–346 (1983).
[15] Katori, et al., "Evidence for the Involvement of a Plasma Kallikrein/Kinin System in the Immediate Hypotension Produced by Endotoxin in Anaesthetized Rats", *Br. J. Pharmacol.*, 98:1383–1391 (1989).
[16] Marceau, et al., "Pharmacology of Kinins: Their Relevance to Tissue Injury and Inflammation", *Gen. Pharmacol.*, 14:209–229 (1982).
[17] Weipert, et al, *Brit J. Pharm.*, 94:282–284 (1988).
[18] Haberland, "The Role of Kininogenases, Kinin Formation and Kininogenase Inhibitor in Post Traumatic Shock and Related Conditions", *Klinische Woochen-Schrift*, 56:325–331 (1978).
[19] Ellis, et al., "Inhibition of Bradykinin-and Kallikrein-Induced Cerebral Arteriolar Dilation by Specific Bradykinin Antagonist", *Stroke*, 18:792–795 (1987).
[20] Kamitani, et al., "Evidence for a Possible Role of the Brain Kallikrein-Kinin System in the Modulation of the Cerebral Circulation", *Circ. Res.*, 57:545–552 (1985).
[21] Barnes, "Inflammatory Mediator Receptors and Asthma", *Am. Rev. Respir. Dis.*, 135:S26-S31 (1987).
[22] Burch, et al., "Bradykinin Receptor Antagonists", *J. Med. Chem.*, 30:237–269 (1990).
[23] Fuller, et al., "Brakykinin-induced Bronchoconstriction in Humans", *Am. Rev. Respir. Dis.*, 135:176–180 (1987).
[24] Jin, et al., "Inhibition of Bradykinin-Induced Bronchoconstriction in the Guinea-Pig by a Synthetic $B_2$ Receptor Antagonist", *Br. J. Pharmacol.*, 97:598–602 (1989).
[25] Polosa, et al., "Contribution of Histamine and Prostanoids to Bronchoconstriction Provoked by Inhaled Bradykinin in Atopic Asthma", Allergy, 45: 174–182 (1990).
[26] Baumgarten, et al., "Concentrations of Glandular Kallikrein in Human Nasal Secretions Increase During Experimentally Induced Allergic Rhinitis", *J. Immunology*, 137:1323–1328 (1986).
[27] Proud, et al., "Nasal Provocation with Bradykinin Induces Symptoms of Rhinitis and a Sore Throat", *Am. Rev. Respir Dis.*, 137:613–616 (1988).
[28] Steward and Vavrek in "Chemistry of Peptide Bradykinin Antagonists" *Basic and Chemical Research*, R. M. Burch (Ed.), pages 51–96 (1991).
[29] Seabrook, et al., Expression of B1 and B2 Bradykinin Receptor mRNA and Their Functional Roles in Sympathetic Ganglia and Sensory Dorsal Root Ganglia Neurons from Wild-type and B2 Receptor Knockout Mice, *Neuropharmacology*, 36(7): 1009–17 (1997)
[30] Elguero, et al., Nonconventional Analgesics: Bradykinin Antagonists, *An. R. Acad. Farm.*, 63(1):173–90 (Spa) (1997)
[31] McManus, U.S. Pat. No. 3,654,275, Quinoxalinecarboxamide Antiinflammatory Agents, issued Apr. 4, 1972.

All of the above identified publications are herein incorporated by reference in their entirety to the same extent as if each individual publication was specifically and individually incorporated by reference in its entirety.

STATE OF THE ART

Bradykinin is known to be one of the most potent naturally occurring stimulators of C-fiber afferents mediating pain. It also is a potent vasodilator, edema-producing agent, and stimulator of various vascular and non-vascular smooth muscles in tissues such as uterus, gut and bronchiole. The kinin/kiniogen activation pathway has also been described as playing a pivotal role in a variety of physiologic and pathophysiologic processes, being one of the first systems to be activated in the inflammatory response and one of the most potent simulators of: (i) phospholipase $A_2$ and, hence, the generation of prostaglandins and leukotrienes; and (ii) phospholipase C and thus, the release of inositol phosphates and diacylgylcerol. These effects are mediated predominantly via activation of BK receptors of the $BK_2$ type.

Bradykinin (BK) is a peptide composed of nine amino acides ($Arg^1$-$Pro^2$-$Pro^3$-$Gly^4$-$Phe^5$- $Ser^6$-$Pro^7$-$Phe^8$-$Arg^9$) (SEQ. ID. NO. 1) which, along with lysyl-BK (kallidin), is released from precursor kininogens by proteases termed kallikreins. Plasma kallikrein circulates as an inactive zymogen, from which active kallikrein is released by Hageman factor. Tissue kallikrein appears to be located predominantly on the outer surface of epithelial cell membranes at sites thought to be involved in transcellular electrolyte transport.

B2 receptors are receptors for bradykinin and kallidin; they predominate and are normally found in most tissues. B1 receptors are specific for [des-$Arg^9$] bradykinin and [des-$Arg^{10}$] kallidin. The B1 subtype is induced by inflammatory processes. Bradykinin receptors have been cloned for different species, notably the human B1 receptor (see J. G. Menke et al.[1], and human B2 receptor J. F. Hess[2]).

The distribution of receptor B1 is very limited since this receptor is only expressed during states of inflammation. Two generations of peptidic antagonists of the B2 receptor have been developed. The second generation has compounds two orders of magnitude more potent as analgesics than first generation compounds and the most important derivative was icatibant. The first non-peptidic antagonist of the B2 receptor, described in 1993, has two phosphonium cations separated by a modified amino acid. Many derivatives of this di-cationic compound have been prepared. Another non-peptidic compound antagonist of B2 is the natural product Martinelline. See Elguero[30]. See also Seabrook[29].

Two major kinin precursor proteins, high molecular weight and low molecular weight kininogen are synthesized in the liver, circulate in plasma, and are found in secretions such as urine and nasal fluid. High molecular weight kininogen is cleaved by plasma kallikrein, yielding BK, or by tissue kallikrein, yielding kallidin. Low molecular weight kininogen, however, is a substrate only for tissue kallikrein. In addition, some conversion of kallidin to BK may occur inasmuch as the amino terminal lysine residue of kallidin is removed by plasma aminopeptidases. Plasma half-lives for kinins are approximately 15 seconds, with a single passage through the pulmonary vascular bed resulting in 80–90% destruction. The principle catabolic enzyme in vascular beds is the dipeptidyl carboxypeptidase kininase II or angiotensin-converting enzyme (ACE). A slower acting enzyme, kininase I, or carboxypeptidase N, which removes the carboxyl terminal Arg, circulates in plasma in great abundance. This suggests that it may be the more important catabolic enzyme physiologically. Des-$Arg^9$-bradykinin as well as des-$Arg^{10}$-kallidin formed by kininase I acting on BK or kallidin, respectively, are acting $BK_1$ receptor agonists, but are relatively inactive at the more abundant $BK_2$ receptor at which both BK and kallidin are potent agonists.

Direct application of bradykinin to denuded skin or intra-arterial or visceral injection results in the sensation of pain in mammals including humans. Kinin-like materials have been isolated from inflammatory sites produced by a variety of stimuli. In addition, bradykinin receptors have been localized to nociceptive peripheral nerve pathways and BK has been demonstrated to stimulate central fibers mediating pain sensation. Bradykinin has also been shown to be capable of causing hyperalgesia in animal models of pain. See, Burch et al,[3] and Clark, W. G.[4]

These observations have led to considerable attention being focused on the use of BK antagonists as analgesics. A number of studies have demonstrated that bradykinin antagonists are capable of blocking or ameliorating both pain as well as hyperalgesia in mammals including humans. See, Ammons[5], Clark[4], Costello[6], Lanuville[7], Steranka[8] and Steranka[9].

Currently accepted therapeutic approaches to analgesia have significant limitations. While mild to moderate pain can be alleviated with the use of non-steroidal anti-inflammatory drugs and other mild analgesics, severe pain such as that accompanying surgical procedures, burns and severe trauma requires the use of narcotic analgesics. These drugs carry the limitations of abuse potential, physical and psychological dependence, altered mental status and respiratory depression which significantly limit their usefulness.

Prior efforts in the field of BK antagonists indicate that such antagonists can be useful in a variety of roles. These include use in the treatment of burns, perioperative pain, migraine and other forms of pain, shock, central nervous system injury, asthma, rhinitis, premature labor, inflammatory arthritis, inflammatory bowel disease, etc. For example, Whalley[10] has demonstrated that BK antagonists are capable of blocking BK-induced pain in a human blister base model. This suggests that topical application of such antagonists would be capable of inhibiting pain in burned skin, e.g., in severely burned patients that require large doses of narcotics over long periods of time and for the local treatment of relatively minor burns or other forms of local skin injury.

The management of perioperative pain requires the use of adequate doses of narcotic analgesics to alleviate pain while not inducing excessive respiratory depression. Post-operative narcotic-induced hypoventilation predisposes patients to collapse of segments of the lungs, a common cause of post-operative fever, and frequently delays discontinuation of mechanical ventilation. The availability of a potent non-narcotic parenteral analgesic could be a significant addition to the treatment of perioperative pain. While no currently available BK antagonist has the appropriate pharmacodynamic profile to be used for the management of chronic pain, frequent dosing and continuous infusions are already commonly used by anesthesiologists and surgeons in the management of perioperative pain.

Several lines of evidence suggest that the kallikrein/kinin pathway may be involved in the initiation or amplification of vascular reactivity and sterile inflammation in migraine. (See, Back[11]). Because of the limited success of both prophylactic and non-narcotic therapeutic regimens for migraine as well as the potential for narcotic dependence in these patients, the use of BK antagonists offers a highly desirable alternative approach to the therapy of migraine.

Bradykinin is produced during tissue injury and can be found in coronary sinus blood after experimental occlusion of the coronary arteries. In addition, when directly injected into the peritoneal cavity, BK produces a visceral type of pain. (See, Ness[12]). While multiple other mediators are also clearly involved in the production of pain and hyperalgesia in settings other than those described above, it is also believed that antagonists of BK have a place in the alleviation of such forms of pain as well.

Shock related to bacterial infections is a major health problem. It is estimated that 400,000 cases of bacterial sepsis occur in the United States yearly; of those 200,000 progress to shock, and 50% of these patients die. Current therapy is supportive, with some suggestion in recent studies that monoclonal antibodies to Gram-negative endotoxin may have a positive effect on disease outcome. Mortality is still high, even in the face of this specific therapy, and a significant percentage of patents with sepsis are infected with Gram-positive organisms which would not be amenable to anti-endotoxin therapy.

Multiple studies have suggested a role for the kallikrein/kinin system in the production of shock associated with endotoxin. See, Aasen[13], Aasen[14], Katori[15] and Marceau[16]. Recent studies using newly available BK antagonists have demonstrated in animal models that these compounds can profoundly affect the progress of endotoxic shock. (See, Weipert[17]). Less data is available regarding the role of BK and other mediators in the production of septic shock due to Gram-positive organisms. However, it appears likely that similar mechanisms are involved. Shock secondary to trauma, while frequently due to blood loss, is also accompanied by activation of the kallikrein/kinin system. (See, Haberland[18].)

Numerous studies have also demonstrated significant levels of activity of the kallikrein/kinin system in the brain. Both kallikrein and BK dilate cerebral vessels in animal models of CNS injury. (See Ellis[19] and Kamitani[20]). Bradykinin antagonists have also been shown to reduce cerebral edema in animals after brain trauma. Based on these data, it is believed that BK antagonists should be useful in the management of stroke and head trauma.

Other studies have demonstrated that BK receptors are present in the lung, that BK can cause bronchoconstriction in both animals and man and that a heightened sensitivity to the bronchoconstrictive effect of BK is present in asthmatics. Some studies have been able to demonstrate inhibition of both BK and allergen-induced bronchoconstriction in animal models using BK antagonists. These studies indicate a potential role for the use of BK antagonists as clinical agents in the treatment of asthma. (See Barnes, [21] Burch[22], Fuller [23], Jin[24] and Polosa[25].) Bradykinin has also been implicated in the production of histamine and prostanoids to bronchoconstriction provoked by inhaled bradykinin in atopic asthma. [25] Bradykinin has also been implicated in the production of symptoms in both allergic and viral rhinitis. These studies include the demonstration of both kallikrein and BK in nasal lavage fluids and that levels of these substances correlate well with symptoms of rhinitis. (See, Baumgarten[26], Jin[24], and Proud[27].)

In addition, studies have demonstrated that BK itself can cause symptoms of rhinitis. Stewart and Vavrek[28] discuss peptide BK antagonists and their possible use against effects of BK. A great deal of research effort has been expended towards developing such antagonists with improved properties. However, notwithstanding extensive efforts to find such improved BK antagonists, there remains a need for additional and more effective BK antagonists. Two of the major problems with presently available BK antagonists are their low levels of potency and their extremely short durations of activity. Thus there is a special need for BK antagonists having increased potency and for duration of action.

U.S. Pat. No. 3,654,275[31] teaches that certain 1,2,3,4-tetrahydro-1-acyl-3-oxo-2-quinoxalinecarboxamides have anti-inflammatory activity and describes the preparation of certain intermediates which can also be used as intermediates in the preparation of the compounds hereafter described.

In view of the above, compounds which are bradykinin antagonists would be particularly advantageous in treating those diseases mediated by bradykinin.

SUMMARY OF THE INVENTION

This invention is directed, in part, to compounds which are bradykinin antagonists and are useful to treat diseases or relieve adverse symptoms associated with disease conditions in mammals mediated by bradykinin. Certain of the compounds exhibit increased potency and are expected to also exhibit an increased duration of action.

In one embodiment, this invention provides compounds of Formula I:

wherein one of bonds characterized by ---is a double bond and the other two are single bonds;

n is an integer from 0 to 4;

p is zero or one;

q is zero or one;

Y is selected from the group consisting of =O, =S, —OR$^8$, —NHR$^8$, =NR$^8$, —SR$^8$, and, when Y is —NHR$^8$ or =NR$^8$, R$^7$ and R$^8$, together with the nitrogen atoms to which they are attached, can form a heteroaryl, a substituted heteroaryl, a unsaturated heterocyclic, or a substituted unsaturated heterocyclic; provided that:

when Y is =O, =S, or =NR$^8$, then the bonds characterized by ---between the 2–3 and 3–4 position are single covalent bonds and p is one;

when Y is —OR$^8$, —SR$^8$, or —NHR$^8$ and p is zero, then the bond characterized by ---between the 3–4 position is a double bond; or when Y is —OR$^8$, —SR$^8$, or —NHR$^8$ and p=1 and R$^7$ is other than hydrogen, then the bond characterized by ---between the 2–3 position is a double bond;

W is selected from the group consisting of O, S, and N, wherein:

when W is O or S, then q is zero; and when W is N, then q is one;

R is selected from the group consisting of aryl, substituted aryl, heteroaryl, substituted heteroaryl, heterocyclic and substituted heterocyclic;

R$^1$ and R$^2$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic and substituted heterocyclic, or R$^1$ and R$^2$ together with the nitrogen atom to which they are attached form a heteroaryl, substituted heteroaryl, heterocyclic, or substituted heterocyclic;

each R$^3$ is independently selected from the group consisting of alkyl, substituted alkyl, alkenyl, substituted alkenyl, alkynyl, substituted alkynyl, amino, substituted amino, cycloalkyl, substituted cycloalkyl, alkoxy, substituted alkoxy, aryl, substituted aryl, aryloxy, substituted aryloxy, heteroaryl, substituted heteroaryl, heteroaryloxy, substituted heteroaryloxy, heterocyclic, substituted heterocyclic, heterocyclyloxy, substituted heterocyclyloxy, acyl, acyloxy, halogen, nitro, cyano, hydroxy, carboxy, —C(O)OR$^{10}$ wherein R$^{10}$ is alkyl, substituted alkyl, aryl, or substituted aryl, and —C(O)NR$^{11}$R$^{12}$ wherein R$^{11}$ and R$^{12}$ are independently selected from the group consisting of hydrogen, alkyl, substituted alkyl, aryl, substituted aryl, cycloalkyl, substituted cycloalkyl, heteroaryl, substituted heteroaryl, heterocyclic and substituted heterocyclic, or R$^{11}$ and R$^{12}$ together with the nitrogen atoms to which they are joined form a heteroaryl, substituted heteroaryl, heterocyclic a substituted heterocyclic group;

or two or more of R$^3$ together with the carbon atoms to which they are joined form a fused ring cycloalkenyl, substituted cycloalkenyl, aryl, substituted aryl, heteroaryl, substituted heteroaryl, unsaturated heterocyclic or substituted unsaturated heterocyclic;

R$^7$ is selected from the group consisting of hydrogen, alkyl, substituted alkyl, alkenyl, substituted alkenyl, cycloalkyl, substituted cycloalkyl, aryl, substituted aryl, heteroaryl, substituted heteroaryl, heterocyclic, substituted heterocyclic, acyl and acyloxy;

or $R^7$ together with at least one of $R^3$ and the nitrogen and carbon atoms to which they are joined forms a fused ring heteroaryl, substituted heteroaryl, unsaturated heterocyclic or substituted unsaturated heterocyclic;

$R^8$ is selected from the group consisting of alkyl, substituted alkyl, alkenyl, substituted alkenyl, cycloalkyl, substituted cycloalkyl, aryl, substituted aryl, heteroaryl, substituted heteroaryl, heterocyclic, substituted heterocyclic, acyl and acyloxy;

and pharmaceutically acceptable salts thereof;

with the proviso that when W=N and Y=O, at least $R^1$ and/or $R^2$ is selected from the group consisting of I alkylene-C(=O)$R^a$, wherein alkylene is optionally substituted and $R^a$ is selected from the group consisting of hydroxyl, —$NR^bR^b$, —$OR^b$, alkyl, substituted alkyl, alkenyl, substituted alkenyl, alkynyl, substituted alkynyl, aryl, substituted aryl, cycloalkyl, substituted cycloalkyl, heteroaryl, substituted heterocyclyl, substituted heterocyclyl wherein each $R^b$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic and substituted heterocyclic;

II alkylene-$X^a$, wherein alkylene is optionally substituted and $X^a$ is selected from the group consisting of —OH, cyano, and —$NR^bR^b$ wherein each $R^b$ is independently as defined above;

III —$NHR^b$, wherein $R^b$ is as defined above;

IV —$OR^b$, wherein $R^b$ is as defined above;

V alkylene-het$^a$-C(=O)—CH($R^b$)$NR^bR^b$, wherein alkylene is optionally substituted and het$^a$ is a nitrogen containing heterocycyl attached to the —C(O)— group through a ring nitrogen atom of the het$^a$ group and each $R^b$ is as defined above;

VI alkylene-het$^a$-C(=O)-het$^b$, wherein alkylene is optionally substituted and het$^a$ is as defined above and het$^b$ is a heterocyclyl;

VII alkylene-$R^c$—$NR^bC$(=$NR^b$)$NR^bR^b$, wherein alkylene is optionally substituted, each $R^b$ is as defined above and $R^c$ is selected from the group consisting of aryl, substituted aryl, cycloalkyl, substituted cycloalkyl, heteroaryl, substituted heteroaryl, heterocyclic and substituted heterocyclic;

VIII alkylene-$R^c$—$NR^b$ C(=O)—$NR^bR^b$, wherein alkylene is optionally substituted, each $R^b$ is as defined above and $R^c$ is as defined above;

IX alkylene-$R^c$-alkylene-C(=O)$R^b$, wherein alkylene is optionally substituted and $R^b$ and $R^c$ are as defined above;

X alkylene-$R^c$—C(=O)-alkylene-($X^b$)$_{n'}$, wherein alkylene is optionally substituted, $X^b$ is selected from the group consisting of —OH, halo, cyano, and —$NR^bR^b$, n' is one except when $X^b$ is halo then n' can be 1–3; and further wherein each $R^b$ is independently as defined above and $R^c$ is as defined above;

XI alkylene-$R^c$—C(=O)—$R^d$, wherein alkylene is optionally substituted and $R^c$ is selected from the group consisting of aryl, substituted aryl, cycloalkyl, substituted cycloalkyl, heteroaryl, substituted heteroaryl, heterocyclic and substituted heterocyclic and $R^d$ is selected from the group consisting of substituted alkyl, aryl, heteroaryl, heterocyclic and cycloalkyl;

XII alkylene-$R^c$—$NR^bC$(=O)$R^e$ wherein alkylene is optionally substituted, $R^b$ and $R^c$ are as defined above, and where $R^e$ is substituted alkyl, alkenyl, substituted alkenyl, aryl, substituted aryl, cycloalkyl, substituted heteroarynyl XIII alkynylene-$R^d$ where $R^d$ is as defined above;

XIV or where $R^1$ and $R^2$ are joined, together with the nitrogen atom bond thereto, to form a nitrogen containing substituted heterocyclyl with 1 to 2 substituents selected from substituted alkyl, heteroaryl, heterocyclyl;

XV alkenylene-$R^d$ where $R^d$ is as defined above; and

XVI alkylene-$R^c$—$NR^b$—C(=$NR^b$)$R^b$, wherein alkylene is optionally substituted, and each of $R^b$ and $R^c$ are as defined above; with the further provisos that:

A. when W is N, $R^1$ is hydrogen, $R^2$ is benzyl, $R^7$ is methyl, n is zero, p is one, and Y is =O, then R is not 2,4,6-trimethylphenyl;

B. when W is N, $R^1$ and $R^7$ are hydrogen, $R^2$ is 2-(pyrid-4-yl)ethy-1-yl, n is zero, p is one, and Y is =O, then R is not 1-methylpyrazol-4-yl;

C. when W is N, $R^1$ and $R^7$ are hydrogen, $R^2$ is benzyl, n is zero, p is one, and Y is =O, then R is not 2,4-difluorophenyl;

D. when W is N, $R^1$, $R^2$ and $R^7$ are hydrogen, n is zero, p is one, and Y is =O, then R is not 2,4-difluorophenyl;

E. when W is N, $R^1$ is hydrogen, $R^2$ and $R^7$ are 3-chlorobenzyl, n is zero, p is one, and Y is =O, then R is not 4-chloro-2,5-dimethylphenyl;

F. when W is N, $R^1$ and $R^7$ are hydrogen, $R^2$ is benzyl, n is zero, p is one, and Y is =O, then R is not phenyl;

G. when W is N, $R^1$ and $R^7$ are hydrogen, $R^2$ is phenyl, n is zero, p is one, and Y is =O, then R is not quinolin-8-yl; and H. when W is N, $R^1$ and $R^7$ are hydrogen, $R^2$ is benzyl, n is zero, p is one, and Y is =O, then R is not thien-2-yl; and with the further proviso excluding the following known compounds:

I. when $R^1$ and $R^7$ are hydrogen, $R^2$ is 2-methoxyphenyl, n is zero, p is one, and Y' is =O, then R is not 4-methylphenyl; and J. when $R^1$ and $R^7$ are hydrogen, $R^2$ is 2-ethoxyphenyl, n is zero, p is one, and Y' is =O, then R is not 4-methylphenyl.

Preferred R groups include, for example, phenyl; naphth-1-yl; 5-dimethylamino-naphth-1-yl; 2-fluorophenyl; 2-chlorophenyl; 2-cyanophenyl; 2-methylphenyl; 2-nitrophenyl; 2-trifluoromethylphenyl; 3-chlorophenyl; 4-methylphenyl (tolyl); 2,5-dibromophenyl; 4-bromo-2-ethylphenyl; 4-bromo-2-trifluoromethoxyphenyl; 2,3-dichlorophenyl; 2,4-dichlorophenyl; 3,4-dichlorophenyl; 2,5-dichlorophenyl; 3,5-dichlorophenyl; 2,6-dichlorophenyl; 2-chloro-4-cyanophenyl; 2-chloro-4-fluorophenyl; 3-chloro-2-methylphenyl; 2-chloro-6-methylphenyl; 5-chloro-2-methoxyphenyl; 2-chloro-4-trifluoromethylphenyl; 2,4-difluorophenyl; 5-fluoro-2-methylphenyl; 2,5-dimethoxyphenyl; 2-methoxy-4-methylphenyl; 2-methoxy-5-bromophenyl; 2-methoxy-5-methylphenyl; 2,5-dimethylphenyl; 2-methyl-5-nitrophenyl; 3,5-di(trifluoromethyl)phenyl; 4-bromo-2,5-difluorophenyl; 2,3,4-trichlorophenyl; 2,4,5-trichlorophenyl; 2,4,6-trichlorophenyl; 2,4-dichloro-5-methylphenyl; 4-chloro-2,5-dimethylphenyl; 2,4,6-tri(iso)propylphenyl; 2,4,6-trimethylphenyl; 2,3,5-trimethyl-4-chlorophenyl; 2,3,6-trimethyl-4-methoxyphenyl; 2,3,4,5,6-pentamethylphenyl; 5-chloro-1,3-dimethylpyrazol-4-yl; 2-methoxycarbonyl-thiophen-3-yl; 2,3-dimethylimidazol-5yl; 2-methylcarbonylamino-4-methyl-thiazol-5-yl; quinolin-8-yl; thiophen-2-yl; 1-methylimidiazol-4-yl; 3,5-dimethylisoxazol-4-yl; and N-morpholino.

Particularly preferred R groups include 4-chloro-2,5-dimethylphenyl and 2,3-dichlorophenyl.

When W is N, preferred R¹ groups include, for example,
2-[(4-amidino)phenyl]1-(R)-(pyrrolidin-N-ylcarbonyl)eth-1-yl,
amino,
2-[N-(α-aminoacetyl)piperid-4-yl]eth-1-yl,
2-[4-(aminoethyleneamidino)phenyl]eth-1-yl,
2-[N-(1-amino-1-methylethylcarbonyl)piperid-4-yl]eth-1-yl,
1-(S)-carboxamide-2-(indol-3-yl)eth-1-yl,
carboxamidemethyl,
1-carboxamide-2-(S)-methyl-but-1-yl,
1-(S)-carboxamide-2-(phenyl)eth-1-yl,
1-(R)-carboxamide-2-(phenyl)eth-1-yl,
cyanomethyl,
2-(4-cyanophenyl)-1-(R)-(pyrrolidin-N-ylcarbonyl)eth-1-yl,
2-(4-cyanophenyl)-1-(S)-(pyrrolidin-N-ylcarbonyl)eth-1-yl,
2-(N-cyclopropylpiperidin-4-yl)-1-(R)-(pyrrolidin-N-ylcarbonyl)eth-1-yl,
1-(R)-1,3-di(benzyloxycarbonyl)prop-1-yl,
1-(S)-1,3-dicarboxamideprop-1-yl,
(2-dimethylamino)eth-1-yl,
3-(dimethylamino)prop-1-yl,
1-(S)-ethoxycarbonyleth-1-yl,
1-(R)-(1-N-ethylamino-carbonyl)-4-amino-n-butyl,
1-(S)-(1-N-ethylamino-carbonyl)-4-amino-n-butyl,
1-(R)-(1-N-ethylaminocarbonyl)-5-(t-butoxycarbonylamino)-pent-5-yl,
1-(S)-(1-N-ethylaminocarbonyl)-5-(t-butoxycarbonylamino)-pent-5-yl,
1-(R)-(1-N-ethylaminocarbonyl)-4-(N'-t-butoxycarbonylamino)-n-but-1-yl,
1-(S)-(1-N-ethylaminocarbonyl)-4-(N'-t-butoxycarbonylamino)-n-but-1-yl,
1-(R)-(1-N-ethylaminocarbonyl)-5-guanadino-n-pent-5-yl,
1-(S)-(1-N-ethylaminocarbonyl)-5-guanadino-n-pent-5-yl,
1-R,S-(1-N-ethylaminocarbonyl)-4-(N'-t-butoxycarbonyl)-guanadino-n-but-1-yl,
1-(R)-(1-N-ethylaminocarbonyl)-5-(N'-t-butoxycarbonylamino)-n-pent-5-yl,
1-(S)-(1-N-ethylaminocarbonyl)-5-(N'-t-butoxycarbonylamino)-n-pent-5-yl,
2-hydroxyeth-1-yl,
2-(4-hydroxyphenyl)-1-(S)-(methoxycarbonyl)eth-1-yl,
2-(4-hydroxyphenyl)-1-(S)-(isopropoxycarbonyl)eth-1-yl,
2-(4-hydroxyphenyl)-1-(R)-(methoxycarbonyl)eth-1-yl,
2-(N-hydroxypyrid-4-yl)eth-1-yl,
2-(imidazol-4-yl)eth-1-yl,
2-[4-(imidazolin-2-yl)phenyl]-1-(R)-(pyrrolidin-1-ylcarbonyl)eth-1-yl,
2-(indol-3-yl)eth-1-yl,
2-(indol-3-yl)-1-(S)-(methoxycarbonyl)eth-1-yl,
2-(indol-3-yl)-1-(R)-(methoxycarbonyl)eth-1-yl,
1-(R)-(isopropoxycarbonyl)-2-(phenyl)eth-1-yl,
methoxy,
1-(R)-(methoxycarbonyl)eth-1-yl,
methoxycarbonylmethyl,
methoxycarbonylphenylmethyl,
2-methoxyeth-1-yl,
1-(R)-(methoxycarbonyl)-2-(N-methylpiperidin-4-yl)eth-1-yl,
1-(R)-(methoxycarbonyl)-2-(N-methyl-1,2,3,6-tetrahydropyrid-4-yl)eth-1-yl,
1-(R)-(methoxycarbonyl)-2-pyrid-4-yl)eth-1-yl,
1-(R)-(N-methyl-N-ethylcarbamoyl)-3-(guanadino)prop-1-yl,
2-(N-methylpiperidin-4-yl)-1-(R)-(pyrrolidin-N-ylcarbonyl)eth-1-yl,
2-(N-methyl-1,2,5,6-tetrahydropyrid-4-yl)-1-(R)-(pyrrolidin-N-ylcarbonyl)eth-1-yl,
3-(2-methylthiazol-4-yl)-pyrazol-5-yl,
1-(R)-2-phenyl-1-(methoxycarbonyl)eth-1-yl,
1-(S)-2-phenyl-1-(methoxycarbonyl)eth-1-yl,
2-(phenyl)-1-(S)-(pyrrolidin-N-ylcarbonyl)eth-1-yl,
(piperidin-1-yl)carbonylmethyl,
1-(R)-(pyrrolidin-N-ylcarbonyl)-2-(4-amidino)phenyl-eth-1-yl,
1-(S)-(pyrrolidin-N-ylcarbonyl)-2-(4-amidino)phenyl-eth-1-yl,
1-(R)-(pyrrolidin-N-ylcarbonyl)-5-amino-n-pent-1-yl,
1-(S)-(pyrrolidin-N-ylcarbonyl)-5-amino-n-pent-1-yl,
1-(R)-(pyrrolidin-N-ylcarbonyl)-2-(4-biphenyl)eth-1-yl,
1-(S)-(pyrrolidin-N-ylcarbonyl)-2-(4-biphenyl)eth-1-yl,
1-(R)-(pyrrolidin-N-ylcarbonyl-2-(4-iodophenyl)eth-1-yl,
1-(S)-(pyrrolidin-N-ylcarbonyl-2-(4-iodophenyl)eth-1-yl,
1-(R)-(pyrrolidin-N-carbonyl)-4-(t-butoxycarbonylamino)-n-but-1-yl,
1-(S)-(pyrrolidin-N-carbonyl)-4-(t-butoxycarbonylamino)-n-but-1-yl,
1-(S)-(pyrrolidin-N-ylcarbonyl)-2-[4-(2-imidazolin-2-yl)phenyl]eth-1-yl,
2-(R)-(pyrrolidin-N-ylcarbonyl-3-phenylprop-2-yl,
1-(R)-(pyrrolidin-N-ylcarbonyl)-2-[4-(N-methylpiperidin-2-yl)eth-1-yl
1-(S)-(pyrrolidin-N-ylcarbonyl)-2-[4-(N-methylpiperidin-2-yl)phenyl]eth-1-yl
1-(R)-(pyrrolidin-N-ylcarbonyl)-2-[N-methyl-1,2,5,6-tetrahydropyridin-4-yl)-phen-4-yl)]eth-1-yl
1-(S)-(pyrrolidin-N-ylcarbonyl)-2-[N-methyl-1,2,5,6-tetrahydropyridin-4-yl)-phen-4-yl)]eth-1-yl
1-(R)-(pyrrolidin-N-ylcarbonyl)-2-[4-(piperidin-2-yl)cyclohexyl)]eth-1-yl,
1-(S)-(pyrrolidin-N-ylcarbonyl)-2-[4-(piperidin-2-yl)cyclohexyl)]eth-1-yl,
1-(R)-(pyrrolidin-N-ylcarbonyl)-2-[N-(phenyl)-piperidin-4-yl)]eth-1-yl
1-(S)-(pyrrolidin-N-ylcarbonyl)-2-[N-(phenyl)-piperidin-4-yl)]eth-1-yl
1-(R)-(pyrrolidin-N-ylcarbonyl)-2-[N-(pyridin-4-yl)-piperidin-4-yl)]eth-1-yl
1-(S)-(pyrrolidin-N-ylcarbonyl)-2-[N-(pyridin-4-yl)-piperidin-4-yl)]eth-1-yl
1-(R)-(pyrrolidin-N-ylcarbonyl)-2-[4-(pyridin-4-yl)phenyl)]eth-1-yl
1-(S)-(pyrrolidin-N-ylcarbonyl)-2-[4-(pyridin-4-yl)phenyl)]eth-1-yl
1-(R)-(pyrrolidin-N-ylcarbonyl)-2-[4-(pyrid-2-yl)phenyl]eth-1-yl,
1-(S)-(pyrrolidin-N-ylcarbonyl)-2-[4-(pyrid-2-yl)phenyl]eth-1-yl,
1-(R)-(pyrrolidin-N-ylcarbonyl)-2-[4-(pyrimidin-2-yl)phenyl]eth-1-yl,
1-(S)-(pyrrolidin-N-ylcarbonyl)-2-[4-(pyrimidin-2-yl)phenyl]eth-1-yl,
1-(R)-(pyrrolidin-N-ylcarbonyl)-2-[4-(N-t-butoxycarbonylpyrrol-2-yl)phenyl]eth-1-yl 1-(S)-(pyrrolidin-N-ylcarbonyl)-2-[4-(N-t-butoxycarbonylpyrrol-2-yl)phenyl]eth-1-yl
1-(S)-(t-butoxycarbonyl)-2-(4-hydroxyphenyl)eth-1-yl,
3-t-butoxycarbonyl-1-methoxycarbonylprop-1-yl,
1-(S)-(t-butoxycarbonyl)-3-methylprop-1-yl,
1-(R)-(t-butoxycarbonyl)-3-methylprop-1-yl,
1-(R)-(t-butoxycarbonyl)-2-(phenyl)eth-1-yl,
1-(R)-1-pyrrolidin-N-ylcarbonyl-2-phenyleth-1-yl
2-phenyl-1-(R)-carboxy-eth-1-yl
2-[N-(α,α dimethylglycine)piperidin-4-yl]eth-1-yl
2-{4-(ethylamino-amidino)phenyl]eth-1-yl
1-(R)-(pyrrolidin-N-ylcarbonyl)-3-(guanadino)but-1-yl
1-(R)-(pyrrolidin-N-ylcarbonyl)-4-(N'-t-butoxycarbonyl)-guanadino-n-but-1-yl
1-(R)-(pyrrolidin-N-ylcarbonyl)-5-(N'-t-butoxycarbonylamino)-n-pent-5-yl
1-(R)-(pyrrolidin-N-ylcarbonyl)-4-amino-n-butyl
1-(R)-(pyrrolidin-N-ylcarbonyl)-4-guanadino-but-4-yl
1-(R)-(pyrrolidin-N-ylcarbonyl)-2-[4-(N-methyl-1,2,3,6-tetrahydropyridin-6-yl)phenyl)]eth-1-yl
1-(R)-(pyrrolidin-N-ylcarbonyl)-2-[4-(N-t-butoxycarbonylpyrrol-2-yl)phenyl]eth-1-yl
4-N-[(N',N'-dimethylaminocarbonyl)amino-phen-4-yl]eth-1-yl
2-[N-(N'-morpholino-carbonyl)piperidin-4-yl]eth-1-yl
2-{N-[(2-(thiophen-2-yl)methylenecarbonyl]-piperidin-4-yl}eth-1-yl
2-[N-(3,5-dimethyloxazol-4-ylcarbonyl)piperidin-4-yl]eth-1-yl
2-[N-(furan-2-ylcarbonyl)-piperidin-4-yl]eth-1-yl
2-[N-(oxazol-5-yl-carbonyl)piperidin-4-yl]eth-1-yl
2-[N-(5-methylpyrazol-3-ylcarbonyl)piperidin-4-yl]eth-1-yl
2-[N-(1-methyl-3-t-butylpyrazol-5-ylcarbonyl)piperidin-4-yl]eth-1-yl
2-[N-(4-methylthiadiazol-5-ylcarbonyl)piperidin-4-yl]eth-1-yl
2-[N-(chloromethylene-carbonyl)piperidin-4-yl]eth-1-yl
2-[N-(benzylcarbonyl)-piperidin-4-yl]eth-1-yl
2-[N-(2-phenylethenyl-carbonyl)piperidin-4-yl]eth-1-yl
2-[N-(methoxymethylene-carbonyl)piperidin-4-yl]eth-1-yl
2-[N-(pyrazin-2-ylcarbonyl)piperidin-4-yl]eth-1-yl
2-[N-(isoquinolin-3-ylcarbonyl)piperidin-4-yl]eth-1-yl
2-[N-(pyrrolidin-5-one-2-ylcarbonyl)piperidin-4-yl]eth-1-yl
2-[N-(N -acetylpyrrolidin-2-ylcarbonyl)piperidin-4-yl]eth-1-yl
2-[N-(dichloromethylenecarbonyl)piperidin-4-yl]eth-1-yl
4-[N-(pyrazin-2-ylcarbonyl)amino]pheneth-1-yl
4-[N-(isoquinolin-2-ylcarbonyl)amino]pheneth-1-yl
4-[N-(N'-acetylpyrrolidin-2-ylcarbonyl)amino]-pheneth-1-yl
4-[N-(1,2-benzothiadiazol-5-ylcarbonyl)amino]-pheneth-1-yl
4-[N-(benzofuran-5-ylcarbonyl)amino]pheneth-1-yl
4-[N-(3-methylisoxazol-5-ylcarbonyl)amino]-pheneth-1-yl
4-[N-(methoxyphen-3-ylcarbonyl)amino]pheneth-1-yl
4-[N-(thiophen-2-ylmethylenecarbonyl)amino]pheneth-1-yl
4-[N-(3,5-dimethyl-isoxazol-4-ylcarbonyl)-amino] pheneth-1-yl
4-[N-(2-(pyrid-3-yl)ethylcarbonyl)amino]pheneth-1-yl
4-[N-(furan-2-ylcarbon-yl)amino]pheneth-1-yl
4-[N-(isoxazol-5-ylcar-bonyl)amino]pheneth-1-yl
4-[N-(3-methylpyrazol-5-yl-5-ylcarbonyl)amino]-pheneth-1-yl
4-[N-(1-methyl-3-t-butyl-pyrazol-5-ylcarbonyl)-amino] pheneth-1-yl
4-[N-(4-methyl-1,2,3-thiadiazol-5-ylcarbonyl)-amino]-pheneth-1-yl
4-[N-(chloromethylene-carbonyl)amino]pheneth-1-yl
4-[N-(chlorophen-2-ylcarbonyl)amino]pheneth-1-yl
4-[N-(phenylcarbonyl)amino]pheneth-1-yl
4-[N-(pyrid-2-ylcarbonyl)-aminopheneth-1-yl
4-[N-(2-phenylethenyl-carbonyl)amino]pheneth-1-yl
4-[N-(2-phenylethenyl-carbonyl)amino]pheneth-1-yl
4-[N-(fluorophen-2-ylcarbonyl)amino]pheneth-1-yl
4-[N-(methoxymethylenecarbonyl)amino]pheneth-1-yl
4-[N-(dichloromethylene-carbonyl)amino]pheneth-1-yl
4-[N-(methylenedioxy-phen-4-ylcarbonyl)amino]-pheneth-1-yl
1-[(R)-(pyrrolidin-N-ylcarbonyl)]-2-[N-methylpyrid-2-yl)phen-4-yl]eth-1-yl
1-[(R)-(pyrrolidin-N-ylcarbonyl)]-2-[(N-methylpyrid-4-yl)phen-4-yl]eth-1-yl
1-[(R)-(pyrrolidin-N-ylcarbonyl)]-2-[(N-methylpyrid-4-yl)phen-4-yl]eth-1-yl
1-[(R)-(pyrrolidin-N-ylcarbonyl)]-2-[1-(piperidin-2-yl) phen-4-yl]eth-1-yl
1-(R)-(pyrrolidin-N-ylcarbonyl)-2-[4-(N-methylpyrid-4-yl)phen-1-yl)eth-1-yl
4-(pyridin-2-yl)but-3-yn-1-yl and
(benzoimidazol-2-ylamino)eth-1-yl.

When W is N, preferred $R^2$ groups include hydrogen, methyl, ethyl, iso-propyl, 2-methoxyeth-1-yl, and pyrid-3-ylmethyl.

In another preferred embodiment, when W is N, $R^1$ and $R^2$ are joined, together with the nitrogen atom to which they are bound, to form an optionally substituted heterocyclic including, by way of example, 4-(2-aminoethyl)piperidin-1-yl; 4-[2-(N-t-butoxycarbonylamino)ethyl]-piperidin-1-yl; and 1-(pyridin-2-yl)piperazin-4-yl.

A particularly preferred $R^2$ group is hydrogen.

Preferred $R^3$ groups include, by way of example, chloro, fluoro and methyl. In one preferred embodiment, the 1,2,3,4-quinoxaline ring is disubstituted at the 6 and 7 positions to provide for 6,7-dichloro; 6,7-difluoro and 6,7-dimethyl substitution.

Most preferably, n is zero (i.e., all of the $R^3$ groups are hydrogen).

Preferred $R^7$ groups include hydrogen, methyl, benzyl, t-butoxycarbonyl-methyl; and the like.

In a particularly preferred embodiment, W is nitrogen, Y is =O, n is zero (all $R^3$ groups are hydrogen), p is one, q is one and $R^2$ and $R^7$ are hydrogen. Such compounds are represented by Formula II as follows:

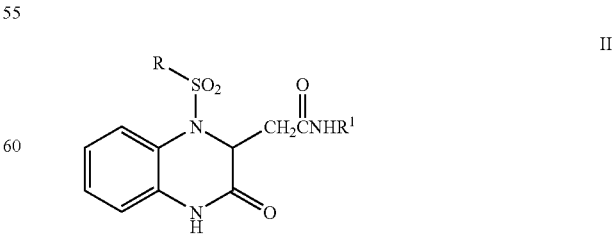

where R and $R^1$ are as defined above; and pharmaceutically acceptable salts thereof.

The present invention further provides intermediates for the compounds of Formula I which can be represented by Formula III below:

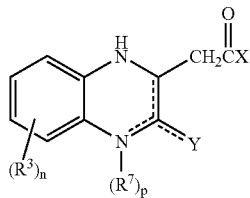

III wherein $R^3$, $R^7$, n, p, Y and the ---bond line are as defined in claim 1 and X is selected from the group consisting of —$NR^1R^2$ wherein $R^1$ and $R^2$ are joined, together with the nitrogen atom bond thereto, to form a nitrogen containing substituted heterocyclyl with 1 to 2 substituents selected from the group consisting of substituted alkyl, heteroaryl, and heterocyclyl, or X is —$OR^{10}$ wherein $R^{10}$ is hydrogen or lower alkyl.

In those cases where the compounds of Formulas I–III exist as optical or geometric isomers, the above formulas are intended to represent isomer mixtures and also the individual BK antagonist or intermediate isomers. Formulas I–III are also intended to represent the individual isomers as well as mixtures thereof; both of which are encompassed within the scope of this invention.

Compounds within the scope of this invention include those set forth in Table I as follows:

TABLE I

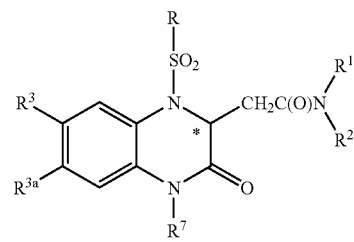

($R^2$, $R^3$, $R^{3a}$, and $R^7$ are all hydrogen unless otherwise specified)

| * | R | $R^1$ | $R^2$, $R^3$, $R^{3a}$, $R^7$ | GP # | Cpd. No. |
|---|---|---|---|---|---|
| R & S | 4-chloro-2,5-dimethyl-phenyl | 1-(R)-1-pyrrolidin-N-ylcarbonyl-2-phenyleth-1-yl | | I | 5 |
| R & S | 4-chloro-2,5-dimethyl-phenyl | (piperidin-1-yl)carbonylmethyl | | I | 6 |
| R & S | 4-chloro-2,5-dimethyl-phenyl | 2-hydroxyeth-1-yl | | II | 11 |
| R or S | 4-chloro-2,5-dimethyl-phenyl | 1-(R)-2-phenyl-1-(methoxycarbonyl)eth-1-yl | | I | 12 |
| R & S | 4-chloro-2,5-dimethyl-phenyl | (2-dimethylamino)eth-1-yl | | II | 16 |
| R & S | 4-chloro-2,5-dimethyl-phenyl | 1-(R)-(methoxycarbonyl)-2-(N-methylpiperidin-4-yl)eth-1-yl | | | 46 |
| R & S | 4-chloro-2,5-dimethyl-phenyl | 1-(R)-1,3-di(benzyloxy-carbonyl)-prop-1-yl | | I | 48 |
| R & S | 4-chloro-2,5-dimethyl-phenyl | 1-(R)-(iso-propoxycarbonyl)-2-(phenyl)eth-1-yl | | I | 49 |
| R & S | 4-chloro-2,5-dimethyl-phenyl | 1-(R)-(methoxycarbonyl)eth-1-yl | | I | 50 |
| R & S | 4-chloro-2,5-dimethyl-phenyl | 1-(R)-(methoxycarbonyl)-2-pyrid-4-yl)eth-l-yl | | I | 51 |
| R & S | 4-chloro-2,5-dimethyl-phenyl | 1-(R)-(methoxycarbonyl)-2-(N-methyl-1,2,3,6-tetrahydropyrid-4-yl)eth-1-yl | | I | 52 |
| R or S | 4-chloro-2,5-dimethyl-phenyl | 1-(R)-(methoxycarbonyl)-2-(N-methylpiperidin-4-yl)eth-1-yl | | I | 53 |
| R & S | 4-chloro-2,5-dimethyl-phenyl | 1-(S)-(pyrrolidin-N-ylcarbonyl)-2-[4-(2-imidazolin-2-yl)phenyl]eth-1-yl | | I | 54 |
| R & S | 4-chloro-2,5-dimethyl-phenyl | 1-(S)-(t-butoxycarbonyl)-3-methylbut-1-yl | | I | 55 |
| R & S | 4-chloro-2,5-dimethyl-phenyl | 1-(R)-(t-butoxycarbonyl)-3-methylprop-1-yl | | I | 56 |
| R & S | 4-chloro-2,5-dimethyl-phenyl | 1-(S)-(t-butoxycarbonyl)-2-(4-hydroxyphenyl)eth-1-yl | | I | 57 |
| R & S | 4-chloro-2,5-dimethyl-phenyl | 1-(R)-(t-butoxycarbonyl)-2-(phenyl)eth-1-yl | | I | 58 |
| R & S | 4-chloro-2,5-dimethyl-phenyl | 1-(S)-carboxamide-2-(indol-3-yl)eth-1-yl | | I | 59 |
| R & S | 4-chloro-2,5-dimethyl-phenyl | 1-(R)-carboxamide-2-(phenyl)eth-1-yl | | I | 60 |
| R & S | 4-chloro-2,5-dimethyl-phenyl | 1-(S)-carboxamide-2-(S)-methylbut-1-yl | | I | 61 |
| R & S | 4-chloro-2,5-dimethyl-phenyl | 1-(S)-carboxamide-2-(phenyl)eth-1-yl | | I | 62 |
| R & S | 4-chloro-2,5-dimethyl-phenyl | 1-(S)-ethoxycarbonyleth-1-yl | | I | 63 |

TABLE I-continued

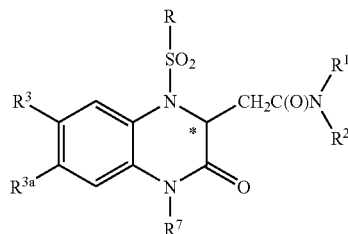

($R^2$, $R^3$, $R^{3a}$, and $R^7$ are all hydrogen unless otherwise specified)

| * | R | $R^1$ | $R^2$, $R^3$, $R^{3a}$, $R^7$ | GP # | Cpd. No. |
|---|---|---|---|---|---|
| R & S | 4-chloro-2,5-dimethyl-phenyl | 1-(S)-1,3-dicarboxamide prop-1-yl | | I | 66 |
| R & S | 4-chloro-2,5-dimethyl-phenyl | 2-(N-cyclopropyl-piperidin-4-yl)-1-(R)-(pyrrolidin-N-ylcarbonyl)eth-1-yl | | I | 71 |
| R & S | 4-chloro-2,5-dimethyl-phenyl | 2-(N-methyl-1,2,5,6-tetrahydropyrid-4-yl)-1-(R)-(pyrrolidin-N-ylcarbonyl)eth-1-yl | | I | 75 |
| R & S | 4-chloro-2,5-dimethyl-phenyl | 2-(N-methylpiperidin-4-yl)-1-(R)-(pyrrolidin-N-ylcarbonyl)eth-1-yl | | I | 78 |
| R & S | 4-chloro-2,5-dimethyl-phenyl | 2-(4-cyanophenyl)-1-(R)-(pyrrolidin-N-ylcarbonyl)eth-1-yl | | I | 85 |
| R & S | 4-chloro-2,5-dimethyl-phenyl | 2-(4-cyanophenyl)-1-(S)-(pyrrolidin-N-ylcarbonyl)eth-1-yl | | I | 86 |
| R & S | 4-chloro-2,5-dimethyl-phenyl | 2-(4-hydroxyphenyl)-1-(S)-(methoxycarbonyl)eth-1-yl | | I | 87 |
| R & S | 4-chloro-2,5-dimethyl-phenyl | 2-(4-hydroxyphenyl)-1-(S)-(t-butoxycarbonyl)eth-1-yl | | I | 88 |
| R & S | 4-chloro-2,5-dimethyl-phenyl | 2-(4-hydroxyphenyl)-1-(R)-(methoxycarbonyl)eth-1-yl | | I | 89 |
| R & S | 4-chloro-2,5-dimethyl-phenyl | 2-(indol-3-yl)-1-(S)-(methoxycarbonyl)eth-1-yl | | I | 92 |
| R & S | 4-chloro-2,5-dimethyl-phenyl | 2-(indol-3-yl)-1-(R)-(methoxycarbonyl)eth-1-yl | | I | 93 |
| R & S | 4-chloro-2,5-dimethyl-phenyl | 2-(phenyl)-1-(S)-(pyrrolidin-N-ylcarbonyl)eth-1-yl | | I | 94 |
| R & S | 4-chloro-2,5-dimethyl-phenyl | 2-(pyrid-4-yl)-1-(R)-(pyrrolidin-N-ylcarbonyl)eth-1-yl | | I | 104 |
| R & S | 4-chloro-2,5-dimethyl-phenyl | 2-phenyl-1-(S)-(methoxy-carbonyl)eth-1-yl | | I | 110 |
| R & S | 4-chloro-2,5-dimethyl-phenyl | 2-phenyl-1-(R)-carboxy-eth-1-yl | | I | 111 |
| R & S | 4-chloro-2,5-dimethyl-phenyl | 2-[N-(α,α dimethyl glycine)piperidin-4-yl]eth-1-yl | | V | 115 |
| R & S | 4-chloro-2,5-dimethyl-phenyl | 2-[N-(α-aminoacetyl)piperidin-4-yl]eth-1-yl | | V | 116 |
| R or S | 4-chloro-2,5-dimethyl-phenyl | 2-[4-(imidazolin-2-yl)phenyl]-1-(R)-(pyrrolidin-1-ylcarbonyl)eth-1-yl | | I | 121 |
| R & S | 4-chloro-2,5-dimethyl-phenyl | 3-(dimethylamino)prop-1-yl | | II | 123 |
| R & S | 4-chloro-2,5-dimethyl-phenyl | 3-t-butoxycarbonyl-1-methoxycarbonylprop-1-yl | | I | 125 |
| R & S | 4-chloro-2,5-dimethyl-phenyl | amino | | III | 129 |
| R & S | 4-chloro-2,5-dimethyl-phenyl | 2-{4-(ethylamino-amidino)phenyl]eth-1-yl | | VII | 130 |
| R & S | 4-chloro-2,5-dimethyl-phenyl | methyl carboxamide | | I | 134 |
| R & S | 4-chloro-2,5-dimethyl-phenyl | cyanomethyl | | II | 135 |
| R or S | 4-chloro-2,5-dimethyl-phenyl | 2-[(4-imidazolin-2-yl)phenyl]-1-(R)-(pyrrolidin-N-ylcarbonyl)eth-1-yl | | I | 139 |
| R & S | 4-chloro-2,5-dimethyl-phenyl | 1-methoxy | $R^2$ = methyl | IV | 140 |
| R & S | 4-chloro-2,5-dimethyl-phenyl | 1-(R)-methoxycarbonylphenylmethyl | | I | 141 |
| R & S | 4-chloro-2,5-dimethyl-phenyl | methoxycarbonylmethyl | | I | 142 |
| R or S | 4-chloro-2,5-dimethyl-phenyl | 2-[(4-amidino)phenyl]-1-(R)-(pyrrolidin-N-ylcarbonyl)eth-1-yl | | I | 169 |

TABLE I-continued

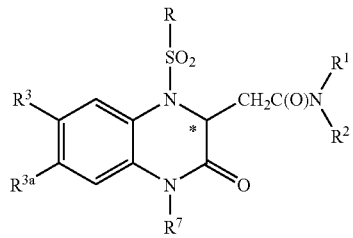

(R², R³, R³ᵃ, and R⁷ are all hydrogen unless otherwise specified)

| * | R | R¹ | R², R³, R³ᵃ, R⁷ | GP # | Cpd. No. |
|---|---|---|---|---|---|
| R or S | 4-chloro-2,5-dimethyl-phenyl | 1-(R)-(pyrrolidin-N-ylcarbonyl)-3-(guanadino)but-1-yl | | I | 170 |
| R or S | 4-chloro-2,5-dimethyl-phenyl | 1-(R)-(pyrrolidin-N-ylcarbonyl)-5-amino-n-pent-1-yl | | I | 172 |
| R & S | 4-chloro-2,5-dimethyl-phenyl | 1-(R)-(pyrrolidin-N-ylcarbonyl)-4-(N'-t-butoxy-carbonyl)-guanadino-n-but-1-yl | | I | 173 |
| R or S | 4-chloro-2,5-dimethyl-phenyl | 1-(R)-(pyrrolidin-N-ylcarbonyl)-5-(N'-t-butoxy-carbonylamino)-n-pent-5-yl | | I | 174 |
| R or S | 4-chloro-2,5-dimethyl-phenyl | 1-(R)-(pyrrolidin-N-ylcarbonyl)-4-amino-n-butyl | | I | 175 |
| R or S | 4-chloro-2,5-dimethyl-phenyl | 1-(R)-(pyrrolidin-N-ylcarbonyl)-4-(N'-t-butoxy-carbonylamino)-n-but-1-yl | | I | 176 |
| R or S | 4-chloro-2,5-dimethyl-phenyl | 1-(R)-(pyrrolidin-N-ylcarbonyl)-2-(4-amidino)phenyl-eth-1-yl | | I | 177 |
| R or S | 4-chloro-2,5-dimethyl-phenyl | 1-(R)-(pyrrolidin-N-ylcarbonyl)-4-guanadino-but-4-yl | | I | 178 |
| R & S | 4-chloro-2,5-dimethyl-phenyl | | —NR¹R² = 4-(2-amino-ethyl)-piperi-din-1-yl | XIV | 179 |
| R or S | 4-chloro-2,5-dimethyl-phenyl | 1-(R)-(pyrrolidin-N-ylcarbonyl)-2-(4-iodophenyl)-eth-1-yl | | I | 180 |
| R & S | 4-chloro-2,5-dimethyl-phenyl | | —NR¹R² = 4-[2-(N-t-butoxy-carbonyl-amino)-ethyl]-piperi-din-1-yl | XIV | 182 |
| R or S | 4-chloro-2,5-dimethyl-phenyl | 1-(R)-(pyrrolidin-N-ylcarbonyl)-4-amino-n-butyl | | I | 187 |
| R or S | 4-chloro-2,5-dimethyl-phenyl | 1-(R)-(pyrrolidin-N-ylcarbonyl)-5-(t-butoxy-carbonylamino)-pent-5-yl | | I | 189 |
| R & S | 4-chloro-2,5-dimethyl-phenyl | | —NR¹R² = 1-(pyridin-2-yl)-pipera-zin-4-yl | XIV | 190 |
| R or S | 4-chloro-2,5-dimethyl-phenyl | 1-(R)-(pyrrolidin-N-ylcarbonyl)-5-amino-n-pent-1-yl | | I | 191 |
| R or S | 4-chloro-2,5-dimethyl-phenyl | 1-(R)-(pyrrolidin-N-ylcarbonyl)-4-(t-butoxy-carbonylamino)-n-but-1-yl | | I | 198 |
| R or S | 4-chloro-2,5-dimethyl-phenyl | 1-(R)-(pyrrolidin-N-ylcarbonyl)-2-(4-iodophenyl)-eth-1-yl | | I | 200 |
| R or S | 4-chloro-2,5-dimethyl-phenyl | 1-(R)-(pyrrolidin-N-ylcarbonyl)-2-[4-(pyrid-2-yl)phenyleth-1-yl | | I | 202 |
| R or S | 4-chloro-2,5-dimethyl-phenyl | 1-(R)-(pyrrolidin-N-ylcarbonyl)-2-[4-(pyrid-2-yl)phenyl]eth-1-yl | | I | 203 |

TABLE I-continued

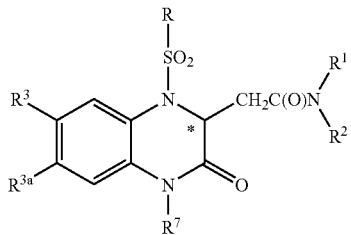

(R², R³, R³ᵃ, and R⁷ are all hydrogen unless otherwise specified)

| * | R | R¹ | R², R³, R³ᵃ, R⁷ | GP # | Cpd. No. |
|---|---|---|---|---|---|
| R or S | 4-chloro-2,5-dimethyl-phenyl | 1-(R)-(pyrrolidin-N-ylcarbonyl)-2-[4-(pyrimidin-2-yl)phenyl]eth-1-yl | | I | 205 |
| R or S | 4-chloro-2,5-dimethyl-phenyl | 1-(R)-(pyrrolidin-N-ylcarbonyl)-2-[4-(pyrimidin-2-yl)phenyl]eth-1-yl | | I | 206 |
| R or S | 4-chloro-2,5-dimethyl-phenyl | 1-(R)-(pyrrolidin-N-ylcarbonyl)-2-[4-(piperidin-2-yl)cyclohexyl]eth-1-yl | | I | 211 |
| R or S | 4-chloro-2,5-dimethyl-phenyl | 1-(R)-(pyrrolidin-N-ylcarbonyl)-2-[4-(piperidin-2-yl)cyclohexyl]eth-1-yl | | I | 212 |
| R or S | 4-chloro-2,5-dimethyl-phenyl | 1-(R)-(pyrrolidin-N-ylcarbonyl)-2-[4-(N-methyl-1,2,3,6-tetrahydropyridin-6-yl)phenyl]eth-1-yl | | I | 213 |
| R or S | 4-chloro-2,5-dimethyl-phenyl | 1-(R)-(pyrrolidin-N-ylcarbonyl)-2-[4-(N-methyl-1,2,3,6-tetrahydropyridin-6-yl)phenyl]eth-1-yl | | I | 214 |
| R or S | 4-chloro-2,5-dimethyl-phenyl | 1-(R)-(pyrrolidin-N-ylcarbonyl)-2-[4-(pyridin-4-yl)phenyl]eth-1-yl | | I | 215 |
| R or S | 4-chloro-2,5-dimethyl-phenyl | 1-(R)-(pyrrolidin-N-ylcarbonyl)-2-[4-(pyridin-4-yl)phenyl]eth-1-yl | | I | 216 |
| R or S | 4-chloro-2,5-dimethyl-phenyl | 1-(R)-(pyrrolidin-N-ylcarbonyl)-2-[N-(phenyl)-piperidin-4-yl)]eth-1-yl | | I | 218 |
| R or S | 4-chloro-2,5-dimethyl-phenyl | 1-(R)-(pyrrolidin-N-ylcarbonyl)-2-[N-(phenyl)-piperidin-4-yl)]eth-1-yl | | I | 219 |
| R or S | 4-chloro-2,5-dimethyl-phenyl | 1-(R)-(pyrrolidin-N-ylcarbonyl)-2-[N-(pyridin-4-yl)-piperidin-4-yl)]eth-1-yl | | I | 220 |
| R or S | 4-chloro-2,5-dimethyl-phenyl | 1-(R)-(pyrrolidin-N-ylcarbonyl)-2-[N-(pyridin-4-yl)-piperidin-4-yl)]eth-1-yl | | I | 221 |
| R or S | 4-chloro-2,5-dimethyl-phenyl | 1-(R)-(pyrrolidin-N-ylcarbonyl)-2-[N-methyl-1,2,5,6-tetrahydropyridin-4-yl)-phen-4-yl]eth-1-yl | | I | 239 |
| R or S | 4-chloro-2,5-dimethyl-phenyl | 1-(R)-(pyrrolidin-N-ylcarbonyl)-2-[N-methyl-1,2,5,6-tetrahydropyridin-4-yl)-phen-4-yl]eth-1-yl | | I | 242 |
| R or S | 4-chloro-2,5-dimethyl-phenyl | 1-(R)-(pyrrolidin-N-ylcarbonyl)-2-(4-biphenyl)eth-1-yl | | I | 243 |
| R or S | 4-chloro-2,5-dimethyl-phenyl | 1-(R)-(pyrrolidin-N-ylcarbonyl)-2-(4-biphenyl)eth-1-yl | | I | 245 |
| R & S | 4-chloro-2,5-dimethyl-phenyl | 1-(R)-(pyrrolidin-N-ylcarbonyl)-2-[4-(N-t-butoxycarbonylpyrrol-2-yl)phenyl]eth-1-yl | | I | 246 |
| R & S | 4-chloro-2,5-dimethyl-phenyl | 4-N-[(N',N'-dimethylaminocarbonyl)amino-phen-4-yl]eth-1-yl | | VIII | 268 |
| R & S | 4-chloro-2,5-dimethyl-phenyl | 2-[N-(methylcarbonyl-methylene)piperidin-4-yl]eth-1-yl | | IX | 272 |

TABLE I-continued

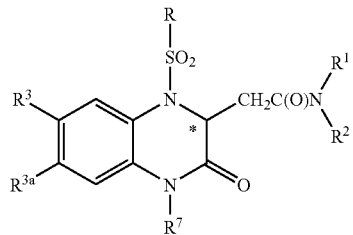

(R$^2$, R$^3$, R$^{3a}$, and R$^7$ are all hydrogen unless otherwise specified)

| * | R | R$^1$ | R$^2$, R$^3$, R$^{3a}$, R$^7$ | GP # | Cpd. No. |
|---|---|---|---|---|---|
| R & S | 2,3-dichlorophenyl | 2-(N',N'-dimethyl-amino)eth-1-yl | | II | 278 |
| R & S | 4-chloro-2,5-dimethyl-phenyl | 2-[N-(N'-morpholino-carbonyl)piperidin-4-yl]eth-1-yl | | VI | 280 |
| R & S | 4-chloro-2,5-dimethyl-phenyl | 2{N-[(2-(thiophen-2-yl)methylenecarbonyl]-piperidin-4-yl}eth-1-yl | | XI | 281 |
| R & S | 4-chloro-2,5-dimethyl-phenyl | 2-[N-(3,5-dimethyloxazol-4-ylcarbonyl)piperidin-4-yl]eth-1-yl | | XI | 282 |
| R & S | 4-chloro-2,5-dimethyl-phenyl | 2[N-(furan-2-ylcarbonyl)-piperidin-4-yl]eth-1-yl | | XI | 283 |
| R & S | 4-chloro-2,5-dimethyl-phenyl | 2-[N-(oxazol-5-yl-carbonyl)piperidin-4-yl]eth-1-yl | | XI | 284 |
| R & S | 4-chloro-2,5-dimethyl-phenyl | 2-[N-(5-methylpyrazol-3-ylcarbonyl)piperidin-4-yl]eth-1-yl | | XI | 285 |
| R & S | 4-chloro-2,5-dimethyl-phenyl | 2-[N-(1-methyl-3-t-butylpyrazol-5-ylcarbonyl)piperidin-4-yl]eth-1-yl | | XI | 286 |
| R & S | 4-chloro-2,5-dimethyl-phenyl | 2-[N-(4-methylthiadiazol-5-ylcarbonyl)piperidin-4-yl]eth-1-yl | | XI | 287 |
| R & S | 4-chloro-2,5-dimethyl-phenyl | 2-[N-(chloromethylene-carbonyl)piperidin-4-yl]eth-1-yl | | X | 288 |
| R & S | 4-chloro-2,5-dimethyl-phenyl | 2-[N-(benzylcarbonyl)-piperidin-4-yl]eth-1-yl | | XI | 289 |
| R & S | 4-chloro-2,5-dimethyl-phenyl | 2-[N-(2-phenylethenyl-carbonyl)piperidin-4-yl]eth-1-yl | | XI | 292 |
| R & S | 4-chloro-2,5-dimethyl-phenyl | 2-[N-(methoxymethylene-carbonyl)piperidin-4-yl]eth-1-yl | | XI | 293 |
| R & S | 4-chloro-2,5-dimethyl-phenyl | 2-[N-(pyrazin-2-ylcarbonyl)piperidin-4-yl]eth-1-yl | | XI | 294 |
| R & S | 4-chloro-2,5-dimethyl-phenyl | 2-[N-(isoquinolin-3-ylcarbonyl)piperidin-4-yl]eth-1-yl | | XI | 295 |
| R & S | 4-chloro-2,5-dimethyl-phenyl | 2-[N-(pyrrolidin-5-one-2-ylcarbonyl)piperidin-4-yl]eth-1-yl | | XI | 296 |
| R & S | 4-chloro-2,5-dimethyl-phenyl | 2-[N-(N'-acetylpyrrolidin-2-ylcarbonyl)piperidin-4-yl]eth-1-yl | | XI | 297 |
| R & S | 4-chloro-2,5-dimethyl-phenyl | 2-[N-(dichloromethylene-carbonyl)piperidin-4-yl]eth-1-yl | | XI | 298 |
| R & S | 4-chloro-2,5-dimethyl-phenyl | 4-[N-(pyrazin-2-ylcarbonyl)amino]pheneth-1-yl | | XII | 301 |
| R & S | 4-chloro-2,5-dimethyl-phenyl | 4-[N-(isoquinolin-2-ylcarbonyl)amino]pheneth-1-yl | | XII | 302 |
| R & S | 4-chloro-2,5-dimethyl-phenyl | 4-[N-(N'-acetylpyrrolidin-2-ylcarbonyl)amino]-pheneth-1-yl | | XII | 303 |
| R & S | 4-chloro-2,5-dimethyl-phenyl | 4-[N-(1,2-benzothiadiazol-5-ylcarbonyl)amino]-pheneth-1-yl | | XII | 304 |
| R & S | 4-chloro-2,5-dimethyl-phenyl | 4-[N-(benzofuran-5-yl carbonyl)amino]pheneth-1-yl | | XII | 305 |

TABLE I-continued

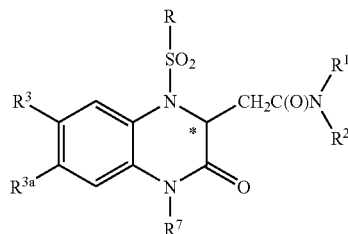

(R², R³, R³ᵃ, and R⁷ are all hydrogen unless otherwise specified)

| * | R | R¹ | R², R³, R³ᵃ, R⁷ | GP # | Cpd. No. |
|---|---|---|---|---|---|
| R & S | 4-chloro-2,5-dimethyl-phenyl | 4-[N-(3-methylisoxazol-5-yl carbonyl)amino]pheneth-1-yl | | XII | 306 |
| R & S | 4-chloro-2,5-dimethyl-phenyl | 4-[N-(N-morpholino-carbonyl)amino]pheneth-1-yl | | XII | 307 |
| R & S | 4-chloro-2,5-dimethyl-phenyl | 4-[N-(methoxyphen-3-yl carbonyl)amino]pheneth-1-yl | | XII | 308 |
| R & S | 4-chloro-2,5-dimethyl-phenyl | 4-[N-(thiophen-2-yl-methylenecarbonyl)amino]pheneth-1-yl | | XII | 309 |
| R & S | 4-chloro-2,5-dimethyl-phenyl | 4-[N-(3,5-dimethyl-isoxazol-4-ylcarbonyl)-amino]pheneth-1-yl | | XII | 310 |
| R & S | 4-chloro-2,5-dimethyl-phenyl | 4-[N-(2-(pyrid-3-yl)ethylcarbonyl)amino]pheneth-1-yl | | XII | 311 |
| R & S | 4-chloro-2,5-dimethyl-phenyl | 4-[N-(furan-2-ylcarbon-yl)amino]pheneth-1-yl | | XII | 312 |
| R & S | 4-chloro-2,5-dimethyl-phenyl | 4-[N-(isoxazol-5-ylcar-bonyl)amino]pheneth-1-yl | | XII | 313 |
| R & S | 4-chloro-2,5-dimethyl-phenyl | 4-[N-(3-methylpyrazol-5-yl-5-ylcarbonyl)amino]-pheneth-1-yl | | XII | 314 |
| R & S | 4-chloro-2,5-dimethyl-phenyl | 4-[N-(1-methyl-3-t-butyl-pyrazol-5-yl carbonyl)-amino]pheneth-1-yl | | XII | 315 |
| R & S | 4-chloro-2,5-dimethyl-phenyl | 4-[N-(4-methyl-1,2,3-thiadiazol-5-ylcarbonyl)-amino]-pheneth-1-yl | | XII | 316 |
| R & S | 4-chloro-2,5-dimethyl-phenyl | 4-[N-(chloromethylene-carbonyl)amino]pheneth-1-yl | | XII | 317 |
| R & S | 4-chloro-2,5-dimethyl-phenyl | 4-[N-(chlorophen-2-ylcar-bonyl)amino]pheneth-1-yl | | XII | 318 |
| R & S | 4-chloro-2,5-dimethyl-phenyl | 4-[N-(phenylcarbonyl)-amino]pheneth-1-yl | | XII | 319 |
| R & S | 4-chloro-2,5-dimethyl-phenyl | 4-[N-(pyrid-2-ylcarbonyl)-aminopheneth-1-yl | | XII | 321 |
| R & S | 4-chloro-2,5-dimethyl-phenyl | 4-[N-(pyrid-4-ylcar-bonyl)amino]pheneth-1-yl | | XII | 322 |
| R & S | 4-chloro-2,5-dimethyl-phenyl | 4-[N-(2-phenylethenyl-carbonyl)amino]pheneth-1-yl | | XII | 325 |
| R & S | 4-chloro-2,5-dimethyl-phenyl | 4-[N-(fluorophen-2-ylcar-bonyl)amino]pheneth-1-yl | | XII | 326 |
| R & S | 4-chloro-2,5-dimethyl-phenyl | 4-[N-(methoxymethylene-carbonyl)amino]pheneth-1-yl | | XII | 327 |
| R & S | 4-chloro-2,5-dimethyl-phenyl | 4-[N-(dichloromethylene-carbonyl)amino]pheneth-1-yl | | XII | 330 |
| R & S | 4-chloro-2,5-dimethyl-phenyl | 4-[N-(methylenedioxy-phen-4-ylcarbonyl)amino]-pheneth-1-yl | | XII | 331 |
| R or S | 4-chloro-2,5-dimethyl-phenyl | 1-[(R)-(pyrrolidin-N-yl-carbonyl)]-2-[N-methyl-pyrid-2-yl)phen-4-yl]eth-1-yl | | I | 332 |
| R or S | 4-chloro-2,5-dimethyl-phenyl | 1-[(R)-(pyrrolidin-N-ylcarbonyl)]-2-[(N-methylpyrid-4-yl)phen-4-yl]eth-1-yl | | I | 333 |
| R or S | 4-chloro-2,5-dimethyl-phenyl | 1-[(R)-(pyrrolidin-N-yl-carbonyl)]-2-[1-(piperidin-2-yl)phen-4-yl]eth-1-yl | | I | 334 |
| R or S | 4-chloro-2,5-dimethyl-phenyl | 1-(R)-(pyrrolidin-N-ylcarbonyl)-2-[4-(N-methylpyrid-4-yl)phen-1-yl)eth-1-yl | R² = methyl | I | 336 |
| R | 4-chloro-2,5-dimethylphenyl | 2-(benzoimidazol-2-ylamino)eth-1-yl | | II | 346 |

TABLE I-continued

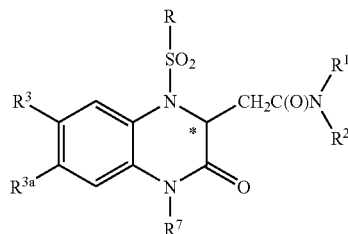

(R², R³, R³ᵃ, and R⁷ are all hydrogen unless otherwise specified)

| * | R | R¹ | R², R³, R³ᵃ, R⁷ | GP # | Cpd. No. |
|---|---|---|---|---|---|
| R | 4-chloro-2,5-dimethylphenyl | 3-(benzoimidazol-2-ylamino)prop-1-yl | | II | 347 |
| R & S | 4-chloro-2,5-dimethylphenyl | 4-(pyridin-2-yl)but-3-yn-1-yl | | XIII | 356 |
| R & S | 4-chloro-2,5-dimethylphenyl | 4-(pyridin-4-yl)but-3-yn-1-yl | | XIII | 357 |

Specific compounds within the scope of this invention include the following:

2-[2-(R,S)-1-(4-chloro-2,5-dimethylbenzenesulfonyl)-3-oxo-1,2,3,4-tetrahydroquinoxalin-2-yl]-N-[1-(R)-1-pyrrolidin-N-ylcarbonyl-2-phenyleth-1yl]acetamide 2-[2-(R,S)-1-(4-chloro-2,5-dimethylbenzenesulfonyl)-3-oxo-1,2,3,4-tetrahydroquinoxalin-2-yl]-N-[(piperidin-1-yl)carbonylmethyl]acetamide 2-[2-(R,S)-1-(4-chloro-2,5-dimethylbenzenesulfonyl)-3-oxo-1,2,3,4-tetrahydroquinoxalin-2-yl]-N-(2-hydroxy-eth-1-yl)acetamide 2-[2-(R or S)-1-(4-chloro-2,5-dimethylbenzenesulfonyl)-3-oxo-1,2,3,4-tetrahydroquinoxalin-2-yl]-N-[1-(R)-2-phenyl-1-(methoxycarbonyl)eth-1-yl]acetamide 2-[2-(S or R)-1-(4-chloro-2,5-dimethylbenzenesulfonyl)-3-oxo-1,2,3,4-tetrahydroquinoxalin-2-yl]-N-[1-(R)-2-phenyl-1-(methoxycarbonyl)eth-1-yl]acetamide 2-[2-(R,S)-1-(4-chloro-2,5-dimethylbenzenesulfonyl)-3-oxo-1,2,3,4-tetrahydroquinoxalin-2-yl]-N-[(2-dimethylamino)eth-1-yl]acetamide 2-[2-(R,S)-1-(4-chloro-2,5-dimethylbenzenesulfonyl)-3-oxo-1,2,3,4-tetrahydroquinoxalin-2-yl]-N-[1-(R)-(methoxycarbonyl)-2-(N-methylpiperidin-4-yl)eth-1-yl]acetamide 2-[2-(R,S)-1-(4-chloro-2,5-dimethylbenzenesulfonyl)-3-oxo-1,2,3,4-tetrahydroquinoxalin-2-yl]-N-[1-(R)-1,3-di(benzyloxycarbonyl)prop-1-yl]acetamide 2-[2-(R,S)-1-(4-chloro-2,5-dimethylbenzenesulfonyl)-3-oxo-1,2,3,4-tetrahydroquinoxalin-2-yl]-N-[1-(R)-(isopropoxycarbonyl)-2-(phenyl)eth-1-yl]acetamide 2-[2-(R,S)-1-(4-chloro-2,5-dimethylbenzenesulfonyl)-3-oxo-1,2,3,4-tetrahydroquinoxalin-2-yl]-N-[1-(R)-(methoxycarbonyl)eth-1-yl]acetamide 2-[2-(R,S)-1-(4-chloro-2,5-dimethylbenzenesulfonyl)-3-oxo-1,2,3,4-tetrahydroquinoxalin-2-yl]-N-[1-(R)-methoxycarbonyl-2-pyrid-4-yl)eth-1-yl]acetamide 2-[2-(R,S)-1-(4-chloro-2,5-dimethylbenzenesulfonyl)-3-oxo-1,2,3,4-tetrahydroquinoxalin-2-yl]-N-[1-(R)-(methoxycarbonyl)-2-(N-methyl-1,2,3,6-tetrahydropyrid-4-yl)eth-1-yl]acetamide 2-[2-(R or S)-1-(4-chloro-2,5-dimethylbenzenesulfonyl)-3-oxo-1,2,3,4-tetrahydroquinoxalin-2-yl]-N-[1-(R)-(methoxycarbonyl)-2-(N-methylpiperidin-4-yl)eth-1-yl]acetamide 2-[2-(S or R)-1-(4-chloro-2,5-dimethylbenzenesulfonyl)-3-oxo-1,2,3,4-tetrahydroquinoxalin-2-yl]-N-[1-(R)-(methoxycarbonyl)-2-(N-methylpiperidin-4-yl)eth-1-yl]acetamide 2-[2-(R,S)-1-(4-chloro-2,5-dimethylbenzenesulfonyl)-3-oxo-1,2,3,4-tetrahydroquinoxalin-2-yl]-N-{1-(S)-[pyrrolidin-N-ylcarbonyl]-2-[4-(2-imidazolin-2-yl)phenyl]eth-1-yl}acetamide 2-[2-(R,S)-1-(4-chloro-2,5-dimethylbenzenesulfonyl)-3-oxo-1,2,3,4-tetrahydroquinoxalin-2-yl]-N-[1-(S)-(t-butoxycarbonyl)-3-methylbut-1-yl]acetamide 2-[2-(R,S)-1-(4-chloro-2,5-dimethylbenzenesulfonyl)-3-oxo-1,2,3,4-tetrahydroquinoxalin-2-yl]-N-[1-(R)-(t-butoxycarbonyl)-3-methylprop-1-yl]acetamide 2-[2-(R,S)-1-(4-chloro-2,5-dimethylbenzenesulfonyl)-3-oxo-1,2,3,4-tetrahydroquinoxalin-2-yl]-N-[1-(S)-(t-butoxycarbonyl)-2-(4-hydroxyphenyl)eth-1-yl]acetamide 2-[2-(R,S)-1-(4-chloro-2,5-dimethylbenzenesulfonyl)-3-oxo-1,2,3,4-tetrahydroquinoxalin-2-yl]-N-[1-(R)-(t-butoxycarbonyl)-2-(phenyl)eth-1-yl]acetamide 2-[2-(R,S)-1-(4-chloro-2,5-dimethylbenzenesulfonyl)-3-oxo-1,2,3,4-tetrahydroquinoxalin-2-yl]-N-[1-(S)-carboxamide-2-(indol-3-yl)eth-1-yl]acetamide 2-[2-(R,S)-1-(4-chloro-2,5-dimethylbenzenesulfonyl)-3-oxo-1,2,3,4-tetrahydroquinoxalin-2-yl]-N-[1-(R)-carboxamide-2-(phenyl)eth-1-yl]acetamide 2-[2-(R,S)-1-(4-chloro-2,5-dimethylbenzenesulfonyl)-3-oxo-1,2,3,4-tetrahydroquinoxalin-2-yl]-N-[1-(S)-carboxamide-2-(S)-methylbut-1-yl]acetamide 2-[2-(R,S)-1-(4-chloro-2,5-dimethylbenzenesulfonyl)-3-oxo-1,2,3,4-tetrahydroquinoxalin-2-yl]-N-[1-(S)-carboxamide-2-(phenyl)eth-1-yl]acetamide 2-[2-(R,S)-1-(4-chloro-2,5-dimethylbenzenesulfonyl)-3-oxo-1,2,3,4-tetrahydroquinoxalin-2-yl]-N-[1-(S)-ethoxycarbonyleth-1-yl]acetamide 2-[2-(R,S)-1-(4-chloro-2,5-dimethylbenzenesulfonyl)-3-oxo-1,2,3,4-tetrahydroquinoxalin-2-yl]-N-[1-(S)-1,3-dicarboxamideprop-1-yl]acetamide 2-[2-(R,S)-1-(4-chloro-2,5-dimethylbenzenesulfonyl)-3-oxo-1,2,3,4-tetrahydroquinoxalin-2-yl]-N-[2-(N-cyclopropylpiperidin-4-yl)-1-(R)-(pyrrolidin-N-ylcarbonyl)eth-1-yl]acetamide 2-[2-(R,S)-1-(4-chloro-2,5-dimethylbenzenesulfonyl)-3-oxo-1,2,3,4-tetrahydroquinoxalin-2-yl]-N-[2-(N-methyl-1,2,5,6-tetrahydropyrid-4-yl)-1-(R)-(pyrrolidin-N-ylcarbonyl)eth-1-yl]acetamide 2-[2-(R,S)-1-(4-chloro-2,5-dimethylbenzenesulfonyl)-3-oxo-1,2,3,4-tetrahydroquinoxalin-2-yl]-N-[2-(N-methylpiperidin-4-yl)-1-(R)-(pyrrolidin-N-ylcarbonyl)eth-1-yl]acetamide 2-[2-(R,S)-1-(4-chloro-2,5-dimethylbenzenesulfonyl)-3-oxo-1,2,3,4-tetrahydroquinoxalin-2-yl]-N-[2-(4-cyanophenyl)-1-(R)-(pyrrolidin-N-ylcarbonyl)eth-1-yl]acetamide 2-[2-(R,S)-1-(4-chloro-2,5-dimethylbenzenesulfonyl)-3-oxo-1,2,3,4-tetrahydroquinoxalin-2-yl]-N-[2-(4-cyanophenyl)-1-(S)-(pyrrolidin-N-ylcarbonyl)eth-1-yl]acetamide 2-[2-(R,S)-1-(4-chloro-2,5-dimethylbenzenesulfonyl)-3-oxo-1,2,3,4-tetrahydroquinoxalin-2-yl]-N-[2-(4-hydroxyphenyl)-1-(S)-(methoxycarbonyl)eth-1-yl]acetamide 2-[2-(R,S)-1-(4-chloro-2,5-dimethylbenzenesulfonyl)-3-oxo-1,2,3,4-tetrahydroquinoxalin-2-yl]-N-[2-(4-hydroxyphenyl)-1-(S)-(t-butoxycarbonyl)eth-1-yl]acetamide 2-[2-(R,S)-1-(4-chloro-2,5-dimethylbenzenesulfonyl)-3-oxo-1,2,3,4-tetrahydroquinoxalin-2-yl]-N-[2-(4-hydroxyphenyl)-1-(R)-(methoxycarbonyl)eth-1-yl]acetamide 2-[2-(R,S)-1-(4-chloro-2,5-dimethylbenzenesulfonyl)-3-oxo-1,2,3,4-tetrahydroquinoxalin-2-yl]-N-[2-(indol-3-yl)-1-(S)-(methoxycarbonyl)eth-1-yl]acetamide 2-[2-(R,S)-1-(4-chloro-2,5-dimethylbenzenesulfonyl)-3-oxo-1,2,3,4-tetrahydroquinoxalin-2-yl]-N-[2-(indol-3-yl)-1-(R)-(methoxycarbonyl)eth-1-yl]acetamide 2-[2-(R,S)-1-(4-chloro-2,5-dimethylbenzenesulfonyl)-3-oxo-1,2,3,4-tetrahydroquinoxalin-2-yl]-N-[2-(phenyl)-1-(S)-(pyrrolidin-N-ylcarbonyl)eth-1-yl]-N-methylacetamide 2-[2-(R,S)-1-(4-chloro-2,5-dimethylbenzenesulfonyl)-3-oxo-1,2,3,4-tetrahydroquinoxalin-2-yl]-N-[2-(pyrid-4-yl)-1-(R)-(pyrrolidin-N-ylcarbonyl)eth-1-yl]acetamide 2-[2-(R,S)-1-(4-chloro-2,5-dimethylbenzenesulfonyl)-3-oxo-1,2,3,4-tetrahydroquinoxalin-2-yl]-N-[2-phenyl-1-(S)-(methoxycarbonyl)eth-1-yl]acetamide 2-[2-(R,S)-1-(4-chloro-2,5-dimethylbenzenesulfonyl)-3-oxo-1,2,3,4-tetrahydroquinoxalin-2-yl]-N-(2-phenyl-1-(R)-carboxy-eth-1-yl)acetamide 2-[2-(R,S)-1-(4-chloro-2,5-dimethylbenzenesulfonyl)-3-oxo-1,2,3,4-tetrahydroquinoxalin-2-yl]-N-{2-[N-(α,α-dimethylglycine)piperidin-4-yl]eth-1-yl}acetamide 2-[2-(R,S)-1-(4-chloro-2,5-dimethylbenzenesulfonyl)-3-oxo-1,2,3,4-tetrahydroquinoxalin-2-yl]-N-{2-[N-(α-aminoacetyl)piperidin-4-yl]eth-1-yl}acetamide 2-[2-(R or S)-1-(4-chloro-2,5-dimethylbenzenesulfonyl)-3-oxo-1,2,3,4-tetrahydroquinoxalin-2-yl]-N-{2-[4-(imidazolin-2-yl)phenyl]-1-(R)-(pyrrolidin-1-ylcarbonyl)eth-1-yl}acetamide 2-[2-(S or R)-1-(4-chloro-2,5-dimethylbenzenesulfonyl)-3-oxo-1,2,3,4-tetrahydroquinoxalin-2-yl]-N-{2-[4-(imidazolin-2-yl)phenyl]-1-(R)-(pyrrolidin-1-ylcarbonyl)eth-1-yl}acetamide 2-[2-(R,S)-1-(4-chloro-2,5-dimethylbenzenesulfonyl)-3-oxo-1,2,3,4-tetrahydroquinoxalin-2-yl]-N-[3-(dimethylamino)prop-1-yl]acetamide 2-[2-(R,S)-1-(4-chloro-2,5-dimethylbenzenesulfonyl)-3-oxo-1,2,3,4-tetrahydroquinoxalin-2-yl]-N-(3-t-butoxycarbonyl-1-methoxycarbonylprop-1-yl)acetamide 2-[2-(R,S)-1-(4-chloro-2,5-dimethylbenzenesulfonyl)-3-oxo-1,2,3,4-tetrahydroquinoxalin-2-yl]-N-aminoacetamide 2-[2-(R,S)-1-(4-chloro-2,5-dimethylbenzenesulfonyl)-3-oxo-1,2,3,4-tetrahydroquinoxalin-2-yl]-N-{2-[4-(ethylaminoamidino)phenyl]eth-1-yl}acetamide 2-[2-(R,S)-1-(4-chloro-2,5-dimethylbenzenesulfonyl)-3-oxo-1,2,3,4-tetrahydroquinoxalin-2-yl]-N-methylcarboxamideacetamide 2-[2-(R,S)-1-(4-chloro-2,5-dimethylbenzenesulfonyl)-3-oxo-1,2,3,4-tetrahydroquinoxalin-2-yl]-N-cyanomethylacetamide 2-[2-(R or S)-1-(4-chloro-2,5-dimethylbenzenesulfonyl)-3-oxo-1,2,3,4-tetrahydroquinoxalin-2-yl]-N-{2-[(4-imidazolin-2-yl)phenyl]-1-(R)-(pyrrolidin-N-ylcarbonyl)eth-1-yl}acetamide 2-[2-(S or R)-1-(4-chloro-2,5-dimethylbenzenesulfonyl)-3-oxo-1,2,3,4-tetrahydroquinoxalin-2-yl]-N-{2-[(4-imidazolin-2-yl)phenyl]-1-(R)-(pyrrolidin-N-ylcarbonyl)eth-1-yl}acetamide 2-[2-(R,S)-1-(4-chloro-2,5-dimethylbenzenesulfonyl)-3-oxo-1,2,3,4-tetrahydroquinoxalin-2-yl]-N-[1-(S)-methoxy]-N-methylacetamide 2-[2-(R,S)-1-(4-chloro-2,5-dimethylbenzenesulfonyl)-3-oxo-1,2,3,4-tetrahydroquinoxalin-2-yl]-N-[1-(R)-methoxycarbonylphenylmethyl)]acetamide 2-[2-(R,S)-1-(4-chloro-2,5-dimethylbenzenesulfonyl)-3-oxo-1,2,3,4-tetrahydroquinoxalin-2-yl]-N-methoxycarbonylmethylacetamide 2-[2-(R or S)-1-(4-chloro-2,5-dimethylbenzenesulfonyl)-3-oxo-1,2,3,4-tetrahydroquinoxalin-2-yl]-N-{2-[(4-amidinophenyl]-1-(R)-(pyrrolidin-N-ylcarbonyl)eth-1-yl}acetamide 2-[2-(S or R)-1-(4-chloro-2,5-dimethylbenzenesulfonyl)-3-oxo-1,2,3,4-tetrahydroquinoxalin-2-yl]-N-{2-[(4-amidinophenyl]-1-(R)-(pyrrolidin-N-ylcarbonyl)eth-1-yl}acetamide 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-3-(guanadino)but-1-yl]acetamide 2-[2-(S or R)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-3-(guanadino)but-1-yl]acetamide 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-5-amino-n-pent-1-yl]acetamide 2-[2-(S or R)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-5-amino-n-pent-1-yl]acetamide 2-[2-(R,S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-4-(N'-t-butoxy-carbonyl)-guanadino-n-but-1-yl]acetamide 2-[2-(R or S)-1-(4-chloro-2,5-dimethylbenzenesulfonyl)-3-oxo-1,2,3,4-tetrahydroquinoxalin-2-yl]-N-[1-(R)-pyrrolidin-N-ylcarbonyl-5-(N'-t-butoxy-carbonylamino)-n-pent-5-yl]acetamide 2-[2-(S or R)-1-(4-chloro-2,5-dimethylbenzenesulfonyl)-3-oxo-1,2,3,4-tetrahydroquinoxalin-2-yl]-N-[1-(R)-pyrrolidin-N-ylcarbonyl-5-(N'-t-butoxy-carbonylamino)-n-pent-5-yl]acetamide 2-[2-(S or R)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-4-amino-n-butyl]acetamide 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-4-(N'-t-butoxy-carbonylamino)-n-but-1-yl]acetamide 2-[2-(S or R)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-4-(N'-t-butoxy-carbonylamino)-n-but-1-yl]acetamide 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-2-(4-amidino)phenyl-eth-1-yl]acetamide 2-[2-(S or R)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-2-(4-amidino)phenyl-eth-1-yl]acetamide 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-4-guanidino-but-1-yl]acetamide 2-[2-(S or R)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-4-guanidino-but-1-yl]acetamide 2-[2-(S,R)-1-(4-chloro-2,5-dimethylbenzenesulfonyl)-3-oxo-1,2,3,4-tetrahydroquinoxalin-2-yl]-methylenecarbonyl-[4-(2-aminoethyl)]piperidin-1-yl]acetamide 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-2-(4-iodophenyl)eth-1-yl]acetamide 2-[2-(R,S)-1-(4-chloro-2,5-dimethylbenzenesulfonyl)-3-oxo-1,2,3,4-tetrahydroquinoxalin-2-yl]-methylenecarbonyl-{[4-(2-(N-t-butoxycarbonyl-amino)ethyl)piperidin-1-yl]}acetamide 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-4-amino-n-butyl]acetamide 2-[2-(S or R)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-4-amino-n-butyl]acetamide 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-5-(t-butoxy-carbonylamino)-pent-5-yl]acetamide 2-[2-(S or R)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-5-(t-butoxy-carbonylamino)-pent-5-yl]acetamide 2-[2-(R,S)-1-(4-chloro-2,5-dimethylbenzenesulfonyl)-3-oxo-1,2,3,4-tetrahydroquinoxalin-2-yl]-methylenecarbonyl{[1-(pyridin-2-yl)]-4-piperazin-4-yl}acetamide 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-5-amino-n-pent-1-yl]acetamide 2-[2-(S or R)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-5-amino-n-pent-1-yl]acetamide 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-4-(t-butoxy-carbonylamino)-n-but-1-yl]acetamide 2-[2-(S or R)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-4-(t-butoxy-carbonylamino)-n-but-1-yl]acetamide 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-2-(4-iodophenyl)-eth-1-yl]acetamide 2-[2-(S or R)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-2-(4-iodophenyl)-eth-1-yl]acetamide 2-[2-(R or S)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[4-(pyrid-2-yl)phenyl]eth-1-yl}acetamide 2-[2-(S or R)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[4-(pyrid-2-yl)phenyl]eth-1-yl}acetamide 2-[2-(R or S)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[4-(pyrid-2-yl)phenyl]eth-1-yl}acetamide 2-[2-(S or R)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[4-(pyrid-2-yl)phenyl]eth-1-yl}acetamide 2-[2-(R or S)-1-(4-chloro-2,5-dimethylbenzenesulfonyl)-3-oxo-1,2,3,4-tetrahydroquinoxalin-2-yl]-N-{1-(R)-(pyrrolidin-N-ylcarbonyl)-2-[4-(pyrimidin-2-yl)phenyl]eth-1-yl}acetamide 2-[2-(S or R)-1-(4-chloro-2,5-dimethylbenzenesulfonyl)-3-oxo-1,2,3,4-tetrahydroquinoxalin-2-yl]-N-{1-(R)-(pyrrolidin-N-ylcarbonyl)-2-[4-(pyrimidin-2-yl)phenyl]eth-1-yl}acetamide 2-[2-(R or S)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[4-(piperidin-2-yl)cyclohexyl]eth-1-yl}acetamide 2-[2-(S or R)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[4-(piperidin-2-yl)cyclohexyl]eth-1-yl}acetamide 2-[2-(R or S)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[4-(N-methyl-1,2,3,6-tetrahydropyridin-6-yl)phenyl]eth-1-yl}acetamide 2-[2-(S or R)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[4-(N-methyl-1,2,3,6-tetrahydropyridin-6-yl)phenyl]eth-1-yl}acetamide 2-[2-(R or S)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[4-(pyridin-4-yl)phenyl]eth-1-yl}acetamide 2-[2-(S or R)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[4-(pyridin-4-yl)phenyl]eth-1-yl}acetamide 2-[2-(R or S)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[N-(phenyl)-piperidin-4-yl)]eth-1-yl}acetamide 2-[2-(S or R)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[N-(phenyl)-piperidin-4-yl)]eth-1-yl}acetamide 2-[2-(R or S)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[N-(pyridin-4-yl)-piperidin-4-yl]eth-1-yl}acetamide 2-[2-(S or R)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[N-(pyridin-4-yl)-piperidin-4-yl]eth-1-yl}acetamide 2-[2-(R or S)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[(N-methyl-1,2,5,6-tetrahydropyridin-4-yl)-phen-4-yl]eth-1-yl}acetamide 2-[2-(S or R)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[(N-methyl-1,2,5,6-tetrahydropyridin-4-yl)-phen-4-yl]eth-1-yl}acetamide 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-2-(4-biphenyl)ethy-1-yl]acetamide 2-[2-(S or R)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-2-(4-biphenyl)eth-1-yl]acetamide 2-[2-(S or R)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[4-(N-t-butoxycarbonylpyrrol-2-yl)phenyl]eth-1-yl}acetamide 2-[2-(R or S)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[4-(N-t-butoxycarbonylpyrrol-2-yl)phenyl]eth-1-yl}acetamide 2-[2-(R,S)-1-(4-chloro-2,5-dimethylbenzenesulfonyl)-3-oxo-1,2,3,4-tetrahydroquinoxalin-2-yl]-N-{2-[N-(N',N'-dimethylaminocarbonyl)aminophen-1-yl]eth-1-yl}acetamide 2-[2-(R,S)-1-(4-chloro-2,5-dimethylbenzenesulfonyl)-3-oxo-1,2,3,4-tetrahydroquinoxalin-2-yl]-N-{2-[N-(methylcarbonylmethylene)piperidin-4-yl]eth-1-yl}acetamide 2-[2-(R,S)-1-(2,3-dichlorobenzenesulfonyl)-3-oxo-1,2,3,4-tetrahydroquinoxalin-2-yl]-N-[2-(N',N'-dimethylamino)eth-1-yl]acetamide 2-[2-(R,S)-1-(4-chloro-2,5-dimethylbenzenesulfonyl)-3-oxo-1,2,3,4-tetrahydroquinoxalin-2-yl]-N-{2-[N-(N'-morpholinocarbonyl)piperidin-4-yl]eth-1-yl}acetamide 2-[2-(R,S)-1-(4-chloro-2,5-dimethylbenzenesulfonyl)-3-oxo-1,2,3,4-tetrahydroquinoxalin-2-yl]-N-{2-[N-[(thiophen-2-yl)methylenecarbonyl]piperidin-4-yl]eth-1-yl}acetamide 2-[2-(R,S)-1-(4-chloro-2,5-dimethylbenzenesulfonyl)]-3-oxo-1,2,3,4-tetrahydroquinoxalin-2-yl]-N-{2-[N-(3,5-dimethyloxazol-4-ylcarbonyl)piperidin-4-yl]eth-1-yl}acetamide 2-[2-(R,S)-1-(4-chloro-2,5-dimethylbenzenesulfonyl)]-3-oxo-1,2,3,4-tetrahydroquinoxalin-2-yl]-N-{2-[(N-furan-2-ylcarbonyl)piperidin-4-yl]eth-1-yl}acetamide 2-[2-(R,S)-1-(4-chloro-2,5-dimethylbenzenesulfonyl)]-3-oxo-1,2,3,4-tetrahydroquinoxalin-2-yl]-N-{2-[N-(3,5-dimethyloxazol-3-ylcarbonyl)piperidin-4-yl]eth-1-yl}acetamide 2-[2-(R,S)-1-(4-chloro-2,5-dimethylbenzenesulfonyl)]-3-oxo-1,2,3,4-tetrahydroquinoxalin-2-yl]-N-{2-[N-(5-methylpyrazol-3-ylcarbonyl)piperidin-4-yl]eth-1-yl}acetamide 2-[2-(R,S)-1-(4-chloro-2,5-dimethylbenzenesulfonyl)]-3-oxo-1,2,3,4-tetrahydroquinoxalin-2-yl]-N- {2-[N-(1-methyl-3-t-butylpyrazol-5-ylcarbonyl)piperidin-4-yl]eth-1-yl}acetamide 2-[2-(R,S)-1-(4-chloro-2,5-dimethylbenzenesulfonyl)]-3-oxo-1,2,3,4-tetrahydroquinoxalin-2-yl]-N-{²-[N-(4-methylthiadiazol-5-ylcarbonyl)piperidin-4-yl]eth-1-yl}acetamide 2-[2-(R,S)-1-(4-chloro-2,5-dimethylbenzenesulfonyl)]-3-oxo-1,2,3,4-tetrahydroquinoxalin-2-yl]-N-{2-[N-(chloromethylenecarbonyl)piperidin-4-yl]eth-1-yl}-acetamide 2-[2-(R,S)-1-(4-chloro-2,5-dimethylbenzenesulfonyl)]-3-oxo-1,2,3,4-tetrahydroquinoxalin-2-yl]-N-{2-[N-(benzylcarbonyl)piperidin-4-yl]eth-1-yl}-acetamide 2-[2-(R,S)-1-(4-chloro-2,5-dimethylbenzenesulfonyl)]-3-oxo-1,2,3,4-tetrahydroquinoxalin-2-yl]-N-{2-[N-(2-phenylethenylcarbonyl)piperidin-4-yl]eth-1-yl}acetamide 2-[2-(R,S)-1-(4-chloro-2,5-dimethylbenzenesulfonyl)]-3-oxo-1,2,3,4-tetrahydroquinoxalin-2-yl]-N-{2-[N-(methoxymethylenecarbonyl)piperidin-4-yl]eth-1-yl}acetamide 2-[2-(R,S)-1-(4-chloro-2,5-dimethylbenzenesulfonyl)]-3-oxo-1,2,3,4-tetrahydroquinoxalin-2-yl]-N-{2-[N-(pyrazin-2-ylcarbonyl)piperidin-4-yl]eth-1-yl}acetamide 2-[2-(R,S)-1-(4-chloro-2,5-dimethylbenzenesulfonyl)]-3-oxo-1,2,3,4-tetrahydroquinoxalin-2-yl]-N-{2-[N-(isoquinolin-3-ylcarbonyl)piperidin-4-yl]eth-1-yl}acetamide 2-[2-(R,S)-1-(4-chloro-2,5-dimethylbenzenesulfonyl)]-3-oxo-1,2,3,4-tetrahydroquinoxalin-2-yl]-N-{2-[N-(pyrrolidin-5-one-2-ylcarbonyl)piperidin-4-yl]eth-1-yl}acetamide 2-[2-(R,S)-1-(4-chloro-2,5-dimethylbenzenesulfonyl)]-3-oxo-1,2,3,4-tetrahydroquinoxalin-2-yl]-N-{2-[N-(N'-acetylpyrrolidin-2-ylcarbonyl)piperidin-4-yl]eth-1-yl}acetamide 2-[2-(R,S)-1-(4-chloro-2,5-dimethylbenzenesulfonyl)]-3-oxo-1,2,3,4-tetrahydroquinoxalin-2-yl]-N-{2-[N-(dichloromethylenecarbonyl)piperidin-4-yl]eth-1-yl}acetamide 2-[2-(R,S)-1-(4-chloro-2,5-dimethylbenzenesulfonyl)]-3-oxo-1,2,3,4-tetrahydroquinoxalin-2-yl]-N-{4-[N-(pyrazin-2-ylcarbonyl)amino]pheneth-1-yl}-acetamide 2-[2-(R,S)-1-(4-chloro-2,5-dimethylbenzenesulfonyl)]-3-oxo-1,2,3,4-tetrahydroquinoxalin-2-yl]-N-{4-[N-(isoquinolin-2-ylcarbonyl)amino]pheneth-1-yl}acetamide 2-[2-(R,S)-1-(4-chloro-2,5-dimethylbenzenesulfonyl)]-3-oxo-1,2,3,4-tetrahydroquinoxalin-2-yl]-N-{4-[N-(N'-acetylpyrrolidin-2-ylcarbonyl)amino]pheneth-1-yl}acetamide 2-[2-(R,S)-1-(4-chloro-2,5-dimethylbenzenesulfonyl)]-3-oxo-1,2,3,4-tetrahydroquinoxalin-2-yl]-N-{4-[N-(1,2-benzothiadiazol-5-ylcarbonyl)amino]pheneth-1-yl}acetamide 2-[2-(R,S)-1-(4-chloro-2,5-dimethylbenzenesulfonyl)]-3-oxo-1,2,3,4-tetrahydroquinoxalin-2-yl]-N-{4-[N-(benzofuran-5-ylcarbonyl)amino]pheneth-1-yl}acetamide 2-[2-(R,S)-1-(4-chloro-2,5-dimethylbenzenesulfonyl)]-3-oxo-1,2,3,4-tetrahydroquinoxalin-2-yl]-N-{4-[N-(3-methylisoxazol-5-ylcarbonyl)amino]pheneth-1-yl}acetamide 2-[2-(R,S)-1-(4-chloro-2,5-dimethylbenzenesulfonyl)]-3-oxo-1,2,3,4-tetrahydroquinoxalin-2-yl]-N-{4-[N-(N-morpholinocarbonyl)amino]pheneth-1-yl}acetamide 2-[2-(R,S)-1-(4-chloro-2,5-dimethylbenzenesulfonyl)]-3-oxo-1,2,3,4-tetrahydroquinoxalin-2-yl]-N-{4-[N-(methoxyphen-3-ylcarbonyl)amino]pheneth-1-yl}acetamide 2-[2-(R,S)-1-(4-chloro-2,5-dimethylbenzenesulfonyl)]-3-oxo-1,2,3,4-tetrahydroquinoxalin-2-yl]-N-{4-[N-(thiophen-2-ylmethylenecarbonyl)amino]pheneth-1-yl}acetamide 2-[2-(R,S)-1-(4-chloro-2,5-dimethylbenzenesulfonyl)]-3-oxo-1,2,3,4-tetrahydroquinoxalin-2-yl]-N-{4-[N-(3,5-dimethylisoxazol-4-ylcarbonyl)amino]pheneth-1-yl}acetamide 2-[2-(R,S)-1-(4-chloro-2,5-dimethylbenzenesulfonyl)]-3-oxo-1,2,3,4-tetrahydroquinoxalin-2-yl]-N-{4-[N-(2-(pyrid-3-yl)ethylcarbonyl)amino]pheneth-1-yl}acetamide 2-[2-(R,S)-1-(4-chloro-2,5-dimethylbenzenesulfonyl)]-3-oxo-1,2,3,4-tetrahydroquinoxalin-2-yl]-N-{4-[N-(furan-2-ylcarbonyl)amino]pheneth-1-yl}acetamide 2-[2-(R,S)-1-(4-chloro-2,5-dimethylbenzenesulfonyl)]-3-oxo-1,2,3,4-tetrahydroquinoxalin-2-yl]-N-{4-[N-(isoxazol-5-ylcarbonyl)amino]pheneth-1-yl}acetamide 2-[2-(R,S)-1-(4-chloro-2,5-dimethylbenzenesulfonyl)]-3-oxo-1,2,3,4-tetrahydroquinoxalin-2-yl]-N-{4-[N-(3-methylpyrazol-5-ylcarbonyl)amino]pheneth-1-yl}acetamide 2-[2-(R,S)-1-(4-chloro-2,5-dimethylbenzenesulfonyl)]-3-oxo-1,2,3,4-tetrahydroquinoxalin-2-yl]-N-{4-[N-(1-methyl-3-t-butylpyrazol-5-ylcarbonyl)amino]pheneth-1-yl}acetamide 2-[2-(R,S)-1-(4-chloro-2,5-dimethylbenzenesulfonyl)]-3-oxo-1,2,3,4-tetrahydroquinoxalin-2-yl]-N-{4-[N-(4-methyl-1,2,3-thiadiazol-5-ylcarbonyl)amino]pheneth-1-yl}acetamide 2-[2-(R,S)-1-(4-chloro-2,5-dimethylbenzenesulfonyl)]-3-oxo-1,2,3,4-tetrahydroquinoxalin-2-yl]-N-{4-[N-(chloromethylenecarbonyl)amino]pheneth-1-yl}acetamide 2-[2-(R,S)-1-(4-chloro-2,5-dimethylbenzenesulfonyl)]-3-oxo-1,2,3,4-tetrahydroquinoxalin-2-yl]-N-{4-[N-(chlorophen-2-ylcarbonyl)amino]pheneth-1-yl}acetamide 2-[2-(R,S)-1-(4-chloro-2,5-dimethylbenzenesulfonyl)]-3-oxo-1,2,3,4-tetrahydroquinoxalin-2-yl]-N-{4-[N-(phenylcarbonyl)amino]pheneth-1-yl}acetamide 2-[2-(R,S)-1-(4-chloro-2,5-dimethylbenzenesulfonyl)]-3-oxo-1,2,3,4-tetrahydroquinoxalin-2-yl]-N- {4-[N-(pyrid-2-ylcarbonyl)amino]pheneth-1-yl}acetamide 2-[2-(R,S)-1-(4-chloro-2,5-dimethylbenzenesulfonyl)]-3-oxo-1,2,3,4-tetrahydroquinoxalin-2-yl]-N-{4-[N-(pyrid-4-ylcarbonyl)amino]pheneth-1-yl}acetamide 2-[2-(R,S)-1-(4-chloro-2,5-dimethylbenzenesulfonyl)]-3-oxo-1,2,3,4-tetrahydroquinoxalin-2-yl]-N-{4-[N-(2-phenylethenylcarbonyl)amino]pheneth-1-yl}acetamide 2-[2-(R,S)-1-(4-chloro-2,5-dimethylbenzenesulfonyl)]-3-oxo-1,2,3,4-tetrahydroquinoxalin-2-yl]-N-{4-[N-(fluorophen-2-ylcarbonyl)amino]pheneth-1-yl}acetamide 2-[2-(R,S)-1-(4-chloro-2,5-dimethylbenzenesulfonyl)]-3-oxo-1,2,3,4-tetrahydroquinoxalin-2-yl]-N-{4-[N-(methoxymethylenecarbonyl)amino]pheneth-1-yl}acetamide 2-[2-(R,S)-1-(4-chloro-2,5-dimethylbenzenesulfonyl)]-3-oxo-1,2,3,4-tetrahydroquinoxalin-2-yl]-N-{4-[N-(dichloromethylenecarbonyl)amino]pheneth-1-yl}acetamide 2-[2-(R,S)-1-(4-chloro-2,5-dimethylbenzenesulfonyl)]-3-oxo-1,2,3,4-tetrahydroquinoxalin-2-yl]-N- {4-[N-(methylenedioxyphen-4-ylcarbonyl)amino]pheneth-1-yl}acetamide 2-[2-(R or S)-1-(4-chloro-2,5-dimethylbenzenesulfonyl)]-3-oxo-1,2,3,4-tetrahydroquinoxalin-2-yl]-N-{1-[(R)-(pyrrolidin-N-ylcarbonyl)]-2-[N-(methylpyrid-2-yl)phen-4-yl]eth-1-yl}acetamide 2-[2-(S or R)-1-(4-chloro-2,5-dimethylbenzenesulfonyl)]-3-oxo-1,2,3,4-tetrahydroquinoxalin-2-yl]-N-{1-[(R)-(pyrrolidin-N-ylcarbonyl)]-2-[N-(methylpyrid-2-yl)phen-4-yl]eth-1-yl}acetamide 2-[2-(R or S)-1-(4-chloro-2,5-dimethylbenzenesulfonyl)]-3-oxo-1,2,3,4-tetrahydroquinoxalin-2-yl]-N-{1-[(R)-(pyrrolidin-N-ylcarbonyl)]-2-[N-(methylpyrid-4-yl)phen-4-yl]eth-1-yl}acetamide 2-[2-(S or R)-1-(4-chloro-2,5-dimethylbenzenesulfonyl)]-3-oxo-1,2,3,4-tetrahydroquinoxalin-2-yl]-N-{1-[(R)-(pyrrolidin-N-ylcarbonyl)]-2-[N-(methylpyrid-4-yl)phen-4-yl]eth-1-yl}acetamide 2-[2-(R or S)-1-(4-chloro-2,5-dimethylbenzenesulfonyl)]-3-oxo-1,2,3,4-tetrahydroquinoxalin-2-yl]-N-{1-[(R)-(pyrrolidin-N-ylcarbonyl)]-2-[1-(piperidin-2-yl)phen-4-yl]eth-1-yl}acetamide 2-[2-(S or R)-1-(4-chloro-2,5-dimethylbenzenesulfonyl)]-3-oxo-1,2,3,4-tetrahydroquinoxalin-2-yl]-N-{1-[(R)-(pyrrolidin-N-ylcarbonyl)]-2-[1-(piperidin-2-yl)phen-4-yl]eth-1-yl }acetamide 2-[2-(R or S)-1-(4-chloro,2,5-dimethylbenzenesulfonyl)]-3-oxo-1,2,3,4-tetrahydroquinoxalin-2-yl]-N-methyl-N-{1-[(R)-pyrrolidin-N-ylcarbonyl)-2-[4-(N-methylpyrid-4-yl)phen-1-yl)eth-1-yl]}acetamide 2-[2-(S or R)-1-(4-chloro-2,5-dimethylbenzenesulfonyl)]-3-oxo-1,2,3,4-tetrahydroquinoxalin-2-yl]-N-methyl-N-{1-[(R)-pyrrolidin-N-ylcarbonyl )-2-[4-(N-methylpyrid-4-yl)phen-1-yl)eth-1-yl]}acetamide 2-[2-(R,S)-1-(2,5-dimethyl-4-chlorobenzenesulfonyl)-3-oxo-1,2,3,4-tetrahydroquinoxalin-2-yl]-N-[4-(pyridin-2-yl)-3-butyn-1-yl]acetamide 2-[2-(R,S)-1-(4-chloro-2,5-dimethylbenzenesulfonyl)-3-oxo-1,2,3,4-tetrahydroquinoxalin-2-yl]-N-[4-(pyrid-4-yl)but-3-yn-1-yl]acetamide 2-[2-(R,S)-1-(4-chloro-2,5-dimethylbenzenesulfonyl)-3-oxo-1,2,3,4-tetrahydroquinoxalin-2-yl]-N-[2-(benzoimidazol-2-ylamino)eth-1-ylacetamide 2-[2-(R,S)-1-(4-chloro-2,5-dimethylbenzenesulfonyl)-3-oxo-1,2,3,4-tetrahydroquinoxalin-2-yl]-N-[3-(benzoimidazol-2-ylamino)prop-1-yl]acetamide and pharmaceutically acceptable salts thereof.

Further included within the scope of the compounds of this invention is the following:

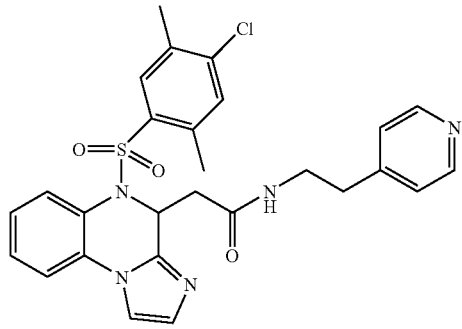

This invention also provides a pharmaceutical composition comprising a pharmaceutically acceptable carrier and a therapeutically effective amount of a compound of Formula I or II (including mixtures thereof) or a pharmaceutically acceptable salt thereof to treat or palliate adverse symptoms in mammals which symptoms are mediated, at least in part, by the presence of bradykinin.

This invention further provides a method for treating or palliating adverse symptoms in a mammal associated with the presence or secretion of bradykinin in the mammal which comprises administering thereto a therapeutically effective amount of a compound Formula I or II (including mixtures thereof) or a pharmaceutically acceptable salt thereof or, as is more generally the case, administering a pharmaceutical composition as described above.

This invention also provides a method for treating or ameliorating pain, hyperalgesia, hyperthermia and/or edema in a mammal which is associated with the release of bradykinin in the mammal which comprises administering to the mammal a therapeutically effective amount of a compound Formula I or II (including mixtures thereof) or a pharmaceutically acceptable salt thereof or, as is more generally the case, administering a pharmaceutical composition as described above.

This invention still further provides a method for treating or ameliorating adverse symptoms in a mammal associated with the release of bradykinin relative to spinal cord injuries, neuropathic pain, back pain, burns, perioperative pain, migraine, shock, central nervous system injury, asthma, rhinitis, premature labor, inflammatory arthritis, or inflammatory bowel disease which comprises administering to the mammal a therapeutically effective amount of a compound Formula I or II (including mixtures thereof) or a pharmaceutically acceptable salt thereof or, as is more generally the case, administering a pharmaceutical composition as described above.

This invention also provides intermediates and processes for synthesizing the compounds of Formulas I–III.

DETAILED DESCRIPTION OF THE PREFERRED EMBODIMENTS

As noted above, this invention is directed, in part, to certain 1,2,3,4-tetrahydrosulfonylquinoxalone acetamide derivatives represented by Formula I above. In turn, the compounds of Formula I can also be represented by the following subgeneric Formulas I(a) through I(i):

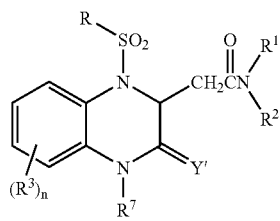

I(a)

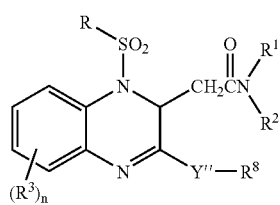

I(b)

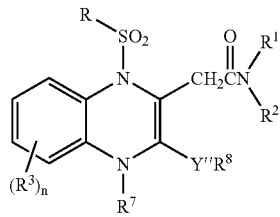

I(c)

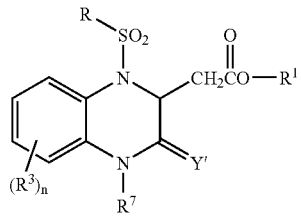

I(d)

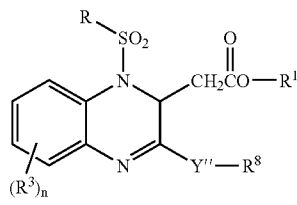

I(e)

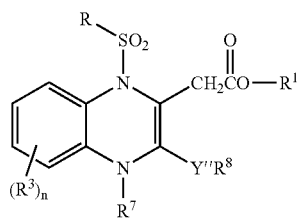

I(f)

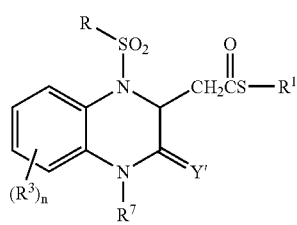

I(g)

-continued

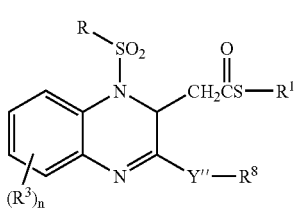

I(h)

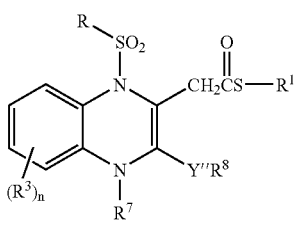

I(i)

wherein Y' is =O or =S; Y" is —O— or —S— and R⁷ is as defined above but, in Formula I(c), R⁷ is not hydrogen; and n, R, R¹, R², R³ and R⁸ are as defined above.

In terms of preferred substituents, the preferred compounds of Formula I of this invention in terms of potency, duration of action manufacture ease and/or ease of administration are compounds having at least one of the following preferred substituents.

In one preferred embodiment, p is one, R⁷ is hydrogen and n is zero.

In another preferred embodiment, p is one, R⁷ is hydrogen, n is one or two and each of R³ is independently hydrogen, alkyl or halo more preferably chloro or fluoro.

In still another preferred embodiment, R is a substituted phenyl, naphthyl, or substituted naphthyl group. More preferably, R is 4-chloro-2,5-dimethylphenyl, or 2,3-dichlorophenyl.

Preferably, W is nitrogen and one and only one of R¹ and R² is hydrogen or R¹ and R² together with the nitrogen atom to which they are joined form a heteroaryl, substituted heteroaryl, heterocyclic or substituted heterocyclic group.

Definitions

Unless otherwise expressly defined with respect to a specific occurrence of the term, the following terms as used herein shall have the following meanings regardless of whether capitalized or not.

The term 1,2,3,4-tetrahydroquinoxaline refers to the ring structure set forth below in which positions 1–4 are numbered according to convention.

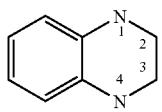

The term "alkyl" refers to alkyl groups having from 1 to 10 carbon atoms and more preferably 1 to 6 carbon atoms and includes both straight chain and branched chain alkyl groups. This term is exemplified by groups such as methyl, t-butyl, n-heptyl, octyl and the like. The term "alkylene" refers to a divalent alkyl group.

The term "substituted alkyl" refers to an alkyl group, of from 1 to 10 carbon atoms, more preferably 1 to 6 carbon atoms, having from 1 to 5 substituents, preferably 1 to 3 substituents, independently selected from the group consisting of alkoxy, substituted alkoxy, acyl, acylamino, thiocarbonylamino, acyloxy, amino, substituted amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxylaryl, substituted aryloxyaryl, cyano, halogen, hydroxyl, nitro, oxo, thioxo, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)₂-alkyl, —OS(O)₂-substituted alkyl, —OS(O)₂-aryl, —OS(O)₂-substituted aryl, —OS(O)₂—OS(O)₂-heteroaryl, —OS(O)₂-substituted heteroaryl, —OS(O)₂-heterocyclic, —OS(O)₂-substituted heterocyclic, —OSO₂—NRR where R is hydrogen or alkyl, —NRS(O)₂—NR-alkyl, —NRS(O)₂—NR-substituted alkyl, —NRS(O)₂—NR-aryl, —NRS(O)₂—NR-substituted aryl, —NRS(O)₂—NR-heteroaryl, —NRS(O)₂—NR-substituted heteroaryl, —NRS(O)₂—NR-heterocyclic, and —NRS(O)₂—NR-substituted heterocyclic where R is hydrogen or alkyl. The term "substituted alkylene" refers to a divalent substituted alkyl.

"Lower alkyl" and "substituted lower alkyl" are defined as above, wherein the number of carbon atoms is from 1 to 5, more preferably, 1–3 carbon atoms.

"Alkoxy" refers to the group "alkyl-O—" which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Substituted alkoxy" refers to the group "substituted alkyl-O—".

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)— provided that a nitrogen atom of the heterocyclic or substituted heterocyclic is not bound to the —C(O)— group wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Amino" refers to the group —NH₂.

"Substituted amino" refers to the group —NRR, where each R group is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, substituted heterocyclic, —SO₂-alkyl, —SO2-substituted alkyl, —SO₂-alkenyl, —SO₂-substituted alkenyl, —SO₂-cycloalkyl, —SO₂-substituted cycloalkyl, —SO₂-aryl, —SO₂-substituted aryl, —SO₂-heteroaryl, —SO₂-substituted heteroaryl, —SO₂-heterocyclic, —SO₂-substituted heterocyclic, provided that both R groups are not hydrogen; or the R groups can be joined together with the nitrogen atom to form a heterocyclic or substituted heterocyclic ring.

The term "acylamino" or as a prefix "carbamoyl" or "carboxamide" or "substituted carbamoyl" or "substituted carboxamide" refers to the group —C(O)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form together with the nitrogen atom a heterocyclic or substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thiocarbonylamino" or as a prefix "thiocarbamoyl" "thiocarboxamide" or "substituted thiocarbamoyl" or "substituted thiocarboxamide" refers to the group —C(S)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form, together with the nitrogen atom a heterocyclic or substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups acyl-O— where acyl is as defined herein.

"Alkenyl" refers to alkenyl group having from 2 to 10 carbon atoms and more preferably 2 to 6 carbon atoms and having at least 1 and preferably from 1–2 sites of alkenyl unsaturation. The term "alkenylene" refers to a divalent alkenyl group.

"Substituted alkenyl" refers to alkenyl groups having from 1 to 5 substituents, preferably 1 to 3 substituents, independently selected from the group of substituents defined for substituted alkyl. The term "substituted alkenylene" refers to a divalent substituted alkenyl group.

"Alkynyl" refers to alkynyl group having from 2 to 10 carbon atoms and more preferably 3 to 6 carbon atoms and having at least 1 and preferably from 1–2 sites of alkynyl unsaturation. The term "alkynylene" refer to a divalent substituted alkynylene group.

"Substituted alkynyl" refers to alkynyl groups having from 1 to 5, preferably 1 to 3 substituents, selected from the same group of substituents as defined for substituted alkyl. The term "substituted alkynylene" refers to as divalent substituted alkynylene group.

"Amidino" refers to the group $H_2NC(=NH)—$ and the term "alkylamidino" refers to compounds having 1 to 3 alkyl groups (e.g., alkylHNC(=NH)—) where alkyl is as defined herein.

"Thioamidino" refers to the group RSC(=NH)— where R is hydrogen or alkyl where alkyl is as defined herein.

"Aminoacyl" refers to the groups —NRC(O)alkyl, —NRC(O)substituted alkyl, —NRC(O)cycloalkyl, —NRC(O)substituted cycloalkyl, —NRC(O)alkenyl, —NRC(O)substituted alkenyl, —NRC(O)alkynyl, —NRC(O)substituted alkynyl, —NRC(O)aryl, —NRC(O)substituted aryl, —NRC(O)heteroaryl, —NRC(O)substituted heteroaryl, —NRC(O)heterocyclic, and —NRC(O)substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are defined herein.

"Aminocarbonyloxy" refers to the groups —NRC(O)O-alkyl, —NRC(O)O-substituted alkyl, —NRC(O)O-alkenyl, —NRC(O)O-substituted alkenyl, —NRC(O)O-alkynyl, —NRC(O)O-substituted alkynyl, —NRC(O)O-cycloalkyl, —NRC(O)O-substituted cycloalkyl, —NRC(O)O-aryl, —NRC(O)O-substituted aryl, —NRC(O)O-heteroaryl, —NRC(O)O-substituted heteroaryl, —NRC(O)O-heterocyclic, and —NRC(O)O-substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxycarbonylamino" or as a prefix "carbamoyloxy" or "substituted carbamoyloxy" refers to the groups —OC(O)NRR where each R is independently hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic or where each R is joined to form, together with the nitrogen atom a heterocyclic or substituted heterocyclic and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxythiocarbonylamino" refers to the groups —OC(S)NRR where each R is independently hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic or where each R is joined to form, together with the nitrogen atom a heterocyclic or substituted heterocyclic and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the group —NR'C(O)NR"R" where R' is selected from the group consisting of hydrogen and alkyl and each R" is independently selected from hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic or where each R" is joined to form together with the nitrogen atom a heterocyclic or substituted heterocyclic and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the group —NR'C(S)NR"R" where R' is selected from the group consisting of hydrogen and alkyl and each R" is independently selected from hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic or where each R" is joined to form together with the nitrogen atom a heterocyclic or substituted heterocyclic, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" or "Ar" refers to an aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like). Preferred aryls include phenyl and naphthyl.

"Substituted aryl" refers to aryl groups which are substituted with from 1 to 4, preferably 1–3, substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, substituted amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, wherein each of the terms is as defined herein.

"Aryloxy" refers to the group aryl-O— which includes, by way of example, phenoxy, naphthoxy, and the like wherein aryl is as defined herein.

"Substituted aryloxy" refers to substituted aryl-O— groups where substituted aryl is as defined herein.

"Aryloxyaryl" refers to the group -aryl-O-aryl where aryl is as defined herein.

"Substituted aryloxyaryl" refers to aryloxyaryl groups substituted with from 1 to 4, preferably 1 to 3 substituents on either or both aryl rings independently selected from the same group consisting of substituents as defined for substituted aryl.

"Cycloalkyl" refers to cyclic alkyl groups of from 3 to 10 carbon atoms having a single or multiple cyclic rings including, by way of example, cyclopropyl, cyclobutyl, cyclopentyl, cyclooctyl, adamantanyl, and the like.

"Cycloalkenyl" refers to cyclic alkenyl groups of from 3 to 8 carbon atoms having single or multiple unsaturation but which are not aromatic.

"Substituted cycloalkyl" and "substituted cycloalkenyl" refer to a cycloalkyl and cycloalkenyl groups, as defined herein, having from 1 to 5, preferably 1–3 substituents independently selected from the same group of substituents as defined for substituited alkyl.

"Cycloalkoxy" refers to —O-cycloalkyl groups where cycloalkyl is as defined herein.

"Substituted cycloalkoxy" refers to —O-substituted cycloalkyl groups where substituted cycloalkyl is as defined herein.

"Guanidino" or "substituted guanidino" refers to the groups —NR'C(=NR')NR"R" where each R' is independently hydrogen or alkyl and each R" is independently selected from the group consisting of hydrogen, alkyl, substituted alkyl, alkenyl, substituted alkenyl, alkynyl, substituted alkynyl, aryl, substituted aryl, cycloalkyl, heteroaryl, substituted heteroaryl, heterocyclic, and substituted heterocyclic and wherein alkyl, substituted alkyl, alkenyl, substituted alkenyl, alkynyl, substituted alkynyl, cycloalkyl, substituted cycloalkyl, alkoxy, substituted alkoxy, acyloxy, aryl, substituted aryl, heteroaryl, substituted heteroaryl, heterocyclic and substituted heterocyclic are as defined herein.

"Guanidinosulfone" refers to the groups —NR'C(=NR')NR'SO$_2$-alkyl, —NR'C(=NR')NR'SO$_2$-substituted alkyl, —NR'C(=NR')NR'SO$_2$-alkenyl, —NR'C(=NR')NR'SO$_2$-substituted alkenyl, —NR'C(=NR')NR'SO$_2$-alkynyl, —NR'C(=NR')NR'SO$_2$-substituted alkynyl, —NR'C(=NR')NR'SO$_2$-aryl, —NR'C(=NR')NR'SO$_2$-substituted aryl, —NR'C(=NR')NR'SO$_2$-cycloalkyl, —NR'C(=NR')NR'SO$_2$-substituted cycloalkyl, —NR'C(=NR')NR'SO$_2$-heteroaryl, —NR'C(=NR')NR'SO$_2$-substituted heteroaryl, —NR'C(=NR')NR'SO$_2$-heterocyclic, and —NR'C(=NR')NR'SO$_2$-substituted heterocyclic where each R' is independently hydrogen and alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Halo" or "halogen" refers to fluoro, chloro, bromo and iodo and preferably is either chloro or fluoro.

"Heteroaryl" refers to an aromatic group of from 1 to 10 ring carbon atoms and 1 to 4 ring heteroatoms selected from oxygen, nitrogen and sulfur within the ring. Such heteroaryl groups can have a single ring (e.g., pyridyl or furyl) or multiple condensed rings (e.g., indolizinyl or benzothienyl). Preferred heteroaryls include pyridyl, pyrrolyl, indolyl and furyl.

"Substituted heteroaryl" refers to heteroaryl groups, as defined above, which are substituted with from 1 to 3 substituents independently elected from the same group of substituents as defined for "substituted aryl".

"Heteroaryloxy" refers to the group —O-heteroaryl and "substituted heteroaryloxy" refers to the group —O-substituted heteroaryl where heteroaryl and substituted heteroaryl are as defined above.

"Heterocycle," "heterocyclyl" or "heterocyclic" refers to a saturated or unsaturated group having a single ring or multiple condensed rings, from 1 to 10 ring carbon atoms and from 1 to 4 ring hetero atoms selected from nitrogen, sulfur or oxygen within the ring wherein, in fused ring systems, one or more of the rings can be aryl or heteroaryl.

"Saturated heterocyclic" refers to heterocycles of single or multiple condensed rings lacking unsaturation in any ring (e.g., carbon to carbon unsaturation, carbon to nitrogen unsaturation, nitrogen to nitrogen unsaturation, and the like).

"Unsaturated heterocyclic" refers to non-aromatic heterocycles of single or multiple condensed rings having unsaturation in any ring (e.g., carbon to carbon unsaturation, carbon to nitrogen unsaturation, nitrogen to nitrogen unsaturation, and the like).

"Substituted heterocyclic" refers to heterocycle groups, as defined above, which are substituted with from 1 to 3 substituents independently selected from the group consisting of oxo (═O), thioxo (═S), plus the same group of substituents as defined for substituted aryl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholino, thiomorpholino, piperidinyl, pyrrolidine, tetrahydrofuranyl, and the like.

"Substituted saturated heterocyclic" refers to substituted heterocycles, as defined above, of single or multiple condensed rings lacking unsaturation in any ring (e.g., carbon to carbon unsaturation, carbon to nitrogen unsaturation, nitrogen to nitrogen unsaturation, and the like).

"Substituted unsaturated heterocyclic" refers to non-aromatic substituted heterocycles of single or multiple condensed rings having unsaturation in any ring (e.g., carbon to carbon unsaturation, carbon to nitrogen unsaturation, nitrogen to nitrogen unsaturation, and the like).

"Heterocyclyloxy" refers to the group —O-heterocyclic and "substituted heterocyclyloxy" refers to the group —O-substituted heterocyclic where heterocyclic and substituted heterocyclyoxy are as defined above.

"Thiol" refers to the group —SH.

"Thioalkyl" refers to the groups —S-alkyl where alkyl is as defined above.

"Substituted thioalkyl" refers to the group —S-substituted alkyl where substituted alkyl is as defined above.

"Thiocycloalkyl" refers to the groups —S-cycloalkyl where cycloalkyl is as defined above.

"Substituted thiocycloalkyl" refers to the group —S-substituted cycloalkyl where substituted cycloalkyl is as defined above.

"Thioaryl" refers to the group —S-aryl and "substituted thioaryl" refers to the group —S-substituted aryl where aryl and substituted aryl are as defined above.

"Thioheteroaryl" refers to the group —S-heteroaryl and "substituted thioheteroaryl" refers to the group —S-substituted heteroaryl where heteroaryl and substituted heteroaryl are as defined above.

"Thioheterocyclic" refers to the group —S-heterocyclic and "substituted thioheterocyclic" refers to the group —S-substituted heterocyclic where heterocyclic and substituted heterocyclic are as defined above.

"Pharmaceutically acceptable salt" refers to pharmaceutically acceptable salts of a compound of Formula I which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

Compound Preparation

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Second Edition, Wiley, N.Y., 1991, and references cited therein.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

In one embodiment, the compounds of Formula I, wherein W is N and $R^1$ and $R^2$ are H, can be prepared via the following reaction scheme, Scheme 1:

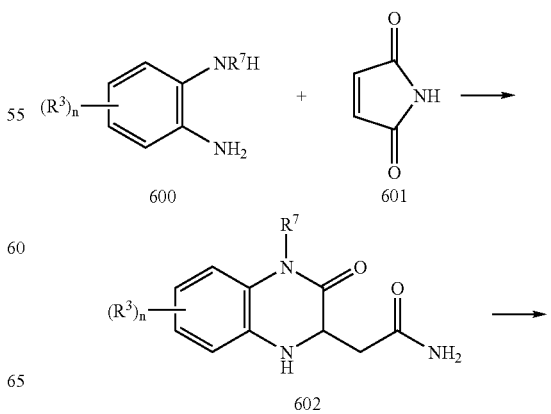

-continued

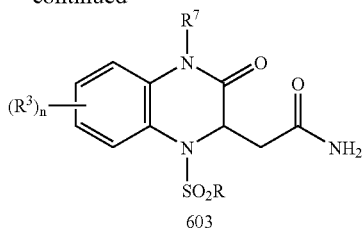

603 wherein R, $R^3$, and $R^7$ are as defined herein above.

In Scheme 1, an appropriately substituted 1,2-diaminobenzene compound (600) is condensed with at least a stoichiometric equivalent, and preferably an excess of maleimide (601) to provide a quinoxalone acetamide intermediate (602). This reaction is typically performed in an inert organic solvent, for example, methanol, water, and the like, and is typically conducted at temperatures in the range of 20 to 100° C. until the reaction is complete, which typically occurs within 1 to 2 hours. The resulting product can be recovered by conventional methods, such as chromatography, filtration, crystallization, and the like, or can be used in the next step without purification or isolation.

The quinoxalone acetamide intermediate (602) can then be sulfonated with the desired sulfonyl chloride ($RSO_2Cl$) to yield the sulfonated quinoxalone acetamide (603). The sulfonation is typically effected by contacting the quinoxalone acetamide intermediate (602) with about a stoichiometric amount, or slight excess, of the desired sulfonyl chloride in the presence of a scavenger base, such as pyridine, and the like in an inert diluent. The reaction is typically conducted at temperatures in the range of about 0° C. to about room temperature for a period of time to effect sulfonation, which is typically 2 to 12 hours. Suitable inert solvents which can be used include, dichloromethane, and the like. The resulting product can be recovered by conventional methods, such as chromatography, filtration, crystallization, and the like, or can be used in the next step without purification or isolation.

The compounds of Formula I, wherein W is N, O, or S, can also be prepared as illustrated below in Scheme 2.

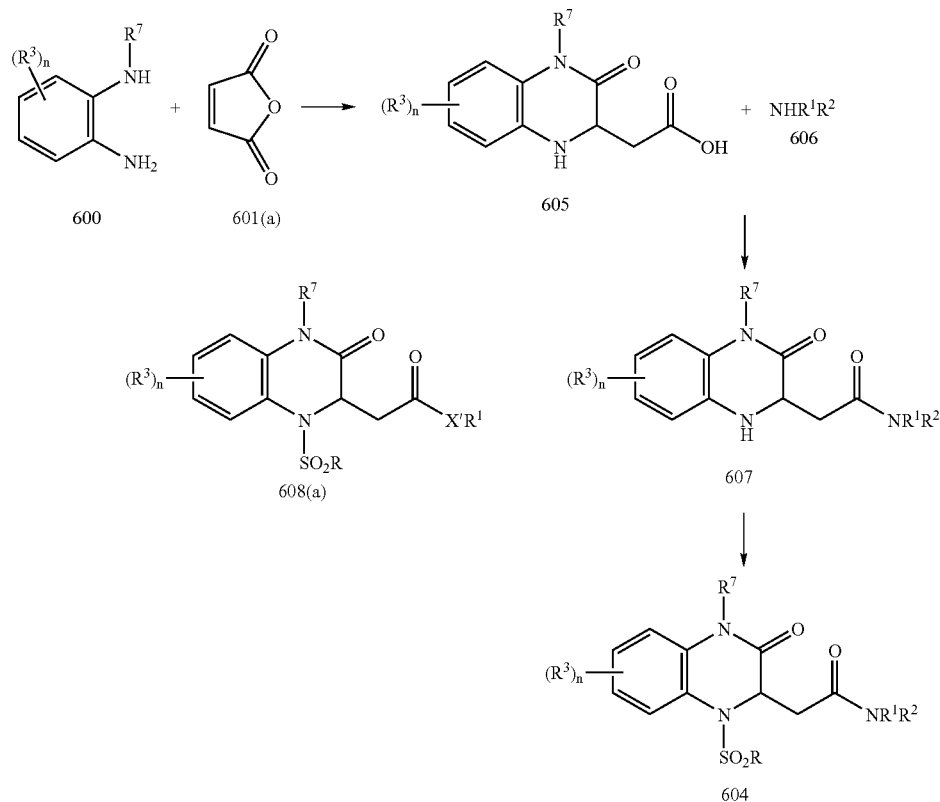

wherein R, $R^1$, $R^2$, $R^3$, and $R^7$ are as defined herein above and X' is O or S.

In Scheme 2, an appropriately substituted 1,2-diaminobenzene compound (600) is condensed with at least a stoichiometric equivalent, and preferably a slight excess of maleic anhydride (601(a)) to provide a quinoxalone acetic acid intermediate (605). This reaction is typically performed in an inert organic solvent, for example, methanol, water, and the like, and is typically conducted at temperatures in the range of 20 to 100° C. until the reaction is complete, which typically occurs within 1 to 2 hours. The resulting product can be recovered by conventional methods, such as chromatography, filtration, crystallization, and the like, or can be used in the next step without purification or isolation.

Compounds of Formula I (where W is N) are prepared by reaction of the carboxyl group of the quinoxalone acetic acid intermediate (605) with a slight excess of a primary or secondary amine or nitrogen heterocycle (606) under reactive conditions, preferably in the presence of an inert organic solvent, a coupling agent and an organic base using amidation methods well known in the art. This reaction is preferably conducted using an excess of an amine (606) (about from 0.99 to 1.2 molar equivalents per mole of quinoxalone acetic acid) at temperatures in the range of about −20° C. to room temperature. The reaction is continued until completion, which typically occurs in 2 to 12 hours. Suitable inert organic solvents which can be used include, for example, N,N-dimethylformamide, acetonitrile, dichloromethane, and the like. Suitable coupling agents which may be used include 1-hydroxybenzotriazole hydrate (HOBT) and 1-(3-dimethylaminopropyl)-3-ethylcarbodiimide hydrochloride (EDCI), diphenylphosphoryl azide (DPPA), and the like. Suitable organic bases include triethylamine (TEA), pyridine, N-methyl morpholine, diisopropylethyl amine (DIEA), and the like. The resulting product can be recovered by conventional methods, such as chromatography, filtration, crystallization, and the like, or can be used in the next step without purification or isolation.

The quinoxalone acetamide compound (607) is then sulfonated with the desired sulfonyl chloride $RSO_2Cl$, as described above, to yield the sulfonated quinoxalone acetamide (604).

For compounds of Formula I wherein W is O or S, the carboxyl group of the quinoxalone acetic acid intermediate (605) is esterified or thioesterified by contacting the quinoxalone acetic acid intermediate (605) with an appropriate alcohol or thiol ($HX'R^1$ wherein X' is O or S). The esterification reaction may be catalyzed by $H^+$. The thioesterification is typically performed in an inert organic solvent, for example, pyridine, and is typically conducted with a stoichiometric amount of a dehydration agent, chlorinating agent, or activating agent, such as $POCl_3$. The reaction is typically conducted at temperatures in the range of −20° C. to −10° C. until reaction completion, which typically occurs in 1 to 3 hours. The resulting intermediate is then sulfonated with the desired sulfonyl chloride $RSO_2Cl$, as described above, to yield the sulfonated quinoxalone ester or thioester (608(a)). Alternatively, for compounds where W is O, esterification can be achieved by reaction of the sulfonated carboxylic acid with alkyl iodide in a suitable solvent such as DMF in the presence of weak base such as potassium carbonate wherein the reaction is maintained at about room temperature or by reaction with the alkyl halide in acetone maintained at reflux.

Alternatively, the sulfonation and transesterification/transthioesterification steps can be reversed such that the sulfonation is performed prior to the transesterification or transthioesterification.

In another embodiment for compounds of Formula I where W is N, the sulfonation and amidation steps of Scheme 2 can be reversed. Specifically, as illustrated in Scheme 3 below, reaction of a sulfonated quinoxalone acetic acid intermediate (608), with a primary or secondary amine provides for the sulfonated quinoxalone acetamide (604).

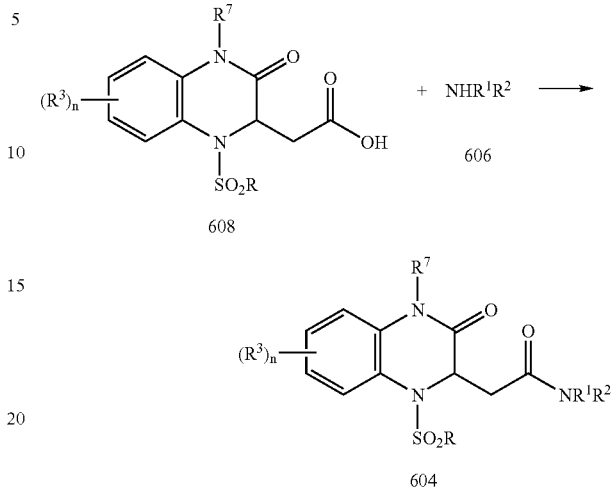

Scheme 3 wherein R, $R^1$, $R^2$, $R^3$, and $R^7$ are as defined herein above.

Specifically in this embodiment, a sulfonated quinoxalone acetic acid intermediate (608) (prepared by sulfonation of intermediate 605 in the manner described above) is contacted with a primary or secondary amine or nitrogen heterocycle (606) under reactive conditions, preferably in an inert organic solvent, in the presence of a coupling agent and an organic base to yield the sulfonated quinoxalone acetamide (604). The resulting product can be recovered by conventional methods, such as chromatography, filtration, crystallization, and the like, or can be used in the next step without purification or isolation. The conditions for this coupling reaction to provide the amide are as described above for Scheme 2.

In yet another embodiment, the quinoxalone acetic acid intermediate (605) can be prepared by hydrolysis of amide (602) using conditions well known in the art and then sulfonating as above to provide for the sulfonated quinoxalone acetic acid intermediate (608) which reaction scheme is illustrated below in Scheme 4.

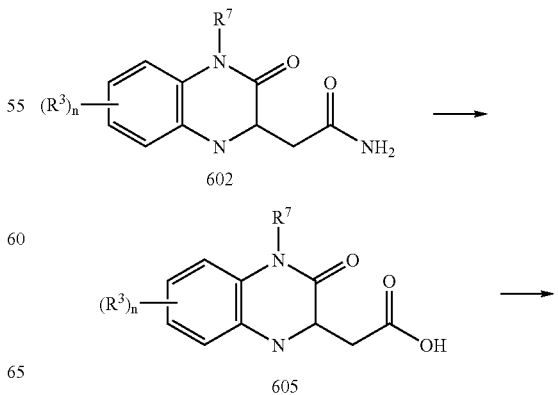

Scheme 4

-continued

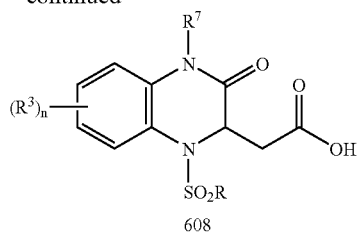
608 wherein R, R³, and R⁷ are as defined herein above.

The first step of this process is typically effected by hydrolyzing the quinoxalone acetamide compound (602) in a suitable solvent such as an aqueous solution in the presence of a base to promote hydrolysis (10% sodium hydroxide). This reaction is typically conducted at elevated temperatures of about 50 to 100° C., and more preferably at reflux in the reaction system used. The reaction is continued until completion, which typically occurs in about 1 to 5 hours. Suitable bases include NaOH, LiOH, and the like. After hydrolysis of the amide yielding the carboxylate, the quinoxalone acetic acid intermediate (605) may be yielded by contact with an acid, such as HCl, and the like. The resulting product can be recovered by conventional methods, such as chromatography, filtration, crystallization, and the like, or can be used in the next step without purification or isolation.

The quinoxalone acetic acid intermediate (605) may then be sulfonated with the desired RSO₂Cl, as described above, to yield the sulfonated quinoxalone acetic acid intermediate (608). The process illustrated in Scheme 4 is, however, not preferred.

In still another embodiment, the quinoxalone acetic acid intermediate (605) can also be prepared as illustrated below in Scheme 5. This alternative embodiment to prepare the quinoxalone acetic acid intermediate (605) is useful for providing an approximately 50/50 mixture of R and S isomers.

wherein R³ and R⁷ are as defined herein above and R⁶⁰ is preferably lower alkyl.

In Scheme 5, an optionally substituted 1,2-diaminobenzene compound (600) is condensed with a stoichiometric amount or a slight excess of a dialkyl ester of 2-ketosuccinic acid (e.g. diethyl 2-keto succinate) (609) in an inert organic solvent, for example, dichloromethane, methanol, and the like, to yield an unsaturated quinoxalone ester intermediate (610). This reaction is typically conducted at or near room temperature. The reaction is continued until completion, which typically occurs in 10 minutes to 1 hour. The resulting product can be recovered by conventional methods, such as chromatography, filtration, crystallization, and the like, or can be used in the next step without purification or isolation.

The unsaturated side chain of the quinoxalone ester intermediate (610) is then reduced to yield a quinoxalone ester (611). The reduction reaction may be conveniently effected by contacting the unsaturated quinoxalone ester intermediate (610) with a stoichiometric amount of a suitable reducing agent, such as sodium cyanoborohydride, and the like. The reduction reaction is typically conducted in a polar organic solvent, for example a THF and acetic acid mixture, methanol and acetic acid, and the like. This reaction is typically conducted at or near room temperature. The reaction is continued until completion, which typically occurs in 10 min. to 2 hours. The resulting product can be recovered by conventional methods, such as chromatography, filtration, crystallization, and the like, or can be used in the next step without purification or isolation.

In the next step, the quinoxalone ester (611) is hydrolyzed to yield the corresponding quinoxalone acetic acid intermediate (605). This reaction may be conveniently effected by contacting the quinoxalone ester (611) with a strong base, for example, lithium hydroxide monohydrate or sodium hydroxide, in a suitable solvent. When lithium hydroxide monohydrate is used, the reaction is typically conducted at about 0° C. for about 10 min to 6 hours in a suitable solvent, e.g., mixtures of tetrahydrofuran and water. The resulting sodium or lithium salt can be converted to carboxylic acid form (—COOH) by contact with a dilute mineral acid, typically dilute aqueous hydrochloric acid. If desired, the Scheme 5

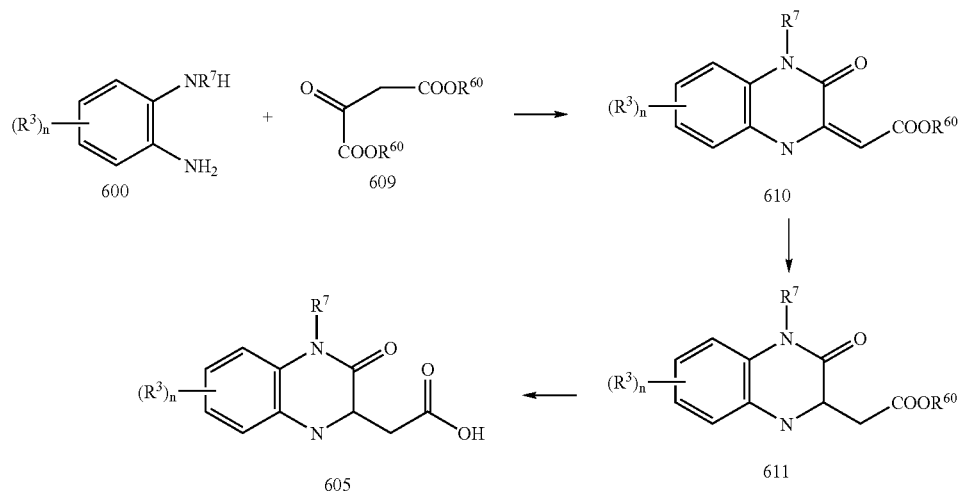

R,S isomers formed can be separated by conventional techniques such as chiral column chromatography, chiral resolving agents, and the like.

The quinoxalone acetic acid intermediate (605(a)), wherein R⁷ is H, may also be prepared as illustrated below in Scheme 6. This reaction scheme is useful for introducing chirality and thus providing pure stereoisomers.

The ester intermediate (614) may be reduced and cyclized to the quinoxalone ester (611) by contact with hydrogen in the presence of a noble metal catalyst, e.g., platinum, in an inert organic solvent, e.g., methanol. This reaction is typically conducted at temperatures in the range of 20 to 30° C., and pressures of about from 30 to 60 psi for about from 3 to 12 hours. The resulting product can be recovered by con-

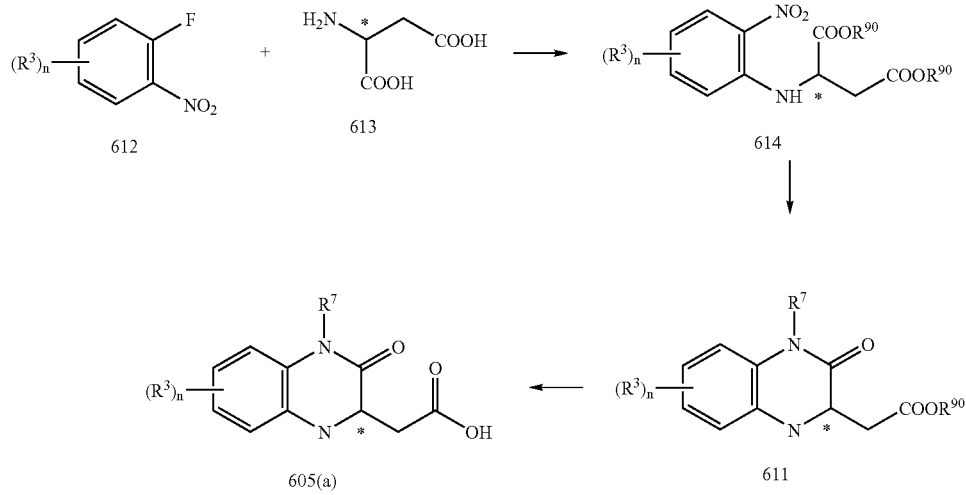

Scheme 6 wherein $R^3$ is as defined herein above and $R^{60}$ is lower alkyl (where * represents the chiral center).

In the first step of this process, an appropriately substituted 1,2-fluoronitrobenzene (612) may be coupled with aspartic acid (613) yielding the diacid, and this may be followed by treatment with a lower alkyl iodide, typically methyl iodide, to yield the diester intermediate (614). When the aspartic acid reagent (613) is optically active, a pure stereoisomer ester intermediate (614) is formed. The coupling reaction is typically conducted using stoichiometric amounts of reagents (612) and (613), or a modest stoichiometric excess of reactant (612), and a weak base e.g., sodium carbonate, in a suitable solvent, e.g., mixtures of methanol and water. The coupling reaction is typically conducted at temperatures in the range of 80 to 130° C. The coupling reaction is continued until completion, which typically occurs in 1 to 12 hours.

ventional methods, such as chromatography, filtration, crystallization, and the like, or can be used in the next step without purification or isolation.

In the next step, the ester group of the quinoxalone ester (611) is hydrolyzed to provide for the quinoxalone acetic acid intermediate (605) as described above for Scheme 5. If optically active starting materials (i.e., aspartic acid) are used, the resulting product (605) is isolated as a pure stereoisomer. To ensure retention of optical center, no more than about 1.05 equivalents and preferably from 0.99 to 1.00 equivalents of base should be used during hydrolysis. In any event, the quinoxalone acetic acid intermediate (605) is then converted to compounds of this invention in the manner described above.

In another embodiment, compounds of Formula I in which W is N and one of $R^1$ and $R^2$ is H and the other is 2-(pyrid-4-yl)eth-1-yl or 2-(piperidin-4-yl)eth-1-yl can be prepared as illustrated below in Scheme 7.

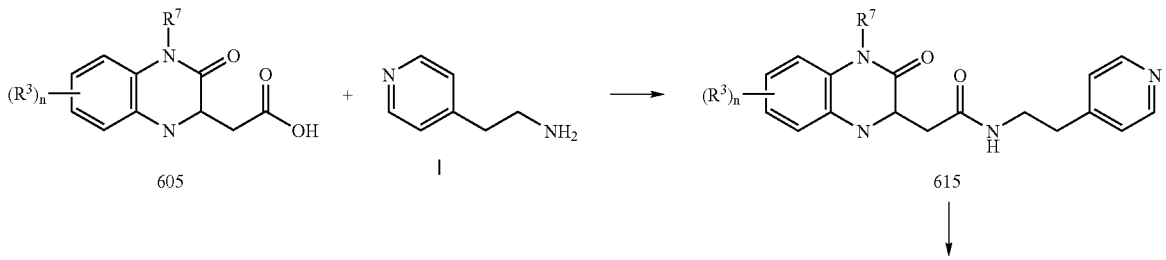

Scheme 7

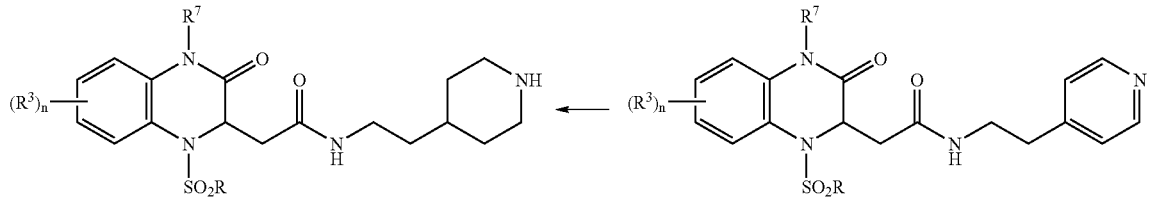

617                            616 wherein R, $R^3$, and $R^7$ are as defined herein above.

In the first step of this process, a quinoxalone acetic acid intermediate (605) is contacted with 4-(2-aminoethyl)pyridine under reactive conditions, preferably in an inert organic solvent in the presence of a coupling agent and an organic base to yield the quinoxalone 2-(pyrid-4-yl)eth-1-yl amide derivative (615). The conditions for this coupling reaction to provide the amide (615) are as described above for Scheme 2. The resulting product can be recovered by conventional methods, such as chromatography, filtration, crystallization, and the like, or can be used in the next step without purification or isolation.

The quinoxalone 2-(pyrid-4-yl)eth-1-yl amide derivative (615) is then sulfonated with the desired $RSO_2Cl$, as described above, to yield the sulfonated quinoxalone amide derivative (616). The resulting product can be recovered by conventional methods, such as chromatography, filtration, crystallization, and the like, or can be used in the next step without purification or isolation.

As an optional step, the pyridine ring can be hydrogenated to yield the quinoxalone 2-(piperidin-4-yl)eth-1-yl amide derivative (617) by contact with hydrogen in the presence of a noble metal catalyst, e.g., platinum, in an organic solvent, e.g., acetic acid. This reaction is typically conducted at temperatures in the range of 20 to 30° C., and pressures of about from 30 to 60 psi for 1 to 12 hours.

The compounds of Formula I where W is nitrogen and one of $R^1$ and $R^2$ is H and the other is 2-(anilin-4-yl)eth-1-yl can be prepared as illustrated below in Scheme 8.

Scheme 8

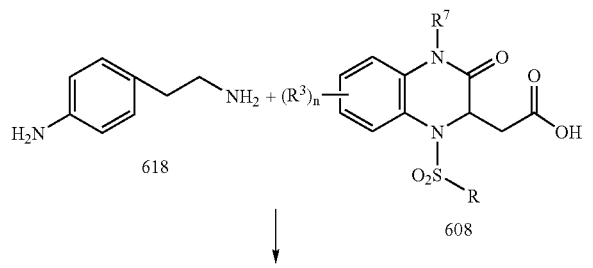

-continued

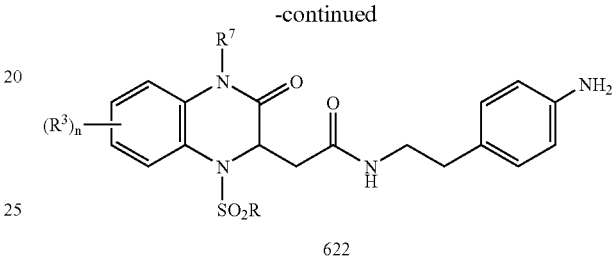

622 wherein R, $R^3$, and $R^7$ are as defined herein above.

Specifically, a sulfonated quinoxalone acetic acid intermediate (608) is contacted with a 4-(2-aminoethyl)aniline (618) under reactive conditions, preferably in an inert organic solvent in the presence of a coupling agent and an organic base to yield the quinoxalone 2-(anilin-4-yl)eth-1-yl amide derivative (622). The conditions for this coupling reaction to provide the amide are as described above for Scheme 2. The resulting product can be recovered by conventional methods, such as chromatography, filtration, crystallization, and the like, or can be used in the next step without purification or isolation.

In the above reaction, the basicity of the aliphatic amine provides a vehicle for the direct reaction with the aliphatic amine without the necessity to block the aniline amine group. Contrarily, when amidation of the quinoxalone acetic acid intermediate (605) is conducted using a polyamine, e.g., a diamine, having two or more similarly reactive amino groups, the use of blocking groups to provide for a single reactive amino functionality will be necessary. Suitable conditions for differentially protecting and deprotecting amines on a polyamine are well known in the art.

The sulfonated quinoxalone 2-(piper-4-yl)eth-1-yl amide derivative (617) and the sulfonated 2-(anilin-4-yl)eth-1-yl quinoxalone amide derivative (622) may be further derivatized as illustrated below in Scheme 9.

Scheme 9

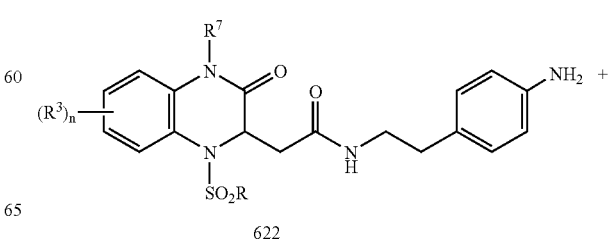

622

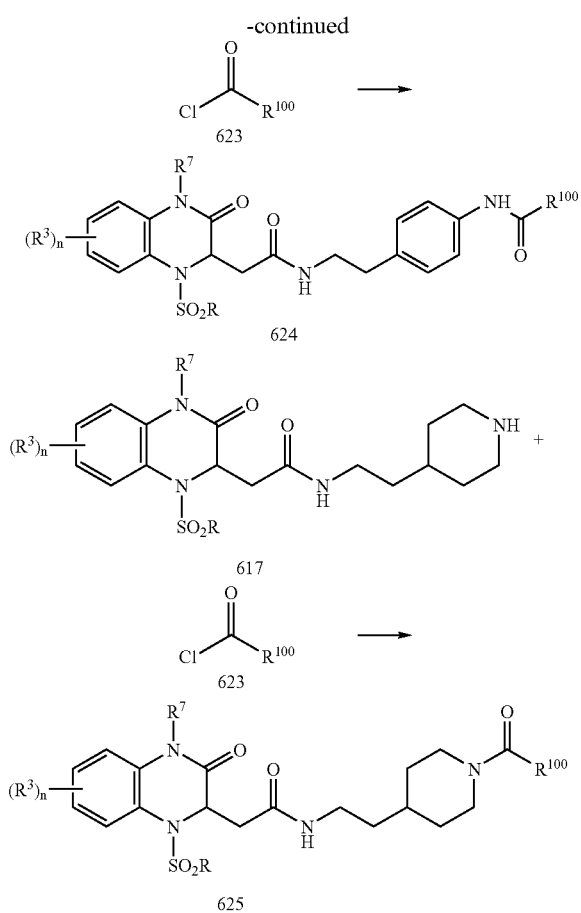

wherein R, $R^3$, and $R^7$ are as defined herein above and $R^{100}$ is selected from the group consisting of alkyl, substituted alkyl, cycloalkyl, substituted cycloalkyl, heterocycle, substituted heterocycle, aryl, substituted aryl, heteroaryl, and substituted heteroaryl.

In this process, aniline intermediate (622) or piperidine intermediate (617) is acylated with an acid chloride having the desired substitutent $R^{100}$ (623) in the presence of an organic base, such as diisopropylethylamine (DIEA). This reaction is typically conducted in an inert organic solvent, such as dichloromethane, dioxane, and the like. The reaction is preferably conducted at room temperature for 1 to 12 hours. If conversion is incomplete, an organic base (e.g., triethylamine (TEA)) may be added to assist in driving the reaction to completion.

In some instances generation of the acid chloride from the carboxylic acid may be necessary prior to the acylation step. This conversion can be accomplished by dissolving the carboxylic acid in an inert organic solvent (e.g., dichloromethane, dioxane, and the like) adding oxalyl chloride plus a catalytic amount of N,N-dimethylformamide and shaking. This conversion can be conducted conveniently at room temperature for 2 to 5 hours.

The compounds of Formula I, wherein Y and $R^7$ together with the carbon atom and nitrogen atom to which they are joined forms an optionally substituted fused heteroaryl or an optionally substituted fused saturated or unsaturated heterocyclic structure, can be prepared as illustrated below in Scheme 10.

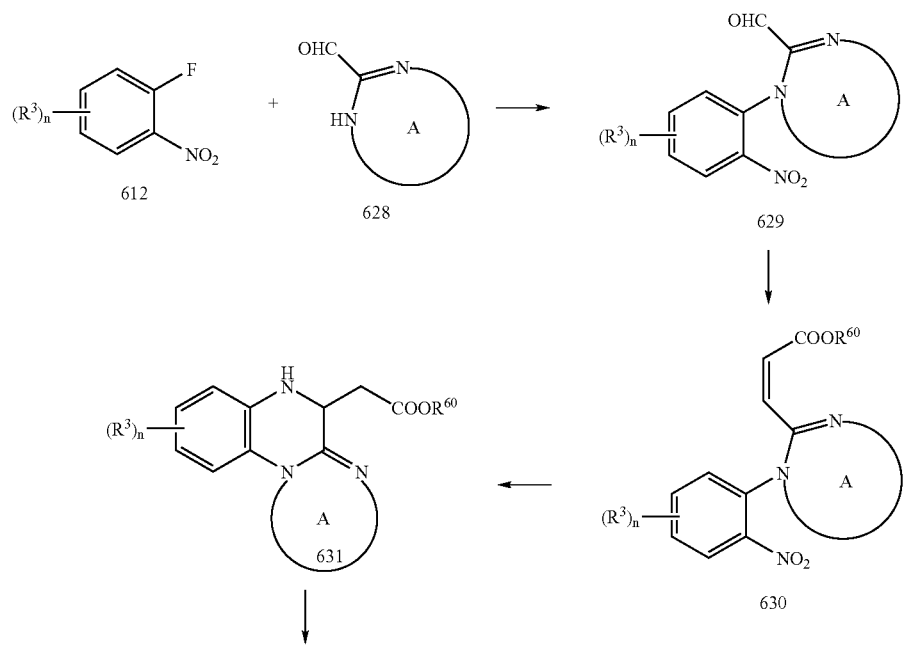

-continued

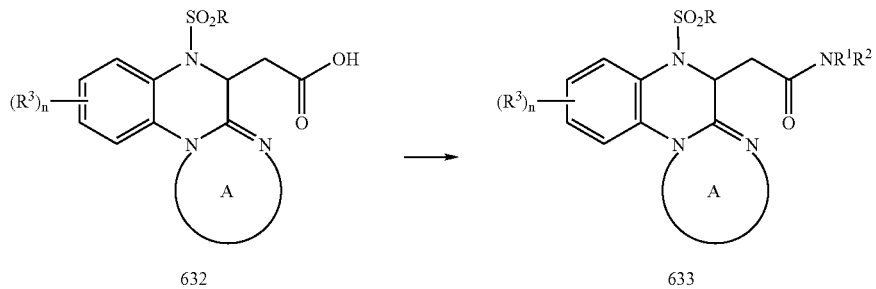

wherein R, $R^1$, $R^2$, and $R^3$ are as defined herein above and $R^{60}$ is lower alkyl.

In the first step of this process, an appropriately substituted 1,2-fluoronitrobenzene (612) is coupled with an amino containing optionally substituted heteroaryl or unsaturated heterocyclic compound having an aldehyde group alpha to both the amino group and an unsaturated ethylene amine moiety (628), for example, the commercially available 2-imidazolecarboxaldehyde. The coupling reaction is typically conducted using stoichiometric amounts of reagents (612) and (628), or a modest stoichiometric excess of reagent (612), and a weak base, e.g., sodium carbonate, in an aqueous inert organic solvent, e.g., mixtures of methanol and water or mixtures of ethanol and water. The coupling reaction is typically conducted at temperatures in the range of 80° C. to 130° C. for 4 to 10 hours. The resulting product can be recovered by conventional methods, such as chromatography, filtration, crystallization, and the like, or can be used in the next step without purification or isolation.

The intermediate from the coupling reaction (629) is reacted with a phosphonium ylide in a conventional Wittig reaction to form an alkene intermediate (630). The Wittig reaction is typically conducted in an inert organic solvent such as tetrahydrofuran and the like and may conveniently be conducted at approximately room temperature. The resulting product can be recovered by conventional methods, such as chromatography, filtration, crystallization, and the like, or can be used in the next step without purification or isolation.

The alkene intermediate is reduced and cyclized to a quinoxalone ester (631) by contact, for example, with iron and acetic acid in an inert organic solvent, e.g., ethanol, methanol, and the like. The reaction is typically conducted at temperatures in the range of 20 to 90° C. The resulting product can be recovered by conventional methods, such as chromatography, filtration, crystallization, and the like, or can be used in the next step without purification or isolation.

In the next step, the ester group of the quinoxalone ester (631) is hydrolyzed under conventional conditions to yield the corresponding carboxyl group (—COOH) or a suitable salt thereof. This reaction is conventionally effected by contacting the quinoxalone ester (631) with a suitable base, for example, lithium hydroxide monohydrate or sodium hydroxide, in a solvent such as an aqueous inert organic solvent, e.g., mixtures of tetrahydrofuran and water. The quinoxalone acetic acid intermediate is sulfonated in the manner described above with the desired sulfonyl choloride $RSO_2Cl$ to yield the sulfonated quinoxalone acid intermediate (632).

The sulfonated quinoxalone acetic acid intermediate (632) is then contacted with a primary or secondary amine $NHR^1R^2$ (606) (not shown) also in the manner described above to provide for compound 633, a compound of Formula I.

The compounds of Formula I, wherein Y is =S, —$OR^8$, —$NR^8$, or —$SR^8$, can be prepared as illustrated below in Scheme 11.

Scheme 11

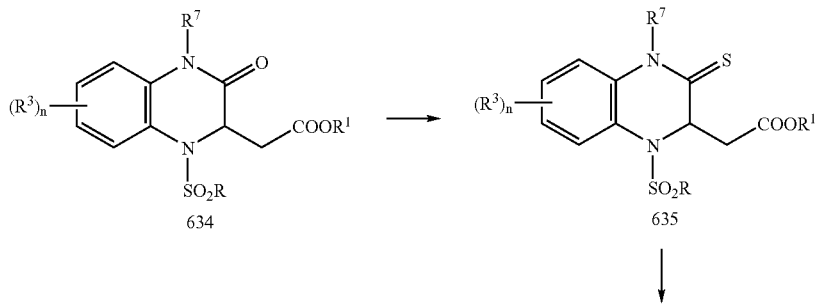

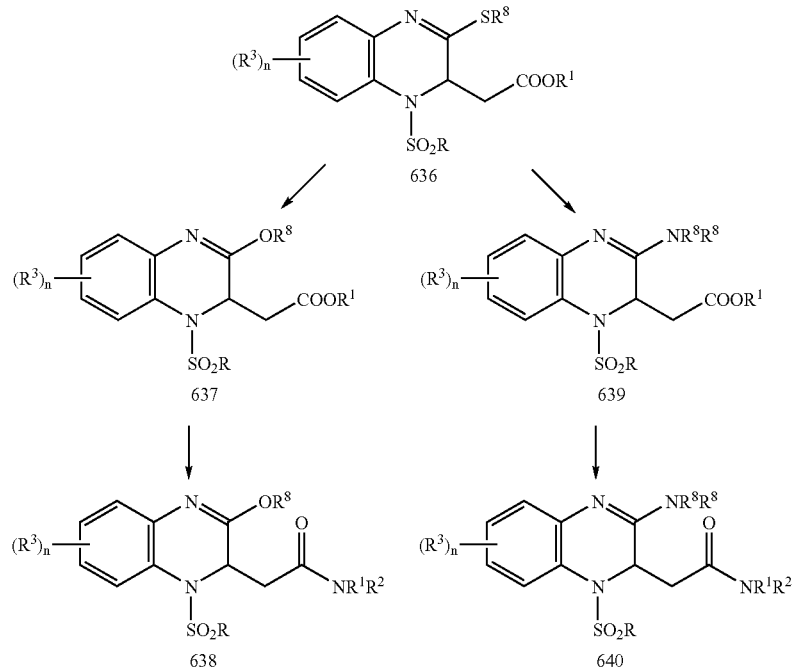

wherein R, $R^1$, $R^2$, $R^3$, and $R^8$ are as defined herein above with the exception that for $NR^8R^8$ one of $R^8$ can be hydrogen.

The carbonyl group of the sulfonated quinoxalone ester (634) is converted to the thiocarbonyl by conventional techniques such as contact with a sulfurization agent such as Lawessen reagent. The sulfurization reaction is conducted in an inert organic solvent, such as tetrahydrofuran, at temperatures in the range of 20° C. to 100° C. for 1 to 6 hours. The resulting product can be recovered by conventional methods, such as chromatography, filtration, crystallization, and the like, or can be used in the next step without purification or isolation.

The thiocarbonyl compound (635) can then be alkylated to provide the desired thioalkoxy derivative, compound 636. The alkylation reaction is effected by conventional techniques such as by contacting the thiocarbonyl compound (635) with a lower alkyl iodide $R^8I$ (not shown), such as methyl iodide. The alkylation reaction is typically conducted in an inert organic solvent such as acetone, at temperatures at or near room temperature. The reaction is run to completion which typically occurs within 1 to 6 hours. The resulting product can be recovered by conventional methods, such as chromatography, filtration, crystallization, and the like, or can be used in the next step without purification or isolation.

Compound 636 can then be converted to the corresponding alkoxy compound —$OR^8$ (637), wherein $R^8$ is the same or different, by refluxing the thioquinoxalone (636) in an appropriate alcohol ($R^8OH$). This reaction is typically conducted from 1 to 12 hours. The resulting product can be recovered by conventional methods, such as chromatography, filtration, crystallization, and the like, or can be used in the next step without purification or isolation.

The ester side chain at the 2-position of the quinoxalone (637) is then amidated by contact with a primary or secondary amine $NHR^1R^2$ (606) in the manner described above.

As is apparent, this procedure may require conversion of the ester to the corresponding carboxyl group prior to amidation.

The thioquinoxalone (636) can also be converted to an amine —$NR^8R^8$, wherein each $R^8$ is the same or different, by refluxing the thioquinoxalone (636) in the presence of appropriate amine ($NHR^8R^8$) in an inert organic solvent such as ethanol, methanol, and the like to provide for compound 639. This reaction is typically conducted 6 to 15 hours. The resulting product can be recovered by conventional methods, such as chromatography, filtration, crystallization, and the like, or can be used in the next step without purification or isolation.

The ester side chain at the 2-position of the quinoxalone (639) is then amidated by contact with a primary or secondary amine $NHR^1R^2$ (606) in the manner described above. As is apparent, this procedure may require hydrolysis of the ester to the corresponding carboxyl group prior to amidation.

As is apparent, the ester group in intermediates 635 and 636 can be directly hydrolyzed and then amidated in the manner described above to provide for compounds of Formula I where Y is =S or —$SR^8$.

The starting materials for the above reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1–15 (John Wiley and Sons, 1991), Rodd's Chemistry of Carbon Compounds, Volumes 1–5 and Supplementals (Elsevier Science Publishers, 1989), Organic Reactions, Volumes 1–40 (John Wiley and Sons, 1991), March's Advanced Organic Chemistry, (John Wiley and Sons, 4$^{th}$ Edition), and Larock's Comprehensive Organic Transformations (VCH Publishers Inc., 1989).

Sulfonyl chlorides of the formula RSO$_2$Cl as employed in the above reaction are either known compounds or compounds that can be prepared from known compounds by conventional synthetic procedures. Such compounds are typically prepared from the corresponding sulfonic acid, i.e., from compounds of the formula R—SO$_3$H where R is as defined above, using phosphorous trichloride and phosphorous pentachloride. This reaction is generally conducted by contacting the sulfonic acid with about 2 to 5 molar equivalents of phosphorous trichloride and phosphorous pentachloride, either neat or in an inert solvent, such as dichloromethane, at temperature in the range of about 0° C. to about 80° C. for about 1 to about 48 hours to afford the sulfonyl chloride. Alternatively, the sulfonyl chlorides can be prepared from the corresponding thiol compound, i.e., from compounds of the formula R—SH where R is as defined herein, by treating the thiol with chlorine (Cl$_2$) and water under conventional reaction conditions.

Examples of sulfonyl chlorides suitable for use in this invention include, but are not limited to, benzenesulfonyl chloride, 1-naphthalenesulfonyl chloride, 2-naphthalenesulfonyl chloride, p-toluenesulfonyl chloride, α-toluenesulfonyl chloride, 4-acetamidobenzenesulfonyl chloride, 4-amidinobenzenesulfonyl chloride, 4-tert-butylbenzenesulfonyl chloride, 4-bromobenzenesulfonyl chloride, 2-carboxybenzenesulfonyl chloride, 4-cyanobenzenesulfonyl chloride, 3,4-dichlorobenzenesulfonyl chloride, 3,5-dichlorobenzenesulfonyl chloride, 3,4-dimethoxybenzenesulfonyl chloride, 3,5-ditrifluoromethylbenzenesulfonyl chloride, 4-fluorobenzenesulfonyl chloride, 4-methoxybenzenesulfonyl chloride, 2-methoxycarbonylbenzenesulfonyl chloride, 4-methylamidobenzenesulfonyl chloride, 4-nitrobenzenesulfonyl chloride, 4-thioamidobenzenesulfonyl chloride, 4-trifluoromethylbenzenesulfonyl chloride, 4-trifluoromethoxybenzenesulfonyl chloride, 2,4,6-trimethylbenzenesulfonyl chloride, 2-phenylethanesulfonyl chloride, 2-thiophenesulfonyl chloride, 5-chloro-2-thiophenesulfonyl chloride, 2,5-dichloro-4-thiophenesulfonyl chloride, 2-thiazolesulfonyl chloride, 2-methyl-4-thiazolesulfonyl chloride, 1-methyl-4-imidazolesulfonyl chloride, 1-methyl-4-pyrazolesulfonyl chloride, 5-chloro-1,3-dimethyl-4-pyrazolesulfonyl chloride, 3-pyridinesulfonyl chloride, 2-pyrimidinesulfonyl chloride and the like. If desired, a sulfonyl fluoride, sulfonyl bromide or sulfonic acid anhydride may be used in place of the sulfonyl chloride in the above reactions.

Optionally substituted α,β-diaminobenzene compounds of the formula:

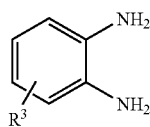

641 are either commercially available or can be prepared by conventional methods such as reduction of the corresponding α,β-dinitrobenzene, α-nitro-β-aminobenzene compounds and the like. When R$^7$ is other than hydrogen, derivatization of the amino group of the commercially available α-nitro-β-aminobenzene compound (2-nitroaniline (Aldrich) followed by reduction of the nitro group yields a compound of the formula:

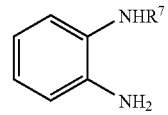

641(a)

Attachment of appropriate R$^3$ groups can occur at any appropriate time during synthesis using conventional reactions.

Similarly, amines of the formula HNR$^1$R$^2$ (606) are either commercially available or can be prepared by methods well known in the art.

In some cases it may be more convenient to prepare a given product compound or intermediate by preparing it from another product of Formula I or intermediate, by applying known synthesis procedures. For example, as noted above, thiocarbonyl compounds (Y=S) are preferably prepared from the corresponding carbonyl compounds (Y=O) which are themselves compounds of Formula I. Similarly, compounds where Y is —OR$^8$, —SR$^8$ or —NHR$^8$ are prepared from the corresponding thiocarbonyl compounds (Y=S).

In a similar manner, when a compound of Formula I or an intermediate thereof has a substituents containing a hydroxyl group, the hydroxyl group can be further modified or derivatized either before or after the above coupling reactions to provide, by way of example, ethers, aldehydes, carboxylic acids, carbamates and the like.

Alternatively, a hydroxyl group present on a substituents of a compound of Formula I or an intermediate thereof can be O-alkylating using the Mitsunobu reaction. In this reaction, an alcohol, such as 3-(N,N-dimethylamino)-1-propanol and the like, is reacted with about 1.0 to about 1.3 equivalents of triphenyl-phosphine and about 1.0 to about 1.3 equivalents of diethyl azodicarboxylate in an inert diluent, such as tetrahydrofuran, at a temperature ranging −10° C. to about 5° C. for about 0.25 to about 1 hour. About 1.0 to about 1.3 equivalents of a hydroxy compound, such as N-tert-butyltyrosine methyl ester, is then added and the reaction mixture is stirred at a temperature of about 0° C. to about 30° C. for about 2 to about 48 hours to provide the O-alkylated product.

In a similar manner, a compound of Formula I or an intermediate thereof containing a aryl hydroxy group can be reacted with an aryl iodide to provide a diaryl ether. Generally, this reaction is conducted by forming the alkali metal salt of the hydroxyl group using a suitable base, such as sodium hydride, in an inert diluent such as xylenes at a temperature of about −25° C. to about 10° C. The salt is then treated with about 1.1 to about 1.5 equivalents of cuprous bromide dimethyl sulfide complex at a temperature ranging 10° C. to about 30° C. for about 0.5 to about 2.0 hours, followed by about 1.1 to about 1.5 equivalents of an aryl iodide, such as sodium 2-iodobenzoate and the like. The reaction is then heated to about 70° C. to about 150° C. for about 2 to about 24 hours to provide the diaryl ether.

Additionally, a hydroxy-containing compound can also be readily derivatized to form a carbamate. In one method for preparing such carbamates, a hydroxy compound of Formula I or an intermediate thereof is contacted with about 1.0 to about 1.2 equivalents of 4-nitrophenyl chloroformate in an inert diluent, such as dichloromethane, at a temperature ranging −25° C. to about 0° C. for about 0.5 to about 2.0 hours. Treatment of the resulting carbonate with an excess, preferably about 2 to about 5 equivalents, of a trialkylamine, such as triethylamine, for about 0.5 to 2 hours, followed by about 1.0 to about 1.5 equivalents of a primary or secondary amine provides the carbamate. Examples of amines suitable for using in this reaction include, but are not limited to, piperazine, 1-methylpiperazine, 1-acetylpiperazine, morpholine, thiomorpholine, pyrrolidin, piperidine and the like.

Alternatively, in another method for preparing carbamates, a hydroxy-containing compound is contacted with about 1.0 to about 1.5 equivalents of a carbamyl chloride in an inert diluent, such as dichloromethane, at a temperature ranging 25° C. to about 70° C. for about 2 to about 72 hours. Typically, this reaction is conducted in the presence of a suitable base to scavenge the acid generated during the reaction. Suitable bases include, by way of example, tertiary amines, such as triethylamine, disopropylethylamine, N-methylmorpholine and the like. Additionally, at least one equivalent (based on the hydroxy compound) of 4-(N,N-dimethylamino)pyridine is preferably added to the reaction mixture to facilitate the reaction. Examples of carbamyl chlorides suitable for use in this reaction include, by way of example, dimethylcarbamyl chloride, diethylcarbamyl chloride and the like.

Likewise, when a compound of Formula I or an intermediate thereof contains a primary or secondary hydroxyl group, such hydroxyl groups can be readily converted into a leaving group and displaced to form, for example, amines, sulfides and fluorides.

These reactions are typically conducted by first converting the hydroxyl group into a leaving group, such as a tosylate, by treatment of the hydroxy compound with at least one equivalent of a sulfonyl halide, such as p-toluenesulfonyl chloride and the like, in pyridine. This reaction is generally conducted at a temperature of 0° C. to about 70° C. for about 1 to about 48 hours. The resulting tosylate can then be readily displaced with sodium azide, for example, by contacting the tosylate with at least one equivalent of sodium azide in an inert diluent, such as a mixture of N,N-dimethylformamide and water, at a temperature ranging 0° C. to about 37° C. for about 1 to about 12 hours to provide the corresponding azido compound. The azido group can then be reduced by, for example, hydrogenation using a palladium on carbon catalyst to provide the amino ($—NH_2$) compound.

A further elaboration of appropriate reactions to form various intermediates useful in this invention is found in, for example, allowed U.S. patent application Ser. No. 09/126,958 which is incorporated herein by reference in its entirety.

Pharmaceutical Formulations

When employed as pharmaceuticals, the compounds of Formula I and II are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds of Formula I and II above associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner.

The following formulation examples illustrate the pharmaceutical compositions of the present invention.

FORMULATION EXAMPLE 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
| --- | --- |
| Active Ingredient | 5 |
| Lactose | 95 |

The active mixture is mixed with the lactose and the mixture is added to a dry powder inhaling appliance.

FORMULATION EXAMPLE 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinyl-pyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

FORMULATION EXAMPLE 5

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, cellulose, starch, an magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 ml dose are made as follows:

| Ingredient | Amount |
|---|---|
| Active Ingredient | 50.0 mg |
| Xanthan gum | 4.0 mg |
| Sodium carboxymethyl cellulose (11%) | |
| Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 560 mg quantities.

FORMULATION EXAMPLE 9

An intravenous formulation may be prepared as follows:

| Ingredient | Quantity |
|---|---|
| Active Ingredient | 250.0 mg |
| Isotonic saline | 1000 mL |

FORMULATION EXAMPLE 10

A topical formulation may be prepared as follows:

| Ingredient | Quantity |
|---|---|
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, which is incorporated herein by reference in its entirety. Such patches may be constructed for continuous, pulsatile, or on demand delivery of pharmaceutical agents.

When it is desirable or necessary to introduce the pharmaceutical composition to the brain, either direct or indirect techniques may be employed. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is incorporated herein by reference in its entirety.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Utility

The compounds of this invention are bradykinin antagonists and therefore are suitable for use in blocking or ameliorating pain as well as hyperalgesia in mammals. Pain blocked or ameliorated by the compounds of this invention include, for example, pain associated with surgical procedures, burns, trauma, migraine, and the like.

The compounds of this invention are also useful in the treatment of disease conditions in a mammal which are mediated at least in part by bradykinin. Examples of such disease conditions include asthma, rhinitis, premature labor, inflammatory arthritis, inflammatory bowel disease, endotoxic shock related to bacterial infections, central nervous system injury, back pain, neuropathic pain, spinal cord injury and the like.

As noted above, the compounds of this invention are typically administered to the mammal in the form of a pharmaceutical composition. Pharmaceutical compositions of the invention are suitable for use in a variety of drug delivery systems. Suitable formulations for use in the present invention are found in *Remington's Pharmaceutical Sciences*, Mace Publishing Company, Philadelphia, Pa., 17th ed. (1985).

In order to enhance serum half-life, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

The amount administered to the patient will vary depending upon what is being administered, the purpose of the administration, such as prophylaxis or therapy, the state of the patient, the manner of administration, and the like all of which are within the skill of the attending clinician. In therapeutic applications, compositions are administered to a patient already suffering from a disease in an amount sufficient to cure or at least partially arrest the symptoms of the disease and its complications. An amount adequate to accomplish this is defined as "therapeutically effective dose." Amounts effective for this use will depend on the disease condition being treated as well as by the judgment of the attending clinician depending upon factors such as the severity of the inflammation, the age, weight and general condition of the patient, and the like.

The compositions administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention will vary according to, for example, the particular use for which the treatment is made, the manner of administration of the compound, the health and condition of the patient, and the judgment of the prescribing physician. For example, for intravenous administration, the dose will typically be in the range of about 20 μg to about 500 μg per kilogram body weight, preferably about 100 μg to about 300 μg per kilogram body weight. Suitable dosage ranges for intranasal administration are generally about 0.1 pg to 1 mg per kilogram body weight. Effective doses can be extrapolated from dose-response curves derived from in vitro or animal model test systems.

In addition to the above, the esters and thioesters of Formula I are useful intermediates in the preparation of the amides of Formula I (W=N).

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

| | |
|---|---|
| Boc = | t-butoxycarbonyl |
| brd = | broad doublet |
| brm = | broad multiplet |
| brt = | broad triplet |
| bs = | broad singlet |
| conc. = | concentrated |
| dba = | dibenzyledene acetone |
| dd = | doublet of doublets |
| DCC = | dicyclohexylcarbodiimide |
| DIAD = | diisopropyl azo dicarboxylate |
| DIEA = | diisopropylethyl amine |
| DMAP = | 4-N,N-dimethylaminopyridine |
| DME = | dimethoxyethane |
| DMF = | N,N-dimethylformamide |
| DPPA = | diphenylphosphoryl azide |
| dppf = | 1,1'-bis(diphenylphosphino)ferrocene |
| dt = | doublet of triplets |
| EDCI = | 1-(3-dimethylaminopropyl)-3-ethylcarbodiimide hydrochloride |
| eq. = | equivalents |
| g = | gram |
| h = | hours |
| HATU = | O-(7-azabenzotriazol-1-yl)-N,N,N',N'-tetraethyluronium hexafluorophosphate |
| HOAc = | acetic acid |
| HOBT = | 1-hydroxybenzothiazole hydrate |
| HPLC = | high performance liquid chromatography |
| LC/MS = | liquid chromatography/mass spectroscopy |
| m = | multiplet |
| M = | molar |
| mg = | milligram |
| min. = | minutes |
| mL = | milliliter |
| mm = | millimeter |
| mmol = | millimol |
| N = | normal |
| psi = | pounds per square inch |
| PS-DCC = | polysupported dicyclohexylcarbodiimide |
| PS-DIEA = | polysupported diisopropylethyl amine |
| q = | quartet |
| rpm = | rotations per minute |
| rt = | room temperature |
| $R_t$ = | retention time |
| s = | singlet |
| t = | triplet |
| TEA = | triethylamine |
| TFA = | trifluoroacetic acid |
| THF = | tetrahydrofuran |
| TLC = | thin layer chromatography |
| μL = | microliters |
| % mol = | mol percent |

In the following examples and procedures, the term "Aldrich" indicates that the compound or reagent used in the procedure is commercially available from Aldrich Chemical Company, Inc., Milwaukee, Wis. 53233 USA; the term "Lancaster" indicates that the compound or reagent is commercially available from Lancaster Synthesis, Inc., NH 03087 USA; the term "Sigma" indicates that the compound or reagent is commercially available from Sigma, St. Louis Mo. 63178 USA; the term "Maybridge" indicates that the compound or reagent is commercially available from Maybridge Chemical Co. Trevillett, Tintagel, Cornwall PL34 OHW United Kingdom; and the term "TCI" indicates that the compound or reagent is commercially available from TCI America, Portland Oreg. 97203; the term "Frontier Scientific" indicates that the compound or reagent is commercially available from Frontier Scientific, Utah, USA; the term "Specs" indicates that the compound or reagent is commercially available from Netherlands; and "Bachem" indicates that the compound or reagent is commercially available from Bachem, Torrance, Calif., USA.

Unless otherwise specified, the following equipment, settings and materials were used in the foregoing examples.

NMR spectra were recorded on a Varian or Bruker 300 spectrometer. $^{13}C$ and $^1H$ were referenced to TMS. Exact mass measurements were performed on an Agilent 1100-MSD mass spectrometer, equipped with a standard electrospray ionization interface. Routine HPLC's were acquired on an Agilent 1100-MSD, using an acetonitrile:water-0.1% TFA solvent system-1.5 ml/mn. The gradient of acetonitrile ranged from 20% to 70% over a period of 2.33 min.

The procedures set forth in Methods A-C below are illustrated in the following reaction scheme:

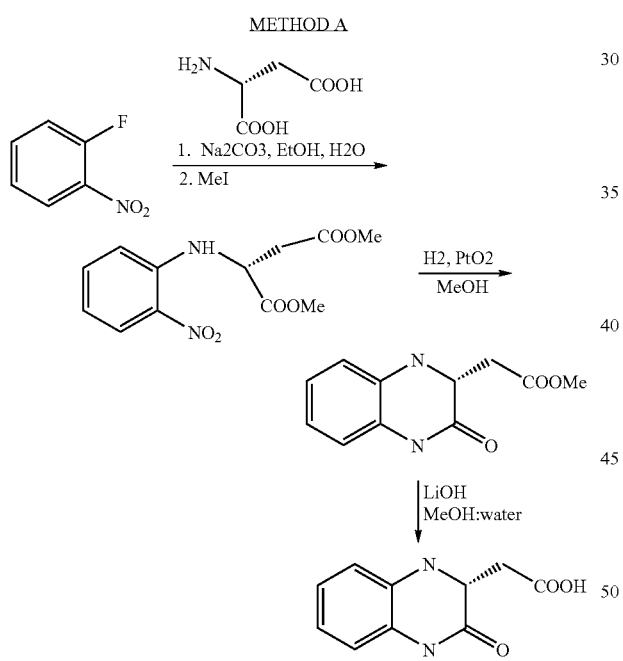

GENERAL PROCEDURE FOR THE COUPLING REACTION BETWEEN 1,2-FLUORONITROBENZENE AND AN AMINOACID

Exemplified by Preparation of (R)-2-(2-Nitrophenylamino)-succinic acid dimethyl ester A mixture of 1,2-fluoronitrobenzene (27.5 g, 19.5 mmol), D-aspartic acid (20.7 g, 15.6 mmol) and sodium carbonate (49.5 g, 46.7 mmol) in a mixed solvent system of ethanol-water (5:1, 300 mL) was heated at 105° C. overnight. The solvent was removed under reduced pressure and DMF (200 mL) was then added to the residue. Methyl iodide (24 mL, 38.5 mmol) was added to the mixture and the resulting mixture was stirred at rt overnight. Solvent was removed under reduced pressure and EtOAc was added to the residue. The heterogeneous mixture was then washed with brine, dried with $MgSO_4$, and concentrated under reduced pressure. The resulting yellow oil was purified by column chromatography over silica gel with EtOAc/hexane (1:2) as eluent to give a yellow oil as the title compound: $^1H$ NMR $(CDCl_3)$ δ=10.24 (bs, 1H), 8.03 (t, 1H, J=5.4 Hz), 7.30–7.15 (m, 5H), 6.75–6.70 (m, 3H), 6.61–6.56 (m, 1H), 5.79 (bs, 1H), 4.08–4.04 (m, 1H), 3.30–3.24 (m, 2H), 2.71 (t, 2H, J=7.8 Hz), 2.60 (dd, 1H, J=3.9, 15.3 Hz), 2.31 (dd, 1H, J=8.7, 15.3 Hz).

METHOD B

GENERAL PROCEDURE OF THE PREPARATION OF THE QUINOXALINE SKELETON USING REDUCTION-CYCLIZATION SEQUENCE

Exemplified by Preparation of (R)-(3-Oxo-1,2,3,4-tetrahydro-quinoxalin-2-yl)-acetic acid methyl ester A mixture of 2-(R)-(2-nitrophenylamino)succinic acid dimethyl ester (2.15 g, 7.62 mmol) (prepared below), and $PtO_2$ (210 mg) in methanol (35 mL) was shaken on a Parr apparatus at 48 psi for 6 hours. The reaction was filtered through celite, rinsed with methanol and was evaporated in vacuo to a very sticky oil as the title compound (1.69 g, 100%): $^1H$ NMR $(CDCl_3)$ δ=8.23 (bs, 1H), 6.91 (dt, 1H, J=1.8, 7.5 Hz), 6.80–6.70 (m, 3H), 4.74 (bs, 1H), 4.34 (dt, 1H, J=2.4, 10.5 Hz), 3.75 (s, 3H), 3.14 (dd, 1H, J=2.4, 17.4 Hz), 2.75 (dd, 1H, J=10.5, 17.4 Hz).

METHOD C

GENERAL PROCEDURE OF ETHYL CHLOROFORMATE COUPLING REACTION

Exemplified by Preparation of 2-(3-oxo-1,2,3,4-tetrahydroquinoxalin-2-yl)-N-phenethyl-acetamide To the solution of (3-oxo-1,2,3,4-tetrahydroquinoxalin-2-yl)-acetic acid (510 mg, 2.48 mmol) in THF (18 mL) was added triethylamine (0.38 ml, 2.74 mmol) and ethyl chloroformate (0.24 ml, 2.74 mmol). The mixture was stirred at rt for 1.5 hours and then phenethylamine (0.34 ml, 2.74 mmol) was added. The resulting mixture was again stirred at rt for 4.5 hours. The precipitate was filtered off and washed with small amount of THF a few times. The solvent was removed under the reduced pressure to give the title compound as a yellow solid: $^1H$ NMR $(DMSO-d_6)$ δ=10.24 (bs, 1H), 8.03 (t, 1H, J=5.4Hz), 7.30–7.15 (m, 5H), 6.75–6.70 (m, 3H), 6.61–6.56 (m, 1H), 5.79 (bs, 1H), 4.08–4.04 (m, 1H), 3.30–3.24 (m, 2H), 2.71 (t, 2H, J=7.8 Hz), 2.60 (dd, 1H, J=3.9, 15.3 Hz), 2.31 (dd, 1H, J=8.7, 15.3 Hz).

METHOD D

GENERAL PROCEDURE OF ETHYL CHLOROFORMATE COUPLING REACTION

Exemplified by Preparation of 2-(3-oxo-1,2,3,4-tetrahydroquinoxalin-2-yl)-N-phenethyl-acetamide To the solution of (3-oxo-1,2,3,4-tetrahydroquinoxalin-2-yl)-acetic acid (510 mg, 2.48 mmol) in THF (18 mL) was added triethylamine (0.38 ml, 2.74 mmol) and ethyl chloroformate (0.24 ml, 2.74 mmol). The mixture was stirred at rt for 1.5 hours and then phenethylamine (0.34 ml, 2.74 mmol) was added. The resulting mixture was again stirred at rt for 4.5 hours. The precipitate was filtered off and washed with small amount of THF a few times. The solvent was removed under the reduced pressure to give the title compound as a yellow solid: $^1$H NMR (DMSO-$d_6$) δ=10.24 (bs, 1H), 8.03 (t, 1H, J=5.4 Hz), 7.30–7.15 (m, 5H), 6.75–6.70 (m, 3H), 6.61–6.56 (m, 1H), 5.79 (bs, 1H), 4.08–4.04 (m, 1H), 3.30–3.24 (m, 2H), 2.71 (t, 2H, J=7.8 Hz), 2.60 (dd, 1H, J=3.9, 15.3 Hz), 2.31 (dd, 1H, J=8.7, 15.3 Hz).

Method E below illustrates an alternative method for ester hydrolysis using sodium hydroxide.

METHOD E

GENERAL PROCEDURE FOR ESTER HYDROLYSIS USING SODIUM HYDROXIDE

Exemplified by Preparation of (3-Oxo-1,2,3,4-tetrahydro-quinoxalin-2-yl)-acetic acid 2-(3-Oxo-1,2,3,4-tetrahydroquinoxalin-2-yl)-acetamide (22 g, 0.11 mol) was dissolved in 10% NaOH (600 mL) and was heated under reflux for 3 hours. The mixture was cooled down via an ice-bath and was acidified with pre-cooled 10% HCl to pH -6. The solvent was concentrated and the resulting precipitate was isolated via filtration to give a gray solid as the title product: $^1$H NMR (DMSO-$d_6$) δ=12.35 (bs, 1H), 10.25 (bs, 1H), 6.74–6.68 (m, 3H), 6.61–6.58 (m, 1H), 5.91 (bs, 1H), 4.08–4.04 (m, 1H), 2.69 (dd, 1H, J=5.1, 16.2 Hz), 2.51 (dd, 1H, J=6.9, 16.2 Hz)

The procedures set forth in Methods F-G below are illustrated in the following reaction scheme:

METHOD F

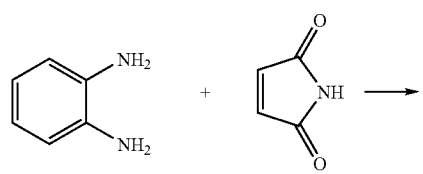

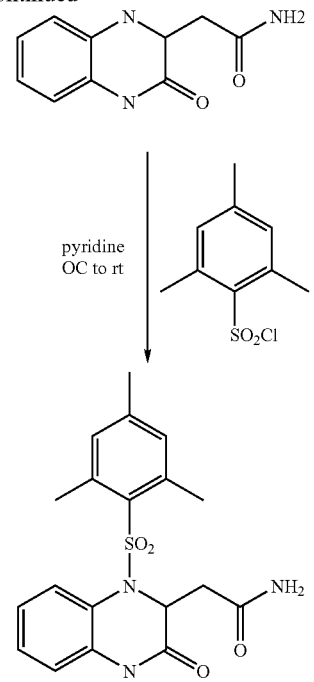

GENERAL PROCEDURE OF THE PREPARATION OF THE QUINOXALINE SKELETON USING MALEIMIDE AND PHENYLENEDIAMINE

Exemplified by Preparation of 2-(3-Oxo-1,2,3,4-tetrahydro-quinoxalin-2-yl)-acetamide To a solution of 1,2-phenylenediamine (21.5 g, 0.2 mol) in water (450 mL) was added dropwise a solution of maleimide, (20.0 g, 0.2 mol) in methanol (180 mL) over 60 min. The mixture was then stirred at 95° C. for 2 hours followed at rt overnight. The precipitate was collected via filtration and was washed with small amount of water for a few times to yield the title compound as a pale gray solid (pure product): $^1$H NMR (DMSO-$d_6$) δ=10.2 (bs, 1H), 7.37 (bs, 1H) 6.88 (bs, 1H), 6.74–6.68 (m, 3H), 6.31–6.57 (m, 1H), 5.78 (bs, 1H), 4.08–4.04 (m, 1H), 2.63 (dd, 1H, J=3.6, 15.5 Hz), 2.32 (dd, 1H, J=3.3, 15.5 Hz); HPLC (CH$_3$CN—H$_2$O-0.1% TFA): R$_f$=9.49 min.

METHOD G

GENERAL PROCEDURE FOR THE PREPARATION OF SULFONATED QUINOXALINYL CARBOXYAMIDE

Exemplified by Preparation of [3-oxo-1-arylsulfonyl-1,2,3,4-tetrahydroquinoxalin-2-yl]-acetamide Arylsulfonyl chloride (1 mmole) was added to a stirred solution of 3-oxo-1,2,3,4-tetrahydroquinoxalin-2-yl-acetamide (1 mmole) in pyridine at 0° C. The reaction was allowed to warm up to rt. Additional stirring was continued at rt for 18–24 h. Excess solvent was removed under reduced pressure and the residue was washed with saturated NaHCO$_3$ solution. The solid residue was filtered off and dried. The title product is obtained either by recrystallization (MeOH) or by using a column chromatography (CH$_2$Cl$_2$—MeOH, 95:5)

Method H below illustrates an alternative method for the preparation of sulfonated quinoxalinyl carboxyacids.

METHOD H

GENERAL PROCEDURE FOR THE PREPARATION OF SULFONATED QUINOXALINYL CARBOXYLIC ACID

Exemplified by Preparation of [3-Oxo-1-(2,4,6-trimethyl-benzenesulfonyl)-1,2,3,4-tetrahydro-quinoxalin-2-yl]-acetic acid The solution of starting material lithium salt (81.7 mmol, 17.3g) in water (500 mL) was stirred in a 3-necked round bottom flask at room temperature under an argon atmosphere. To the solution was added 2,5-dimethyl-4-chlorobenzene sulfonyl chloride (32.2 g, 135 mmol) in portions over 20 min. The reaction mixture was left to stir for 18 hours at room temperature under an argon atmosphere. The pH dropped from 9.0 to weakly acidic (approximately pH 5). A light yellowish solid was filtered off, and rinsed with water. The solid was transferred to a flask containing water (200 mL) and 10% NaOH (15–20 mL) was added to a pH of approximately 9.0. Not all of the solid dissolved. The insoluble material was filtered off and the filtrate was extracted with EtOAc (100 mL) to remove traces of sulfonyl chloride. The aqueous phase was cooled in an ice bath then acidified with 2M HCl to approximately 4.0. A precipitate was filtered off and rinsed with cold water then air dried.

$^1$H NMR (DMSO-d$_6$) δ=12.51 (s, 1H), 10.71 (bs, 1H), 7.28 (dt, 1H, J=1.6, 8.4 Hz), 7.07–7.10 (m, 3H), 7.01 (dt, 1H, J=1.6, 8.4 Hz), 6.95 (dd, 1H, J=1.6, 8.4 Hz), 4.66 (dd, 1H, J=4.4, 10.4 Hz), 2.45–2.49 (m, 1H), 2.36 (s, 6H), 2.28 (s, 3H), 2.13 (dd, 1H, J=10.4, 15.2 Hz).

The procedures set forth in Method I below are illustrated in the following reaction scheme:

METHOD I

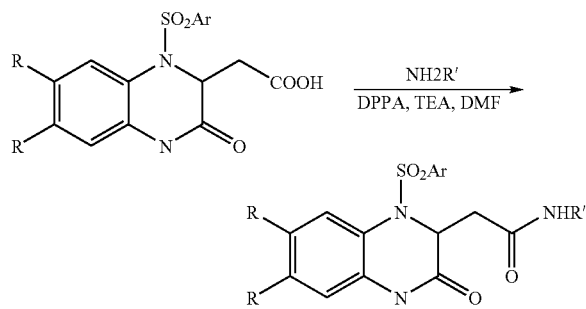

GENERAL PROCEDURE FOR PREPARING SULFONATED QUINOXALINYL CARBOXYAMIDE

Exemplified by Preparation of [3-Oxo-1-arylsulfonyl-1,2,3,4-tetrahydroquinoxalin-2-yl]-acetamide The 3-oxo-1-arylsulfonyl-1,2,3,4-tetrahydroquinoxalin-2-yl carboxylic acid (12.19 mmol), a primary or secondary amine (14.73 mmol) and TEA (34.34 mmol) were dissolved in dry DMF (50 mL) and cooled to 0° C. To the above stirred solution, DPPA (14.62 mmol neat) was added slowly over 20 min. and the reaction was allowed to warm to rt. After stirring for 18 h at rt, excess DMF was removed under reduced pressure. Water (50 mL), saturated NaHCO$_3$ (50 mL) and ethyl acetate (100 mL) were added to a crude residue and the reaction mixture was sonicated for 10 min. The title product was filtered off and dried.

The procedures set forth in Method J below are illustrated in the following reaction scheme:

METHOD J

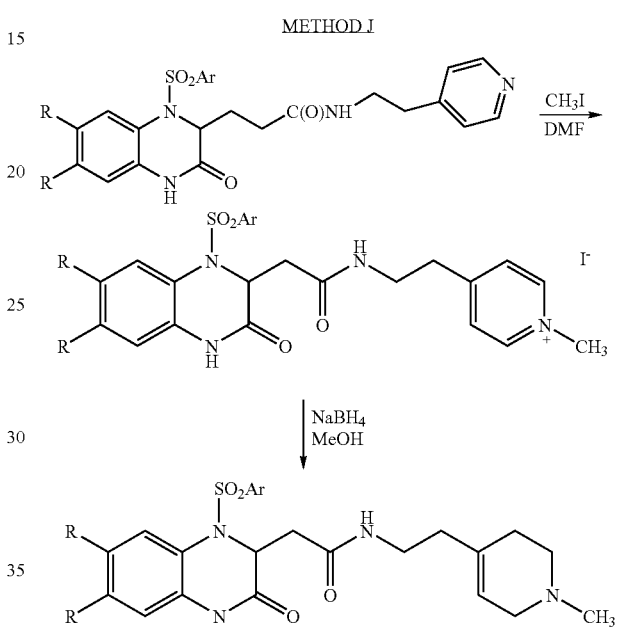

GENERAL PROCEDURE FOR THE PREPARATION OF 1,2,3,6-TETRAHYDRO-N-ALKYLPYRIDINE DERIVATIVES

A suitable starting material comprising a 2-acetamide group on the 1,2,3,4-tetrahydroquinoxaline having a pyridine functionality attached thereto (2.92 mmol) was added to dry DMF (15 ml) and heated with a heat-gun (if required) to form a clear solution and cooled to rt. Methyl iodide (5 mL, excess) was added to it and stirring continued for 18 h at rt. Excess DMF was removed under reduced pressure and the pyridinium salt formed was taken to the next step without further purification. The methyl iodide salt was dissolved in methanol (25 mL) and NaBH$_4$ (13.78 mmol) was added to it and stirred for 1 h. Excess MeOH was removed and water (50 ml) was added to the crude product and sonicated for 10 min. A solid product containing the 1,2,3,6-tetrahydro-N-methylpyridine group was filtered off or extracted with CH$_2$Cl$_2$ and used in the next step without further purification.

The remaining double bond in the 1,2,3,6-tetrahydro-N-methylpyridine group can optionally be hydrogenated to provide for the N-methylpiperidin-4-yl derivative.

A process for reduction of the heterocyclic double bond is provided in Method K and is illustrated in the reaction scheme below:

METHOD K

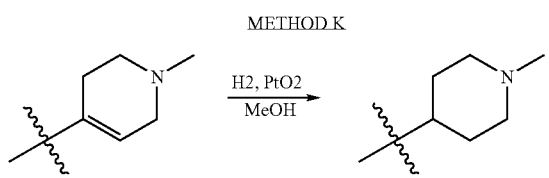

GENERAL PROCEDURE OF THE PREPARATION OF N-ALKYLPIPERIDINE DERIVATIVES FROM 1,2,3,6-TETRAHYDRO-N-ALKYLPYRIDINE COMPOUNDS

N-methyl- 1,2,3,6-tetrahydropyridine (0.1 moles) was dissolved in methanol (25 mL) and transferred to a Parr hydrogenation bottle. 10% Dilute HCl (10 mL) and PtO$_2$ (300 mg) were added to it and the mixture was hydrogenated at 45 psi for 18 h. The catalyst was filtered off over celite. Excess solvent was removed and the crude material was dried overnight on high vacuum pump to afford the title compound.

The processes set forth in Method L are illustrated in the following reaction schemes:

METHOD L

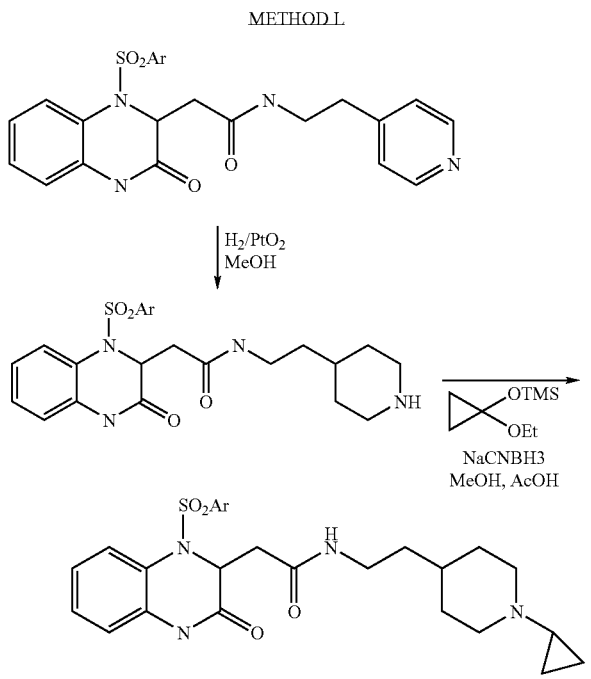

GENERAL PROCEDURE FOR THE PREPARATION OF N-CYCLOPROPYLPIPERIDINYLETHYL ACETAMIDES

Exemplified by Preparation of 2-[2-(R,S)-1-(4-chloro-2,5-dimethylbenzenesulfonyl)-3-oxo-1,2,3,4-tetrahydroquinoxalin-2-yl]-N-[2-(N-cyclopropylpiperidin-4-yl)eth-1-yl]acetamide Step A: 2-[2-(R,S)-1-(4-chloro-2,5-dimethylbenzenesulfonyl)-3-oxo-1,2,3,4-tetrahydroquinoxalin-2-yl]-N-[2-(pyrid-4-yl)eth- 1-yl]acetamide, prepared by amidation of the corresponding carboxylic acid with 2-(2-aminoethyl)pyridine (TCI) in the manner described above was hydrogenated in the presence of platinum oxide (PtO$_2$) in methanol to provide for 2-[2-(R,S)-1-(4-chloro-2,5-dimethylbenzenesulfonyl)-1,2,3,4-tetra-hydroquinoxalin-2-yl]-N-[2-(piperidin-4-yl)eth-1-yl]acetamide.

Step B: Sodium cyanoborohydride (1.5 mmol) was added to a stirred solution of 2-[2-(R,S)-1-(4-chloro-2,5-dimethyl-benzenesulfonyl)-3-oxo-1,2,3,4-tetrahydro-quinoxalin-2-yl]-N-[2-(N-cyclopropylpiperidin-4-yl)eth-1-yl]acetamide (1 mmol), with 1-ethoxy-1-trimethylsiloxy cyclopropane (1 mmol) (Aldrich Chemical Company) and AcOH (1 mmol) in MeOH (20 mL) at rt. After being stirred at rt, the reaction mixture was refluxed for 18 h. The excess solvent was removed and washed with saturated NaHCO$_3$ solution. The aqueous solution was extracted with CH$_2$Cl$_2$ (2×100 mL). The combined organic layers were dried and concentrated. The resulting residue was then purified by silica gel column chromatography (CH$_2$Cl$_2$—MeOH 95:5) to afford the title compound as a solid.

The process set forth in Method M is illustrated in the following reaction scheme:

METHOD M

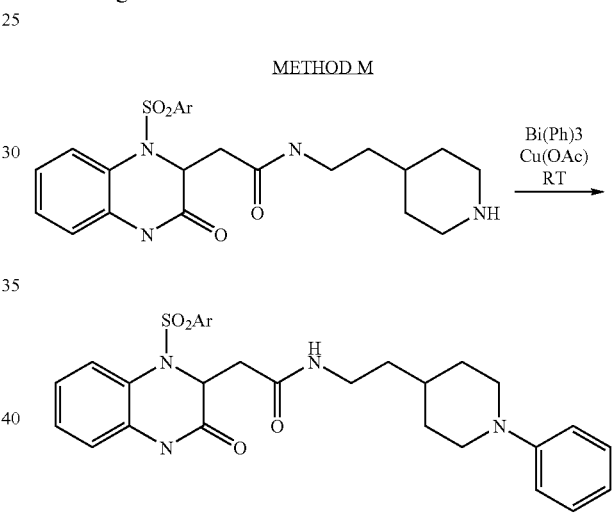

GENERAL PROCEDURE FOR THE PREPARATION OF N-PHENYLPIPERIDINYLETHYL ACETAMIDES

Exemplified by Preparation of 2-[2-(R,S)-1-(4-chloro-2,5-dimethylbenzenesulfonyl)-3-oxo-1,2,3,4-tetrahydroquinoxalin-2-yl]-N-[2-(N-phenylpiperidin-4-yl)eth-1-yl]acetamide Triphenylbismuth diacetate (Ph$_3$Bi(OAc)$_2$ (1.2 eq.) and Cu(OAc)$_2$ (0.12 eq.) were added to a stirred solution of 2-[2-(R,S)-1-(4-chloro-2,5-dimethyl-enzenesulfonyl)-3-oxo-1,2,3,4-tetra-hydroquinoxalin-2-yl]-N-[2-(piperidin-4-yl)eth-1-yl]acetamide (1 mmol) in dichloromethane at rt and stirred for 18 h. The reaction mixture was partitioned between dichloromethane (50 mL) and water (50 mL) and stirred for 2 h. The organic layer was separated, dried and concentrated. The residue was chromatographed on silica gel using (CH$_2$Cl$_2$—MeOH 90:10) affording the title compound.

The process set forth in Method N is illustrated in the following reaction scheme:

METHOD N

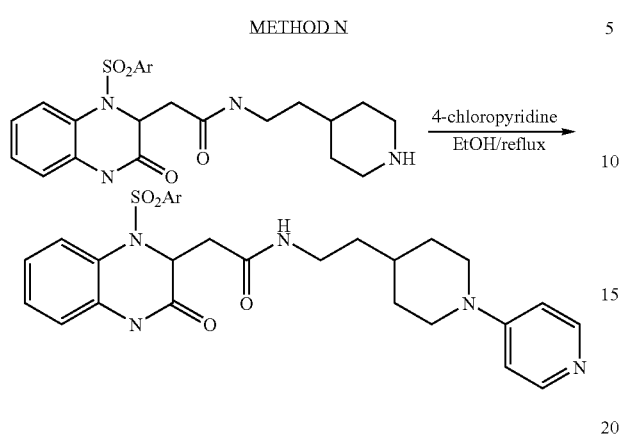

GENERAL PROCEDURE FOR THE PREPARATION OF N-PYRIDYLPIPERIDINYLETHYL ACETAMIDES

Exemplified by Preparation of 2-[2-(R,S)-1-(4-chloro-2,5-dimethylbenzenesulfonyl)-3-oxo-1,2,3,4-tetrahydroquinoxalin-2-yl]-N-[2-((N-pyrid-4-yl)piperidin-4-yl)eth-1-yl]acetamide A solution of 2-[2-(R,S)-1-(4-chloro-2,5-dimethyl-benzenesulfonyl)-3-oxo-1,2,3,4-tetrahydroquinoxalin-2-yl]-N-[2-(piperidin-4-yl)eth-1-yl]acetamide (0.1 mmol) and 4-chloropyridine (excess) in EtOH (5 mL) was heated in a sealed tube at 110° C. for 16 h. Excess solvent was removed and the residue purified by preparative HPLC (acetonitrile-water-0.1% TFA) and the title compound was isolated as the TFA salt.

METHOD O

GENERAL PROCEDURE FOR REMOVAL OF BOC PROTECTING GROUPS FROM AMINO GROUPS

To a stirred solution of Boc-amine (0.01 mole) in dry ethyl acetate (25 mL) at 0° C., HCl gas was bubbled for 15 min. The reaction solution was stirred for 5 h at rt after which the HCl salt was recovered by filtration. The HCl salt was used in the next step without further purification.

METHOD P

GENERAL PROCEDURE FOR REMOVAL OF BOC PROTECTING GROUPS FROM AMINO GROUPS

HCl gas was bubbled for 2 h into a solution of Boc amino acid in dry MeOH (100 mL) at rt. The reaction solution was stirred for 18 h at rt after which the product was recovered upon solvent removal. The HCl salt was used in the next step without further purification.

The processes set forth in Methods Q and R are illustrated in the following reaction scheme:

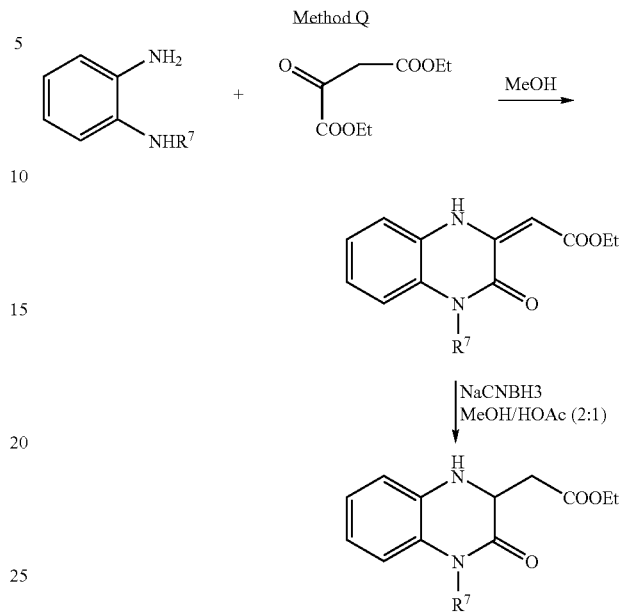

GENERAL PROCEDURE FOR THE PREPARATION OF VINYLIDENE GROUPS AT THE 2-POSITION OF 3-OXO-3,4-DIHYDRO-1-H-QUINOXALINES

Exemplified by Preparation of 2-[3-oxo-3,4-dihydro-1H-quinoxalin-2-ylidine acetic acid ethyl ester Phenylene diamine (0.1 mmol) (available, e.g., from Aldrich) in $CH_2Cl_2$ was added to a stirred solution of 2-keto-glutonoic acid diethyl ester (0.1 mmol) (Aldrich) in MeOH at rt. After being stirred 1 h, at rt, a solid product was filtered out and purified by washing with $CH_2Cl_2$. The product formed was used in the next step without further purification.

METHOD R

GENERAL PROCEDURE FOR HYDROGENATION OF VINYLIDENE GROUPS

Exemplified by Preparation of 2-[2-(R,S)-3-oxo-1,2,3,4-tetrahydroquinoxalin-2-yl]-Acetic Acid Ethyl Ester Sodium cyanoborohydride (7.95 mmol) was added to a stirred solution of 2-[3-oxo-3,4-dihydro-1H-quinoxalin-2-ylidene acetic acid ethyl ester (2.23 mmol), in THF-AcOH (25.5 mL, 2:1) under argon at rt. After stirring for 20 min, the solvent was evaporated under reduced pressure, the crude residue was resuspended in water (200 mL) and extracted with $CH_2Cl_2$ (3×50 mL) or filtered. The combined organic layers were washed with water and dried over anhydrous $Na_2SO_4$. After evaporation of the solvent, the crude oil was purified by silica gel column chromatography (eluents: $CH_2Cl_2$+MeOH (95:5), to give the title compound.

METHOD S

GENERAL PROCEDURE FOR MAKING THE SULFONATED QUINOXALINYL CARBOXYAMIDE FROM THE CORRESPONDING CARBOXYLIC ACID

The starting carboxylic acid (200 mg; 0.48 mmol) was dissolved in dry DMF (50 mL) maintained at rt under $N_2$. To this was added $Et_3N$ (3.0 eq), HOBT (1.1 eq) and the amine of choice (1.1 eq). The reaction was stirred at −10° C. for about 15 min. EDCI (1.1 eq) was then added and the reaction mixture warmed up to rt and stirred overnight. EtOAc (100 mL) was added. The organic layer was washed with saturated $NaHCO_3$ (3×50 mL); 10% HCl (3×50 mL) and brine (6×50 mL). The organic layer was dried over $MgSO_4$. Upon filtration, the solvent was removed under reduced pressure. A column chromatography (silica gel) using EtOAc/hexanes 1:4 afforded the amidated product.

The processes set forth in Method T are illustrated in the following reaction scheme:

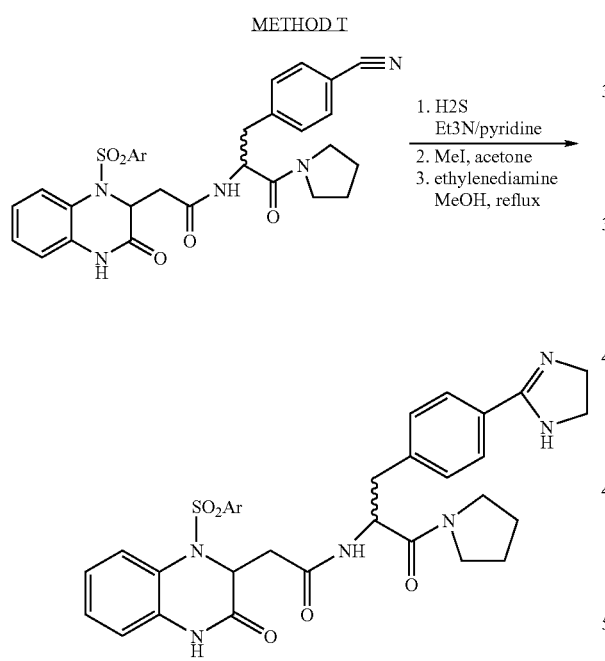

GENERAL PROCEDURE FOR CONVERSION OF A CYANOPHENYL GROUP TO A 4,5-DIHYDROIMIDAZOL-2-YLPHENYL GROUP

Exemplified by the Preparation of 2-[2-(R,S)-1-arylsulfonyl)-3-oxo-1,2,3,4-tetrahydroquinoxalin-2-yl]-N-[1-(N-pyrrolidinylcarbonyl)-2-(4-(4,5-dihydroimidazol-2-yl)phenyl)eth-1-yl]acetamide 2-[2-(R,S)-1-Arylsulfonyl)-3-oxo-1,2,3,4-tetrahydroquinoxalin-2-yl]-N-[1-(N-pyrrolidinylcarbonyl)-2-(4-cyanophenyl)eth-1-yl]acetamide] (1 g; 1.57 mmol) was dissolved in a solution of $Et_3N$/pyridine (6 mL/60 mL) at rt. $H_2S$ was bubbled through for 15 min. at rt. The reaction mixture was then capped and stirred at rt overnight. The solvent mixture was removed under reduced pressure and the resulting residue was then dissolved in a mixture of acetone/iodomethane (60 mL: 5 mL). The solution was heated to reflux for 1.5 h whereupon the solvent was removed under reduced pressure. The crude material was dissolved in dry MeOH (15 mL), with $Et_3N$ (1.0 eq; 220 μL) and ethylenediamine (1.1 eq; 120 μL). The solution was refluxed for 2 days. The solvent was evaporated under reduced pressure. The crude material was submitted for purification by reverse phase HPLC (acetonitrile/water-0.1% TFA), and the resulting product isolated.

The processes set forth in Method U are illustrated in the following reaction scheme:

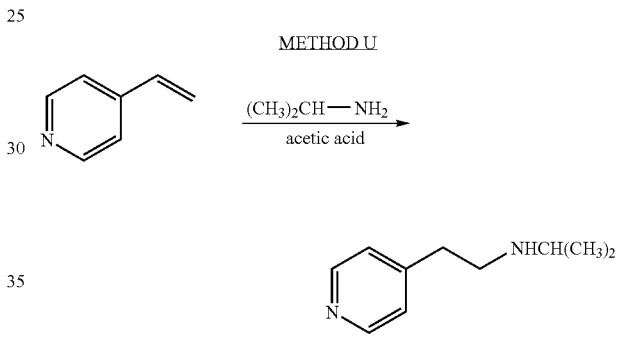

GENERAL PROCEDURE FOR CONVERSION OF A VINYLPYRIDINE GROUP TO A 2-AMINOETHYLPYRIDINE GROUP

Exemplified by the Preparation of 2-(N-isopropyl)-eth-1-yl-pyridine

4-Vinyl pyridine (1.6 mL; 15 mmol) was dissolved in acetic acid (12.5 mmol; 0.72 mL) and isopropylamine (12.5 mmol; 1.06 mL). The reaction mixture was refluxed for 6 h. The solvent was evaporated under reduced pressure. To the resulting solid was added EtOAc as well as saturated $NaHCO_3$. The organic layer was isolated, dried over $MgSO_4$. The solvent was removed under reduced pressure. The desired material was isolated as a foam. $H^1$ NMR ($CDCl_3$) δ=8.4 (m, 2H); 7.05 (m, 2H); 2.75 (m, 2H); 2.65 (m, 3H); 0.99 (d, 6H). $C^{13}$ NMR ($CDCl_3$) 149.87; 149.54; 149.09; 123.93; 48.19; 47.20; 35.56; 22.43. MS (ES) m/e (API-ES)=165 (M+H).

The processes set forth in Method V are illustrated in the following reaction scheme:

METHOD V

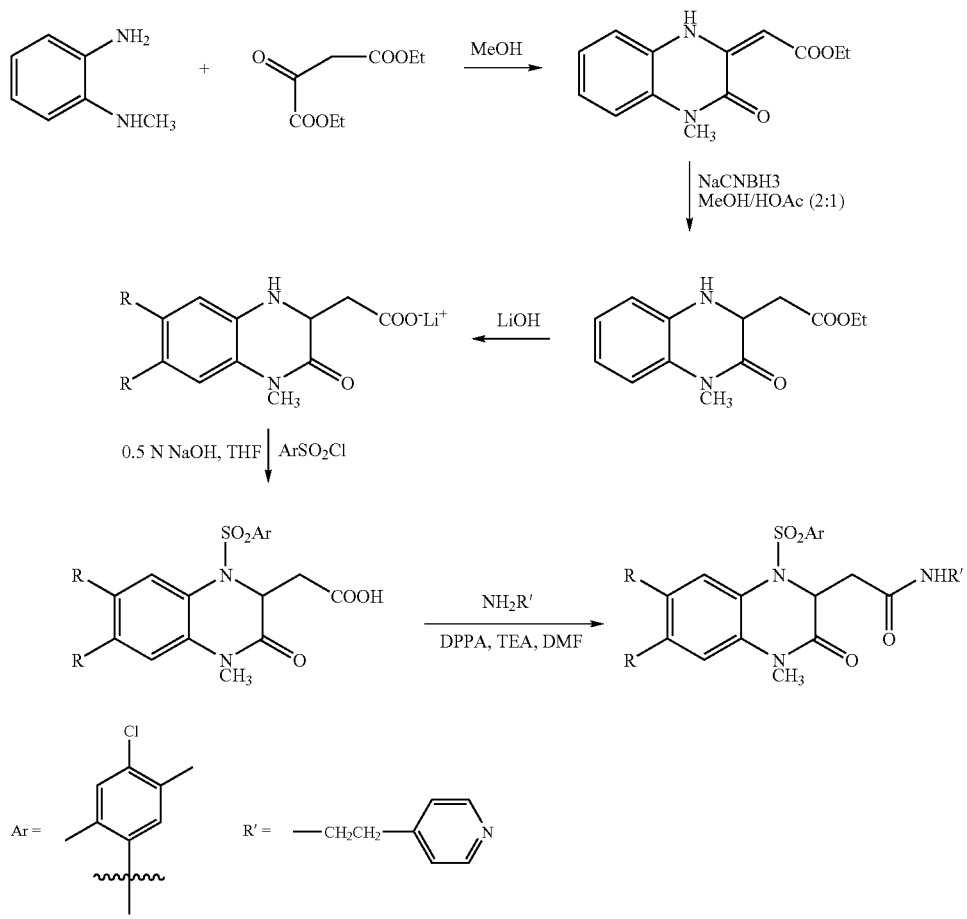

GENERAL PROCEDURE FOR THE PREPARATION OF N-METHYL-N-(2-PYRID-4-YL-ETHYL) ACETAMIDES

Exemplified by the Preparation of 2-[1-(4-Chloro-2, 5-dimethyl-benzenesulfonyl)-4-methyl-3-oxo-1,2,3, 4-tetrahydro-quinoxalin-2-yl]-N-methyl-N-(2-pyridin-4-yl-ethyl)-acetamide Step A: Preparation of 4-methyl-3-oxo-3,4-dihydro-1H-quinoxalin-2-ylidene-acetic acid ethyl ester To a solution of N-methyl-1,2-phenylenediamine (6.1 g, 4.99 mmol) in MeOH (50 mL) was added in portion of oxalacetic acid diethyl ester (9.9 g, 5.26 mmol). The mixture was then stirred at rt for 1 h. The precipitate was collected via filtration and was washed with small amount of methanol to yield a pale brownish solid as the pure product: $^1$H NMR (DMSO-$d_6$) δ=11.1 (bs, 1H), 7.45–7.42 (m, 1H), 7.32–7.29 (m, 1H), 7.15–7.10 (m, 2H), 5.53 (s, 1H), 4.14 (q, J=9.0 Hz, 2H), 3.51 (s, 3H), 1.23 (t, J=9.0 Hz, 3H); HPLC (CH$_3$CN—H$_2$O-0.1% TFA) (short column): R$_t$=3.91 min.

Step B: Preparation of 4-methyl-3-oxo-1,2,3,4-tetrahydro-quinoxalin-2-yl-acetic acid ethyl ester 4-Methyl-3-oxo-3,4-dihydro-1H-quinoxalin-2-ylidene-acetic acid ethyl ester (1.1 g, 4.47 mmol) was suspended in 25 mL of MeOH/HOAc (2:1) at rt and sodium cyanoborohydride was added portionwise (281 mg, 4.47 mmol). The mixture became clear after five minutes and was continuously stirred at rt for 2 hours. The solvent was removed under reduced pressure. The crude residue was mixed with water (50 mL) and extracted with EtOAc (3×40 mL). The organic layers were combined, washed with water, brine and dried over MgSO$_4$. After removal of the solvent, a pale brown oil was obtained as the desired pure product: $^1$H NMR (CDCl$_3$) δ=6.97–6.94 (m, 3H), 6.74 (d, J=9.0 Hz, 1H), 4.28 (dd, J=3.0, 9.0 Hz, 1H), 4.23 (q, J=9.0 Hz, 2H), 3.37 (s, 3H), 3.11 (dd, J=3.0, 18.0 Hz, 1H), 2.68 (dd, J=9.0, 19.0 Hz, 1H), 1.28 (t, J=9.0 Hz, 3H).

Step C: Preparation of lithium [(4-methyl-3-oxo-1,2,3,4-tetrahydro-quinoxalin-2-yl)]-acetate 4-Methyl-3-oxo-1,2,3,4-tetrahydro-quinoxalin-2-yl-acetic acid ethyl ester (1.05 g, 4.23 mmol) was dissolved in a mixed solvent THF/H$_2$O (1:1, 39 mL) and cooled to 0° C. in an ice-bath. Lithium hydroxide monohydrate (174 mg, 4.15 mmol) was then added and the resulting mixture was stirred at 0° C. for 6 h (monitored by TLC). Solvent was removed under reduced pressure and the residue was triturated with EtOAc to give the title compound as a gray solid: $^1$H NMR (D$_2$O) δ=7.03–6.79 (m, 4H), 4.06 (dd, 1H, J=4.5, 9.6 Hz), 3.21 (s, 3H), 2.48 (dd, 1H, J=9.3, 15.6 Hz), 2.33 (dd, 1H, J=4.5, 15.6 Hz).

Step D: Preparation of 1-[(4-Chloro-2,5-dimethyl-benzenesulfonyl)-4-methyl-3-oxo-1,2,3,4-tetrahydro-quinoxalin-2-yl]-acetic acid Lithium (4-methyl-3-oxo-1,2,3,4-tetrahydroquinoxalin-2-yl)-acetate and 4-chloro-2,5-dimethylbenzenesulfonyl chloride (Lancaster) were reacted using Method H above to provide the title compound for this step.

$^1$H NMR (DMSO-$d_6$) δ=7.51–7.44 (m, 4H), 7.28 (dt, J=1.2, 7.8 Hz, 1H), 7.18 (d, J=7.8 Hz, 1H), 4.97 (dd, J=3.9, 10.5 Hz, 1H), 2.76 (s, 3H), 2.56–2.49 (m, 1H), 2.28 (s, 3H), 2.16 (dd, J=10.5, 15.3 Hz, 1H), 2.00 (s, 3H).

Step E: Preparation of 2-[1-(4-Chloro-2,5-dimethylbenzenesulfonyl)-4-methyl-3-oxo-1,2,3,4-tetrahydro-quinoxalin-2-yl]-N-(2-pyridin-4-yl-ethyl)]-acetamide 1-(4-Chloro-2,5-dimethyl-benzenesulfonyl)-4-methyl-3-oxo-1,2,3,4-tetrahydro-quinoxalin-2-yl]-acetic acid and 4-(2-aminoeth-1-yl)pyridine (TCI) were coupled using Method I to give the desired material. $^1$H NMR (D$_2$O) δ=8.52–8.50 (m, 2H), 8.04 (t, J=5.4 Hz, 1H), 7.49–7.39 (m, 4H), 7.27–7.22 (m, 3H), 7.16 (d, J=8.1 Hz, 1H), 5.03 (dd, J=4.8, 8.7 Hz, 1H), 3.37–3.21 (m, 2H), 2.77–2.67 (m, 5H), 2.27 (s, 3H), 2.27–2.11 (m, 2H), 2.00 (s, 3H); ); HPLC (CH$_3$CN—H$_2$O-0.1% TFA) (short column): R$_t$=3.71 min.

The procedures set forth in Methods W through Z below are illustrated in the following general reaction scheme. It is noted that this reaction scheme merely illustrates the amidation of the carboxyl group with the appropriate amine and that the specific conditions used in each Method varies to account for the particulars of that Method. It is further noted that while a primary amine is illustrated below, secondary amines can also be used:

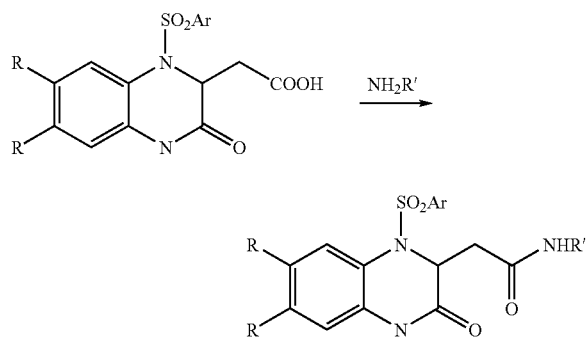

METHOD W

GENERAL PROCEDURE FOR AMIDATING A CARBOXYLIC ACID

Into a vial was placed 0.22 mg of an amine or amine hydrochloride salt. A solution was then prepared by dissolving 2.45 g of acid (5.99 mol), 0.90 g of 1-hydroxy-7-azabenzotriazole, and 2.5 mL of triethylamine in sufficient dimethylacetamide to give a total volume of 30 mL. The amine was treated with 1.0 mL of this solution and briefly agitated, and then treated with 1.0 mL of 0.26 M solution of 1-(3-dimethylaminopropyl)-3-ethylcarbodiimide in dimethylacetamide. The mixtures was agitated for 24 h then diluted with 3 mL of dimethylacetamide and treated with 2.5 mL of Biorad AG 50W-8X strong acid ion exchange resin and 2.5 mL of Amerlite MP-3 mixed bed ion exchange evaporated at reduced pressure. The product was then dissolved in diethyl ether or in ethyl acetate and precipitated by the addition of hexane and collected by filtration and dried in a stream of air.

METHOD X

GENERAL PROCEDURE FOR AMIDATING A CARBOXYLIC ACID 5.5 mmol of HOBT in 10 mL of dry DMF was added via a pipette to 10 mL of the carboxylic acid compound dissolved in DMF at 0.5 mmol/mL at rt. To this solution was added 5 mL of DCC in DMF (5.5 mmol), as well as DIEA (15 mmol, 1.62 mL) and this solution was allowed to stir for 30 min.

1 mL of the coupling cocktail described above was added to 0.5 mmol of an alpha amino ester or alpha amino amide of choice. The reaction was stirred at rt for 3 hours. The solvent was removed under vacuum. The residue was dissolved in 1 mL of EtOAc, and washed with 0.5 N NaOH (3 times), then 0.5 N HCl (3 times), and water. The organic layer was dried over MgSO4, filtered then evaporated under vacuum.

METHOD Y

GENERAL PROCEDURE FOR AMIDATING A CARBOXYLIC ACID

To an alpha amino amide or alpha amino ester in DMF (0.25 mmol in 200 μL) was added 1-[(4-chloro-2,5-dimethylbenzenesulfonyl)-4-methyl-3-oxo-1,2,3,4-tetrahydroquinoxalin-2-yl]-acetic acid in DMF (0.25 mmol in 200 μL), followed by EDC free amine (0.275 mmol) and PS-DIEA (150 mg). The reaction was gently stirred overnight at rt.

The solids were removed by filtration and 3 mL of water was added. A precipitate crashed out and was collected by filtration, washed again with water. The residue was dried on high vacuum.

METHOD Z

GENERAL PROCEDURE FOR AMIDATING A CARBOXYLIC ACID

A stock solution of 1-[(4-chloro-2,5-dimethyl-benzenesulfonyl)-4-methyl-3-oxo-1,2,3,4-tetrahydro-quinoxalin-2-yl]-acetic acid in DMF (0.25 mmol/ml) was prepared.

To each solution of alpha amino acid or amide (0.25 mmol/mL) was added 1 mL of the above stock solution. To this was added 5 mL of DMF, 35 mg of PS-DIEA (2 eq) and PS-DCC (530 mg, 2 eq). The reaction vessel was shaken overnight at 150 rpm. Afterwards, each reaction system was filtered to remove solids. 1N HCl (1 mL) was added to each filtrate and the solution was evaporated under vacuum. The residue was collected, and analyzed.

The processes set forth in Methods A' and B' are illustrated in the following reaction scheme:

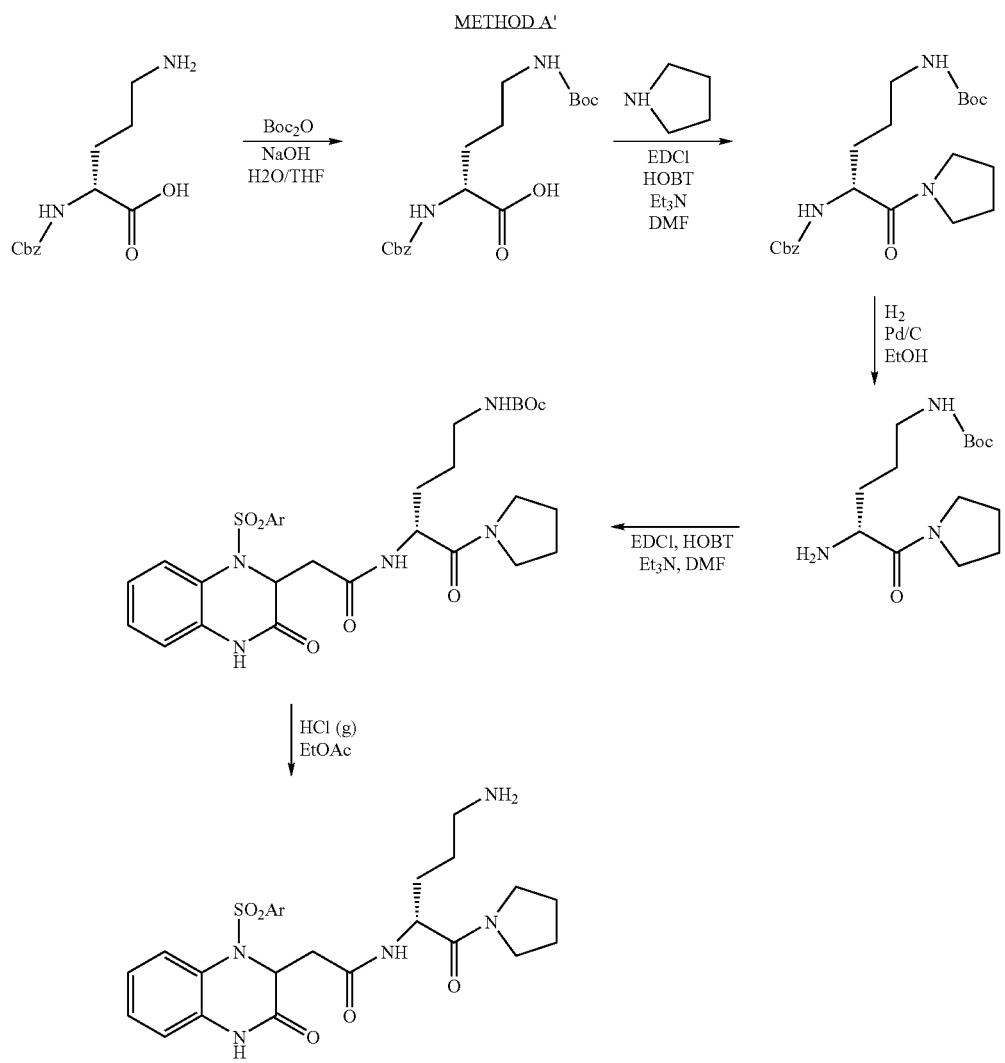

GENERAL PROCEDURE FOR FORMING A BOC PROTECTED AMINE

Exemplified by Preparation of α-Cbz-γ-Boc-lysine

Cbz-protected D-lysine (5 g, 0.016 mol) (Sigma) was dissolved in H₂O and THF (500 mL, 1:1). To this was first added NaOH (2 eq.) followed by di-tert-butyl dicarbonate (0.016 mmol). The reaction was stirred at rt overnight. EtOAc (100 mL) was then added and the aqueous layer set aside. The aqueous layer was then acidified to pH 2–3 using 1N HCl and then extracted with EtOAc (100 mL, 2×). The extracted layers were combined, washed with brine (100 mL, 2×) and dried over Na₂SO₄. Upon evaporation of the solvent under reduced pressure, the desired material was isolated in good yield and used in the next step without further purification.

The carboxylic acid of the Cbz and Boc protected lysine was then amidated with pyrrolidine in the manner described in Method S above to provide for 1-(R)-1-(pyrrolidin-1-ylcarbonyl)-1-carbobenzyloxyamino-4-butoxycarbonylaminobutane.

METHOD B'

GENERAL PROCEDURE FOR REMOVING A CBZ GROUP FROM A CBZ PROTECTED AMINE

Exemplified by Preparation of 1-(R)-1-(pyrrolidin-1-ylcarbonyl)-1-amino-4-butoxycarbonylaminobutane 1-(R)-1-(pyrrolidin-1-ylcarbonyl)-1-carbobenzyloxyamino-4-butoxycarbonylaminobutane (1.5 g, 3.6 mmol) was dissolved in EtOH (30 mL) and then transferred to a Parr hydrogenation bottle. 10% Pd/C was added (100 mg) and the mixture was hydrogenated at 50 psi for 2 hrs. The reaction mixture was filtered through celite and the solvent evaporated under reduced pressure to afford the title compound.

1-(R)-1-(pyrrolidin-1-ylcarbonyl)-1-amino-4-butoxycarbonylaminobutane can then be reacted with 2-(R,S)-1-[(arylsulfonyl)-3-oxo-1,2,3,4-tetrahydroquinoxalin-2-yl]-acetic acid in the manner described in Method S above to provide for the resulting amide, 2-(R,S)-[1-(arylsulfonyl)-3-oxo-1, 2,3,4-tetrahydroquinoxalin-2-yl]-N-[1-pyrrolidin-1-ylcarbonyl-4-(t-butoxylcarbonylamino)butyl]acetamide.

Removal of the t-butoxylcarbonyl (Boc) group in the manner provided in Method P above provides for the 2-(R,S)-[1-(arylsulfonyl)-3-oxo-1,2,3,4-tetrahydro-quinoxalin-2-yl]-N-[1-pyrrolidin-1-ylcarbonyl-4-aminobutyl]acetamide.

The processes set forth in Method C' is illustrated in the following reaction scheme:

lidine in the manner described in Method S above provided for 1-(R)-[1-(t-butoxycarbonylamino)-1-(pyrrolidin-1-ylcarbonyl)-2-(4-iodophenyl)]ethane and this amino acid derivative is sometimes referred to herein as compound 1061.

Removal of the Boc protecting group and coupling with 2-(R,S)-1-[(arylsulfonyl)-3-oxo-1,2,3,4-tetrahydroquinoxalin-2-yl]acetic acid, in the manner described in Methods O and S above gave the 2-(R,S)-[1-(arylsulfonyl)-3-oxo-1,2, 3,4-tetrahydroquinoxalin-2-yl]-N-(R)-(1-pyrrolidin-1-ylcarbonyl-2-(4-iodophenyl)eth-1-yl)acetamide.

2-(R,S)-2-[1-(arylsulfonyl)-3-oxo-1,2,3,4-tetrahydroquinoxalin-2-yl]-N-(R)-(1-pyrrolidin-1-ylcarbonyl-2-(4-iodophenyl)eth-1-yl)acetamide. (250 mg, 0.34 mmol), was dissolved in dry DME (6 mL) under nitrogen. To this was added Pd(OAc)$_2$ (0.1 eq), P(O-tolyl)$_3$ (0.1 eq), 2M Na$_2$CO$_3$ (1.7 mL) and 1-(t-butoxycarbonyl)pyrrole-2-boronic acid (2

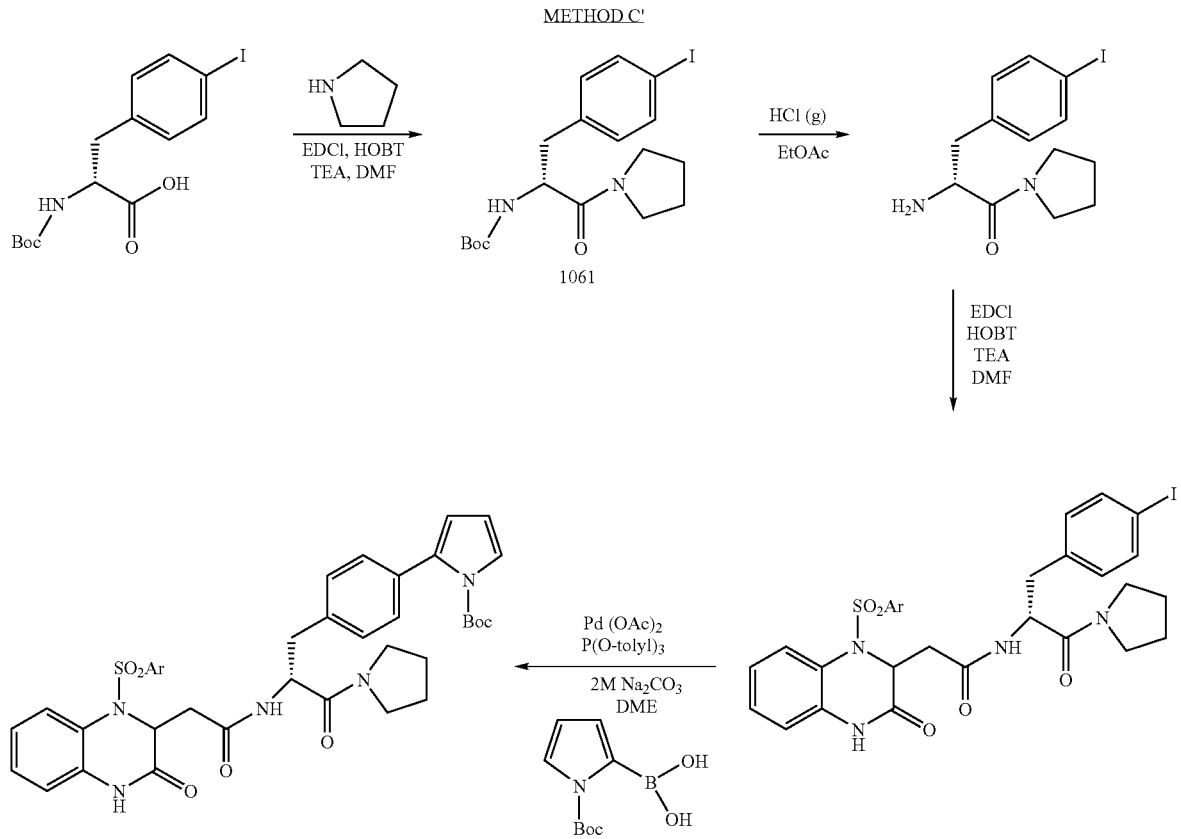

METHOD C'

GENERAL PROCEDURE FOR FORMING A HETEROARYL SUBSTITUENT ON A PHENYL GROUP

Exemplified by Preparation of 2-(R,S)-[1-(arylsulfonyl)-3-oxo-1,2,3,4-tetrahydroquinoxalin-2-yl]-N-[(1-(R)-1-pyrrolidin-1-ylcarbonyl-2-(4-(N-t-butoxycarbonylpyrrol-2-yl)phenyl)eth-1-yl]acetamide (D)-N-t-butoxycarbonyl-p-iodophenylalanine can be prepared by Boc protecting the commercially available p-iodophenylalanine (Aldrich) in the manner described above. This compound was then amidated by reaction with pyrroeq) (Frontier Scientific). The reaction mixture was stirred overnight at 80° C. The solvent was removed under vacuum and EtOAc (20 mL) was added. The organic layer was washed with H$_2$O (10 mL, 2x), brine (10 mL, 1x) and dried over Na$_2$SO$_4$. Upon filtration, the solvent was removed under vacuum and the title compound was purified on column chromatography (silica gel) eluted with EtOAc, followed by a prep plate (silica gel) eluted with EtOAc.

Optionally, the Boc protecting group can then be removed via Method O above to provide for $^2$-(R,S)-[1-(arylsulfonyl)-3-oxo-1,2,3,4-tetrahydroquin-oxalin-2-yl]-N-[(1-(R)-1-pyrrolidin-1-ylcarbonyl-2-(4-(pyrrol-2-yl)phenyl)eth-1-yl]acetamide.

The processes set forth in Methods D' and E' are illustrated in the following reaction scheme:

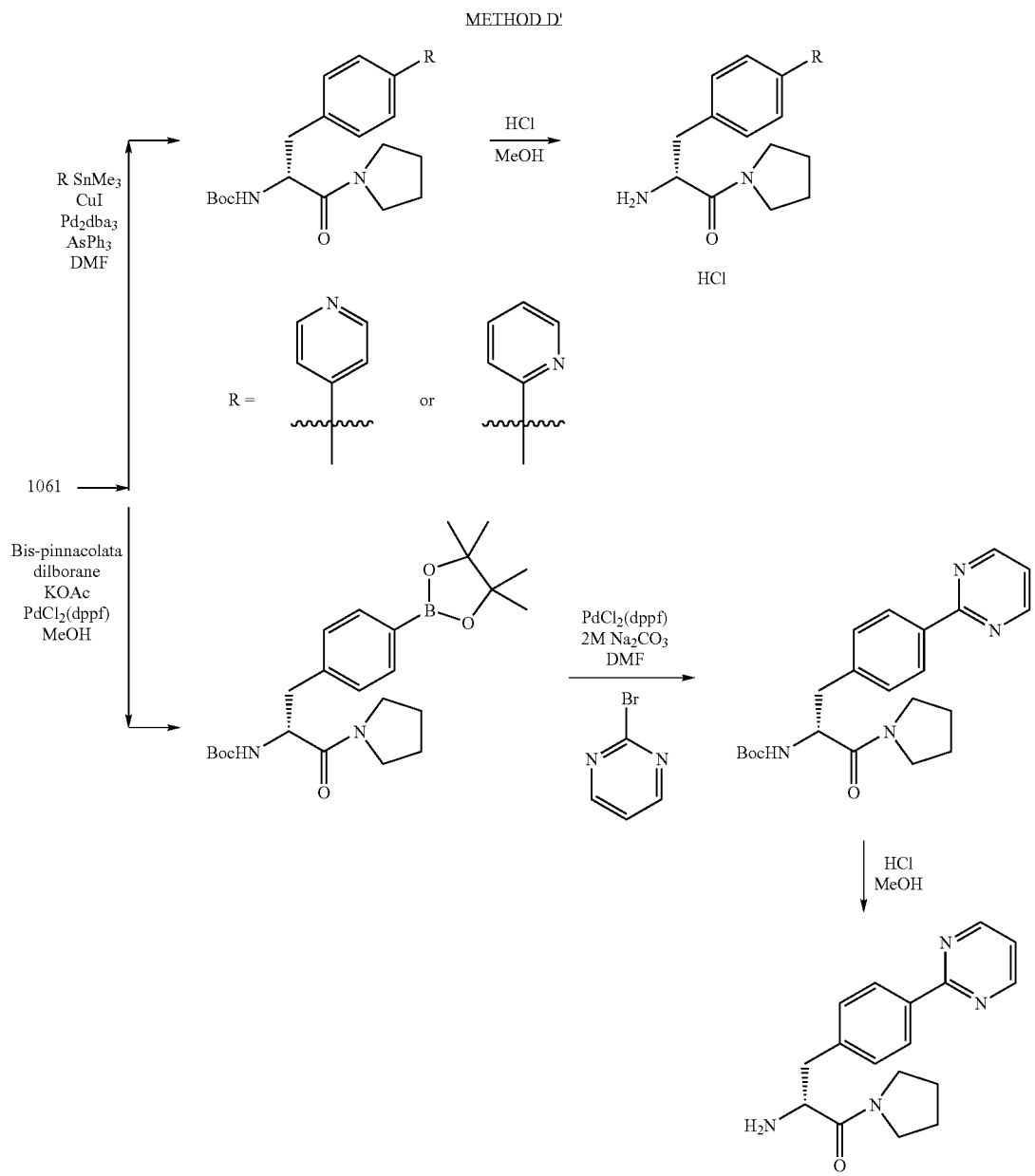

GENERAL PROCEDURE FOR FORMING A 2- OR 4-PYRIDYL SUBSTITUENT ON A PHENYL GROUP

Exemplified by the Preparation of 1-[(R)-1-Pyrrolidin-1-ylcarbonyl-1-amino-2-(4-(2-or 4-pyridyl)phenyl]ethane 1-(R)-[1-(t-butoxycarbonylamino)-1-(pyrrolidin-1-ylcarbonyl)-2-(4-iodophenyl)]ethane (compound 1061) (300 mg, 0.68 mmol), was added to a 50 mL round-bottom flask with CuI (8% mol) in dry DMF (10 mL). The resulting solution was flushed under nitrogen for 2–3 min. Pd$_2$dba$_3$ (2% mol) (Aldrich) and AsPh$_3$ (16% mol) (Aldrich) were weighed together in a small vial to which 1 mL of DMF was added. This solution was added to the reaction mixture and it was flushed under nitrogen for an additional 2–3 minutes. An oil bath was heated to 60° C. and the reaction mixture was immersed into it and allowed to thermally equilibrate. The commercially available pyridyl stannane (1.15 eq.) (Frontier) was then weighed out into a small vial to which 1 mL of DMF was added and this solution was then added to the previous reaction mixture and heated at 60° C. for 6 hours. The solvent was removed under vacuum. The crude residue was dissolved in EtOAc (30 mL). The organic layer was washed with brine (10 mL, 2×), and dried over MgSO$_4$. Upon filtration and evaporation of the solvent under reduced pressure, the crude material was purified on column chromatography (silica gel), eluted with EtOAc-Hexanes 3:2 to afford 1-[(R)-1-(pyrrolidin-1-ylcarbonyl)-1-(t-butoxycarbonylamino)-2-(4-(2-or 4-pyridyl)phenyl]ethane in good yield.

Subsequent removal of the Boc protecting group with HCl/methanol in the manner described above provides for the title compound as the HCl salt.

METHOD E'

GENERAL PROCEDURE FOR FORMING A 2-PYRIMIDINYL SUBSTITUENT ON A PHENYL GROUP

Exemplified by the Preparation of 1-[(R)-1-Pyrrolidin-1-ylcarbonyl-1-amino-2-(4-(2-pyrimidinyl)phenyl]ethane 1-(R)-[1-(t-butoxycarbonylamino)-1-(pyrrolidin-1-ylcarbonyl)-2-(4-iodophenyl)]ethane (compound 1061)(100 mg, 0.22 mmol), was dissolved in dry MeOH (5 mL) to which was added KOAc (1.5 eq.) and bis-pinnacolato diboron (1.1 eq.) (Aldrich) and the mixture was flushed under nitrogen for 5 minutes. The catalyst, PdCl$_2$(dppf) (0.03 eq.) (Aldrich), was then added and the reaction was heated at 60° C. overnight. The reaction mixture was filtered through Celite and condensed under vacuum. The residue was then treated with bromopyrimidine (3 eq.) (Aldrich), Na$_2$CO$_3$ (5 eq., 0.55 mL) and PdCl$_2$(dppf) (0.03 eq.) in DMF (1 mL) and stirred at 80° C. overnight. The solvent was removed under vacuum. The crude residue was purified on column chromatography (silica gel), eluted with EtOAc-Hexanes, 3:2 to afford 1-[(R)-1-pyrrolidin-1-ylcarbonyl-1-(t-butoxycarbonylamino)-2-(4-(2-pyrimidinyl)phenyl]ethane in good yield.

Subsequent removal of the Boc protecting group with HCl/methanol in the manner described above provides for the title compound as the HCl salt.

The processes set forth in Methods F' and G' are illustrated in the following reaction scheme:

GENERAL PROCEDURE FOR THE PREPARATION OF 1,2,3,6-TETRAHYDRO-N-ALKYLPYRIDINE DERIVATIES

Boc protected 2-aminoethylpyridine (or the N-methyl analog thereof) (120 mg, 0.18 mmol), was dissolved in MeOH/CH$_2$Cl$_2$ (2:1) to make a 2.5 M solution. To this was added MeI (4 eq.) and the mixture was heated in a sealed tube for 3.5 h. The solvent was removed under vacuum and the resulting crude mixture was used directly in Method G' without purification and/or isolation.

METHOD G'

GENERAL PROCEDURE FOR THE REDUCTION/HYDROGENATION OF A PYRIDIUM SALT

The methyl pyridinium iodide salt produced above, (60 mg, 0.083 mmol), was dissolved in dry MeOH (4 mL) and the resulting mixture cooled to 0° C. Excess NaBH$_4$ was added and the mixture was allowed to stir for 30 min. The solvent was then removed under vacuum and water (5–10 mL) was added to the crude product and sonicated for 10 mins. Upon filtration, the solvent was evaporated to provide for Boc protected 2-aminoethyl-1,2,3,6-tetrahydropyridine in good yields.

If desired, the remaining unsaturated bond in the Boc protected 2-aminoethyl-1,2,3,6-tetrahydropyridine can be hydrogenated with hydrogen/PtO$_2$ maintained at about 35 psi.

The Boc protecting group of the saturated or unsaturated compound can then be removed by conventional methods (e.g., HCl/methanol).

The process set forth in Method H' is illustrated in the following reaction scheme:

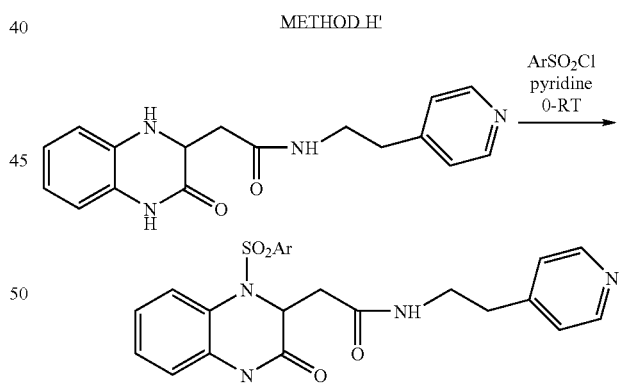

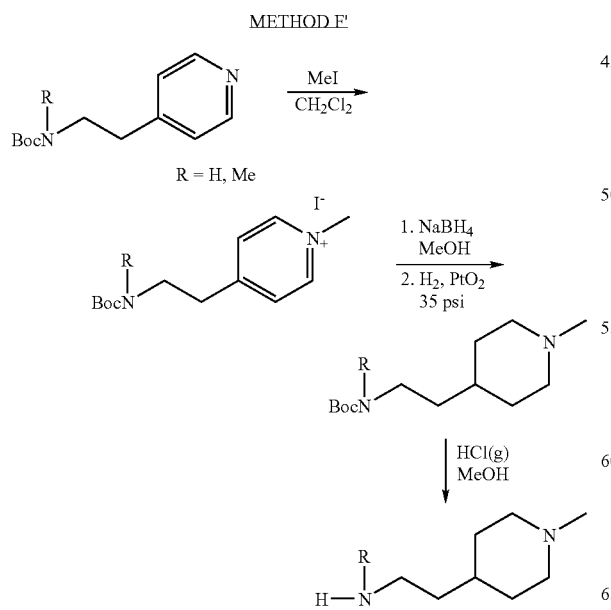

GENERAL PROCEDURE FOR PREPARING LIBRARIES OF DIFFERENT ARYLSULFONYL GROUPS 0.33 mmol of 2-(R,S)-[3-oxo-1,2,3,4-tetrahydroquinoxalin-2-yl]-N-[2-(pyrid-4-yl)eth-1-yl]acetamide dissolved in 1 mL of pyridine, was added to 0.50 mmol of each separate sulfonyl chloride, dissolved in 1.5 mL of pyridine at 0° C., in the proposed library set. All reactions were prepared in 1-dram reaction vials and placed on a J-Kem Orbit Shaker. The reactions were then brought up to rt and left for 16 h.

Afterwards, LC-MS analysis for each product mixture was completed on an Agilent 1050 series HPLC coupled to a Thermo-Finnigan Mass Spectrometer, utilizing a 6-minute 5%–100% CH₃CN:H₂O gradient with 0.05% TFA on a Phenomenex 50×2.00 mm, 5 micron column. Products were purified via the Varian Pro Star Preparative HPLC, using a 17-minute 10%–100% CH₃CN:H₂O gradient with 0.1% TFA on a Phenomenex 60×21.20 mm, 50 micron column.

The process set forth in Method I' is illustrated in the following reaction scheme:

METHOD I'

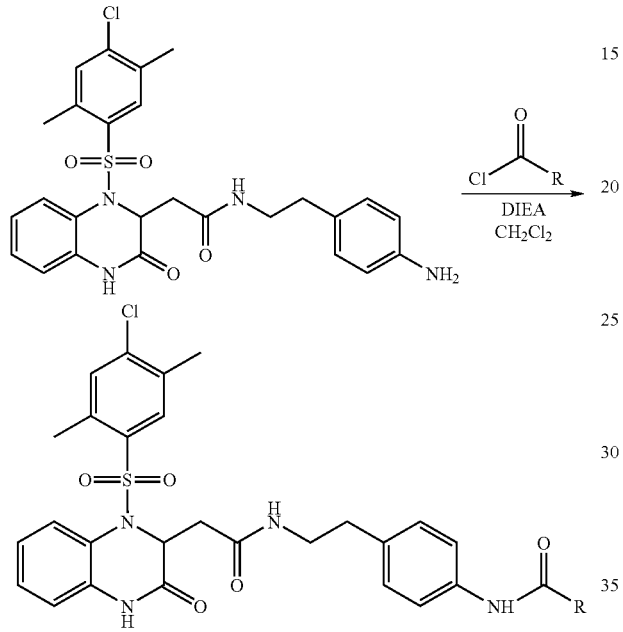

GENERAL PROCEDURE FOR CONVERTING AN ANILINE AMINO GROUP TO AN AMIDE IN A LIBRARY MANNER

Exemplified by the Preparation of a Library of 2-(R,S)-[1-(4-chloro-2,5-dimethylphenylsulfonyl)-3-oxo-1,2,3,4-tetrahydroquinoxalin-2-yl]-N-[2-((4-RC(O)NH-)phenyl)eth-1-yl]acetamide 2-(R,S)-[1-(4-Chloro-2,5-dimethylphenylsulfonyl)-3-oxo-1,2,3,4-tetrahydroquinoxalin-2-yl]-N-[2-((4-amino)phenyl)eth-1-yl]acetamide (20.0 mg, 0.038 mmole) was dissolved in dioxane (600 μL) and treated with PS-DIEA (31.0 mg, 0.0114 mmole). After shaking at rt for 15 minutes, each respective acid chloride (RC(O)Cl) (0.038 mmole) was added. In a few instances, generation of the acid chloride from the carboxylic acid was necessary prior to this acylation step. This conversion was accomplished by dissolving the acid (0.076 mmole) in CH₂Cl₂ (500 μL), adding oxalyl chloride (9.0 μL) plus a catalytic amount of DMF and allowing to shake at rt for 3 h. The solvent was subsequently removed by reduced pressure, THF (500 μL) was added and removed by the same means, to ensure complete removal of excess oxalyl chloride. The isolated acid chloride was then used in the acylation procedure, without further characterization.

Following addition of each acid chloride to a separate reaction vessel containing the 2-(R,S)-[1-(4-chloro-2,5-dimethylphenylsulfonyl)-3-oxo-1,2,3,4-tetrahydroquinoxalin-2-yl]-N-[2-((4-amino)phenyl)eth-1-yl]acetamide, the reaction mixtures were stirred (shaken) at rt for 18 h. Confirmation of acylation and product purity were determined by LC-MS. A portion of the reactions exhibited incomplete conversion, therefore, additional acid chloride (0.038 mmole) and Et₃N (100 μL) were added. These reactions were then allowed to shake at 50° C. for 4 h, followed by 8 h of shaking at rt. The resin was removed by filtration, and the samples were purified by prep HPLC, using a Phenomenex 60×21.20 mm, 50-micron column; 16 minute gradient, 0–100% CH₃CN to H₂O, with 0.1% TFA. The purity of each isolated product was confirmed by LC-MS.

The process set forth in Method J' is illustrated in the following reaction scheme:

METHOD J'

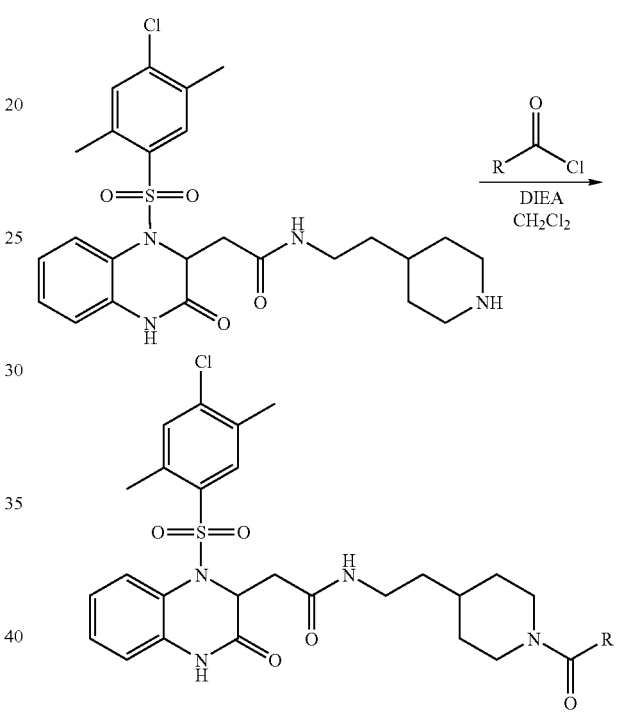

GENERAL PROCEDURE FOR CONVERTING THE AMINO NITROGEN OF PIPERIDINE TO AN AMIDE IN A LIBRARY MANNER

Exemplified by the Preparation of a Library of 2-(R,S)-[1-(4-chloro-2,5-dimethylphenylsulfonyl)-3-oxo-1,2,3,4-tetrahydroquinoxalin-2-yl]-N-[2-(1-RC(O)-piperidin-4-yl)eth-1-yl]acetamide Into separate vials, 2-(R,S)-[1-(4-chloro-2,5-dimethylphenylsulfonyl)-3-oxo-1,2,3,4-tetrahydroquinoxalin-2-yl]-N-[2-(piperidin-4-yl)eth-1-yl]acetamide (25.0 mg, 0.04825 mmole) was dissolved in CH₂Cl₂ (600 μL) and treated with PS-DIEA (39.4 mg, 0.0145 mmole). After shaking the respective vials at rt for 15 min., each respective acid chloride (0.0531 mmole) was added to a separate vial. Similar to the acylation set forth in Method I' above, there were a few cases in which the acid chloride required conversion from the carboxylic acid prior to this acylation. The conversion was completed as mentioned in the acylation set forth in Method I' above.

Following the addition of the acid chlorides, the reactions were allowed to shake at rt for 18 h. Confirmation of acylation and determination of purity was analyzed by LC-MS. A portion of the library exhibited incomplete conversion, therefore, additional acid chloride (0.0531 mmole) and TEA (20 μL) were added. These reactions were allowed to shake at 70° C. for 4 h, adding additional $CH_2Cl_2$ as necessary, followed by shaking at rt for an additional 8 h. The resin was removed by filtration, and the samples were purified by prep HPLC using a Phenomenex 60×21.20 mm, 50-micron column; 16 minute gradient, 0–100% $CH_3CN$ to $H_2O$, with 0.1% TFA. The purity of each isolated product was confirmed by LC-MS.

The processes set forth in Method K' are illustrated in the following reaction scheme:

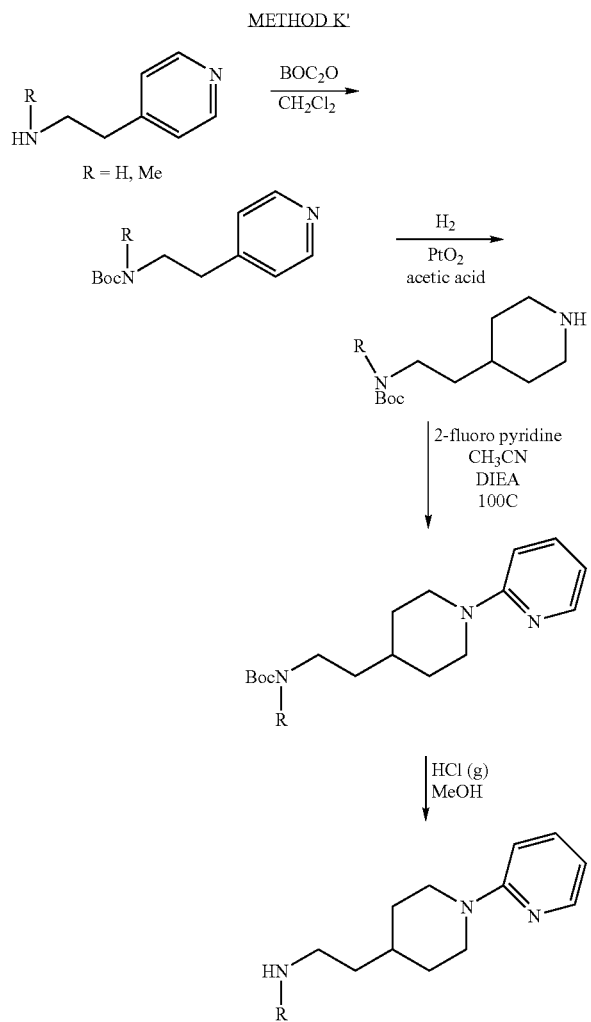

GENERAL PROCEDURE FOR PREPARING N-(PYRID-2-YL)PIPERIDINE COMPOUNDS

Exemplified by the Preparation of 2-[1-(pyrid-2-yl)piperidin-4-yl]ethylamine

Step A: Synthesis of N-t-butoxycarbonyl 2-(pyrid-2-yl)ethylamine

4-Aminoethylpyridine (5.0 g, 40 mmol) and di-t-butyl dicarbonate (8.9 g, 40 mmol) were dissolved in $CH_2Cl_2$ (50 mL) and the resulting solution was stirred at rt for overnight. Solvent was removed under reduced pressure to afford N-t-butoxycarbonyl 2-(pyrid-2-yl)ethylamine as a reddish liquid (9.1 g, 100%).

Step B: Synthesis of N-t-butoxycarbonyl 2-(piperidin-2-yl)ethylamine

The product from step A was mixed with $PtO_2$ (640 mg) in HOAc (30 mL) and hydrogenation was carried out at 58 psi on a Parr apparatus for overnight. Catalyst was removed and solvent was evaporated under reduced pressure to give N-t-butoxycarbonyl 2-(piperidin-2-yl) ethylamine as a black liquid.

Step C: Synthesis of N-t-butoxycarbonyl 2-[1-(pyrid-2-yl)piperidin-4-yl]ethylamine To a solution of N-t-butoxycarbonyl 2-(piperidin-2-yl)ethylamine (8.1 g) and DIEA (14.1 mL) in $CH_3CN$ (29 mL) was added 2-fluoropyridine (3.5 mL) and the resulting mixture was heated in a sealed-tube at 100° C. for three days. Solvent was removed and the crude product was purified via column chromatography (20% EtOAc/hexane) to afford 3.9 g of N-t-butoxycarbonyl 2-[1-(pyrid-2-yl)piperidin-4-yl]ethylamine. $^1H$ NMR ($CDCl_3$) δ=8.16 (dd, J=1.8, 5.0 Hz, 1H), 7.44–7.38 (m, 1H), 6.61 (d, J=8.7 Hz, 1H), 6.53 (dd, J=5.0, 7.2, 1H 4.58 (bs, 1H), 4.23 (d, J=12.6 Hz, 2H), 3.15 (q, J=6.6 Hz, 2H), 2.76 (dt, J=2.7, 12.6 Hz, 2H), 1.75 (d, J=12.6 Hz, 2H), 1.55–1.35 (m, 11H), 1.28–1.15 (m, 3H);

MS (ES) m/e: m/z (EI+) 306 (M+H);

HPLC ($CH_3CN$—$H_2O$-0.1% TFA) (short column) $R_t$=2.27 min.

Step D: Synthesis of 2-[1-(pyrid-2-yl)piperidin-4-yl]ethylamine

To a solution of N-t-butoxycarbonyl 2-[1-(pyrid-2-yl)piperidin-4-yl]ethylamine (3.9 g) in EtOAc (15 mL) was bubbled HCl (g) for 15 min. The suspension was then stirred under positive pressure ($N_2$) for 30 min. Solvent was removed under vacuum to afford the 2-[1-(pyrid-2-yl)piperidin-4-yl]ethylamine (pure) as the hydrochloride salt (white solid) (3.4 g, 98%).

The processes set forth in Method L' are illustrated in the following reaction scheme:

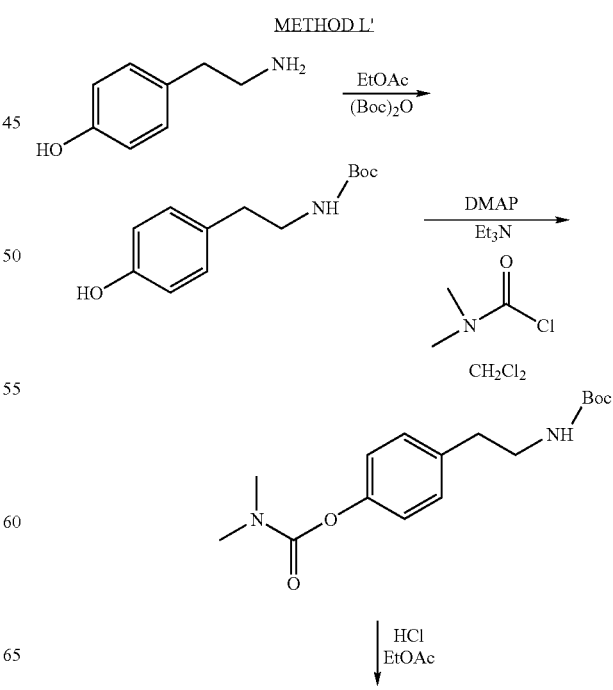

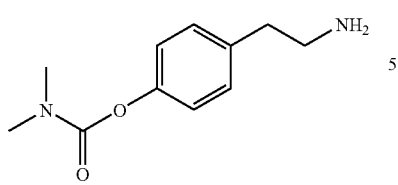

GENERAL PROCEDURE FOR THE PREPARATION OF CARBAMOYLOXY SUBSTITUTED PHENYLETHYL AMINE COMPOUNDS

Exemplified by the Preparation of 2-[4-(N',N'-dimethylaminocarbonyloxy)phenyl]ethylamine Step A: Synthesis of N-t-butoxycarbonyloxy 2-(4-hydroxyphenyl)ethylamine The amine group of 2-(4-hydroxyphenyl) ethylamine was protected with a Boc protecting group in the manner described above in Method K' to provide for N-t-butoxycarbonyloxy 2-(4-hydroxyphenyl) ethylamine.

Step B: Synthesis of N-t-butoxycarbonyloxy 2-[4-(N',N'-dimethylaminocarbonyloxy)phenyl]ethylamine N-t-butoxycarbonyloxy 2-(4-hydroxyphenyl) ethylamine (2.53 g, 10.7 mmol), Et$_3$N (2.96 mL, 2 eq.), a catalytic amount of DMAP (131 mg) and dimethylcarbamyl chloride (2.0 mL, 2 eq) were mixed in CH$_2$Cl$_2$ at 0° C. The resulting mixture was stirred for overnight. EtOAc was added to dilute the reaction mixture and then was washed with 1N HCl, sat.Na$_2$CO$_3$ and brine. Solvent was removed under reduced pressure to give pure t-butoxycarbonyloxy 2-[4-(N',N'-dimethylaminocarbonyloxy)phenyl]ethylamine a colorless solid.

Step C: Synthesis of 2-[4-(N',N'-dimethylaminocarbonyloxy)phenyl]ethylamine

The Boc protecting group on the t-Butoxycarbonyloxy 2-[4-(N',N'-dimethylaminocarbonyloxy)phenyl]ethylamine was removed in a manner similar to that set forth in Step D, of Method K' to provide for the title compound a white solid, and this compound was used "as is" in the next step.

The processes set forth in Method M' are illustrated in the following reaction scheme:

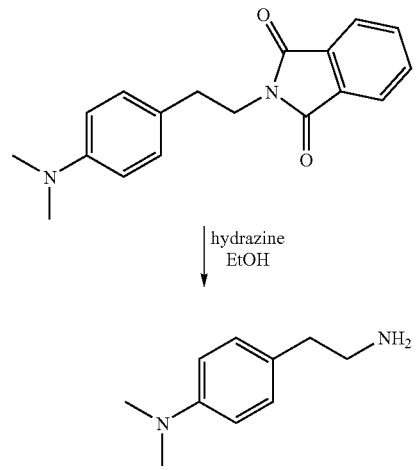

GENERAL PROCEDURE FOR CONVERTING 2-[4-(N,N-DIMETHYLAMINOPHENYL]ETHANOL TO 2-[4-(N',N'-DIMETHYLAMINOPHENYL]ETHYLAMINE

Step A: Synthesis of 2-[2-(4-N,N-dimethylaminophenyl)-ethyl]-isoindole-1,3-dione 2-[4-(N,N-dimethylaminophenyl]ethanol (2.05 g, 17.4 mmol), phthalimide (2.19 g, 14.9 mmol) and PPh$_3$ (3.93 g, 14.9 mmol) (Aldrich) were mixed in 100 mL of THF maintained at 0° C. The mixture was then treated with DIAD (2.68 mL) (Aldrich) which was added dropwise. After stirring overnight, the solvent was removed under reduced pressure to give a pale yellow solid. The solid was triturated with EtOAc three times. The combined EtOAc layers were treated with gaseous HCl to precipitate the product, and the desired product was isolated through filtration.

Step B: Synthesis of 2-[4-(N',N'-dimethylaminophenyl] ethylamine

2-[2-(4-N,N-dimethylaminophenyl)-ethyl]-isoindole-1,3-dione (606 mg, 1.84 mmol) and hydrazine hydrate (30%, 0.64 mL) in ethanol was heated at 65° C. for 5 h. The precipitate was removed via filtration. The filtrate was concentrated to give the title compound as a white solid. This product was used in the next step without further purification.

The processes set forth in Method N' are illustrated in the following reaction scheme:

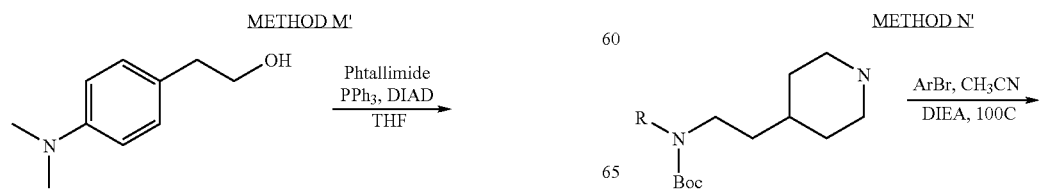

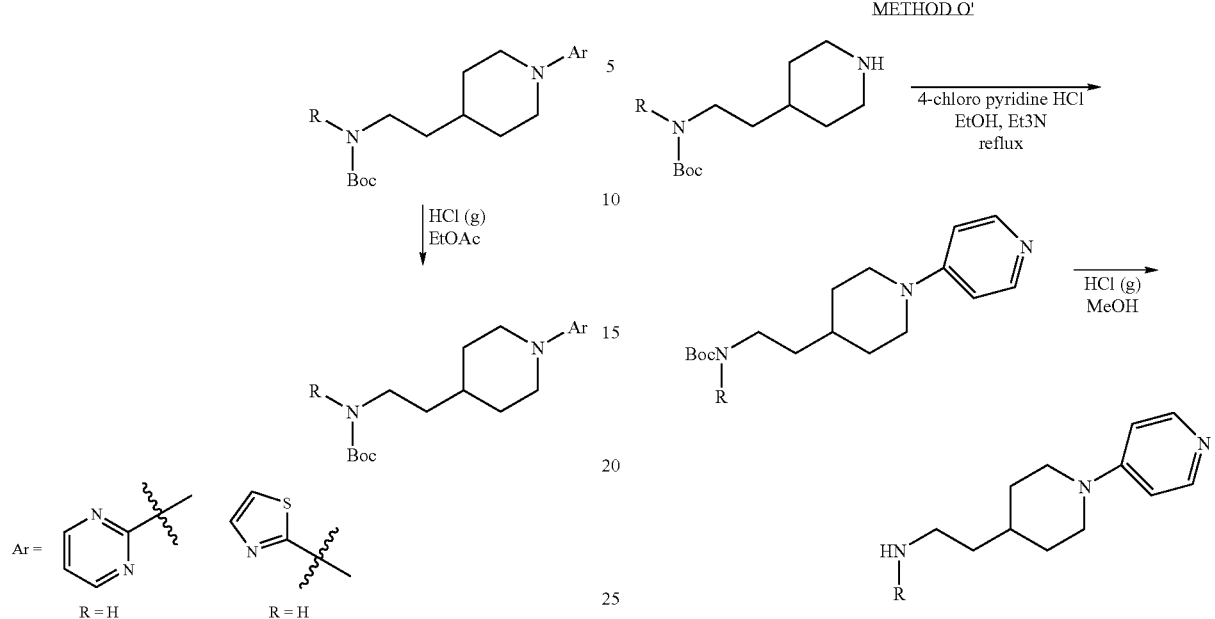

GENERAL PROCEDURE FOR PREPARING 2-[(1-PYRIMIDIN-2-YL)PIPERIDIN-4-YL]-ETHYLAMINE

Step A: Synthesis of N-t-butoxycarbonyloxy 2-[1-(pyrimidin-2-yl)piperidin-4-yl]-ethylamine N-t-butoxycarbonyloxy 2-(piperidin-4-yl)-ethylamine (prepared per Method K' above), DIEA (0.75 mL) and 2-bromopyrimidine (204 mg) (Aldrich) in acetonitrile (5 mL) were heated under reflux overnight. The solvent was removed under reduced pressure and the black liquid was subjected to a column chromatography, eluted with 1:1 EtOAc/hexanes, to give pure N-t-butoxy-carbonyloxy 2-[1-(pyrimidin-2-yl)piperidin-4-yl]-ethylamine as a pale yellow oil.

$^1$H NMR (CDCl$_3$) δ=8.21 (d, J=5.1 Hz, 2H), 6.36 (t, J=5.1 Hz, 1H), 4.64 (d, J=13.8 Hz, 2H), 3.14–3.07 (m, 2H), 2.76 (dt, J=2.7, 13.2 Hz, 1H), 1.69 (d, J=13.8 Hz, 1H), 1.57–1.30 (m, 11H), 1.20–1.03 (m, 3H); MS: m/z (EI$^+$) 307 (M+H); HPLC (CH$_3$CN—H$_2$O-0.1% TFA) (short column) R$_f$=2.63 min.

Step B: Synthesis of 2-[(1-pyrimidin-2-yl)piperidin-4-yl]-ethylamine

The Boc protecting group on N-t-butoxy-carbonyloxy 2-[1-(pyrimidin-2-yl)piperidin-4-yl]-ethylamine was removed using Step D of Method K' to afford the title compound.

The processes set forth in Method O' are illustrated in the following reaction scheme:

GENERAL PROCEDURE FOR PREPARING N-(PYRID-4-YL)PIPERIDINE COMPOUNDS

Step A: Synthesis of N-t-butoxycarbonyloxy 2-[1-(pyrid-4-yl)piperidin-4-yl]-ethylamine N-t-butoxycarbonyloxy 2-(piperidin-4-yl)-ethylamine (prepared per Method K' above) (14.4 g, 50 mmol), 4-chloropyridine HCl (1.0 eq., 8.0 g), TEA (2.2 eq.) were mixed in ethanol, and maintained under reflux overnight. The desired compound, N-t-butoxycarbonyloxy 2-[1-(pyrid-4-yl)piperidin-4-yl]-ethylamine, was isolated by column chromatography, (silica gel) eluted with EtOAc and carried in the next step.

Step B: Synthesis of 2-[1-(pyrid-4-yl)piperidin-4-yl]-ethylamine

The Boc protecting group on N-t-butoxycarbonyloxy 2-[1-(pyrid-4-yl)piperidin-4-yl]-ethylamine was then removed using Method K', Step D, to provide the title compound.

Method P' is the same as Methods F' and G'. Any reaction referencing Method P' in the examples below, may be accomplished by Method F' or G'.

The processes set forth in Method Q' are illustrated in the following reaction scheme:

METHOD Q'

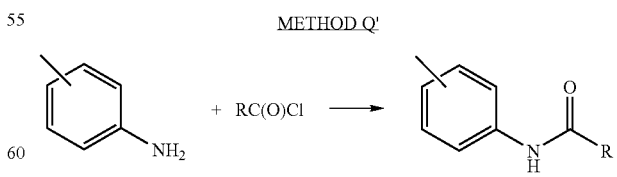

To a solution of the starting aniline (100 mg; 0.19 mmol) in dry pyridine (5 mL), was added acetic anhydride (20 μL). The mixture was stirred at rt overnight. Water (3 mL) was added to the mixture and the product was precipitated from the solution.

The processes set forth in Method R' are illustrated in the following reaction scheme:

METHOD R'

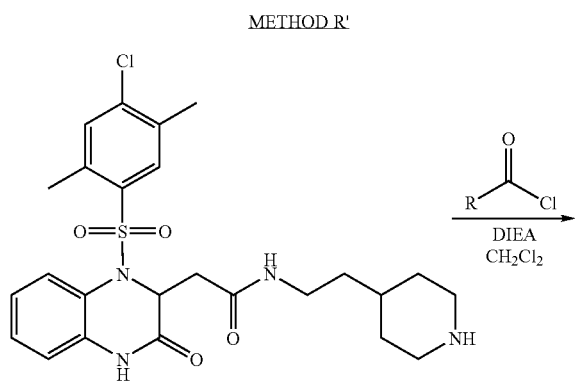

GENERAL PROCEDURE FOR CONVERTING THE AMINO NITROGEN OF PIPERIDINE TO AN AMIDE

Exemplified by the Preparation of a Library of 2-(R,S)-[1-(4-chloro-2,5-dimethylphenylsulfonyl)-3-oxo-1,2,3,4-tetrahydroquinoxalin-2-yl]-N-[2-(1-RC(O)-piperidin-4-yl)eth-1-yl]acetamide

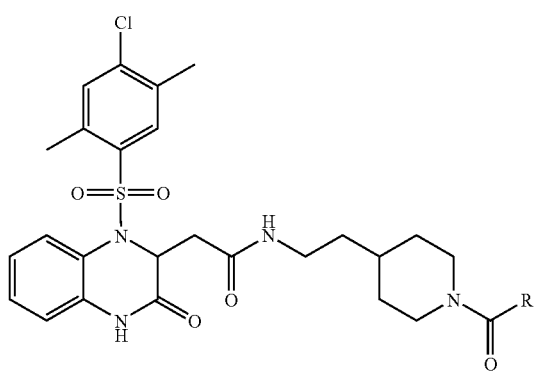

2-(R,S)-[1-(4-chloro-2,5-dimethylphenylsulfonyl)-3-oxo-1,2,3,4-tetrahydroquinoxalin-2-yl]-N-[2-(piperidin-4-yl)eth-1-yl]acetamide (25.0 mg, 0.04825 mmol) was dissolved in $CH_2Cl_2$ (600 μL) and treated with DIEA (2.0 eq.). After shaking at rt for 15 minutes, each respective acid chloride (0.0531 mmole) was added. The reaction was stirred at rt overnight. The organic layer was washed with brine, dried over $MgSO_4$. Upon filtration over celite, the crude material was purified over column chromatography (silica gel) eluted with $CHCl_3$:MeOH 9:1.

METHOD S'

GENERAL PROCEDURE FOR AMIDATING A CARBOXYLIC ACID

To a solution of the carboxylic acid (916 mg) in dry pyridine (5 mL), at −20° C. was added the amine hydrochloride salt piece (280 mg) in pyridine (5 mL), followed by $POCl_3$ (0.11 ml). The mixture was stirred at this temperature for 1.5 hours. The reaction was then quenched with ice. The mixture was diluted with water and was extracted with EtOAc. The organic solvent was concentrated to give the crude product, which was purified through a column chromatography (silica gel) system, eluted with EtOAc/hexanes to give the desired pure product.

METHOD T'

GENERAL PROCEDURE FOR CONVERSION OF A VINYLPYRIDINE GROUP TO A 2-AMINOETHYLPYRIDINE GROUP

Exemplified by the preparation of 2-N-ethyl-eth-1-yl-pyridine

4-Vinyl pyridine (1.6 mL; 15 mmol) was dissolved in acetic acid (12.5 mmol; 0.72 mL) and ethylamine (12.5 mmol). The reaction mixture was refluxed for 6 hours. The solvent was evaporated under reduced pressure. A solid was evaporated. EtOAc was added as well as saturated $NaHCO_3$. The organic layer was isolated, dried over $MgSO_4$. The solvent was removed under reduced pressure. The desired material was isolated as a foam.

$H^1$ ($CDCl_3$) 8.5 (m, 2H); 7.1 (m, 2H); 2.9 (m, 2H); 2.8 (m, 2H); 2.7 (m, 2H); 1.1 (m, 3H).

METHOD U'

GENERAL PROCEDURE FOR AMIDATING A CARBOXYLIC ACID

A mixture of the amine hydrochloride or trifluoroacetate salt, R,S-[1-(4-chloro-2,5-dimethyl-benzenesulfonyl)-3-oxo-1,2,3,4-tetrahydroquinoxalin-2-yl]-acetic acid, and triethyl amine (3.0 equ) in 5 mL of acetonitrile, with a small amount of DMF added for solubility, was treated with HATU (1.0 eq). The resulting homogeneous solution was stirred at room temperature for 2 hours then concentrated and diluted with a mixture of chloroform and isopropanol (3:1). The organic layer was washed with saturated aqueous odium bicarbonate solution and brine, dried in vacuo, and concentrated. The residue was purified by HPLC to give the title compound The process set forth in Method V' is illustrated in the following scheme

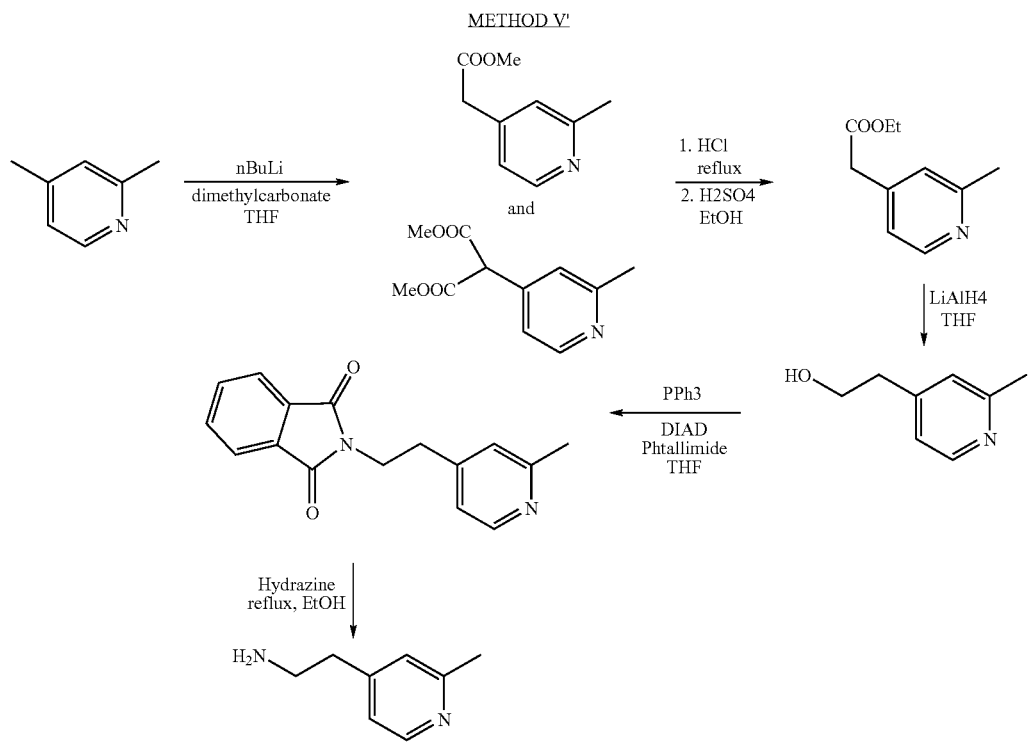

PREPARATION OF 2-(2-METHYLPYRIDIN-2-YL)ETHYLAMINE

Step A: Synthesis of (2-Methyl-pyridin-4-yl)-acetic acid methyl ester (and bis adduct)

A solution of diisopropyl amine (7.52 mL, 53.66 mmol) in 30 mL of THF was cooled to −78° C. and a solution of 2.5 M n-butylithium in hexanes (21.46 mL, 53.66 mmol) was added slowly. The solution was allowed to warm to room temperature and 2,4-dimethyl-pyridine (5.39 mL, 46.66 mmol) in 5 mL of THF was added dropwise.

The reaction was stirred for 4 hours at room temperature then transferred via an addition funnel to a room temperature solution of dimethyl carbonate (3.93 mL, 46.66 mmol) in 30 mL of THF. The resulting solution was stirred overnight and quenched with saturated aqueous ammonium chloride. The mixture was extracted several times with ethyl acetate and the combined organic layers were dried over anhydrous sodium sulfate. Flash chromatography on silica using a hexane/ethyl acetate gradient (20–60%) afforded 2.29 g of the title compound as a thick oil. MS(ES): m/e (EI*) 166.1 [M+H]

Step B: Synthesis of (2-Methyl-pyridin-4-yl)-acetic acid ethyl ester

The mixture of (2-methyl-pyridin-4-yl)-acetic acid methyl ester and the bis adduct (20 g) was dissolved in concentrated hydrochloric acid and heated to reflux for 1 hour. The solution was cooled, diluted with toluene, and concentrated in vacuo to give the crude acid. The acid was dissolved in ethanol, treated with a catalytic amount of sulfuric acid, and heated to reflux for 3 h. The solution was cooled to room temperature and concentrated in vacuo. The residue was dissolved in ethyl acetate and washed with saturated aqueous sodium chloride solution. The mixture was filtered and the filtrate concentrated to give 14 g of the title compound as a crude oil. MS(ES): m/e (EI*) 180.1 [M+H]

Step C: Synthesis of 2-(2-Methyl-pyridin-4-yl)-ethanol

A solution of (2-methyl-pyridin-4-yl)-acetic acid ethyl ester (3.75 g, 20.2 mmol) in 100 mL of THF was cooled in an ice bath and a 1.0M solution of LAH in THF was added (15.7 mL, 15.7 mmol). The reaction mixture was allowed to warm to room temperature and stirred overnight. The mixture was cooled in an ice bath and quenched with the successive addition of water, 15% aqueous sodium hydroxide solution and additional water. The resulting mixture was stirred at room temperature for 1 hour then dried over anhydrous sodium sulfate and filtered. The filtrate was concentrated to give 2.8 g of the title compound as a light brown oil. MS(ES): m/e (EI*) 138.1 [M+H]

Step D: Synthesis of 2-[2-(2-methyl-pyridin-4-yl)ethyl]isoindole-1,3-dione

A solution of triphenylphosphine (3.18 g, 12.12 mmol) and diisopropylazodicarbocylate (2.39 μL, 12.12 mmol) in 10 mL of THF was stirred at 0° C. for 30 min and combined with a solution of 2-(2-methyl-pyridin-4-yl)-ethanol and phthalimide (1.33 g, 9.7 mmol) in 10 mL of THF. The resulting solution was stirred overnight at room temperature and concentrated in vacuo. The residue was dissolved in ethyl acetate and the organic layer was washed successively with saturated aqueous sodium bicarbonate and saturated aqueous sodium chloride solutions. The organic layer was dried over sodium sulfate and concentrated in vacuo. Flash chromatography on silica using a dichloromethane/methanol gradient (2–10%) gave 2.5 g of the title product. MS(ES): m/e (EI*) 267.1 [M+H]

Step E: Synthesis of 2-(2-Methyl-pyridin-4-yl)-ethylamine

A solution of 2-[2-(2-methyl-pyridin-4-yl)-ethyl]-isoindole-1,3-dione (2.58 g, 9.69 mmol) in 20 mL of ethanol was heated to reflux for 5 hours. The reaction was allowed to cool and stirred overnight. The resulting slurry was filtered and the filtrate was concentrated. The residue was dissolved in ethyl acetate and extracted several times with 10% aqueous hydrogen chloride solution. The aqueous layers were combined and neutralized with sodium carbonate and extracted with a mixture of chloroform and isopropanol (3:1). The organic layer was dried over anhydrous sodium sulfate, filtered, and concentrated to give the tile compound as a clear colorless oil. MS(ES): m/e (EI*) 137.1 [M+H]

The reaction set forth in Method W' is exemplified below

METHOD W'

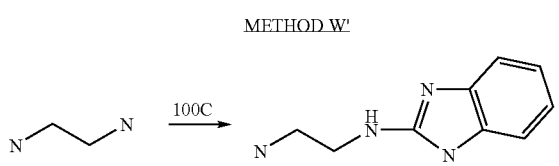

PREPARATION OF N1-(1H-BENZOIMIDAZOL-2-YL)-ETHANE-1,2-DIAMINE

A mixture of 2-chloro-1H-benzoimidazole (1 g) in 4 mL of ethane-1,2-diamine was heated to 100 C. for several hours until complete by HPLC. The reaction was allowed to cool and diluted with a mixture of chloroform and isopropanol (3:1). The organic phase was washed with water then dried and concentrated to give 216 mg of product as a solid which was used in the next step without further purification. MS(ES): m/c (EI*) 177.1 [M+H]

The process set forth in Method X' is illustrated below

METHOD X'

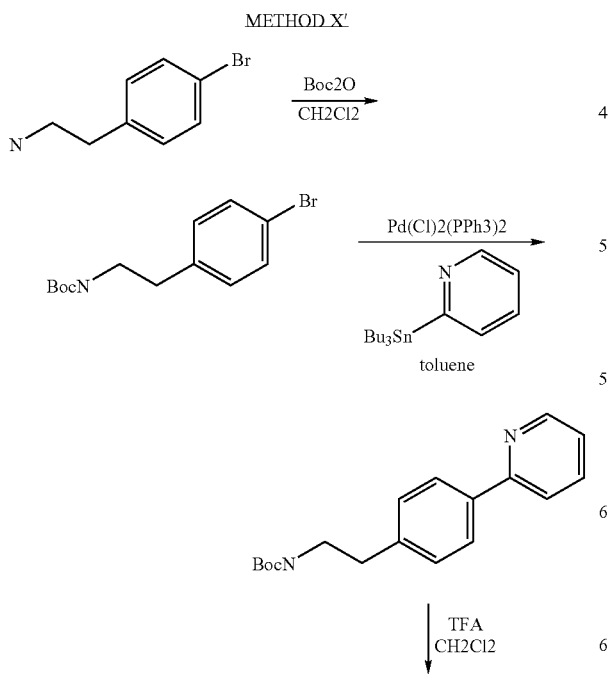

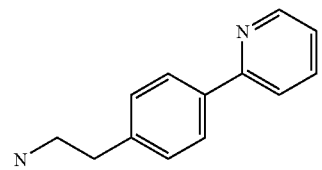

PREPARATION OF 2-(4-PYRIDIN-2-YL-PHENYL)-ETHYLAMINE

Step A: Synthesis of [2-(4-Bromo-phenyl)-ethyl]-carbamic acid tert-butyl ester 2-(4-Bromo-phenyl-ethylamine was protected with a Boc protecting group in the manner described in step A of Method K' to provide [2-(4-Bromo-phenyl)-ethyl]-carbamic acid tert-butyl ester, in quantitative yields. The compound was used as is in the next step.

Step B: Synthesis of [2-(4-Pyridin-2-yl-phenyl)-ethyl]-carbamic acid tert-butyl ester

[2-(4-Bromo-phenyl)-ethyl]-carbamic acid tert-butyl ester (1.5 g, 4.99 mmol) was dissolved in toluene (0.2 M) in a 100 mL round-bottom flask. To this was added LiCl (10.6 mg, 0.25 mmol, 0.05 eq) and the resulting solution was flushed under nitrogen for 2–3 minutes. PdCl$_2$(PPh$_3$)$_2$ (175.4 mg, 0.25 mmol, 0.05 eq) was added to the reaction mixture and the solution was again flushed under nitrogen for 2–3 minutes. 2-Tributylstannanyl-pyridine, from Frontier (1.84 g, 4.99 mmol, 1 eq) was added last and the reaction mixture was heated to 110° C. overnight. The solvent was removed under vacuum. The crude material was purified on column chromatography (silica gel), and eluted with EtOAc-Hexanes 15:85 to afford [2-(4-Pyridin-2-yl-phenyl)-ethyl]-carbamic acid tert-butyl ester in good yield.

Step C: Synthesis of 2-(4-Pyridin-2-yl-phenyl)-ethylamine

[2-(4-Pyridin-2-yl-phenyl)-ethyl]-carbamic acid tert-butyl ester was dissolved in a 1:1 mixture of trifluroacetic acid:dichloromethane. The reaction mixture was stirred at room temperature overnight after which the product was recovered upon solvent removal. The TFA salt was used in the next step without further purification.

The process set forth in Method Y' is outlined below

METHOD Y'

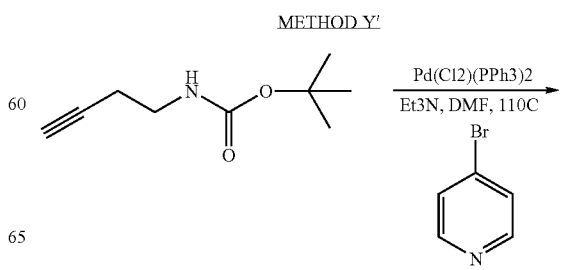

-continued

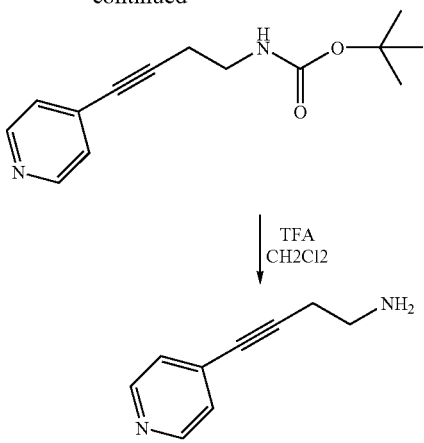

PREPARATION OF
4-(PYRIDIN-4-YL)BUT-3-YNYLAMINE

Step A: Synthesis of but-3-ynyl-carbamic acid tert-butyl ester
The procedure described in Taylor, *Tetrahedron*. 1987, Volume 43, page 5145 was followed. This reference is incorporated by reference herein in its entirety.

Step B: But-3-ynyl-carbamic acid tert-butyl ester was reacted with
4-bromo pyridine (Aldrich) using a catalytic amount of $PdCl_2(PPh3)_2$, and CuI, according to the procedure reported by Glase, S. A et al. in *J. Med. Chem.* 1996, Volume 39, pages 3179–3187.

Step C: Deprotection took place using neat TFA. Upon evaporation of the solvent under reduced pressure, an oil was isolated. HPLC (acetonitrile-water-0.1% TFA) $R_t$=0.79 mn. MS (ES): m/e 147 (M+H).

Example 1

Preparation of 2-[2-(R,S)-1-(4-chloro-2,5-dimethyl-benzenesulfonyl)-3-oxo-1,2,3,4-tetrahydroquinoxalin-2-yl]-methylenecarbonyl-{[4-(2-(N-t-butoxycarbonylamino)ethyl)piperidin-1-yl]}

The title compound was prepared from[2-(R,S)-1-(4-chloro-2,5-dimethyl-benzenesulfonyl)-3-oxo-1,2,3,4-tetrahydroquinoxalin-2-yl]acetic acid, and 4-(2-(N-t-butoxycarbonyl-amino)ethyl)piperidine using Method I.
$^1$H NMR (DMSO-$d_6$): δ=0.77–1.59(m, 7H), 1.40(s, 9H), 1.95(s, 3H), 2.01(s, 3H), 2.20–2.52(m, 2H), 2.70–2.92 (m, 4H), 3.47(brd, 1H), 3.30(brd, 1H), 4.83(m, 1H), 6.73–7.49 (m,6H)10.53(s, 1H); MS (ES): m/e 643 (M+Na); HPLC ($CH_3CN$—$H_2O$-0.1% TFA) (short column): $R_t$=6.35 min.

Example 2

Preparation of 2-[2-(R,S)-1-(4-chloro-2,5-dimethyl-benzenesulfonyl)-3-oxo-1,2,3,4-tetrahydroquinoxalin-2-yl]-methylenecarbonyl-[4-(2-aminoethyl)]piperidin-1-yl]

The title compound was prepared from 2-[2-(R,S)-1-(4-chloro-2,5-dimethylbenzenesulfonyl)-3-oxo-1,2,3,4-tetrahydroquinoxalin-2-yl]methylenecarbonyl-{4-(2-(N-t-butoxycarbonyl-amino)ethyl)piperidin-1-yl} using Method P in ethyl acetate. The desired material was isolated as an HCl salt.
$^1$H NMR (DMSO-$d_6$): δ=0.84–1.60 (m, 7H), 2.00(s, 3H), 2.20(s, 3H), 2.36–2.47(m, 2H), 2.75–2.83(m, 2H), 3.48–3.52(brd, 1H), 4.28–4.3 1(brd, 1H), 4.81(m, 1H), 6.84–7.47(m, 6H), 8.05(brs, 2H, $NH_2$)10.56(s, 1H); MS (ES): m/e 520.1 (M+H); HPLC ($CH_3CN$—$H_2O$-0.1% TFA) (short column): $R_t$=3.48 min.

Example 3

Preparation of [2-(R,S)-1-(4-Chloro-2,5-dimethyl-benzenesulfonyl)-3-oxo-1,2,3,4-tetrahydroquinoxalin-2-yl]-S-(p-tolyl)thioacetic acid ester The title compound was prepared from [2-(R,S)-1-(4-chloro-2,5-dimethylbenzenesulfonyl)-3-oxo-1,2,3,4-tetrahydroquinoxalin-2-yl]acetic acid and p-thiocresol using Method I.
$^1$H NMR (DMSO-$d_6$): δ=1.97 (s, 3H), 2,21 (s, 3H), 2.32 (s, 3H), 2.64–2.89 (m, 2H), 4.85 (m, 1H), 6.82–7.5 (m, 8H), 10.63 (s, 1H); MS (ES): m/e 516.1 (M+H); HPLC ($CH_3CN$—$H_2O$-0.1% TFA) (short column) $R_t$=8.034 min.

Example 4

Preparation of 2-[2-(R,S)-1-(2,3-dichlorobenzene-sulfonyl)-3-oxo-1,2,3,4-tetrahydroquinoxalin-2-yl]-N-methyl-N-[2-(N-methylpiperidin-4-yl)eth-1-yl}acetamide The title compound was prepared from 2-[2-(R,S)-1-(2,3-dichloro-benzenesulfonyl)-3-oxo-1,2,3,4-tetrahydroquinoxalin-2-yl]acetic acid and N-methyl-(2-(N-methyl-piperidin-4-yl)eth-1-yl)amine using Method I and purified by preparative HPLC.
$^1$H NMR (DMSO-$d_6$): δ=1.06–1.91 (m, 7H), 2. 32–2.60 (m, 2H), 2.75–3.40 (m, 6H), 2.44 (s, 3H), 2.47 (s, 3H), 4.84 (dd, 1H, J=3.3 Hz,) 4.96 (dd, 1H, J=3.3 Hz), 6.85–7.94 (m, 8H), 10.71(s, 1H, NH), 10.76 (s, 1H, NH), MS (ES): m/e 548.1 (M+H); HPLC ($CH_3CN$—$H_2O$-0.1% TFA) (short column): $R_t$=2.53 min.

Example 5

Preparation of 2-[2-(R)-1-(4-chloro-2,5-dimethyl-benzenesulfonyl)-3-oxo-1,2,3,4-tetrahydroquinoxalin-2-yl]-N-{2-[N-(pyridin-4-yl)piperidin-4-yl]eth-1-yl}acetamide The title compound was prepared from [2-(R)-1-(4-chloro-2,5-dimethylbenzenesulfonyl)-3-oxo-1,2,3,4-tetrahydroquinoxalin-2-yl]acetic acid and 2-[N-(pyridin-4-yl)piperidin-4-yl]ethylamine using Method I.
$^1$H NMR (DMSO-$d_6$): δ=1.03–1.80 (m, 7H), 1.98 (s, 3H), 2.20 (s, 3H), 2.09–2.24 (m, 2H), 2.75–3.13 (m, 4H), 3.88 (brd, 2H), 4.85 (dd, 1H, J=5.1 Hz), 6.76 (brd, 2H), 6.78–7.47 (m, 6H), 7.85 (brt, 1H, NH), 8.08 (brd, 2H); MS (ES): m/e 596.2(M+H); HPLC ($CH_3CN$—$H_2O$-0.1% TFA) (short column): $R_t$=2.66 min.

Example 6

Preparation of 2-[2-(S)-1-(4-chloro-2,5-dimethyl-benzenesulfonyl)-3-oxo-1,2,3,4-tetrahydroquinoxalin-2-yl]-N-2-[N-(pyrid-4-yl)]piperidin-4-yl}acetamide The title compound was prepared from [2-(S)-1-(4-chloro-2,5-dimethyl-benzene-sulfonyl)-3-oxo-1,2,3,4-tetrahydroquinoxalin-2-yl]acetic acid and 2-[N-(pyridin-4-yl)piperidin-4-yl]ethylamine using Method I.

$^1$H NMR (DMSO-$d_6$): δ=1.03–1.80 (m, 7H), 1.97 (s, 3H), 2.19 (s, 3H), 2.10–2.30 (m, 2H), 2.75–3.12 (m, 4H), 3.87 (brd, 2H), 6.75 (brd, 2H, Py), 6.78–7.41 (m, 6H), 7.83 (brt, 1H, NH), 8.05 (brd, 2H, Py), 10.42 (s, 1H, NH); MS (ES): m/e 597(M+H); HPLC (CH$_3$CN—H$_2$O-0.1% TFA) (short column): R$_t$=2.65 min.

Example 7

Preparation of 2-[2-(R,S)-1-(3-chloro-2-methylbenzenesulfonyl)-3-oxo-1,2,3,4-tetrahydroquinoxalin-2-yl]-N-benzylacetamide The title compound was obtained from 2-[2-(R,S)-3-oxo-1,2,3,4-tetrahydro-quinoxalin-2-yl]-N-benzylacetamide using Method G and 2-methyl-3-chloro benzene sulfonyl chloride.

$^1$H NMR (300 MHz, CD$_3$OD) δ=8.42 (1H, t), 7.77 (1H, d, J=8.7 Hz), 7.67 (1H, d, J=8.1 Hz), 7.33 (8H, m), 7.11 (1H, m), 6.87 (1H, d, J=7.8 Hz), 4.89 (1H, q), 4.32 (1H, dd), 4.05 (1H, dd), 2.35 (2H, m), 2.18 (3H, s); $^{13}$C NMR (300 MHz, CD$_3$OD) ppm 167.12, 166.48, 139.29, 137.47, 136.60, 135.44, 135.01, 133.84, 133.71, 129.64, 128.91, 128.53, 128.35, 127.90, 127.47, 127.10, 123.25, 121.23, 116.21, 56.17, 55.23, 16.56; MS (ES): m/e 484.1 (M+H); HPLC (CH$_3$CN—H$_2$O-0.1% TFA): R$_t$=5.20 min.

Example 8

Preparation of 2-[2-(R,S)-1-(2,5-dimethylbenzenesulfonyl)-3-oxo-1,2,3,4-tetrahydroquinoxalin-2-yl]-N-benzylacetamide The title compound was obtained from 2-[2-(R,S)-3-oxo-1,2,3,4-tetrahydro-quinoxalin-2-yl]-N-benzylacetamide using Method G, and 2,5-dimethylbenzene sulfonyl chloride.

$^1$H NMR (300 MHz, CD$_3$OD) δ=10.42 (1H, s), 8.40 (1H, t), 7.34 (9H, m), 7.17 (1H, d, J=8.4 Hz), 7.08 (1H, t), 6.81 (1H, d, J=7.8 Hz), 4.95 (1H, q), 4.32 (1H, dd), 4.13 (1H, dd), 2.33 (2H, m), 2.22 (3H, s), 2.05 (3H, s); $^{13}$C NMR (300 MHz, CD$_3$OD) ppm 167.32, 166.63, 139.36, 136.28, 135.06, 134.67, 134.52, 133.73, 133.01, 130.33, 128.52, 128.31, 127.47, 127.07, 122.99, 121.65, 116.09, 56.21, 42.47, 36.77, 20.54, 19.67; MS (ES): m/e 464 (M+H); HPLC (CH$_3$CN—H$_2$O-0.1% TFA): R$_t$=5.25 min.

Example 9

Preparation of 2-[2-(R,S)-1-(2-methylbenzenesulfonyl)-3-oxo-1,2,3,4-tetrahydroquinoxalin-2-yl]-N-benzylacetamide The title compound was obtained from 2-[2-(R,S)-3-oxo-1,2,3,4-tetrahydro-quinoxalin-2-yl]-N-benzylacetamide, using Method G, and 2-methylbenzene sulfonyl chloride.

$^1$H NMR (300 MHz, CD$_3$OD) δ=10.46 (1H, s), 8.40 (1H, t), 7.52 (2H, m), 7.29 (9H, m), 7.10 (1H, m), 6.79 (1H, q), 4.99 (1H, m), 4.35 (1H, m), 4.14 (1H, dd), 2.34 (3H, s), 2.28 (2H, m); $^{13}$C NMR (300 MHz, CD$_3$OD) ppm 167.37, 167.30, 166.70, 144.56, 139.36, 137.69, 135.52, 134.16, 133.66, 133.19, 130.21, 129.96, 128.52, 128.17, 127.48, 127.41, 127.07, 126.97, 126.88, 123.05, 121.66, 116.17, 60.08, 56.40, 56.11, 42.47, 36.76, 21.36, 21.09, 20.12, 14.41; MS (ES): m/e 450.1 (M+H); HPLC (CH$_3$CN—H$_2$O-0.1% TFA): R$_t$=4.85 min.

Example 10

Preparation of 2-[2-(R,S)-1-(benzenesulfonyl)-3-oxo-1,2,3,4-tetrahydroquinoxalin-2-yl]-N-[2-(pyrid-4-yl)eth-1-yl]acetamide The title material was obtained from 2-[2-(R,S)-3-oxo-1,2,3,4-tetrahydroquinoxalin-2-yl]-N-(pyrid-4-yl)ethylacetamide using Method G and benzene sulfonyl chloride.

$^1$H NMR (CD$_3$OD) δ=10.31 (1H, s), 8.48 (2H, q), 8.01 (1H, t), 7.64 (1H, t), 7.45 (3H, m), 7.25 (5H, m), 7.10 (1H, m), 6.75 (1H, d, J=9.0 Hz), 4.98 (1H, q), 2.70 (2H, t), 2.21 (2H, m); $^{13}$C NMR ($^1$H) δ=167.32, 166.18, 149.73, 148.73, 136.82, 134.16, 133.29, 129.55, 128.60, 128.21, 126.89, 124.56, 123.09, 116.13, 56.30, 36.81, 34.35; MS m/z (M+H) 451.1; HPLC (CH$_3$CN—H$_2$O-0.1% TFA): R$_t$=1.41 min.

Example 11

Preparation of 2-[2-(R,S)-1-(4-chloro-2,5-dimethyl-benzenesulfonyl)-3-oxo-1,2,3,4-tetrahydro-6,7-dimethylquinoxalin-2-yl]-N-benzylacetamide The title material was prepared from 4,5-dimethyl-1,2-phenylenediamine using Method F, followed by Method H using 2,5-dimethyl-4-chlorobenzene sulfonyl chloride.

$^1$H NMR (DMSO-$d_6$) δ=2.0–2.5 (dd, m, s 14H), 4.15 (dd, J=14.5 Hz, 1H), 4.3 (dd, J=14.5 Hz, 1H), 4.89 (dd, J=4.5 Hz, 1H), 7.14–7.49 (m, ArH, 8H), 8.36 (t, 1H, NH), 10.35 (s, 1H, NH); MS (ES): m/e 527.3 (M+H), 550.3 (M+Na).

Example 12

Preparation of 2-[2-(R or S)-1-(4-chloro-2.5-dimethylbenzenesulfonyl)-3-oxo-1,2,3,4-tetrahydroquinoxalin-2-yl]-N-[1-(R)-(methoxycarbonyl)-2-(N-methylpiperidin-4-yl)eth-1-yl]acetamide The title compound was obtained as a single diastereomer by recrystallization of 2-[2-(R,S)-1-(4-chloro-2,5-dimethyl-benzene-sulfonyl)-3-oxo-1,2,3,4-tetrahydroquinoxalin-2-yl]-N-[1-(R)-(methoxycarbonyl)-2-(N-methylpiperidin-4-yl)eth-1-yl]acetamide with ethyl acetate.

$^1$H NMR (DMSO-$d_6$) δ=1.06–2.40 (brm, 10H), 1.99(s, 3H), 2.22(s, 3H), 2.75(br. d, 2H), 3.60(s, 3H), 4.30(m, 1H), 4.82(t, J=6 Hz, 1H), 6.79–7.42(m, Ar—H, 6H), 8.32(d, J=7.5 Hz, 1H); MS (ES): m/e: 590.1 (M+H), 613(M+Na); HPLC (CH$_3$CN—H$_2$O-0% TFA) (short column): R$_t$=4.01 min.

Example 13

Preparation of 2-[2-(R,S)-1-(4-chloro-2,5-dimethyl-benzenesulfonyl)-3-oxo-1,2,3,4-tetrahydroquinoxalin-2-yl]-N-[2-(pyrid-4-yl)eth-1-yl]-N-iso-propylacetamide Iso-propyl-(2-pyridin-4-yl-ethyl)-amine, obtained from 4-vinylpyridine using Method U, and was subsequently reacted with 2-[2-(R,S)-1-(4-chloro-2,5-dimethylbenzenesulfonyl)-3-oxo-1,2,3,4-tetrahydroquinoxalin-2-yl]acetic acid using Method I to afford the title material.
$^1$H NMR (DMSO-$d_6$) δ=0.79–1.08 (m, 6H), 1.90 (s, 3H), 2.18 (s, 3H), 2.30–2.70 (brm, 4H), 2.90–3.28(m, 4H), 3.74, (m, 1H), 4.28(m,1H), 4.93 (m, 1H), 6.71–7.46(m, 8H), 8.23(d, 2H), 8.43(d, 2H); MS (ES): m/e 556.1 (M+H), 579 (M+Na); HPLC (CH$_3$CN—H$_2$O-0.1% TFA) (short column) $R_t$=3.94 min.

Example 14

Preparation of 2-[2-(R,S)-1-(4-chloro-2,5-dimethyl-benzenesulfonyl)-3-oxo-1,2,3,4-tetrahydroquinoxalin-2-yl]-methylenecarbonyl{[1-(pyridin-2-yl]-4-piperazin-4-yl}

2-[2-(R,S)-1-(4-Chloro-2, 5-dimethylbenzenesulfonyl)-3-oxo-1,2,3,4-tetrahydro-quinoxalin-2-yl]acetic acid was reacted with 1-pyridin-2-yl-piperazine using Method I to afford the title material as a solid.
$^1$H NMR (DMSO-$d_6$) δ=2.02 (s, 3H), 2.21 (s,3H), 2.53 (m, 2H), 3.30–3.48 (m, 8H), 4.89 (m, 1H), 6.62–8.75 (m, 10H,Ar—H), 10.55 (s, 1H, NH); MS (ES): m/e: 555 (M+H); HPLC (CH$_3$CN—H$_2$O-0.1% TFA) (short column): $R_t$=3.77 min.

Example 15

Preparation of 2-[2-(R,S)-1-(4-methoxy-2,3,6-trimethylbenzenesulfonyl)-3-oxo-1,2,3,4-tetrahydroquinoxalin-2-yl]-N-[2-(pyrid-4-yl)-eth-1-yl]acetamide The title compound was synthesized from 2-[2-(R,S)-3-oxo-1,2,3,4-tetrahydroquinoxalin-2-yl]-N-(pyrid-4-yl)ethylacetamide and 4-methoxy 2,3,6-trimethylbenzene sulfonyl chloride using Method G.
$^1$H NMR (DMSO-$d_6$) δ=10.30 (1H, s), 8.44 (2H, d, J=6.0 Hz), 7.95 (1H, t), 7.22 (3H, m), 6.95 (3H, m), 6.84 (1H, s), 4.71 (1H, q), 3.86 (3H, s), 2.66 (2H, t), 2.38 (3H, s), 2.29 (3H, s), 2.05 (3H, s); MS m/z (M+H) 523.2; HPLC (CH$_3$CN—H$_2$O-0.1% TFA): $R_t$=3.33 min.

Example 16

Preparation of 2-[2-(R,S)-1-(2,3-dichlorobenzenesulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and 2,3-dichlorobenzenesulfonyl chloride using Method G.
$^1$H NMR (DMSO-$d_6$) δ=10.25 (1H, s), 8.46 (2H, d, J=6.0 Hz), 7.91(2H, m), 7.50 (2H, m), 7.22 (3H,m), 7.06 (1H, y), 6.87 (1H, d, J=9.0 Hz), 4.91 (1H, q), 2.69 (2H, t), 2.25 (2H, m); MS m/z (M+H) 520.4; HPLC (CH$_3$CN—H$_2$O-0.1% TFA): $R_t$=2.95 min.

Example 17

Preparation of2-[2-(R,S)-1-(2.3-dichlorobenzenesulfonyl)-3-oxo-1,2,3,4-tetrahydroquinoxalin-2-yl]-N-[(2-pyrid-4-yl)-eth-1-yl]-N-methylacetamide 2-[2-(R,S)-3-Oxo-1,2,3,4-tetrahydroquinoxalin-2-yl]acetic acid was coupled to commercially available 4-[2-(methylamino)ethyl]pyridine using Method I, followed by sulfonylation with 2,3-dichlorobenzene sulfonyl chloride using Method G.
$^1$NMR (DMSO-$d_6$) δ=10.76 (1H, d, J=7.2 Hz), 8.46 (1H, d, J=5.7 Hz), 8.37 (1H, d, J=6.0 Hz), 7.94 (2H, m), 7.53 (2H, m), 7.25 (2H, m), 7.05 (1H, t), 6.94 (2H, m), 4.98 (m, 1H), 4.88 (1H, dd), 2.69 (3H, s), 2.27 (1H, m); MS m/z (M+H) 534.4; HPLC (CDCl$_3$CN—H$_2$O-0.1% TFA): $R_t$=3.16 min.

Example 18

Preparation of2-[2-(R,S)-1-(4-methoxy-2,3,6-trimethylbenzenesulfonyl)-3-oxo-1,2,3,4-tetrahydroquinoxalin-2-yl]-N-[2-(pyrid-4-yl)eth-1-yl]-N-methylacetamide 2-[2-(R,S)-3-Oxo-1,2,3,4-tetrahydroquinoxalin-2-yl]acetic acid was coupled to commercially available 4-[2-(methylamino)ethyl]pyridine using Method I, followed by sulfonylation with 4-methoxy-2,3,6-trimethylbenzenesulfonyl chloride using Method G.
$^1$H NMR (DMSO-$d_6$) δ=10.72 (1H, m), 8.45 (1H, d, J=6.0 Hz), 8.37 (1H, d, J=6.0 Hz), 8.20 (1H, d, J=5.7 Hz), 7.24 (1H, m), 6.99 (4H, m), 6.85 (1H, s), 4.73 (1H, m), 4.56 (1H, m), 3.85 (3H d, J=3.0 Hz), 2.74 (3H, s), 2.65 (3H, s), 2.39 (2H, d, J=4.8 Hz), 2.31 (2H, d, J=3.0 Hz), 2.04 (2H, d, J=9.0 Hz); MS m/z (M+H) 537.2; HPLC (CH$_3$CN—H$_2$O-0.1% TFA): $R_t$=3.46 min.

Example 19

Preparation of 2-[2-(R,S)-1-(4-chloro-2,5-dimethyl-benzenesulfonyl)-3-oxo-1,2,3,4-tetrahydroquinoxalin-2-yl]-N-[1-(R)-(pyrrolidin-N-ylcarbonyl)-4-(N'-t-butoxycarbonyl)guanadino-n-but-1-yl]acetamide Z-D-Arg-OH amino acid was protected using Method A' followed by coupling with pyrrolidine using Method I. Deprotection using Method B' followed by coupling to 2-[2-(R,S)-1-(4-chloro-2,5-dimethylbenzenesulfonyl)-3-oxo-1,2,3,4-tetrahydroquinoxalin-2-yl]acetic acid using Method S led to the desired material. The crude product was purified via column chromatography (silica gel) eluted with CH$_2$Cl$_2$—MeOH-ammonia 9:1:0.1 and washed with a citric acid buffer to afford the title compound as a mixture of diastereomers.
$^1$H NMR (CDCl$_3$) δ=8.04 (1H, s), 7.63 (2H, m), 7.55 (1H, s), 7.49 (1H, s), 7.21 (1H, d, J=7.8 Hz), 7.11 (1H, m), 2.90 (3H, s), 2.90 (3H, s), 2.23 (2H, d, J=9.3 Hz), 2.07 (2H, d, J=8.4 Hz), 2.00 (1H, m), 1.86 (1H, m), 1.51 (9H, s); MS m/z (M+H) 719.2; HPLC (CH$_3$CN—H20–0.1% TFA): $R_t$=4.40 min.

Example 20

Preparation of 2-[2-[(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-5-(t-butoxy-carbonylamino)-pent-5-yl]acetamide Z-D-Lys(Boc)-OH amino acid was coupled to pyrrolidine using Method I followed by deprotection using Method B', followed by coupling to 2-[2-(R,S)-1-(4-chloro-2,5-dimethylbenzenesulfonyl)-3-oxo-1,2,3,4-tetrahydroquinoxalin-2-yl]acetic acid using Method S. The crude material was purified via column chromatography (silica gel) eluted with EtOAc-CH$_3$CN 95:5, separating the diastereomers to afford the title compound as a single diastereomer.
$^1$H NMR (DMSO-d$_6$) δ=10.44 (1H, s), 8.16 (1H, d, J=9.0 Hz), 7.45 (1H, s), 7.32 (3H, m), 7.10 (1H, m), 6.81 (1H, d, J=8.7 Hz), 6.74 (1H, t), 4.87 (1H, m), 4.45 (1H, m), 3.62 (1H, m), 3.43 (1H, m), 2.85 (2H, m), 2.73 (1H, s), 2.29 (1H, m), 2.23 (3H, s), 1.92 (4H, m), 1.571H, m), 1.36 (9H, s); MS m/z (M+H-Boc) 590.2; HPLC (CH$_3$CN—H$_2$O-0.1% TFA): R$_t$=6.01 min.

Example 21

Preparation of 2-[2-(R or S)-1-(4-chloro-2,5-dimethylbenzenesulfonyl)-3-oxo-1,2,3,4-tetrahydroquinoxalin-2-yl]-N-[1-(R)-pyrrolidin-N-ylcarbonyl-5-(N'-t-butoxycarbonylamino)-pent-5-yl]acetamide Z-D-Lys(Boc)-OH amino acid was coupled to pyrrolidine using Method I, followed by deprotection using Method B', followed by coupling to 2-[2-(R,S)-1-(4-chloro-2,5-dimethylbenzenesulfonyl)-3-oxo-1,2,3,4-tetrahydroquinoxalin-2-yl]acetic acid using Method S. The resulting material was purified via column chromatography (silica gel) eluted with EtOAc-CH$_3$CN 95:5 separating the diastereomers to afford the title compound as a single diastereomer.
$^1$H NMR (DMSO-d$_6$) δ=10.45 (1H, s), 8.13 (1H, d, J=9.0 Hz), 7.40 (3H, m), 7.26 (1H, t), 7.11 (1H, t), 6.77 (2H, m), 4.84 (1H, m), 4.44 (1H, m), 3.55 (1H, m), 3.42 (1H, m), 3.22 (2H, m), 2.91 (2H, m), 2.73 (1H, s), 2.24 (3H, s), 1.99 (2H, m), 1.86 (2H, m), 1.76 (1H, m), 1.38 (9H, s); MS m/z (M+H-Boc) 590.2; HPLC (CH$_3$CN—H$_2$O-0.1% TFA): R$_t$=5.92 min.

Example 22

Preparation of 2-[2-(S or R)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-4-guanidino-but-1-yl]acetamide 2-[2-(R,S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-4-(N'-t-butoxycarbonyl)-guanadino-n-but-1-yl]acetamide was deprotected using Method O. The resulting pair of diastereomers was purified by preparative HPLC (CH$_3$CN—H$_2$O-0.1% TFA) to afford the title compound as a single diastereomer.
$^1$H NMR (DMSO-d$_6$) δ=10.45 (1H, s), 8.26 (1H, d, J=8.7 Hz), 7.35 (5H, m), 7.12 (2H, t), 6.80 (1H, d, J=9.0 Hz), 4.89 (1H, m), 4.55 (1H, m), 3.06 (2H, m), 2.73 (1H, s), 2.30 (2H, m), 2.25 (3H, s), 1.97 (4H, m), 1.83 (2H, m), 1.42 (3H, m); MS m/z (M+H) 619.2; HPLC (CH$_3$CN—H$_2$O-0.1% TFA): R$_t$=3.45 min.

Example 23

Preparation of 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-4-(guanadino)but-1-yl]acetamide 2-[2-(R,S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-4-(N'-t-butoxycarbonyl)-guanadino-n-but-1-yl]acetamide was deprotected using Method O. The resulting pair of diastereomers was purified by preparative HPLC (CH$_3$CN—H$_2$O-0.1% TFA) to afford the title compound as a single diastereomer.
$^1$H NMR (DMSO-d$_6$) δ=10.45 (1H, s), 8.24 (1H, d, J=8.4 Hz), 7.40 (4H, m), 7.29 (1H, m), 7.11 (2H, m), 6.80 (1H, d, J=8.4 Hz), 4.87 (1H, t), 4.51 (1H, m), 3.13 (2H, m), 2.73 (1H, s), 2.30 (2H, m), 2.23 (3H, s), 1.99 (3H, s), 1.89 (2H, m), 1.77 (2H, m), 1.42 (3H, m); MS m/z (M+H) 619.2; HPLC (CH$_3$CN—H$_2$O-0.1% TFA): R$_t$=3.68 min.

Example 24

Preparation of 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-4-(t-butoxy-carbonylamino)-n-but-1-yl]acetamide Z-D-Orn(Boc)-OH amino acid was coupled to pyrrolidine using Method I followed by deprotection using Method B', followed by coupling to 2-[2-(R,S)-1-(4-chloro-2,5-dimethylbenzenesulfonyl)-3-oxo-1,2,3,4-tetrahydroquinoxalin-2-yl]acetic acid using Method S. The resulting material was purified via column chromatography (silica gel) eluted with EtOAc-CH$_3$CN 95:5, separating the diastereomers to afford the title compound as a single diastereomer.
$^1$H NMR (DMSO-d$_6$) δ=10.45 (1H, s), 8.16 (1H, d, J=9.0 Hz), 7.32 (4H, m), 7.11 (1H, t), 6.81 (1H, d, J=7.5 Hz), 6.73 (1H, s), 4.87 (1H, t), 4.47 (1H, m), 3.60 (1H, m), 3.45 (1H, m), 2.87 (2H, m), 2.73 (1H, s), 2.30 (2H, m), 2.23 (3H, s), 1.98 (4H, d, J=3.6 Hz), 1.94 (1H, s), 1.83 (2H, m), 1.55 (1H, m) 1.36 (9H, s); MS m/z (M+H-Boc) 576.2; HPLC (CH$_3$CN—H$_2$O-0.1% TFA): R$_t$=5.78 min.

Example 25

Preparation of 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-4-(N'-t-butoxy-carbonylamino)-n-but-1-yl]acetamide Z-D-Orn(Boc)-OH amino acid was coupled to pyrrolidine using Method I followed by deprotection using Method B' followed by coupling to 2-[2-(R,S)-1-(4-chloro-2,5-dimethylbenzenesulfonyl)-3-oxo-1,2,3,4-tetrahydroquinoxalin-2-yl]acetic acid using Method S. The resulting material was purified via column chromatography (silica gel) eluted with EtOAc-CH$_3$CN 95:5 separating the diastereomers to afford the title compound as a single diastereomer.
$^1$H NMR (DMSO-d$_6$) δ=10.45 (1H, s), 8.15 (1H, d, J=8.1 Hz), 7.42 (3H, m), 7.29 (1H, t), 7.10 (1H, t), 6.79 (2H, m), 4.84 (1H, t), 4.46 (1H, m), 3.47 (2H, m), 2.91 (2H, m), 2.73 (1H, s), 2.29 (5H, m), 1.99 (4H, d, J=7.5 Hz), 1.88 (2H, m), 1.80 (2H, m), 1.57 (1H, m) 1.38 (9H, s); MS m/z (M+H-Boc) 576.2; HPLC (CH$_3$CN—H$_2$O-0.1% TFA): R$_t$=5.76 min.

Example 26

Preparation of 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-5-amino-n-pent-1-yl]acetamide 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-5-(t-butoxycarbonylamino)-pent-5-yl] acetamide was deprotected using Method O to afford the title compound as a single diastereomer.
$^1$H NMR (DMSO-$d_6$) δ=8.23 (1H, d, J=9.0 Hz), 7.77 (2H, s), 7.32 (4H, m), 7.12 (1H, t), 6.82 (1H, d, J=6.0 Hz), 4.91 (1H, m), 4.51 (1H, m), 3.59 (2H, m), 3.31 (2H, m), 2.74 (2H, s), 2.32 (2H, m), 2.27 (3H, s), 1.99 (3H,s), 1.82 (3H, m), 1.50 (1H, m); MS m/z (M+H) 591.3; HPLC (CH$_3$CN—H$_2$O-0.1% TFA): R$_t$=3.56 min.

Example 27

Preparation of 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-5-amino-n-pent-1-yl]acetamide 2-[2-(R or S)-1-(4-chloro-2,5-dimethylbenzene-sulfonyl)-3-oxo-1,2,3,4-tetrahydroquinoxalin-2-yl]-N-[1-(R)-pyrrolidin-N-ylcarbonyl-5-(N'-t-butoxycarbonylamino)-n-pent-5-yl]acetamide was deprotected using Method O to afford the title compound as a single diastereomer.
$^1$H NMR (DMSO-$d_6$) δ=8.20 (1H, d, J=8.4 Hz), 7.83 (2H, s), 7.39 (3H, m), 7.30 (1H, t), 7.15 (1H, t), 6.81 (1H, d, J=7.8 Hz), 4.87 (1H, m), 4.51 (1H, m), 3.27 (2H, m), 2.80 2H, m), 2.30 (2H, m), 2.23 (3H, s), 1.91 (4H, m), 1.79 (2H, m), 1.60 (3H, m) 1.39 (2H, m); MS m/z (M+H) 591.3; HPLC (CH$_3$CN—H$_2$O-0.1% TFA): R$_t$=3.32 min.

Example 28

Preparation of 2-[2-(R or S)-1-(4-chloro-2.5-dimethylbenzenesulfonyl)-3-oxo-1,2,3,4-tetrahydroquinoxalin-2-yl]-N-[1-(R)-(pyrrolidin-N-ylcarbonyl)-4-amino-n-butyl]acetamide 2-[2-(R or S)-1-(4-chloro-2,5-dimethylbenzene-sulfonyl)-3-oxo-1,2,3,4-tetrahydroquinoxalin-2-yl]-N-[1-(R)-(pyrrolidin-N-ylcarbonyl)-4-(t-butoxycarbonylamino)-n-butyl]acetamide was deprotected using Method O to afford the title compound as a single diastereomer.
$^1$H NMR (DMSO-$d_6$) δ=10.47 (1H, s), 8.27 (1H, d, J=8.4 Hz), 7.69 (2H, s), 7.33 (4H, m), 7.15 (1H, t), 6.81 (1H, d, J=9.6 Hz), 4.91 (1H, m), 4.56 (1H, m), 3.47 (2H, m), 2.75 (2H, m), 2.28 (2H, m), 2.22 (3H, s), 1.88 (4H, m), 1.50 (1H, m), 1.18 (3H, m); MS m/z (M+H) 577.2; HPLC (CH$_3$CN—H$_2$O-0.1% TFA): R$_t$=3.25 min.

Example 29

Preparation of 2-[2-(S or R)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-4-amino-n-butyl]acetamide 2-[2-(R or S)-1-(4-chloro-2,5-dimethylbenzene-sulfonyl)-3-oxo-1,2,3,4-tetrahydroquinoxalin-2-yl]-N-[1-(R)-(pyrrolidin-N-ylcarbonyl)-4-(N'-t-butoxycarbonylamino)-n-butyl]acetamide was deprotected using Method O to afford the title compound as a single diastereomer.
$^1$H NMR (DMSO-$d_6$) δ=10.46 (1H, s), 8.29 1H, d, J=8.4 Hz), 7.72 (2H, s), 7.42 (1H, m), 7.30 (1H, t), 7.12 (1H, t), 6.80 (1H, d, J=7.8 Hz), 4.91 (1H, m), 4.50 (1H, m), 3.49 (2H, m), 2.79 (2H, m), 2.30 (2H, m), 2.22 (3H, s), 1.88 (4H, m), 1.53 (4H, m); MS m/z (M+H)577.2; HPLC (CH$_3$CN—H$_2$O-0.1% TFA): R$_t$=3.36 min.

Example 30

Preparation of 2-[2-(R,S)-1-(4-chloro-2,5-dimethylbenzenesulfonyl)-3-oxo-4-methyl-1,2,3, 4-tetrahydroquinoxalin-2-yl]-N-[2-(N-methyl-1,2,5,6-tetrahydropyrid-4-yl)eth-1-yl]acetamide The title compound was synthesized from 2-[2-(R,S)-1-(4-chloro-2,5-dimethylbenzenesulfonyl)-3-oxo-4-methyl-1,2,3,4-tetrahydroquinoxalin-2-yl]-N-[2-(pyrid-4-yl)eth-1-yl]acetamide by Method J.
$^1$H NMR (d$_6$-DMSO HCl salt) δ=8.02–7.99 (m, 1H), 7.47–7.41 (m, 4H), 7.30–7.25 (m, 1H), 7.16 (d,J=8.1 Hz, 1H), 5.43–5.38 (m, 1H), 5.05–4.99 (m, 1H), 3.70–3.47 (m, 3H), 3.22–2.97 (m, 3H), 2.77–2.74 (m, 6H), 2.60–2.47 (m, 1H), 2.33–2.16 (m, 6H), 2.13–2.07 (m, 2H), 1.98–1.97 (s, 3H); MS (ES): m/e 546 (M+H); HPLC (CH$_3$CN—H$_2$O-0.1% TFA) (short column): R$_t$=3.85 min.

Example 31

Preparation of 2-[2-(R,S)-1-(4-chloro-2,5-dimethylbenzenesulfonyl)-3-oxo-1,2,3,4-tetrahydroquinoxalin-2-yl]-methylenecarbonyl-(N-morpholino)

The title compound was synthesized from 2-[2-(R,S)-1-(4-chloro-2,5-di-methylbenzenesulfonyl)-3-oxo-1,2,3,4-tetrahydroquinoxalin-2-yl]acetic acid and morpholine using Method I.
$^1$H NMR (d$_6$-DMSO) δ=10.60 (s), 7.54–7.46 (m, 3H), 7.32 (t, J=7.8 Hz, 1H), 7.18–7.14 (m, 1H), 6.88 (d, J=7.8 Hz, 1H), 4.93 (t, J=6.0 Hz, 1H), 3.57–3.50 (m, 4H), 3.47–3.40 (m, 2H), 3.35 (d, J=6.6 Hz, 2H), 3.29–3.24 (m,2H), 2.28 (s, 3H), 2.07 (s, 3H); ); MS: m/z (EI+) 479 (M+H); HPLC (CH$_3$CN—H$_2$O-0.1% TFA) (short column): R$_t$=4.98 min.

Example 32

Preparation of 2-[2-(R,S)-1-(4-chloro-2,5-dimethylbenzenesulfonyl)-3-oxo-1,2,3,4-tetrahydroquinoxalin-2-yl]-N-{[2-N-(t-butoxycarbonylmethyl)pyridin-4-yl]eth-1-yl]acetamide This title compound was synthesized from 2-[2-(R,S)-1-(4-chloro-2,5-dimethylbenzenesulfonyl)-3-oxo-1,2,3,4-tetrahydroquinoxalin-2-yl]-N-[2-(pyrid-4-yl)eth-1-yl]acetamide and t-butyl bromoacetate using the procedure described for the synthesis of 2-[2-(R,S)-1-(4-chloro-2,5-dimethylbenzenesulfonyl)-3-oxo-4-t-butoxy-carbonylmethyl-1,2,3,4-tetrahydroquinoxalin-2-yl]-N-{2-[N-(t-butoxy-carbonylmethyl)piperidin-4-yl]eth-1-yl}acetamide.
$^1$H NMR (d$_6$-DMSO) δ=10.47 (s, 1H), 8.90 (d, J=7.8 Hz, 2H), 8.13 (bs, 1H), 8.05 (d, J=7.8 Hz, 2H), 7.41–7.25 (m, 4H), 7.09 (t, J=7.8 Hz, 1H), 6.81 (d, J=7.8 Hz, 1H), 5.49 (s, 2H), 4.85–4.81 (m, 1H), 3.42 (bs, 2H), 3.02 (bs, 2H), 2.27–2.06 (m, 5H), 1.96 (s, 3H), 1.45 (s, 9H); $^{13}$C NMR (d$_6$-DMSO) δ=167.92, 166.77, 166.09, 161.72, 145.94, 139.19, 137.31, 134.65, 134.24, 133.98, 133.33, 132.63, 129.23, 128.84, 128.47, 123.56, 121.60, 116.50, 84.28, 60.53, 56.40, 38.53, 36.72, 35.34, 28.12, 19.39, 19.35; MS: m/z (EI+) 628 (M+H); HPLC (CH$_3$CN—H$_2$O-0.1% TFA) (short column): R$_t$=4.33 min.

Example 33

Preparation of 2-[2-(R,S)-1-(4-chloro-2,5-dimethyl-sulfonyl)-3-oxo-4-methyl-1,2,3,4-tetrahydroquinoxalin-2-yl]-N-[2-(pyrid-4-yl)eth-1-yl]-N-methylacetamide This compound was synthesized from 2-[2-(R,S)-1-(4-chloro-2,5-dimethylsulfonyl)-3-oxo-4-methyl-1,2,3,4-tetrahydroquinoxalin-2-yl]acetic acid and 4-methyl aminoethylpyridine using Method I.

$^1$H NMR (d$_6$-DMSO) δ=8.83 (d, J=6.6 Hz, 1.5H), 8.72 (d, J=6.6 Hz, 0.5H), 7.93 (d, J=6.6 Hz, 1.5H), 7.58 (d, J=6.6 Hz, 0.5H), 7.51–7.39 (m, 4H), 7.29–7.16 (m, 2H), 5.11–5.01 (m, 1H), 3.71–3.80 (m, 1H), 3.53–3.62 (m, 1H), 3.06 (t, J=6.6 Hz, 2H), 2.82 2.74 (m, 6H), 2.48–2.30 (m, 2H), 2.27 (s, 3H), 2.00 (s, 0.5H), 1.96 (s, 1.5H); MS: m/z (EI+) 542 (M+H); HPLC (CH$_3$CN—H$_2$O-0.1% TFA) (short column): R$_t$=3.92 min.

Example 34

Preparation of 2-[2-(R,S)-1-(4-chloro-2,5-dimethyl-benzenesulfonyl)-3-oxo-4-benzyl-1,2,3,4-tetrahydroquinoxalin-2-yl]-N-[2-(pyrid-4-yl)eth-1-yl]acetamide This compound was synthesized from 2-[2-(R,S)-1-(4-chloro-2,5-dimethyl-benzenesulfonyl)-3-oxo-4-benzyl-1,2,3,4-tetrahydroquinoxalin-2-yl]acetic acid and 4-aminoethyl pyridine using Method I.

$^1$H NMR (d$_6$-DMSO) δ=8.74 (d, J=5.4 Hz, 2H), 8.13 (t, J=4.5 Hz, 1H), 7.84 (d, J=5.4 Hz, 2H), 7.59–7.42 (m, 3H), 7.36–7.16 (m, 6H), 7.06 (d, J=7.2 Hz, 1H), 6.94 (d, J=7.2 Hz, 1H), 5.12–5.07 (m, 1H), 4.84 (d, J=16.8 Hz, 1H), 4.48 (d, J=16.8 Hz, 1H), 3.35–3.45 (m, 2H), 2.97–2.87 (m, 2H), 2.41–2.26 (m, 5H), 2.09 (s, 3H).

Example 35

Preparation of 2-[2-(R,S)-1-(4-chloro-2,5-dimethyl-benzenesulfonyl)-3-oxo-1,2,3,4-tetrahydroquinoxalin-2-yl]-N-{2-[N-(pyrid-2-yl)piperidin-4-yl]eth-1-yl}acetamide This compound was synthesized from 2-[(R,S)-1-(4-chloro-2,5-dimethylbenzenesulfonyl)-3-oxo-1,2,3,4-tetrahydroquinoxalin-2-yl]-acetic acid and [N-(pyrid-2-yl)piperidin-4-yl]eth-1-ylamine using Method I.

$^1$H NMR (d$_6$-DMSO, parent) δ=10.51 (s, 1H), 8.11 (d, J=6.6 Hz, 1H), 7.92 (bs, 1H), 7.55–7.44 (m, 4H), 7.33 (t, J=7.8 Hz, 1H), 7.15 (t, J=7.8 Hz, 1H), 6.85 (t, J=7.8 Hz, 2H), 6.60 (dd, J=5.7, 7.8 Hz, 1H), 4.91 (dd, J=4.5, 9.3 Hz, 1H), 4.33–4.29 (m, 2H), 3.21–3.13 (m, 1H), 3.04–2.97 (m, 1H), 2.81 (t, J=12.0 Hz, 2H), 2.33–2.13 (m, 5H), 2.04 (s, 3H), 1.81–1.05 (m, 7H); $^{13}$C-NMR (d$_6$-DMSO) δ=166.70, 147.82, 138.75, 137.73, 137.01, 134.26, 134.02, 132.95, 132.37, 128.83, 128.48, 123.15, 121.38, 112.48, 107.29, 56.32, 45.15, 36.24, 36.10, 33.00, 31.54, 31.43, 19.31, 19.21; MS: m/z (EI+) 597 (M+H); HPLC (CH$_3$CN—H$_2$O-0.1% TFA) (short column): R$_t$=3.92 min.

Example 36

Preparation of 2-[2-(R,S)-1-(4-chloro-2,5-dimethyl-benzenesulfonyl)-3-oxo-1,2,3,4-tetrahydroquin-2-yl]-N-(4-fluorophenethyl)acetamide This compound was synthesized from 2-[(R,S)-1-(4-chloro-2,5-dimethyl-benzenesulfonyl)-3-oxo-1,2,3,4-tetrahydroquinoxalin-2-yl]acetic acid and 4-fluorophenyl ethylamine using Method I.

$^1$H NMR (d$_6$-DMSO) δ=10.46 (s, 1H), 7.96 (t, J=5.4 Hz, 1H), 7.47–7.06 (m, 9H), 6.81 (d, J=8.1 Hz, 1H), 4.86 (dd, J=5.1, 9.0 Hz, 1H), 3.26–3.10 (m, 2H), 2.63 (t, J=7.2 Hz, 2H), 2.25–2.10 (m, 5H), 2.01 (s, 3H); MS: m/z (EI+) 531 (M+H); HPLC (CH$_3$CN—H$_2$O-0.1% TFA) (short column): R$_t$=6.17 min.

Example 37

Preparation of 2-[2-(R,S)-1-(4-chloro-2,5-dimethyl-benzenesulfonyl)-3-oxo-1,2,3,4-tetrahydroquinoxalin-2-yl]-N-[2-(4-acetamidophenethyl)]acetamide This compound was synthesized from 2-[2-(R,S)-1-(4-chloro-2,5-dimethylbenzenesulfonyl)-3-oxo-1,2,3,4-tetrahydroquinoxalin-2-yl]-N-[2-(4-aminophenyl)eth-1-yl]acetamide and acetic anhydride using Method Q'.

$^1$H NMR (d$_6$-DMSO) δ=10.52 (s, 1H), 9.90 (s, 1H), 8.00 (bs, 1H), 7.54–7.41 (m, 5H), 7.32 (t, J=7.8 Hz, 1H), 7.15–7.11 (m, 3H), 6.86 (d, J=7.8 Hz, 1H), 4.91 (dd, J=4.8, 9.0 Hz, 1H), 3.33–3.11 (m, 2H), 2.63 (t, J=6.9 Hz, 2H), 2.19–2.14 (m, 5H), 2.05 (s, 6H); MS: m/z (EI+) 570 (M+H); HPLC (CH$_3$CN—H$_2$O-0.1% TFA) (short column): R$_t$=3.35 min.

Example 38

Preparation of 2-[2-(R,S)-1-(4-chloro-2,5-dimethyl-benzenesulfonyl)-3-oxo-1,2,3,4-tetrahydroquinoxalin-2-yl]-N-{2-[4-(N',N'-dimethylamino)-phenethyl]}acetamide This compound was synthesized from 2-[(R,S)-1-(4-chloro-2,5-dimethylbenzenesulfonyl)-3-oxo-1,2,3,4-tetrahydroquinoxalin-2-yl]acetic acid and 2-[4-(N',N'-dimethylamino)phen-1-yl]eth-1-ylamine using Method I.

$^1$H NMR (d$_6$-DMSO) δ=10.52 (s, 1H), 7.97 (t, J=5.1 Hz, 1H), 7.53–7.41 (m, 3H), 7.32 (t, J=7.8 Hz, 1H), 7.13 (t, J=7.8 Hz, 1H), 7.04 (d, J=7.8 Hz, 2H), 6.87 (d, J=8.1 Hz, 1H), 6.71 (d, J=7.8 Hz, 2H), 4.92 (dd, J=5.1, 8.7 Hz, 1H), 3.23–3.09 (m, 2H), 2.88 (s, 6H), 2.56–2,53 (m, 2H), 2.31–2.15 (m, 5H), 2.07 (s, 3H); MS: m/z (EI+) 556 (M+H); HPLC (CH$_3$CN—H$_2$O-0.1% TFA) (short column): R$_t$=2.58 min.

Example 39

Preparation of 2-[2-(R,S)-1-(2,3-dichlorobenzene-sulfonyl)-3-oxo-1,2,3,4-tetrahydroquinoxalin-2-yl]-N-[2-(4-aminophen 1-yl)ethy-1-yl]acetamide This compound was synthesized from 2-[2-(R,S)-1-(2,3-dichlorobenzene-sulfonyl)-3-oxo-1,2,3,4-tetrahydroquinoxalin-2-yl]acetic acid and 4-amino phenylethyl amine using Method I.

$^1$H NMR (d$_6$-DMSO) δ=10.67 (s, 1H), 7.97–7.87 (m, 3H), 7.51 (t, J=7.8 Hz, 2H), 7.22 (t, J=7.2 Hz, 1H), 7.05 (t,

J=7.2 Hz, 1H), 6.89–6.76 (m, 3H), 6.48 (d, 2H), 4.97–4.87 (m, 1H), 4.82 (bs, 2H), 3.28–2.98 (m, 4H), 2.25–2.16 (m, 2H); MS: m/z (EI+) 534 (M+H); HPLC (CH$_3$CN—H$_2$O-0.1% TFA) (short column): R$_t$=2.20 min.

Example 40

Preparation of 2-[2-(R,S)-1-(4-chloro-2,5-dimethyl-benzenesulfonyl)-3-oxo-1,2,3,4-tetrahydro-6,7-difluoroquinoxalin-2- yl]-N-[(2-pyrid-4-yl)eth-1-yl]acetamide The title compound was synthesized from 2-[2-(R,S)-1-(4-chloro-2,5-dimethylbenzene-sulfonyl)-3-oxo-1,2,3,4-tetrahydro-6,7-difluoroquinoxalin-2-yl]acetic acid and 4-(2-aminoethyl)pyridine using Method I.

$^1$H NMR (d$_6$-DMSO) δ=10.60 (s, 1H), 8.76 (d, J=6.6 Hz, 2H), 8.04 (t, J=3.6 Hz, 1H), 7.79 (d, J=6.6 Hz, 2H), 7.47 (d, J=4.8 Hz, 2H), 7.35 (dd, J=7.8, 11.1 Hz, 1H),6.81 (dd, J=7.8, 11.1 Hz, 1H), 4.92 (dd, J=5.1, 9.6 Hz, 1H), 3.47–3.31 (m, 2H), 2.95–2.91 (m, 2H), 2.25–2.09 (m, 8H); MS: m/z (EI+) 550 (M+H); HPLC (CH$_3$CN—H$_2$O-0.1% TFA) (short column): R$_t$=2.69 min.

Example 41

Preparation of 2-[2-(R,S)-1-(4-chloro-2,5-dimethyl-benzenesulfonyl)-3-oxo-1,2,3,4-tetrahydro-6,7-difluoroquinoxalin-2-yl]-N-[2-(4-aminophenyl)eth-1-yl]acetamide This compound was synthesized from 2-[2-(R,S)-1-(4-chloro-2,5-dimethylbenzenesulfonyl)-3-oxo-1,2,3,4-tetrahydro-6,7-difluoroquinoxalin-2-yl]acetic acid and 4-amino-phenethylamine using Method I.

$^1$H NMR (d$_6$-DMSO) δ=10.61 (s, 1H), 7.99 (t, J=5.1 Hz, 1H), 7.50 (d, J=6.0 Hz, 2H), 7.39 (dd, J=8.1, 11.1 Hz, 1H), 7.25 (d, J=8.1 Hz, 2H), 7.14 (d, J=8.1 Hz, 2H), 6.84 (dd, J=8.1, 11.1 Hz, 1H), 4.79 (dd, J=4.5, 8.7 Hz, 1H), 3.25–3.09 (m, 2H), 2.65 (t, J=7.2 Hz, 2H), 2.26–2.06 (m, 8H); MS: m/z (EI+) 563 (M+H); HPLC (CH$_3$CN—H$_2$O-0.1% TFA) (short column): R$_t$=2.77 min.

Example 42

Preparation of2-[2-(R,S)-1-(4-chloro-2,5-dimethyl-benzenesulfonyl)-3-oxo-1,2,3,4-tetrahydroquinoxalin-2-yl]-N-{2-[N-(N',N'-dimethylaminocarbonyl)piperidin-4-yl]eth-1-yl}acetamide This compound was synthesized from 2-[2-(R,S)-1-(4-chloro-2,5-dimethylbenzenesulfonyl)-3-oxo-1,2,3,4-tetrahydroquinoxalin-2-yl]-N-[2-(piperidin-4-yl)eth-1-yl]acetamide and dimethylcarbamyl chloride using Method R'.

$^1$H NMR (d$_6$-DMSO) δ=10.50 (s, 1H), 7.90 (t, J=5.1 Hz, 1H), 7.49–7.43 (m, 3H), 7.33 (dt, J=1.2, 7.5 Hz, 1H), 7.16 (dt, J=1.2, 7.5 Hz, 1H), 6.87 (dd, J=1.2, 7.5 Hz, 1H), 4.91 (dd, J=4.8, 9.9 Hz, 1H), 3.58–3.53 (m, 2H), 3.19–3.10 (m, 1H), 3.05–2.94 (m, 1H), 2.74–2.65 (m, 8H), 2.32–2.12 (m, 5H), 2.05 (s, 3H), 1.75–1.03 (m, 7H); MS: m/z (EI+) 591 (M+H); HPLC (CH$_3$CN—H$_2$O-0.1% TFA) (short column): R$_t$=3.75 min.

Example 43

Preparation of 2-[2-(R,S)-1-(4-chloro-2,5-dimethyl-benzenesulfonyl)-3-oxo-1,2,3,4-tetrahydroquinoxalin-2-yl]-N-{4-[N-(N',N'-dimethylaminocarbonyl)aminophen-1-yl]}acetamide This compound was synthesized from 2-[2-(R,S)-1-(4-chloro-2,5-dimethylbenzenesulfonyl)-3-oxo-4-t-butoxy-carbonylmethyl-1,2,3,4-tetrahydroquinoxalin-2-yl]-N-{2-[N-(t-butoxycarbonylmethyl)piperidin-4-yl]eth-1-yl}acetamide and dimethylcarbamyl chloride using Method R'.

$^1$H NMR (d$_6$-DMSO) δ=10.52 (s, 1H), 8.23 (s, 1H), 8.01 (t, J=5.7 Hz, 1H), 7.53–7.40 (m, 5H), 7.32 (dt, J=1.2, 7.5 Hz, 1H), 7.16–7.10 (m, 3H), 6.87 (dd, J=1.2, 7.5 Hz, 1H), 4.91 (dd, J=4.8, 9.9 Hz, 1H), 3.28–3.09 (m, 2H), 2.95 (s, 6H), 2.61 (t, J=7.5 Hz, 2H), 2.28–2.09 (m, 5H), 2.07 (s, 3H); MS: m/z (EI+) 599 (M+H); HPLC (CH$_3$CN—H$_2$O-0.1% TFA) (short column): R$_t$=3.78 min.

Example 44

Preparation of 2-[2-(R,S)-1-(4-chloro-2,5-dimethyl-benzenesulfonyl)-3-oxo-1,2,3,4-tetrahydroquinoxalin-2-yl]-N-{2-[N-(pyrimidin-2-yl)piperidin-4-yl]eth-1-yl}acetamide The title compound was synthesized from 2-[2-(R,S)-1-(4-chloro-2,5-dimethylbenzenesulfonyl)-3-oxo-1,2,3,4-tetrahydroquinoxalin-2-yl]acetic acid and 2-[N-(pyrimidin-2-yl)piperidin-4-yl]ethylamine using Method I.

$^1$H NMR (d$_6$-DMSO) δ=10.46 (s, 1H), 8.30 (d, J=5.0 Hz, 2H), 7.86 (t, J=5.7 Hz, 1H), 7.45–7.39 (m, 3H), 7.28 (t, J=7.5 Hz, 1H), 7.11 (t, J=7.5 Hz, 1H), 6.81 (d, J=7.5 Hz, 1H), 6.54 (t, J=5.0 Hz, 1H), 4.86 (dd, J=4.8, 9.3 Hz, 1H), 4.65–4.62 (m, 2H), 3.16–3.09 (m, 1H), 2.98–2.91 (m, 1H), 2.87–2.79 (m, 2H), 2.28–2.07 (m, 5H), 1.99 (s, 3H), 1.77–0.95 (m, 7H); MS: m/z (EI+) 598 (M+H); HPLC (CH$_3$CN—H$_2$O-0.1% TFA) (short column): R$_t$=3.21 min.

Example 45

Preparation of 2-[2-(R,S)-1-(4-chloro-2,5-dimethyl-benzenesulfonyl)-3-oxo-1,2,3,4-tetrahydroquinoxalin-2-yl]-N-{2-[N-(thiazol-2-yl)piperidin-4-yl]eth-1-yl}acetamide The title compound was synthesized from 2-[2-(R,S)-1-(4-chloro-2,5-di-methylbenzenesulfonyl)-3-oxo-1,2,3,4-tetrahydroquinoxalin-2-yl]acetic acid and 2-[N-(thiazol-2-yl)piperidin-4-yl]ethylamine using Method I.

$^1$H NMR (CDCl$_3$) δ=8.10 (s, 1H), 7.64 (dd, J=1.2, 8.1 Hz, 1H), 7.52 (s, 1H), 7.29–7.24 (m, 1H), 7.18–7.12 (m, 3H), 6.74 (dd, J=1.2, 8.1 Hz, 1H), 6.25 (d, J=3.3 Hz, 1H), 6.15 (t, J=5.4 Hz, 1H), 5.05 (dd, J=3.6, 9.9 Hz, 1H), 4.02–3.96 (m, 2H), 3.37–3.27 (m, 2H), 3.11–3.00 (m, 2H), 2.55 (dd, J=4.2, 15.9 Hz, 1H), 2.36 (dd, J=10.5, 15.9 Hz, 1H), 2.25 (s, 3H), 1.97 (s, 3H), 1.88–1.36 (m, 7H); $^{13}$C NMR (CDCl$_3$) δ=167.87, 162.73, 162.16, 135.36, 134.92, 132.17, 130.28, 128.87, 128.51, 127.73, 127.32, 124.28, 123.94, 119.75, 117.00, 111.34, 102.26, 51.44, 44.37, 44.33, 32.44, 32.22, 31.17, 28.30, 26.55, 26.46, 15.04, 14.57; MS: m/z (EI+) 603 (M+H); HPLC (CH$_3$CN—H$_2$O-0.1% TFA) (short column): R$_t$=3.02 min.

Example 46

Preparation of 2-[2-(R,S)-1-(4-chloro-2,5-dimethyl-benzenesulfonyl)-3-oxo-1,2,3,4-tetrahydroquinoxalin-2-yl]-N-[4-N',N'-dimethylaminocarbonyloxy)phenyth-1-yl]acetamide The title compound was synthesized from 2-[2-(R,S)-1-(4-chloro-2,5-dimethylbenzenesulfonyl)-3-oxo-1,2,3,4-tetrahydroquinoxalin-2-yl]-acetic acid and 2-[4-(N,N-dimethylcarbamate)]ethylamine using Method I.

$^1$H NMR (d$_6$-DMSO) δ=10.52 (s, 1H), 8.05 (t, J=5.7Hz, 1H), 7.53 (s, 1H), 7.48 (s, 1H), 7.42 (d, J=8.1 Hz, 1H), 7.32 (t, J=8.1 Hz, 1H), 7.23 (d, J=8.4 Hz, 2H), 7.14 (t, J=8.1 Hz, 1H), 7.06 (d, J=8.4 Hz, 2H), 6.87 (d, J=8.1 Hz, 1H), 4.93 (dd, J=5.1, 9.0 Hz, 1H), 3.32–3.17 (m, 2H), 3.07 (s, 3H), 2.94 (s, 3H), 2.69 (t, J=7.2 Hz, 2H), 2.30–2.16 (m, 5H), 2.07 (s, 3H); MS: m/z (EI+) 600 (M+H); HPLC (CH$_3$CN—H$_2$O-0.1% TFA) (short column): R$_t$=4.33 min.

Example 47

Preparation of 2-[2-(R,S)-1-(4-chloro-2,5-dimethyl-benzenesulfonyl)-3-oxo-1,2,3,4-tetrahydroquinoxalin-2-yl]-N-{2-[N-(methylcarbonylmethylene)piperidin-4-yl]eth-1-yl}acetamide This compound was synthesized by alkylation of 2-[2-(R,S)-1-(4-chloro-2,5-dimethylbenzenesulfonyl)-3-oxo-1,2,3,4-tetrahydroquinoxalin-2-yl]-N-[2-(piperidin-4-yl)eth-1-yl]acetamide with chloroacetone using DIEA in EtOH at room temperature.

$^1$H NMR (d$_6$-DMSO) δ=10.53 (s, 1H), 7.98 (bs, 1H), 7.48–7.43 (m, 3H), 7.34 (t, J=8.1 Hz, 1H), 7.17 (t, J=8.1 Hz, 1H), 6.88 (d, J=8.1 Hz, 1H), 4.92 (dd, J=4.5, 9.3 Hz, 1H), 4.35 (s, 2H), 3.45–3.41 (m, 2H), 3.23–3.15 (m, 2H), 3.05–2.96 (m, 2H), 2.61–2.47 (m, 1H), 2.34–2.11 (m, 7H), 2.03 (s, 3H), 1.95–1.29 (m, 7H); MS: m/z (EI+) 576 (M+H); HPLC (CH$_3$CN—H$_2$O-0.1% TFA) (short column): R$_t$=2.79 min.

Example 48

Preparation of 2-[2-(R)-1-(4-chloro-2,5-dimethyl-benzenesulfonyl)-3-oxo-1,2,3,4-tetrahydroquinoxalin-2-yl]-N-{2-[N-(pyrid-2-yl)piperdin-4-yl]eth-1-yl}acetamide The title compound was synthesized using the same method described for the synthesis of 2-[2-(R,S)-1-(4-chloro-2,5-dimethylbenzene-sulfonyl)-3-oxo-1,2,3,4-tetrahydroquinoxalin-2-yl]-N-{2-[N-(pyrid-2-yl)piperidin-4-yl]eth-1-yl}acetamide starting with 2-[2-(R)-1-(4-chloro-2,5-dimethyl-benzenesulfonyl)-3-oxo-1,2,3,4-tetrahydroquinoxalin-2-yl]acetic acid.

$^1$H NMR (d$_6$-DMSO, HCl salt) δ=10.51 (s, 1H), 8.03–7.96 (m, 3H), 7.55–7.41 (m, 4H), 7.34 (t, J=7.5 Hz, 1H), 7.18 (t, J=7.5 Hz, 1H), 6.94–6.86 (m, 2H), 4.91 (dd, J=5.1, 9.9 Hz, 1H), 4.31–4.27 (m, 2H), 3.39–3.17 (m, 3H), 3.05–3.01 (m, 1H), 2.65–2.46 (m, 1H), 2.34–2.12 (m, 4H), 2.03 (s, 3H), 1.96–1.73 (m, 3H), 1.39–1.09 (m, 4H); MS: m/z (EI+) 597 (M+H); HPLC (CH$_3$CN—H$_2$O-0.1% TFA) (short column): R$_t$=3.03 min.

Example 49

Preparation of 2-[2-(R,S)-1-(2,3-dichlorobenzenesulfonyl)-3-oxo-1,2,3,4-tetrahydroquinoxalin-2-yl]-N-{2-[N-(pyrid-2-yl)piperidin-4-yl]eth-1-yl}acetamide The title compound was synthesized using the procedure described for 2-[2-(R,S)-1-(4-chloro-2,5-dimethylbenzenesulfonyl)-3-oxo-1,2,3,4-tetrahydroquinoxalin-2-yl]-N-{2-[N-(pyrid-2-yl)piperidin-4-yl]eth-1-yl}acetamide using 2-[2-(R,S)-1-(2,3-dichlorobenzenesulfonyl)-3-oxo-1,2,3,4-tetrahydroquinoxalin-2-yl]acetic acid and N-[2-N-(pyrid-2-yl)piperidin-4-yl]eth-1-yl amine as a starting material $^1$H NMR (d$_6$-DMSO) δ=10.71 (s, 1H), 8.12 (d, J=5.1 Hz, 1H), 7.99 (d, J=8.1 Hz, 1H), 7.93–7.89 (m, 2H), 7.57–7.49 (m, 3H), 7.26 (t, J=7.8 Hz, 1H), 7.10 (t, J=7.8 Hz, 1H), 6.92 (d, J=7.5 Hz, 1H), 6.84 (d, J=8.1 Hz, 1H), 6.60 (t, J=7.8 Hz, 1H), 4.97 (dd, J=5.1, 9.3 Hz, 1H), 4.33–4.29 (m, 2H), 3.18–3.09 (m, 1H), 3.07–2.96 (m, 1H), 2.79 (t, J=12.6 Hz, 2H), 2.37–2.32 (m, 2H), 1.81–1.05 (m, 7H); MS: m/z (EI+) 603 (M+,+H); HPLC (CH$_3$CN—H$_2$O-0.1% TFA) (short column): R$_t$=2.71 min.

Example 50

Preparation of 2-[2-(R,S)-1-(2,3-dichlorobenzenesulfonyl)-3-oxo-1,2,3,4-tetrahydroquinoxalin-2-yl]-N-methyl-N-{2-[N-(pyrid-2-yl)piperidin-4-yl]eth-1-yl}acetamide The title compound was synthesized using Method I from N-methyl-N-[(pyrid-2-ylpiperidin-4-yl)eth-1-yl]amine and 2-[2-(R,S)-1-(2,3-dichlorobenzenesulfonyl)-3-oxo-1,2,3,4-tetrahydroquinoxalin-2-yl]acetic acid. MS: m/z (EI+) 617 (M+H); HPLC (CH$_3$CN—H$_2$O-0.1% TFA) (short column): R$_t$=2.86 min.

Example 51

Preparation of 2-[2-(R,S)-1-(2,3-dichlorobenzenesulfonyl)-3-oxo-1,2,3,4-tetrahydroquinoxalin-2-yl]-N-{2-[1-(N-(methylimidizol-4-yl)eth-1-yl]}acetamide The title compound was synthesized from 2-[2-(R,S)-1-(2,3-dichlorobenzenesulfonyl)-3-oxo-1,2,3,4-tetrahydroquinoxalin-2-yl]acetic acid and 1-methyl-histamine using Method I.

$^1$H NMR ($^1$H) δ=7.92 (dd, J=1.8, 7.5 Hz, 1H), 7.75 (dd, J=1.8, 7.5 Hz, 1H), 7.57 (dd, J=1.8, 7.5 Hz, 1H), 7.49 (s, 1H), 7.36 (t, J=7.8 Hz, 1H), 7.19 (dt, J=1.8, 7.5 Hz, 1H), 7.05 (dt, J=1.8, 7.5 Hz, 1H), 6.90–6.84 (m, 2H), 5.23 (dd, J=4.8, 9.9 Hz, 1H3.69 (s, 3H), 3.49–3.3.39 (m, 1H), 3.36–3.26 (m, 1H), 2.70 (t, J=7.2 Hz, 2H), 2.46 (dd, J=4.8, 14.1 Hz, 1H), 2.34 (dd, J=9.9, 14.1 Hz, 1H); $^{13}$C NMR (CD$_3$OD) δ=163.95, 163.12, 134.21, 132.57, 130.73, 130.59, 121.52, 126.76, 125.38, 123.00, 122.81, 121.69, 118.54, 116.99, 112.81, 111.28, 52.06, 34.28, 32.03, 27.43, 22.55; MS: m/z (EI+) 523 (M+H); HPLC (CH$_3$CN—H$_2$O-0.1% TFA) (short column): R$_t$=2.36 min.

Example 52

Preparation of 2-[2-(R,S)-1-(2,3-dichlorobenzenesulfonyl)-3-oxo-1,2,3,4-tetrahydroquinoxalin-2-yl]-N-[2-(N',N'-dimethylamino)eth-1-yl]acetamide This compound was synthesized from 2-[2-(R,S)-1-(2,3-dichlorobenzenesulfonyl)-3-oxo-1,2,3,4-tetrahydroquinoxalin-2-yl]acetic acid and N',N'-dimethylethylenediamine using Method I.

$^1$H NMR ($d_6$-DMSO, parent) δ=10.78 (s, 1H), 8.30 (t, J=5.1 Hz, 1H), 8.01 (dd, J=1.8, 8.4 Hz, 1H), 7.91(dd, J=1.8, 8.4 Hz, 1H), 7.59–7.53 (m, 2H), 7.27 (dt, J=1.8, 7.8 Hz, 1H), 7.10 (t, J=7.8 Hz, 1H), 6.93 (d, J=7.8 Hz, 1H), 5.02 (dd, J=4.2, 8.7 Hz, 1H), 3.43–3.36 (m, 2H), 3.14–3.07 (m, 2H), 2.84 (s, 3H), 2.83 (s, 3H), 2.60–2.26 (m, 2H); MS: m/z (EI+) 486 (M+H); HPLC (CH$_3$CN—H$_2$O-0.1% TFA) (short column): R$_t$=2.38 min.

Example 53

Preparation of 2-[2-(R,S)-1-(2,3-dichlorobenzenesulfonyl)-3-oxo-1,2,3,4-tetrahydroquinoxalin-2-yl]-N-[2-(imidizol-4-yl)eth-1-yl]acetamide This compound was synthesized from 2-[2-(R,S)-1-(2,3-dichlorobenzenesulfonyl)-3-oxo-1,2,3,4-tetrahydroquinoxalin-2-yl]acetic acid and histamine using Method I. MS: m/z (EI+) 509 (M+H); HPLC (CH$_3$CN—H$_2$O-0.1% TFA) (short column, low gradient): R$_t$=13.50 min.

Example 54

Preparation of 2-[2-(R,S)-1-(5-chloro-1,3-dimethylpyrazol-4-ylsulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-(3-oxo-1,2,3,4-tetrahydro-quinoxalin-2-yl]-N-(pyrid-4-yl)ethylacetamide and 2-chloro 3-N-methyl 5-methylpyrazole sulfonyl chloride using Method G.

$^1$H NMR (DMSO-d$_6$) δ=8.47 (2H, d, J=6.0 Hz), 8.00 (1H, t), 7.26 (4H, m), 7.09 (1H, t), 6.84 (1H, d, J=9.0 Hz), 4.92 (1H, m), 4.10 (1H, q), 3.70 (3H, s), 3.23 (2H, m), 2.69 (2H, m), 2.18 (m, 2H), 1.81 (3H, s); $^{13}$C NMR (DMSO-d$_6$) δ=167.26, 166.91, 149.75, 148.69, 148.04, 133.69, 130.01, 129.16, 128.95, 124.56, 123.12, 121.28, 116.03, 112.87, 55.97, 36.94, 36.49, 34.32, 13.01; MS m/z (M+H) 504; HPLC (CH$_3$CN—H$_2$O-0.1% TFA): R$_t$=6.69.

Example 55

Preparation of 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-2-(4-iodophenyl)-eth-1-yl]acetamide Boc-D-p-iodo phenylalanine was coupled with pyrrolidine using Method S to afford N-Boc-{1-(R)-[pyrrolidin-N-ylcarbonyl]-2-(4-iodophenyl)}eth-1-ylamine (compound 1061) which was deprotected using Method O and coupled to 2-[2-(R,S)-1-(4-chloro-2,5-dimethylbenzenesulfonyl)-3-oxo-1,2,3,4-tetrahydroquinoxalin-2-yl]acetic acid using Method S. The resulting material was purified via column chromatography (silica gel) eluted with EtOAc-Hexanes 1:4 separating the diastereomers to afford the title compound as a single diastereomer.

$^1$H NMR (CD$_3$OD) δ=7.59 (3H, m), 7.49 (1H, s), 7.23 (3H, m), 7.01 (2H, d, J=8.1 Hz), 6.82 (1H, d, J=9.3 Hz), 5.07 (1H, m), 3.72 (1H, m), 3.46 (1H, m), 3.06 (1H, m), 2.95 (1H, m), 2.83 (1H, m), 2.38 (2H, m), 2.26 (3H, s), 1.99 (3H, s), 1.75 (2H, m); MS m/z (M+H) 736.

Example 56

Preparation of 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-2-(4-iodophenyl)eth-1-yl]acetamide Boc-D-p-iodo phenylalanine was coupled with pyrrolidine using Method S to afford N-Boc-{1-(R)-[pyrrolidin-N-ylcarbonyl]-2-(4-iodophenyl)}eth-1-yl-amine (compound 1061) which was deprotected using Method O and coupled to 2-[2-(R,S)-1-(4-chloro-2,5-dimethylbenzenesulfonyl)-3-oxo-1,2,3,4-tetrahydroquinoxalin-2-yl]acetic acid using Method S. The resulting material was purified via column chromatography (silica gel) eluted with EtOAc-Hexanes 1:4 separating the diastereomers to afford the title compound as a single diastereomer.

$^1$H NMR (CD$_3$OD) δ=7.56 (2H, d, J=13.2 Hz), 7.51 (1H, s), 7.32 (3H, m), 7.13 (3H, m), 6.81 (1H, d, J=9.0 Hz), 5.08 (1H, m), 3.68 (1H, m), 3.46 (1H, m), 3.01 (1H, m), 2.96 (1H, m), 2.89 (1H, m), 2.40 (2H, m), 2.28 (3H, s), 2.17 (3H, s), 1.91 (2H, m); MS m/z (M+H) 735.

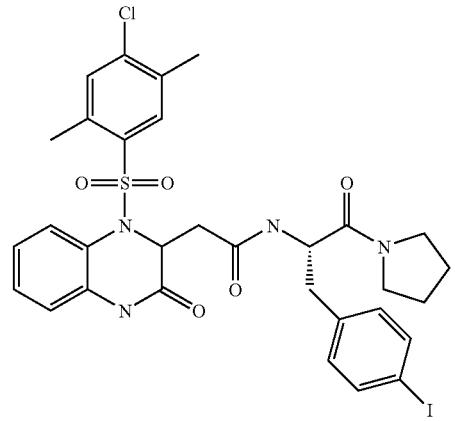

Example 57

Preparation of 2-[2-(R or S)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[4-(N-t-butoxycarbonylpyrrol-2-yl)phenyl]eth-1-yl}acetamide The title compound was synthesized from 2-[2-(R,S)-1-(4-chloro-2,5-dimethyl-benzenesulfonyl)-3-oxo-1,2,3,4-tetrahydroquinoxalin-2-yl]acetic acid and 2-Boc-pyrrole boronic acid using Method C' affording the title compound as a single diastereomer.

$^1$H NMR (CDCl$_3$) δ=8.02 (1H, s), 7.68 (1H, d, J=8.4 Hz), 7.54 (1H, s), 7.35 (3H, m), 7.20 (2H, m), 7.04 (2H, m), 6.74 (1H, d, J=7.8 Hz), 6.22 (1H, m), 6.15 (1H, m), 5.19 (1H, m), 5.00 (1H, m), 3.53 (1H, m), 3.00 (1H, m), 2.42 (2H, m), 2.26 (3H, s), 2.07 (3H, s), 1.42 (9H, s); MS m/z (M+H) 775; HPLC (CH$_3$CN—H$_2$O-0.1% TFA): R$_t$=4.67 min.

Example 58

Preparation of 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-2-(4-biphenyl)eth-1-yl]acetamide D-Biphenylalanine was protected with di-tert butyl dicarbonate using the protection aspects of Method A' followed by coupling with pyrrolidine using Method I, followed by deprotection using Method O, followed by coupling with 2-[2-(R,S)-1-(4-chloro-2,5-dimethylbenzenesulfonyl)-3-oxo-1,2,3,4-tetrahydroquinoxalin-2-yl] acetic acid using Method I. The residue was purified via column chromatography (silica gel) eluted with EtOAc-Hexanes, 1:4 and prep plate (silica gel), eluted with EtOAc-Hex, 1:9 separating the diastereomers to afford the title compound as a single diastereomer.

$^1$H NMR (DMSO-$d_6$) δ=10.47 (1H, s), 8.41 (1H, d, J=9.0 Hz), 7.62 (2H, d, J=9.0 Hz), 7.54 (2H, d, J=9.0 Hz), 7.34 (10H, m), 7.12 (1H, t), 6.82 (1H, d, J=9.0 Hz), 4.83 (1H, m), 4.69 (1H, m), 3.50 (1H, m), 2.90 (1H, m), 2.74 (1H, m), 2.25 (3H, s), 1.99 (3H, s), 1.79 (3H, m); MS m/z (M+H) 686; HPLC (CH$_3$CN—H$_2$O-0.1% TFA): R$_t$=7.03 min

Example 59

Preparation of 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-2-(4-biphenyl)ethy-1-yl]acetamide D-Biphenylalanine was protected using the protection aspects of Method A' followed by coupling with pyrrolidine using Method I, followed by deprotection using Method O, followed by coupling with 2-[2-(R,S)-1-(4-chloro-2,5-dimethylbenzenesulfonyl)-3-oxo-1,2,3,4-tetrahydroquinoxalin-2-yl]acetic acid using Method I. The residue was purified via column chromatography (silica gel) eluted with EtOAc-Hexanes, 1:4 and prep plate (silica gel) eluted with EtOAc-Hex, 1:9 separating the diastereomers to afford the title compound as a single diastereomer.

$^1$H NMR (DMSO-$d_6$) δ=10.47 (1H, s), 8.39 (1H, d, J=6.0 Hz), 7.61 (4H, m), 7.36 (10H, m), 7.04 (1H, t), 6.81 (1H, d, J=9.0 Hz), 4.8 (1H, t), 4.66 (1H, dd), 3.49 (1H, m), 2.91 (1H, m), 2.76 (1H, m), 2.23 (3H, s), 1.99 (3H, s), 1.76 (3H, m); MS m/z (M+H) 686; HPLC (CH$_3$CN—H$_2$O-0.1% TFA): R$_t$=6.99 min.

Example 60

Preparation of 2-[2-(R or S)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[4-(pyrid-2-yl)phenyl]eth-1-yl}acetamide The title compound was synthesized from compound 1061 and 2-pyridyl using Method D', followed by deprotection using Method P, followed by coupling with 2-[2-(R,S)-1-(4-chloro-2,5-dimethylbenzene-sulfonyl)-3-oxo-1,2,3,4-tetrahydro-quinoxalin-2-yl]acetic acid using Method I. The resulting material was purified via column chromatography (silica gel) eluted with EtOAc-CH$_3$CN-95:5. Trituration with MeOH afforded the separation of the diastereomers to afford the title compound as a single diastereomer.

$^1$H NMR (DMSO-$d_6$) δ=10.47 (1H, s), 8.64 (1H, d, J=6.0 Hz), 8.41 (1H, d, J=9.0 Hz), 7.89 (4H, m), 7.33 (6H, m), 7.12 (1H, t), 6.82 (1H, d, J=9.0 Hz), 4.83 (1H, m), 4.72 (1H, m), 3.51 (1H, m), 2.94 (2H, m), 2.70 (2H, m), 2.22 (3H, s), 1.99 (3H, s), 1.81 (3H, m); MS m/z (M+H) 687; HPLC (CH$_3$CN—H$_2$O-0.1% TFA): R$_t$=4.13 min.

Example 61

Preparation of 2-[2-(S or R)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[4-(pyrid-2-yl)phenyl]eth-1-yl}acetamide The title compound was synthesized from compound 1061 and 2-pyridyl stannane using Method D', followed by deprotection using Method P, followed by coupling with 2-[2-(R,S)-1-(4-chloro-2,5-dimethylbenzene-sulfonyl)-3-oxo-1,2,3,4-tetra-hydroquinoxalin-2-yl]acetic acid using Method I. The resulting material was purified via column chromatography (silica gel), eluted with EtOAc-CH$_3$CN-95:5. Trituration with MeOH afforded the separation of the diastereomers to afford the title compound as a single diastereomer.

$^1$H NMR (DMSO-$d_6$) δ=10.48 (1H, s), 8.67 (1H, d, J=3.0 Hz), 8.39 (1H, d, J=6.0 Hz), 7.91 (4H, m), 7.31 (6H, m), 7.03 (1H, t), 6.82 (1H, d, J=6.0 Hz 4.83 (1H, m), 4.64 (1H, m), 3.49 (1H, m), 2.85 (2H, m), 2.76 (2H, m), 2.22 (3H, s), 1.99 (3H, s), 1.75 (3H, m); MS m/z (M+H) 687; HPLC (CH$_3$CN—H$_2$O-0.1% TFA): R$_t$=3.99 min.

Example 62

Preparation of 2-[2-(R or S)-1-(4-chloro-2,5-dimethylbenzenesulfonyl)-3-oxo-1,2,3,4-tetrahydroquinoxalin-2-yl]-N-{1-(R)-(pyrrolidin-N-ylcarbonyl)-2-[4-(pyrimidin-2-yl)phenyl]eth-1-yl}acetamide 1-[(R)-1-pyrrolidin-1-ylcarbonyl-1-(t-butoxycarbonylamino)-1-(4-(2-pyrimidinyl)phenyl]ethane was synthesized from compound 1061 and bromopyrimidine using Method E' followed by deprotection using Method P followed by coupling with 2-[2-(R,S)-1-(4-chloro-2,5-dimethylbenzene-sulfonyl)-3-oxo-1,2,3,4-tetrahydroquinoxalin-2-yl]acetic acid using Method I. The resulting material was purified via column chromatography (silica gel) (EtOAc-CH$_3$CN-95:5) and prep plate (silica gel) (EtOAc-CH$_3$CN-9: 1) separating the diastereomers to afford the title compound as a single diastereomer.

$^1$H NMR (300 MHz, (DMSO-$d_6$) δ=10.47 (1H, s), 8.88 (1H, d, J=6.0 Hz), 8.43 (1H, d, J=6.0 Hz), 8.26 (1H, d, J=9.0 Hz), 7.34 (6H, m), 7.12 (1H, t), 6.82 (1H, d, J=9.0 Hz), 4.82 (1H, m), 4.73 (1H, m), 3.51 (1H, m), 2.99 (2H, m), 2.72 (2H, m), 2.22 (3H, s), 1.99 (3H, s); MS m/z (M+H) 688; HPLC (CH$_3$CN—H$_2$O-0.1% TFA): R$_t$=3.84 min.

Example 63

Preparation of 2-[2-(R or S)-1-(4-chloro-2,5-dimethylbenzenesulfonyl)-3-oxo-1,2,3,4-tetrahydroquinoxalin-2-yl]-N-1-(R)-[pyrrolidin-N-ylcarbonyl]-2-[4-(pyrimidin-2-yl)phenyl]eth-1-yl}acetamide 1-[(R)-1-pyrrolidin-1-ylcarbonyl-1-(t-butoxycarbonylamino)-1-(4-(2-pyrimidinyl)phenyl]ethane was synthesized from compound 1061 and bromopyrimidine using Method E', followed by deprotection using Method P followed by coupling with 2-[2-(R,S)-1-(4-chloro-2,5-dimethylbenzene-sulfonyl)-3-oxo-1,2,3,4-tetrahydroquinoxalin-2-yl]acetic acid using Method I. The resulting material was purified via column chromatography (silica gel), eluted with EtOAc-CH$_3$CN-95:5 and prep plate (silica gel) eluted with EtOAc-CH$_3$CN-9:1 separating the diastereomers to afford the title compound as a single diastereomer.

$^1$H NMR (DMSO-d$_6$) δ=10.48 (1H, s), 8.91 (1H, d, J=3.0 Hz), 8.31 (1H, d, J=6.0 Hz), 7.35 (6H, m), 7.06 (1H, t), 6.82 (1H, d, J=9.0 Hz), 4.83 (1H, m), 4.66 (1H, m), 3.47 (1H, m), 2.91 (2H, m), 2.64 (2H, m), 2.22 (3H, s), 1.98 (3H, s); MS m/z (M+H) 688; HPLC (CH$_3$CN—H$_2$O-0.1% TFA): R$_t$=3.80 min.

Example 64

Preparation of 2-[2-(S or R)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[4-(piperidin-2-yl)cyclohexyl]eth-1-yl}acetamide 2-[2-(R or S)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[4-(pyrid-2-yl)phenyl]eth-1-yl}acetamide (15 mgs, 0.02 mmol) was dissolved in MeOH (5 mL) and transferred to a Parr hydrogenation bottle. PtO$_2$ (50 mgs) and AcOH (2 mL) were added and the mixture was hydrogenated at 40 psi overnight. The reaction mixture was filtered through celite and condensed under reduced pressure. The resulting material was purified by preparative HPLC (CH$_3$CN—H$_2$O-0.1% TFA) to afford the title compound as a single diastereomer.

$^1$H NMR (DMSO-d$_6$) δ=8.11 (1H, m), 7.59 (1H, d, J=7.8 Hz), 7.47 (1H, d, J=4.2 Hz), 7.34 (1H, t), 7.27 (1H, s), 7.21 (1H, t), 6.83 (1H, d, J=8.1 Hz), 5.12 (1H, m), 3.70 (2H, m), 3.09 (3H, m), 2.42 (2H, m), 2.28 (3H, s), 2.04 (3H, s) 1.90 (6H, m), 1.56 (11H, m); MS m/z (M+H) 699; HPLC (CH$_3$CN—H$_2$O-0.1% TFA): R$_t$=2.73 min.

Example 65

Preparation of 2-[2-(R or S)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[4-(piperidin-2-yl)cyclohexyl]eth-1-yl}acetamide 2-[2-(R or S)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[4-(pyrid-2-yl)phenyl]eth-1-yl}acetamide (15 mgs, 0.02 mmol) was dissolved in MeOH (5 mL) and transferred to a Parr hydrogenation bottle. PtO$_2$ (50 mgs) and AcOH (2 mL) were added and the mixture was hydrogenated at 40 psi overnight. The reaction mixture was filtered through celite and condensed under reduced pressure. The resulting material was purified by preparative HPLC (CH$_3$CN—H$_2$O-0.1% TFA) to afford the title compound as a single diastereomer.

$^1$H NMR (CD$_3$OD) δ=8.23 (1H, m), 7.57 (1H, d, J=7.8 Hz), 7.49 (1H, s), 7.30 (1H, t), 7.26 (1H, s), 7.20 (1H, t), 6.81 (1H, d, J=6.6 Hz), 5.11 (1H, m), 3.88 (1H, m), 3.56 (3H, m), 3.09 (2H, m), 2.28 (3H, s), 2.05 (3H, s), 1.56 (11H, m); MS m/z (M+H) 699; HPLC (CH$_3$CN—H$_2$O-0.1% TFA): R$_t$=2.89 min.

Example 66

Preparation of 2-[2-(S or R)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[4-(N-methyl-1,2,3,6-tetrahydropyridin-6-yl)phenyl]eth-1-yl}acetamide The title compound was synthesized from 2-[2-(R or S)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[4-(pyrid-2-yl)phenyl]eth-1-yl}acetamide using Method F' followed by Method G'.

$^1$H NMR (CD$_3$OD) δ=7.59 (1H, d, J=9.0 Hz), 7.51 (1H, s), 7.23 (7H, m), 6.82 (1H, d, J=7.8 Hz), 5.80 (2H, dd), 5.07 (1H, m), 3.67 (1H, m), 2.90 (4H, m), 2.39 (3H, m), 2.28 (3H, s), 2.03 (3H, s), 1.90 (2H, m), 1.67 (3H, m), 0.91 (5H, m); $^{13}$C NMR (CD$_3$OD) δ=168.04, 136.66, 136.10, 134.31, 133.83, 132.86, 132.42, 131.94, 129.23, 128.63, 128.26, 127.63, 124.85, 123.18, 115.53, 59.98, 56.52, 52.54, 37.23, 36.03, 34.33, 25.17, 23.54, 19.29, 18.50, 17.79, 12.90; MS m/z (M+H) 705; HPLC (CH$_3$CN—H$_2$O-0.1% TFA): R$_t$=2.85 min.

Example 67

Preparation of 2-[2-(S or R)-1-(4-chloro-2,5-dimethylbenzenesulfonyl)-3-oxo-1,2,5,6-tetrahydroquinoxalin-2-yl]-N-{1-(R)-[pyrrolidin-N-ylcarbonyl]-2-[4-(N-methyl-1,2,5,6-tetrahydropyridin-6-yl)phenyl]eth-1-yl}acetamide The title compound was synthesized from 2-[2-(R or S)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[4-(pyrid-2-yl)phenyl]eth-1-yl}acetamide using Method F' followed by Method G'.

$^1$H NMR (CD$_3$OD) δ=7.53 (1H, s), 7.31 (7H, m), 7.15 (1H, t), 6.82 (1H, d, J=7.8 Hz), 5.81 (2H, dd), 5.08 (1H, m), 3.61 (2H, m), 3.00 (4H, m), 2.40 (3H, m), 2.29 (3H, s), 2.03 (3H, s), 1.86 (2H, m), 1.69 (2H, m), 0.91 (4H, m); MS m/z (M+H) 705; HPLC (CH$_3$CN—H$_2$O-0.1% TFA): R$_t$=2.74 min.

Example 68

2-[2-(R or S)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[4-(pyridin-4-yl)phenyl]eth-1-yl}acetamide The title compound was prepared from compound 1061 and 4-pyridyl stannane using Method D', followed by deprotection using Method P, followed by coupling with 2-[2-(R,S)-1-(4-chloro-2,5-dimethylbenzenesulfonyl)-3-oxo-1,2,3,4-tetrahydroquinoxalin-2-yl]acetic acid using Method I. The resulting material was purified by preparative HPLC (CH$_3$CN—H$_2$O-0.1% TFA) to afford the title compound as a single diastereomer.

$^1$H NMR (CD$_3$OD) δ=8.78 (2H, d, J=6.6 Hz), 8.41 (1H, d, J=8.1 Hz), 8.27 (2H, d, J=6.6 Hz), 7.97 (2H, d, J=8.4 Hz), 7.56 (2H, d, J=8.1 Hz), 7.45 (1H, d, J=6.6 Hz), 7.31 (3H, m), 7.07 (1H, t), 6.80 (1H, d, J=7.8 Hz), 5.03 (2H, m), 3.71 (1H, m), 3.46 (1H, m), 3.20 (1H, m), 3.08 (1H, m), 2.36 (2H, m), 2.27 (3H, s), 2.01 (3H, s), 1.83 (2H, m) 1.31 (2H, m); MS m/z (M+H) 687; HPLC (CH$_3$CN—H$_2$O-0.1% TFA): R$_t$=2.95 min.

Example 69

Preparation of 2-[2-(S or R)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[4-(pyridin-4-yl)phenyl]eth-1-yl}acetamide The title compound was prepared from compound 1061 and 4-pyridyl stannane using Method D', followed by deprotection using Method P, followed by coupling with 2-[2-(R, S)-1-(4-chloro-2,5-dimethylbenzenesulfonyl)-3-oxo-1,2,3,4-tetra-hydroquinoxalin-2-yl]acetic acid using Method I. The resulting material was purified by preparative HPLC ($CH_3CN$—$H_2O$-0.1% TFA) to afford the title compound as a single diastereomer.

$^1$H NMR ($CD_3OD$) δ=8.76 (2H, d, J=5.7 Hz), 8.41 (1H, d, J=8.7 Hz), 8.19 (2H, d, J=5.4 Hz), 7.87 (2H, d, J=8.1 Hz), 7.57 (2H, d, J=9.3 Hz), 7.49 (3H, m), 7.33 (1H, t), 7.25 (1H, s), 7.19 (1H, t), 6.81 (1H, d, J=8.1 Hz), 5.05 (2H, m), 3.77 (1H, m), 3.53 (2H, m), 3.15 (2H, m), 2.99 (1H, m), 2.37 (2H, m), 2.27 (3H, s), 2.03 (3H, s), 1.79 (2H, m), 1.31 (2H, m); MS m/z (M+H) 687; HPLC ($CH_3CN$—$H_2O$-0.1% TFA): $R_t$=3.13 min.

Example 70

Preparation of 2-[2-(R or S)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[(N-methyl-1,2,5,6-tetrahydropyridin-4-yl)-phen-4-yl]eth-1-yl}acetamide The title compound was synthesized from 2-[2-(S or R)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[4-(pyridin-4-yl)phenyl]eth-1-yl}acetamide using Method J. The resulting solid was purified by preparative HPLC ($CH_3CN$—$H_2O$-0.1% TFA) to afford the title compound as a single diastereomer.

$^1$H NMR ($CD_3OD$) δ=8.35 (1H, d, J=6.0 Hz), 7.57 (1H, d, J=9.3 Hz), 7.45 (3H, m), 7.29 (5H, m), 6.81 (1H, d, J=9.3 Hz), 6.15 (1H, m), 5.05 (2H, m), 4.04 (1H, m), 3.73 (3H, m), 3.53 (2H, m), 3.02 (3H, s), 2.89 (3H, m), 2.28 (3H, s), 2.03 (3H, s), 1.94 (1H, m), 1.76 (2H, m); MS m/z (M+H) 705; HPLC ($CH_3CN$—$H_2O$-0.1% TFA): $R_t$=2.85 min.

Example 71

Preparation of 2-[2-(R or S)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[(N-methyl-1,2,5,6-tetrahydropyridin-4-yl)-phen-4-yl]eth-1-yl}acetamide The title compound was synthesized from 2-[2-(R or S)-1-(4-chloro-2,5-dimethylbenzene-sulfonyl)-3-oxo-1,2,3,4-tetrahydroquinoxalin-2-yl]-N-{1-(R)-[pyrrolidin-N-ylcarbonyl]-2-[4-(pyridin-4-yl)phenyl]eth-1-yl}acetamide using Method J. The resulting solid was purified by preparative HPLC ($CH_3CN$—$H_2O$-0.1% TFA) to afford the title compound as a single diastereomer.

$^1$H NMR ($CD_3OD$) δ=8.34 (1H, d, J=7.8 Hz), 7.50 (3H, m), 7.31 (5H, m), 7.11 (1H, t), 6.81 (1H, d, J=9.3 Hz), 6.17 (1H, m), 5.06 (2H, m), 4.04 (1H, m), 3.56 (3H, m), 3.09 (3H, s), 2.37 (2H, m), 2.28 (3H, s), 2.03 (3H, s), 1.80 (4H, m); mixture was stirred at room temperature overnight. The solid was removed HPLC ($CH_3CN$—$H_2O$-0.1% TFA): $R_t$=2.69 min.

Example 72

Preparation of 2-[2-(R or S)-1-(4-chloro-2,5-dimethylbenzenesulfonyl)-3-oxo-1,2,3,4-tetrahydroquinoxalin-2-yl]-N-{1-[(R)-(pyrrolidin-N-ylcarbonyl)]-2-[N-(methylpyrid-2-yl)phen-4-yl]eth-1-yl}acetamide iodide salt The title compound was synthesized from 2-[2-(R or S)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[4-(pyrid-2-yl)phenyl]eth-1-yl}acetamide using Method F'.

$^1$H NMR (DMSO-$d_6$) δ=9.1 (1H, d, J=6.9 Hz), 8.62 (1H, t), 8.46 (1H, d, J=8.7 Hz), 8.14 (1H, t), 8.02 (1H, d, J=8.1 Hz), 7.55 (2H, d, J=8.4 Hz), 7.41 (9H, m), 7.14 (1H, t), 6.82 (1H, d, J=8.1 Hz), 4.80 (2H, m), 4.10 (3H, s), 3.57 (1H, m), 3.16 (1H, m), 3.03 (1H, m), 2.77 (2H, m), 2.19 (3H, s), 1.98 (3H, s), 1.79 (3H, m); MS m/z (M+H) 701; HPLC ($CH_3CN$—$H_2O$-0.1% TFA): $R_t$=3.41 min

Example 73

Preparation of 2-[2-(R or S)-1-(4-chloro-2,5-dimethylbenzenesulfonyl)-3-oxo-1,2,3,4-tetrahydroquinoxalin-2-yl]-N-{1-[(R)-(pyrrolidin-N-ylcarbonyl)]-2-[N-(methylpyrid-4-yl)phen-4-yl]eth-1-yl}acetamide iodide salt 2-[2-(S or R)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[4-(pyridin-4-yl)phenyl]eth-1-yl}acetamide (300 mg, 0.4 mmol) was dissolved in MeOH (5 mL) and to it added MeI (5 mL). The mixture was stirred at room temperature overnight. The solvent was removed under reduced pressure and the resulting solid purified via column chromatography (silica gel) eluted with $CH_2Cl_2$—MeOH, 9:1 to afford the title compound.

$^1$H NMR (DMSO-$d_6$) δ=10.50 (1H, s), 8.99 (2H, d), 8.49 (3H, d), 8.00 (2H, d), 7.36 (5H, m), 7.16 (1H, t), 6.85 (1H, d), 4.82 (2H, m), 4.34 (3H, s), 3.59 (1H, m), 3.05 (1H, m), 2.75 (2H, m), 2.24 (3H, s), 2.08 (3H, s), 1.81 (3H, m); MS m/z (M+1) 701; HPLC ($CH_3CN$—$H_2O$-0.1% TFA): $R_t$=3.09 min.

Example 74

Preparation of 2-[2-(R or S)-1-(4-chloro-2,5-dimethylbenzenesulfonyl)-3-oxo-1,2,3,4-tetrahydroquinoxalin-2-yl]-N-{1-[(R)-(pyrrolidin-N-ylcarbonyl)]-2-[1-(piperidin-2-yl)phen-4-yl]eth-1-yl}acetamide 2-[2-(R or S)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[4-(pyrid-2-yl)phenyl]eth-1-yl}acetamide (52 mgs, 0.076 mmol) was dissolved in AcOH (3 mL) and transferred to a Parr hydrogenation bottle. $PtO_2$ (50 mg) was added and the mixture was hydrogenated at 40 psi for 1 h. The reaction mixture was filtered through celite and reduced under vacuum to afford the title compound.

$^1$H NMR (DMSO-$d_6$) δ=8.37 (1H, d), 7.25 (9H, m), 6.83 (1H, t), 4.84 (1H, m), 4.60 (1H, m), 3.00 (5H, m), 2.62 (1H, m), 231 (3H, s), 1.99 (3H, s), 1.86 (4H, s), 1.64 (3H, m), 1.30 (2H, m), 1.24 (2H, m); MS m/z (M+H) 693.2; HPLC ($CH_3CN$—$H_2O$-0.1% TFA): $R_t$=3.18 min.

Example 75

Preparation of 2-[2-(R,S)-1-(2-chloro-4-methylpyrid-5-ylsulfonyl)-3-oxo-1,2,3,4-tetrahydroquinoxalin-2-yl]-N-[2-(pyrid-4-yl)eth-1-yl)acetamide 2-Chloro-4-methyl-5-nitropyridine (1 g, 5.8 mmol) was dissolved in EtOH (60 mL). AcOH (4 mL) and Fe (5 eq.) were added and the mixture was refluxed at 80° C. overnight. The mixture was filtered through celite and reduced under vacuum to afford the crude 5-amino-2-chloro-4-methylpyridine which was used in the next step with no further purification. The amine was dissolved in conc. HCl (6 mL), transferred to a 3-neck round bottom flask, and cooled to −5° C. A solution of $NaNO_2/H_2O$ (440 mgs/5 mL) was slowly added and the mixture was allowed to stir for 10 mins. To a second, separate 3-neck round bottom flask was added $H_2O$ (12 mL) and cooled to −5° C. Thionyl chloride (4.5 eq.) was then added dropwise. After complete addition the mixture was allowed to warm to room temp. Whereupon CuCl (0.05 eq.) was added and the mixture was then cooled back down to −5° C. The first reaction mixture, containing the amine precursor, was slowly added to the second reaction mixture. A froth formed and was filtered off to afford 6-chloro-4-methyl-pyridine-3-sulfonyl chloride which was used in the next step with no further purification. The title compound was synthesized from 2-[2-(R,S)-3-oxo-1,2,3,4-tetrahydroquinoxalin-2-yl]-N-(pyrid-4-yl)ethyl acetamide and 6-chloro-4-methyl-pyridine-3-sulfonyl chloride using Method G.

MS m/z (M+H) 501.4; HPLC ($CH_3CN$—$H_2O$-0.1% TFA): $R_t$=2.05 min.

Example 76

Preparation of 2-[2-(R or S)-1-(4-chloro-2,5-dimethylsulfonyl)-3-oxo-1,2,3,4-tetrahydroquinoxalin-2-y]-4-methyl-N-{1-[(R)-pyrrolidin-N-ylcarbonyl)-2-[4-(N-methyl-pyrid-4-yl)phen-1-yl)eth-1-yl]}acetamide iodide salt The TFA salt of 2-[2-(S or R)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[4-(pyridin-4-yl)phenyl]eth-1-yl}acetamide was dissolved in EtOH/1N HCl to form a clear solution. The solution was made alkaline using saturated $K_2CO_3$ and extracted with $CHCl_3$. The solvent was removed in vacuo to afford the free base of 2-[2-(S or R)-1-(4-chloro-2,5-dimethylbenzene-sulfonyl)-3-oxo-1,2,3,4-tetrahydroquinoxalin-2-yl]-N-{1-(R)-[pyrrolidin-N-ylcarbonyl]-2-[4-(pyridin-4-yl)phenyl]eth-1-yl}acetamide (130 mgs, 0.19 mmol) which was dissolved in MeOH (3 mL) and to it was added MeI (3 mL) and the mixture was allowed to stir for 1 week. The resulting solid was purified by preparative HPLC ($CH_3CN$—$H_2O$-0.1% TFA to afford the title compound.

$^1$H NMR (DMSO-$d_6$) δ=8.96 (1H, d, J=6.9 Hz), 8.46 (2H, d, J=6.9 Hz), 7.97 (1H, d, J=8.1 Hz), 7.39 (9H, m), 7.13 (1H, d, J=8.1 Hz), 4.94 (1H, m), 4.78 (1H, m), 4.31 (3H, s), 3.58 (2H, m), 2.75 (1H, m), 2.71 (3H, s), 2.27 (3H, s), 1.93 (3H, s), 1.79 (3H, m); MS m/z (M+H) 715.2; HPLC ($CH_3CN$—$H_2O$-0.1% TFA): $R_t$=3.32 min.

Example 77

Preparation of 2-[2-(R)-1-(2,4,6-trimethylbenzenesulfonyl)-3-oxo-1,2,3,4-tetrahydroquinoxalin-2-yl]-N-benzylacetamide The title material was obtained from 2-[2-(R,S)-3-oxo-1,2,3,4-tetrahydroquinoxalin-2-yl]-N-benzylacetamide and 2,4,6-trimethylphenyl sulfonyl chloride using Method G, followed by a chiral HPLC separation. MS (ES): m/e 478.1 (M).

Example 78

Preparation of 2-[2-(R,S)-1-(p-toluenesulfonyl)-3-oxo-1,2,3,4-tetrahydroquinoxalin-2-yl]-N-benzylacetamide The title material was obtained from 2-[2-(R,S)-3-oxo-1,2,3,4-tetrahydroquinoxalin-2-yl]-N-benzylacetamide and 4-methylphenyl sulfonyl chloride using Method G.

MS (ES): m/e 436 (M).

Example 79

Preparation of 2-[2-(R,S)-1-(p-toluenesulfonyl)-3-oxo-1,2,3,4-tetrahydroquinoxalin-2-yl]-N-(2-methoxyphenyl)acetamide The title material was purchased from Maybridge

Example 80

Preparation of 2-[2-(R,S)-1-(p-toluenesulfonyl)-3-oxo-1,2,3,4-tetrahydroquinoxalin-2-yl]-N-(2-ethoxyphenyl)acetamide The title material was purchased from Specs.

Example 81

Preparation of 2-[2-(R,S)-1-(2,4,6-trimethylbenzenesulfonyl)-3-oxo-1,2,3,4-tetrahydroquinoxalin-2-yl]-N-phenylacetamide The title material was prepared from 2-[2-(R,S)-1-(2,4,6-trimethylbenzenesulfonyl)-3-oxo-1,2,3,4-tetrahydroquinoxalin-2-yl]acetic acid and aniline using Method C.

MS (ES): m/e 464 (M).

Example 82

Preparation of 2-[2-(R,S)-1-(2,5-dichlorobenzenesulfonyl)-3-oxo-1,2,3,4-tetrahydroquinoxalin-2-yl]-N-benzylacetamide The title material was obtained from 2-[2-(R,S)-3-oxo-1,2,3,4-tetrahydroquinoxalin-2-yl]-N-benzylacetamide and 2,5-dichlorophenyl sulfonyl chloride using Method G.

MS (ES): m/e 504 (M).

Example 83

Preparation of 2-[2-(R,S)-1-(3,5-dichlorobenzenesulfonyl)-3-oxo-1,2,3,4-tetrahydroquinoxalin-2-yl]-N-benzylacetamide The title material was obtained from 2-[2-(R,S)-3-oxo-1,2,3,4-tetrahydroquinoxalin-2-yl]-N-benzylacetamide and 3,5-dichlorophenyl sulfonyl chloride using Method G.

MS (ES): m/e 504 (M).

Example 84

Preparation of 2-[2-(R,S)-1-(2,3-dichlorobenzenesulfonyl)-3-oxo-1,2,3,4-tetrahydroquinoxalin-2-yl]-N-benzylacetamide The title material was obtained from 2-[2-(R,S)-3-oxo-1,2,3,4-tetrahydroquinoxalin-2-yl]-N-benzylacetamide and 2,3-dichlorophenyl sulfonyl chloride using Method G.

MS (ES): m/e 504 (M). HPLC (H$_2$O-acetonitrile-0.1% TFA): R$_t$=27.16 min.

Example 85

Preparation of 2-[2-(R,S)-1-(2,3-dichlorobenzenesulfonyl)-3-oxo-1,2,3,4-tetrahydroquinoxalin-2-yl]-N-methylacetamide 2-[2-(R,S)-1-(2,3-dichlorobenzenesulfonyl)-3-oxo-1,2,3,4-tetrahydroquinoxalin-2-yl]acetic acid was coupled to methyl amine HCl using Method C.

HPLC (H$_2$O-acetonitrile-0.1% TFA): R$_t$=20.98 min.

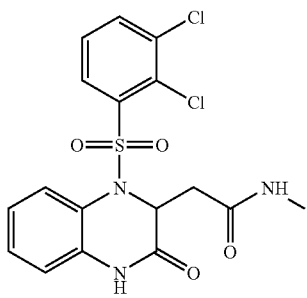

Example 86

Preparation of 2-[2-(R,S)-1-(2,3-dichlorobenzenesulfonyl)-3-oxo-1,2,3,4-tetrahydroquinoxalin-2-yl]-N-cyclohexylmethylacetamide 2-[2-(R,S)-1-(2,3-dichlorobenzenesulfonyl)-3-oxo-1,2,3,4-tetrahydroquinoxalin-2-yl]acetic acid was coupled to cyclohexanemethylamine using Method C.

HPLC (H$_2$O-acetonitrile-0.1% TFA): R$_t$=30.02 min.

Example 87

Preparation of 2-[2-(R,S)-1-(2,4-dichlorobenzenesulfonyl)-3-oxo-1,2,3,4-tetrahydroquinoxalin-2-yl]-N-benzylacetamide The title material was obtained from 2-[2-(R,S)-3-oxo-1,2,3,4-tetrahydroquinoxalin-2-yl]-N-benzylacetamide and 2,4-dichlorophenyl sulfonyl chloride using Method G.

MS (ES): m/e 504 (M).

Example 88

Preparation of 2-[2-(R,S)-1-(2-fluorobenzenesulfonyl)-3-oxo-1,2,3,4-tetrahydroquinoxalin-2-yl]-N-benzylacetamide The title material was obtained from 2-[2-(R,S)-3-oxo-1,2,3,4-tetrahydro-quinoxalin-2-yl]-N-benzylacetamide and 2-fluorophenyl sulfonyl chloride using Method G.

HPLC (H$_2$O-acetonitrile-0.1% TFA): R$_t$=24.12 min.

Example 89

Preparation of 2-[2-(R,S)-1-(4-chloro-2,5-dimethylbenzenesulfonyl)-3-oxo-1,2,3,4-tetrahydroquinoxalin-2-yl]-N-benzylacetamide The title material was obtained from 2-[2-(R,S)-3-oxo-1,2,3,4-tetrahydroquinoxalin-2-yl]-N-benzylacetamide and 2,5-dimethyl 4-chlorophenyl sulfonyl chloride using Method G.

HPLC (H$_2$O-acetonitrile-0.1% TFA): R$_t$=29.46 min.

Example 90

Preparation of 2-[2-(R,S)-1-(2,3,4-trichlorobenzenesulfonyl)-3-oxo-1,2,3,4-tetrahydroquinoxalin-2-yl]-N-benzylacetamide The title material was obtained from 2-[2-(R,S)-3-oxo-1,2,3,4-tetrahydroquinoxalin-2-yl]-N-benzylacetamide and 2,3,4-trichlorophenylsulfonyl chloride using Method G.

HPLC (H$_2$O-acetonitrile-0.1% TFA): R$_t$=29.56 min.

Example 91

Preparation of 2-[2-(R,S)-1-(2,3-dichlorobenzenesulfonyl)-3-oxo-1,2,3,4-tetrahydroquinoxalin-2-yl]-N-phenylacetamide 2-[2-(R,S)-1-(2,3-dichlorobenzenesulfonyl)-3-oxo-1,2,3,4-tetrahydroquinoxalin-2-yl]acetic acid was coupled to aniline using Method C.

HPLC (H$_2$O-acetonitrile-0.1% TFA): R$_t$=27.7 min.

Example 92

Preparation of 2-[2-(S)-1-(2,4,6-trimethylbenzenesulfonyl)-3-oxo-1,2,3,4-tetrahydroquinoxalin-2-yl]-N-benzylacetamide The title material was obtained from 2-[2-(R,S)-3-oxo-1,2,3,4-tetrahydroquinoxalin-2-yl]-N-benzylacetamide and 2,4,6-trimethylphenyl sulfonyl chloride using Method G, followed by a chiral HPLC separation.

MS (ES): m/e 478.1 (M).

Example 93

Preparation of 2-[2-(R,S)-1-(4-chloro-2,5-dimethylbenzenesulfonyl)-3-oxo-1,2,3,4-tetrahydroquinoxalin-2-yl]acetamide The title material was prepared from 1,2-phenylenediamine and maleimide using Method F, followed by Method G using 4-chloro 2,5-dimethyl phenylsulfonyl chloride.

MS (ES): m/e 408 (M+H)

Example 94

Preparation of 2-[2-(R,S)-1-(4-chloro-2,5-dimethyl-benzenesulfonyl)-3-oxo-1,2,3,4-tetrahydroquinoxalin-2-yl]-N-[2-(indol-3-yl)-1-(S)-(methoxycarbonyl)eth-1-yl]acetamide The title compound was prepared using Method Y starting with 2-(indol-3-yl)-1-(S)-(methoxycarbonyl)-1-aminoethane and 2-[2-(R,S)-1-(4-chloro-2,5-dimethylbenzenesulfonyl)-3-oxo-1,2,3,4-tetrahydroquinoxalin-2-yl]acetic acid.
MS (ES): m/e 610 (M+H).

Example 95

Preparation of 2-[2-(R,S)-1-(4-chloro-2,5-dimethyl-benzenesulfonyl)-3-oxo-1,2,3,4-tetrahydroquinoxalin-2-yl]-N-[1-(R)-(t-butoxycarbonyl)-3-methylprop-1-yl]acetamide The title compound was prepared from 2-[2-(R,S)-1-4-(chloro-2,5-dimethylbenzenesulfonyl)-3-oxo-1,2,3,4-tetrahydroquinoxalin-2-yl]acetic acid and D-isoleucine t-butyl ester using Method Y.
HPLC (water-acetonitrile-0.1% TFA): $R_t$=35.38 min

Example 96

Preparation of 2-[2-(R,S)-1-(4-chloro-2,5-dimethyl-benzenesulfonyl)-3-oxo-1,2,3,4-tetrahydroquinoxalin-2-yl]-methylenecarbonyl-[3-(R)-t-butoxycarboxamide-pyrrolidin-N-yl]

The title compound was prepared from 2-[2-(R,S)-1-4-(chloro-2,5-dimethylbenzenesulfonyl)-3-oxo-1,2,3,4-tetrahydroquinoxalin-2-yl]acetic acid and 3-(R)-t-butoxycarboxamide pyrrolidine using Method W.
MS (ES): m/e 599.2 (M+Na)

Example 97

Preparation of 2-[2-(R,S)-1-(4-chloro-2,5-dimethyl-benzenesulfonyl)-3-oxo-1,2,3,4-tetrahydroquinoxalin-2-yl]-methylenecarbonyl-[2-(S)-carboxamidepyrrolidin-N-yl]

The title compound was prepared from 2-[2-(R,S)-1-4-(chloro-2,5-dimethylbenzenesulfonyl)-3-oxo-1,2,3,4-tetrahydroquinoxalin-2-yl]acetic acid and 2-(S)-carbox-amide pyrrolidine using Method W.
MS (ES): m/e 527.1 (M+Na)

Example 98

Preparation of 2-[2-(R,S)-1-(4-chloro-2,5-dimethyl-benzenesulfonyl)-3-oxo-1,2,3,4-tetrahydroquinoxalin-2-yl]-methylenecarbonyl-[3-(R,S)-hydroxy-pyrrolidin-N-yl]

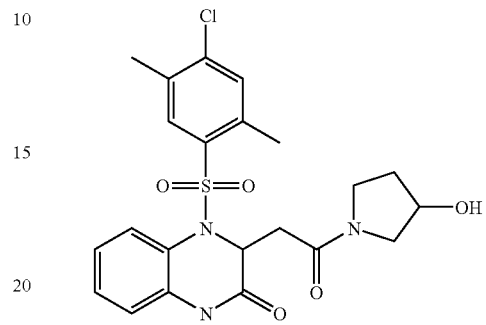

The title compound was prepared from 2-[2-(R,S)-1-4-(chloro-2,5-dimethylbenzenesulfonyl)-3-oxo-1,2,3,4-tetrahydroquinoxalin-2-yl]acetic acid and 3-(R,S)-hydroxypyrrolidine using Method W.
MS (ES): m/e 500.1 (M+Na).

Example 99

Preparation of 2-[2-(R,S)-1-(4-chloro-2,5-dimethyl-benzenesulfonyl)-3-oxo-1,2,3,4-tetrahydroquinoxalin-2-yl]-N,N-(dipyrid-3-ylmethyl)acetamide The title compound was prepared from 2-[2-(R,S)-1-4-(chloro-2,5-dimethylbenzenesulfonyl)-3-oxo-1,2,3,4-tetrahydroquinoxalin-2-yl]acetic acid and N,N-dipyrid-3-ylmethylamine using Method W.
MS (ES): m/e 590.2 (M)

Example 100

Preparation of 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-2-(4-amidino)phenyl-eth-1-yl]acetamide The title material was obtained from 2-[2-(R,S)-1-(4-chloro-2,5-dimethylbenzenesulfonyl)-3-oxo-1,2,3,4-tetrahydro-quinoxalin-2-yl]-N-[2-(4-cyanophenyl)-1-(R)-(pyrrolidin-N-ylcarbonyl)eth-1-yl]acetamide and ammonium acetate using Method T. The desired diastereomer was obtained upon prep HPLC purification.
HPLC (acetonitrile/water-0.1% TFA): $R_t$=3.90 min. MS (ES): m/e 652 (M+H).

Example 101

Preparation of 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-2-(4-amidino)phenyl-eth-1-yl]acetamide The title material was obtained from 2-[2-(R,S)-1-(4-chloro-2,5-dimethylbenzenesulfonyl)-3-oxo-1,2,3,4-tetrahydroquinoxalin-2-yl]-N-[2-(4-cyanophenyl)-1-(R)-(pyrrolidin-N-ylcarbonyl)eth-1-yl]acetamide and ammonium acetate using Method T. The desired diastereomer was obtained upon prep HPLC purification.

HPLC (acetonitrile/water-0.1% TFA): $R_t$=3.60 min. MS (ES): m/e 652 (M+H).

Example 102

Preparation of 2-[2-(R or S)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[N-(phenyl)-piperidin-4-yl)]eth-1-yl}acetamide N-phenylation of N-Boc-1-(R)-[pyrrolidin-N-ylcarbonyl]-2-[N-(piperidin-4-yl]ethylamine using Method M, followed by deprotection using Method P, and subsequent coupling to 2-[2-(R,S)-1-(4-chloro-2,5-dimethylbenzenesulfonyl)-3-oxo-1,2,3,4-tetrahydroquinoxalin-2-yl]acetic acid using Method S, led to the desired material, which was purified by prep HPLC.

HPLC (acetonitrile/water-0.1% TFA): $R_t$=4.15 min. MS (ES): m/e 693 (M+H).

Example 103

Preparation of 2-[2-(S or R)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[N-(phenyl)-piperidin-4-yl)]eth-1-yl}acetamide N-phenylation of N-Boc-1-(R)-[pyrrolidin-N-ylcarbonyl]-2-[N-(piperidin-4-yl]ethylamine using Method M, followed by deprotection using Method P, and subsequent coupling to 2-[2-(R,S)-1-(4-chloro-2,5-dimethylbenzenesulfonyl)-3-oxo-1,2,3,4-tetrahydro-quinoxalin-2-yl]acetic acid using Method S, led to the desired material, which was purified by prep HPLC.

HPLC (acetonitrile/water-0.1% TFA): $R_t$=4.27 min. MS (ES): m/e 693 (M+H).

Example 104

Preparation of 2-[2-(R or S)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[N-(pyridin-4-yl)-piperidin-4-yl]eth-1-yl}acetamide Coupling of N-phenylation of N-Boc-1-(R)-[pyrrolidin-N-ylcarbonyl]-2-[N-(piperidin-4-yl]ethylamine with 4-chloropyridine using Method N, followed by deprotection using Method P, and subsequent coupling to 2-[2-(R,S)-1-(4-chloro-2,5-di-methylbenzenesulfonyl)-3-oxo-1,2,3,4-tetrahydroquinoxalin-2-yl]acetic acid using Method S, led to the desired material, which was purified by prep HPLC.

HPLC (acetonitrile/water-0.1% TFA): $R_t$=2.16 min. MS (ES): m/e 695 (M+H).

Example 105

Preparation of 2-[2-(S or R)-1-(4-chloro-2,5-dimethylbenzenesulfonyl)-3-oxo-1,2,3,4-tetrahydroquinoxalin-2-yl]-N-{1-(R)-[pyrrolidin-N-ylcarbonyl]-2-[N-(pyridin-4-yl)-piperidin-4-yl]eth-1-yl}acetamide Coupling of N-phenylation of N-Boc-1-(R)-[pyrrolidin-N-ylcarbonyl]-2-[N-(piperidin-4-yl]ethylamine with 4-chloropyridine using Method N, followed by deprotection using Method P, and subsequent coupling to 2-[2-(R,S)-1-(4-chloro-2,5-dimethylbenzenesulfonyl)-3-oxo-1,2,3,4-tetrahydroquinoxalin-2-yl]acetic acid using Method S, led to the desired material, which was purified by prep HPLC.

HPLC (acetonitrile/water-0.1% TFA): $R_t$=2.77 min. MS (ES): m/e 695 (M+H).

Example 106

Preparation of 2-[2-(R,S)-1-(4-chloro-2,5-dimethylbenzenesulfonyl)-3-oxo-1,2,3,4-tetrahydroquinoxalin-2-yl]-N-[3-(2-methylthiazol-4-yl)-pyrazol-5-yl]acetamide 2-[2-(R,S)-1-(4-Chloro-2,5-dimethylbenzenesulfonyl)-3-oxo-1,2,3,4-tetrahydroquinoxalin-2-yl]acetic acid was coupled with 2-tert-Butyl-5-(2-methylthiazol-4-yl)-2H-pyrazol-3-ylamine in presence of $POCl_3$ in pyridine at −20° C. for 5 min, then at room temperature for 18h. The reaction mixture was poured on ice, and crude product was filtered off. Pure product, obtained after recrystallization from MeOH, was treated with formic acid at reflux temperature for 4 h. Excess formic acid was removed and crude product purified by recrystallization with ethyl acetate to afford the title compound as a white solid.

$^1$H NMR (DMSO-$d_6$): δ=1.99 (s, 3H), 2.20(s, 3H), 2.42–2.46, (br. s, 2H), 2.68(s, 3H), 4.94(dd, 1H, J=6 Hz), 6.81(s, 1H), 7.45(s, 1H), 6.84–7.39(m, Ar—H, 6H), 7.79(s, 1H, NH), 10.43, 10.51 (s, 1H); MS (ES): m/e 571.1 (M); HPLC ($CH_3CN$—$H_2O$-0.1% TFA) (short column): $R_t$=5.12 min.

Example 107

Preparation of 2-[2-(R,S)-1-(4-chloro-2,5-dimethylbenzenesulfonyl)-3-oxo-1,2,3,4-tetrahydroquinoxalin-2-yl]-N-{2-[N-(N-morpholinocarbonyl)piperidin-4-yl]eth-1-yl}acetamide The title compound was prepared from 2-[2-(R,S)-1-(4-chloro-2,5-dimethylbenzenesulfonyl)-3-oxo-1,2,3,4-tetrahydroquinoxalin-2-yl]-N-(2-piperidin-4-yl)-eth-1-yl acetamide and morpholine carbonyl chloride using Method J'.

MS (ES): m/e (M) 632.2

Example 108

Preparation of 2-[2-(R,S)-1-(4-chloro-2,5-dimethylbenzenesulfonyl)-3-oxo-1,2,3,4-tetrahydroquinoxalin-2-yl]-N-{2-[N-[(thiophen-2-yl)methylenecarbonyl]piperidin-4-yl]eth-1-yl}acetamide The title compound was prepared by Method J' using thiophen-2-yl acetyl chloride and 2-[2-(R,S)-1-(4-chloro-2,5-dimethylbenzenesulfonyl)-3-oxo-1,2,3,4-tetrahydroquinoxalin-2-yl]-N-(2-piperidin-4-yl)-eth-1-yl acetamide.

HPLC ($CH_3CN$—$H_2O$-0.1% TFA): $R_t$=11.07 min. MS (ES): m/e (M+H+) 644.

Example 109

Preparation of 2-[2-(R,S)-1-(4-chloro-2,5-dimethylbenzenesulfonyl)-3-oxo-1,2,3,4-tetrahydroquinoxalin-2-yl]-N-{2-[N-(3,5-dimethyloxazol-4-ylcarbonyl)piperidin-4-yl]eth-1-yl}acetamide The title compound was prepared by Method J' using 3,5-dimethylisoxazol-4-ylcarbonyl chloride and 2-[2-(R,S)-

1-(4-chloro-2,5-dimethylbenzenesulfonyl)-3-oxo-1,2,3,4-tetrahydroquinoxalin-2-yl]-N-(2-piperidin-4-yl)-eth-1-yl acetamide.

HPLC (CH₃CN—H₂O-0.1% TFA): $R_t$=10.596 min. MS (ES): m/e (M+H+) 643.

Example 110

Preparation of 2-[2-(R,S)-1-(4-chloro-2,5-dimethyl-benzenesulfonyl)-3-oxo-12,3,4-tetrahydroquinoxalin-2-yl]-N-{2-[(N-furan-2-ylcarbonyl)piperidin-4-yl]eth-1-yl}acetamide The title compound was prepared by Method J', using furan-2-ylcarbonyl chloride and 2-[2-(R,S)-1-(4-chloro-2,5-dimethylbenzenesulfonyl)-3-oxo-1,2,3,4-tetrahydroquinoxalin-2-yl]-N-(2-piperidin-4-yl)-eth-1-yl acetamide.

HPLC (CH₃CN—H₂O-0.1% TFA): $R_t$=10.852 min. MS (ES): m/e (M+H+) 614.

Example 111

Preparation of 2-[2-(R,S)-1-(4-chloro-2,5-dimethyl-benzenesulfonyl)-3-oxo-1,2,3,4-tetrahydroquinoxalin-2-yl]-N-{2-[N-(isoxazol-5-yl-carbonyl)piperidin-4-yl]eth-1-yl}acetamide The title compound was prepared by Method J', using isoxazol-5-ylcarbonyl chloride and 2-[2-(R,S)-1-(4-chloro-2,5-dimethylbenzenesulfonyl)-3-oxo-1,2,3,4-tetrahydroquinoxalin-2-yl]-N-(2-piperidin-4-yl)-eth-1-yl acetamide.

HPLC (CH₃CN—H₂O-0.1% TFA): $R_t$=10.598 min. MS (ES): m/e (M+H+) 615

Example 112

Preparation of 2-[2-(R,S)-1-(4-chloro-2,5-dimethyl-benzenesulfonyl)-3-oxo-1,2,3,4-tetrahydroquinoxalin-2-yl]-N-{2-[N-(5-methylpyrazol-3-yl-carbonyl)piperidin-4-yl]eth-1-yl}acetamide The title compound was prepared by Method J', using 5-methylpyrazol-3-ylcarbonyl chloride and 2-[2-(R,S)-1-(4-chloro-2,5-dimethylbenzenesulfonyl)-3-oxo-1,2,3,4-tetrahydroquinoxalin-2-yl]-N-(2-piperidin-4-yl)-eth-1-yl acetamide.

HPLC (CH₃CN—H₂O-0.1% TFA): $R_t$=9.695 min. MS (ES): m/e (M+H+) 628.

Example 113

Preparation of 2-[2-(R,S)-1-(4-chloro-2,5-dimethyl-benzenesulfonyl)-3-oxo-1,2,3,4-tetrahydroquinoxalin-2-yl]-N-{2-[N-(1-methyl-3-t-butylpyrazol-5-yl-carbonyl)piperidin-4-yl]-1-yl}acetamide The title compound was prepared by Method J', using 1-methyl-3-t-butylpyrazol-5-ylcarbonyl chloride and 2-[2-(R,S)-1-(4-chloro-2,5-dimethylbenzenesulfonyl)-3-oxo-1,2,3,4-tetrahydroquinoxalin-2-yl]-N-(2-piperidin-4-yl)-eth-1-yl acetamide.

HPLC (CH₃CN—H₂O-0.1% TFA): $R_t$=11.759 min. MS (ES): m/e (M+H+) 684.

Example 114

Preparation of 2-[2-(R,S)-1-(4-chloro-2,5-dimethyl-benzenesulfonyl)-3-oxo-1,2,3,4-tetrahydroquinoxalin-2-yl]-N-{2-[N-(4-methylthiadiazol-5-yl-carbonyl)piperidin-4-yl]eth-1-yl}acetamide The title compound was prepared by Method J' using 4-methyl-2,3-thiadiazole-5-carbonyl chloride and 2-[2-(R,S)-1-(4-chloro-2,5-dimethylbenzenesulfonyl)-3-oxo-1,2,3,4-tetrahydroquinoxalin-2-yl]-N-(2-piperidin-4-yl)-eth-1-yl acetamide.

HPLC (CH₃CN—H₂O-0.1% TFA): $R_t$=10.831 min. MS (ES): m/e (M+H+) 646.

Example 115

Preparation of 2-[2-(R,S)-1-(4-chloro-2,5-dimethyl-benzenesulfonyl)-3-oxo-1,2,3,4-tetrahydroquinoxalin-2-yl]-N-{2-[N-(chloromethylene-carbonyl)piperidin-4-yl]eth-1-yl}acetamide The title compound was prepared by Method J', using chloroacetyl chloride and 2-[2-(R,S)-1-(4-chloro-2,5-dimethylbenzenesulfonyl)-3-oxo-1,2,3,4-tetrahydroquinoxalin-2-yl]-N-(2-piperidin-4-yl)-eth-1-yl acetamide.

HPLC (CH₃CN—H₂O-0.1% TFA): $R_t$=10.663 min. MS (ES): m/e (M+H+) 596.

Example 116

Preparation of 2-[2-(R,S)-1-(4-chloro-2,5-dimethyl-benzenesulfonyl)-3-oxo-1,2,3,4-tetrahydroquinoxalin-2-yl]-N-{2-[N-(phenylcarbonyl)-piperidin-4-yl]eth-1-yl}acetamide The title compound was prepared by Method J', using phenyl chloroformate and 2-[2-(R,S)-1-(4-chloro-2,5-dimethylbenzenesulfonyl)-3-oxo-1,2,3,4-tetrahydroquinoxalin-2-yl]-N-(2-piperidin-4-yl)-eth-1-yl acetamide.

HPLC (CH₃CN—H₂O-0.1% TFA): $R_t$=11.231 min. MS (ES): m/e (M+H+) 624

Example 117

Preparation of 2-[2-(R,S)-1-(4-chloro-2,5-dimethyl-benzenesulfonyl)-3-oxo-1,2,3,4-tetrahydroquinoxalin-2-yl]-N-{2-[N-(isopropylcarbonyl)piperidin-4-yl]eth-1-yl}acetamide The title compound was prepared by Method J', using isopropyl carbonyl chloride and 2-[2-(R,S)-1-(4-chloro-2,5-dimethylbenzenesulfonyl)-3-oxo-1,2,3,4-tetrahydroquinoxalin-2-yl]-N-(2-piperidin-4-yl)-eth-1-yl acetamide.

HPLC (CH₃CN—H₂O-0.1% TFA): $R_t$=10.922 min. MS (ES): m/e (M+H+) 590.2.

Example 118

Preparation of 2-[2-(R,S)-1-(4-chloro-2,5-dimethyl-benzenesulfonyl)-3-oxo-1,2,3,4-tetrahydroquinoxalin-2-yl]-N-{2-[N-(t-butylmethylene-carbonyl)piperidin-4-yl]eth-1-yl}acetamide The title compound was prepared by Method J', using t-butylacetyl chloride and 2-[2-(R,S)-1-(4-chloro-2,5-dimethylbenzene-sulfonyl)-3-oxo-1,2,3,4-tetrahydroquinoxalin-2-yl]-N-(2-piperidin-4-yl)-eth-1-yl acetamide.

HPLC (CH$_3$CN—H$_2$O-0.1% TFA): R$_t$=11.745 min. MS (ES): m/e (M+H+) 618.

Example 119

Preparation of 2-[2-(R,S)-1-(4-chloro-2,5-dimethyl-benzenesulfonyl)]-3-oxo-1,2,3,4-tetrahydroquinoxalin-2-yl]-N-{2-[N-(2-phenylethenyl-carbonyl)piperidin-4-yl]eth-1-yl}acetamide The title compound was prepared by Method J', using cinnamyl chloride and 2-[2-(R,S)-1-(4-chloro-2,5-dimethylbenzenesulfonyl)-3-oxo-1,2,3,4-tetrahydroquinoxalin-2-yl]-N-(2-piperidin-4-yl)-eth-1-yl acetamide.

HPLC (CH$_3$CN—H$_2$O-0.1% TFA): R$_t$=11.894 min. MS (ES): m/e (M+H+) 650.

Example 120

Preparation of 2-[2-(R,S)-1-(4-chloro-2,5-dimethyl-benzenesulfonyl)-3-oxo-1,2,3,4-tetrahydroquinoxalin-2-yl]-N-{2-[N-(methoxymethylenecarbonyl)piperidin-4-yl]eth-1-yl}acetamide The title compound was prepared by Method J', using methoxy acetyl chloride and 2-[2-(R,S)-1-(4-chloro-2,5-dimethylbenzenesulfonyl)-3-oxo-1,2,3,4-tetrahydroquinoxalin-2-yl]-N-(2-piperidin-4-yl)-eth-1-yl acetamide.

HPLC (CH$_3$CN—H$_2$O-0.1% TFA): R$_t$=11.853 min. MS (ES): m/e (M+H+) 592.

Example 121

Preparation of 2-[2-(R,S)-1-(4-chloro-2,5-dimethyl-benzenesulfonyl)-3-oxo-1,2,3,4-tetrahydroquinoxalin-2-yl]-N-{2-[N-(pyrazin-2-ylcarbonyl)piperidin-4-yl]eth-1-yl}acetamide The title compound was prepared by Method J', using pyrazin-2-ylcarbonyl chloride and 2-[2-(R,S)-1-(4-chloro-2,5-dimethylbenzenesulfonyl)-3-oxo-1,2,3,4-tetrahydroquinoxalin-2-yl]-N-(2-piperidin-4-yl)-eth-1-yl acetamide.

HPLC (CH$_3$CN—H$_2$O-0.1% TFA): R$_t$=10.036 min. MS (ES): m/e (M+H+) 626

Example 122

Preparation of 2-[2-(R,S)-1-(4-chloro-2,5-dimethyl-benzenesulfonyl)-3-oxo-1,2,3,4-tetrahydroquinoxalin-2-yl]-N-{2-[N-(isoquinolin-3-ylcarbonyl)piperidin-4-yl]eth-1-yl}acetamide The title compound was prepared by Method J', using isoquinolin-3-ylcarbonyl chloride and 2-[2-(R,S)-1-(4-chloro-2,5-dimethylbenzenesulfonyl)-3-oxo-1,2,3,4-tetrahydroquinoxalin-2-yl]-N-(2-piperidin-4-yl)-eth-1-yl acetamide.

HPLC (CH$_3$CN—H$_2$O-0.1% TFA): R$_t$=10.408 min. MS (ES): m/e (M+H+) 675

Example 123

Preparation of 2-[2-(R,S)-1-(4-chloro-2,5-dimethyl-benzenesulfonyl)-3-oxo-1,2,34-tetrahydroquinoxalin-2-yl]-N-{2-[N-(pyrrolidin-5-one-2-ylcarbonyl)piperidin-4-yl]eth-1-yl}acetamide The title compound was prepared by Method J' using 2-[2-(R,S)-1-(4-chloro-2,5-dimethylbenzenesulfonyl)-3-oxo-1,2,3,4-tetrahydroquinoxalin-2-yl]-N-(2-piperidin-4-yl)-eth-1-yl acetamide and N-pyrrolidin-5-one-2-ylcarbamyl chloride.

HPLC (CH$_3$CN—H$_2$O-0.1% TFA): R$_t$=9.403 min. MS (ES): m/e (M+H+) 631 (M+Na+) 653

Example 124

Preparation of 2-[2-(R,S)-1-(4-chloro-2,5-dimethyl-benzenesulfonyl)-3-oxo-1,2,3,4-tetrahydroquinoxalin-2-yl]-N-{2-[N-(N'-acetylpyrrolidin-2-ylcarbonyl)piperidin-4-yl]eth-1-yl}acetamide The title compound was prepared by Method J', using N-acetylpyrrolidin-2-ylcarbonyl chloride and 2-[2-(R,S)-1-(4-chloro-2,5-dimethylbenzenesulfonyl)-3-oxo-1,2,3,4-tetrahydroquinoxalin-2-yl]-N-(2-piperidin-4-yl)-eth-1-yl acetamide.

HPLC (CH$_3$CN—H$_2$O-0.1% TFA): R$_t$=9.797 min. MS (ES): m/e (M+H+) 659 (M+Na+) 681.

Example 125

Preparation of 2-[2-(R,S)-1-(4-chloro-2,5-dimethyl-benzenesulfonyl)]-3-oxo-1,2,3,4-tetrahydroquinoxalin-2-yl]-N-{2-[N-(dichloromethylenecarbonyl)piperidin-4-yl]eth-1-yl}acetamide The title compound was prepared by Method J', using dichloroacetyl chloride and 2-[2-(R,S)-1-(4-chloro-2,5-dimethylbenzenesulfonyl)-3-oxo-1,2,3,4-tetrahydroquinoxalin-2-yl]-N-(2-piperidin-4-yl)-eth-1-yl acetamide.

HPLC (CH$_3$CN—H$_2$O-0.1% TFA): R$_t$=11.177 min. MS (ES): m/e (M+H+) 631 (M+Na+) 652.

Example 126

Preparation of 2-[2-(R,S)-1-(4-chloro-2,5-dimethyl-benzenesulfonyl)-3-oxo-1,2,3,4-tetrahydroquinoxalin-2-yl]-N-{2-[N-(ethylcarbonyl)piperidin-4-yl]eth-1-yl}acetamide The title compound was prepared by Method J', using propionyl chloride and 2-[2-(R,S)-1-(4-chloro-2,5-dimethylbenzenesulfonyl)-3-oxo-1,2,3,4-tetrahydroquinoxalin-2-yl]-N-(2-piperidin-4-yl)-eth-1-yl acetamide.

HPLC (CH$_3$CN—H$_2$O-0.1% TFA): R$_t$=10.467 min. MS (ES): m/e (M+H+) 576 (M+Na+) 598.

Example 127

Preparation of 2-[2-(R,S)-1-(4-chloro-2,5-dimethyl-benzenesulfonyl)-3-oxo-1,2,3,4-tetrahydroquinoxalin-2-yl]-N-{2-[N-(n-propylcarbonyl)piperidin-4-yl]eth-1-yl}acetamide The title compound was prepared by Method J', using butyryl chloride and 2-[2-(R,S)-1-(4-chloro-2,5-dimethylbenzenesulfonyl)-3-oxo-1,2,3,4-tetrahydroquinoxalin-2-yl]-N-(2-piperidin-4-yl)-eth-1-yl acetamide.

HPLC (CH$_3$CN—H$_2$O-0.1% TFA): R$_t$=10.733 min. MS (ES): m/e (M+H+) 590

Example 128

Preparation of 2-[2-(R,S)-1-(4-chloro-2,5-dimethyl-benzenesulfonyl)-3-oxo-1,2,3,4-tetrahydroquinoxalin-2-yl]-N-{4-[N-(pyrazin-2-ylcarbonyl)amino]pheneth-1-yl}acetamide The title compound was prepared by Method I' using pyrazin-2-yl carbonyl chloride and 2-[2-(R,S)-1-(4-chloro-2,5-dimethylbenzenesulfonyl)-3-oxo-1,2,3,4-tetrahydroquinoxalin-2-yl]-N-2-(4-aminophenyl)eth-1-ylacetamide.

HPLC (CH$_3$CN—H$_2$O-0.1% TFA): R$_t$=10.873 min. MS (ES): m/e (M+H+) 634 (M+Na+) 656.

Example 129

Preparation of 2-[2-(R,S)-1-(4-chloro-2,5-dimethyl-benzenesulfonyl)-3-oxo-1,2,3,4-tetrahydroquinoxalin-2-yl]-N-{4-[N-(isoquinolin-2-yl-carbonyl)amino]pheneth-1-yl}acetamide The title compound was prepared using Method I', starting with 2-[2-(R,S)-1-(4-chloro-2,5-dimethylbenzenesulfonyl)-3-oxo-1,2,3,4-tetrahydroquinoxalin-2-yl]-N-2-(4-aminophenyl)eth-1-ylacetamide and isoquinolin-2-ylcarbonyl chloride.

HPLC (CH$_3$CN—H$_2$O-0.1% TFA): R$_t$=12.312 min. MS (ES): m/e (M+H+) 683 (M+Na+) 705.

Example 130

Preparation of 2-[2-(R,S)-1-(4-chloro-2,5-dimethyl-benzenesulfonyl)-3-oxo-1,2,3,4-tetrahydroquinoxalin-2-yl]-N-{4-[N-(N'-acetylpyrrolidin-2-yl-carbonyl)amino]pheneth-1-yl}acetamide The title compound was prepared using Method I' starting with 2-[2-(R,S)-1-(4-chloro-2,5-dimethylbenzenesulfonyl)-3-oxo-1,2,3,4-tetrahydroquinoxalin-2-yl]-N-[2-(4-aminophenyl)eth-1-yl]acetamide and N-acetylpyrrolidin-2-ylcarbonyl chloride.

HPLC (CH$_3$CN—H$_2$O-0.1% TFA): R$_t$=10.071 min. MS (ES): m/e (M+H+) 667 (M+Na+) 689.

Example 131

Preparation of 2-[2-(R,S)-1-(4-chloro-2,5-dimethyl-benzenesulfonyl)-3-oxo-1,2,3,4-tetrahydroquinoxalin-2-yl]-N-{4-[N-(1,2-benzothiadiazol-5-ylcarbonyl)amino]pheneth-1-yl}acetamide The title compound was prepared using Method I' starting with 2-[2-(R,S)-1-(4-chloro-2,5-dimethylbenzenesulfonyl)-3-oxo-1,2,3,4-tetrahydroquinoxalin-2-yl]-N-[2-(4-aminophenyl)eth-1-yl]acetamide and 1,2-benzothiadiazol-5-ylcarbonyl chloride.

HPLC (CH$_3$CN—H$_2$O-0.1% TFA): R$_t$=11.549 min. MS (ES): m/e (M+H+) 690 (M+Na+) 712.

Example 132

Preparation of 2-[2-(R,S)-1-(4-chloro-2,5-dimethyl-benzenesulfonyl)-3-oxo-1,2,3,4-tetrahydroquinoxalin-2-yl]-N-{4-[N-(benzofuran-5-ylcarbonyl)amino]pheneth-1-yl}acetamide The title compound was prepared using Method I' starting with 2-[2-(R,S)-1-(4-chloro-2,5-dimethylbenzenesulfonyl)-3-oxo-1,2,3,4-tetrahydroquinoxalin-2-yl]-N-[2-(4-aminophenyl)eth-1-yl]acetamide and benzofuran-5-ylcarbonyl chloride.

HPLC (CH$_3$CN—H$_2$O-0.1% TFA): R$_t$=11.325 min. MS (ES): m/e (M+H+) 674 (M+Na+) 696.

Example 133

Preparation of 2-[2-(R,S)-1-(4-chloro-2,5-dimethyl-benzenesulfonyl)-3-oxo-1,2,3,4-tetrahydroquinoxalin-2-yl]-N-{4-[N-(3-methylisoxazol-5-ylcarbonyl)amino]pheneth-1-yl}acetamide The title compound was prepared using Method I' starting with 2-[2-(R,S)-1-(4-chloro-2,5-dimethylbenzenesulfonyl)-3-oxo-1,2,3,4-tetrahydroquinoxalin-2-yl]-N-[2-(4-aminophenyl)eth-1-yl]acetamide and 3-methylisoxazol-5-ylcarbonyl chloride.

HPLC (CH$_3$CN—H$_2$O-0.1% TFA): R$_t$=10.346 min. MS (ES): m/e (M+H+) 637 (M+Na+) 659.

Example 134

Preparation of 2-[2-(R,S)-1-(4-chloro-2,5-dimethyl-benzenesulfonyl)-3-oxo-1,2,3,4-tetrahydroquinoxalin-2-yl]-N-{4-[N-(N'-morpholinocarbonyl)amino]pheneth-1-yl}acetamide The title compound was prepared using Method I' starting with 2-[2-(R,S)-1-(4-chloro-2,5-dimethylbenzenesulfonyl)-3-oxo-1,2,3,4-tetrahydroquinoxalin-2-yl]-N-[2-(4-aminophenyl)eth-1-yl]acetamide and morpholinocarbonyl chloride.

HPLC (CH$_3$CN—H$_2$O-0.1% TFA): R$_t$=10.203 min. MS (ES): m/e (M+H+) 641 (M+Na+) 663

Example 135

Preparation of 2-[2-(R,S)-1-(4-chloro-2,5-dimethyl-benzenesulfonyl)-3-oxo-1,2,3,4-tetrahydroquinoxalin-2-yl]-N-{4-[N-(methoxyphen-3-ylcarbonyl)amino]pheneth-1-yl}acetamide The title compound was prepared using Method I' starting with 2-[2-(R,S)-1-(4-chloro-2,5-dimethylbenzenesulfonyl)-3-oxo-1,2,3,4-tetrahydroquinoxalin-2-yl]-N-[2-(4-aminophenyl)eth-1-yl]acetamide and 3-methoxy benzoyl chloride.

HPLC (CH$_3$CN—H$_2$O-0.1% TFA): R$_t$=11.506 min. MS (ES): m/e (M+H+) 662 (M+Na+) 684.

Example 136

Preparation of 2-[2-(R,S)-1-(4-chloro-2,5-dimethyl-benzenesulfonyl)-3-oxo-1,2,3,4-tetrahydroquinoxalin-2-yl]-N-{4-[N-(thiophen-2-ylmethylenecarbonyl)amino]pheneth-1-yl}acetamide The title compound was prepared using Method I' starting with 2-[2-(R,S)-1-(4-chloro-2,5-dimethylbenzenesulfonyl)-3-oxo-1,2,3,4-tetrahydroquinoxalin-2-yl]-N-[2-(4-aminophenyl)eth-1-yl]acetamide and thiophen-2-ylacetyl chloride.

HPLC (CH$_3$CN—H$_2$O-0.1% TFA): R$_t$=11.273 min. MS (ES): m/e (M+H+) 652 (M+Na+) 674.

Example 137

Preparation of 2-[2-(R,S)-1-(4-chloro-2,5-dimethyl-benzenesulfonyl)-3-oxo-1,2,3,4-tetrahydroquinoxalin-2-yl]-N-{4-[N-(3 5-dimethylisoxazol-4-ylcarbonyl)amino]pheneth-1-yl}acetamide The title compound was prepared using Method I' starting with 2-[2-(R,S)-1-(4-chloro-2,5-dimethylbenzenesulfonyl)-3-oxo-1,2,3,4-tetrahydroquinoxalin-2-yl]-N-[2-(4-aminophenyl)eth-1-yl]acetamide and 3,5-dimethylisoxazol-4-ylcarbonyl chloride.

HPLC (CH$_3$CN—H$_2$O-0.1% TFA): R$_t$=10.943 min. MS (ES): m/e (M+H+) 651 (M+Na+) 673.

Example 138

Preparation of 2-[2-(R,S)-1-(4-chloro-2,5-dimethyl-benzenesulfonyl)-3-oxo-1,2,3,4-tetrahydroquinoxalin-2-yl]-N-{4-[N-(2-(pyrid-3-yl)ethylcarbonyl)amino]pheneth-1-yl}acetamide The title compound was prepared using Method I' starting with 2-[2-(R,S)-1-(4-chloro-2,5-dimethylbenzenesulfonyl)-3-oxo-1,2,3,4-tetrahydroquinoxalin-2-yl]-N-[2-(4-aminophenyl)eth-1-yl]acetamide and pyridin-3-ylpropionyl chloride.

HPLC (CH$_3$CN—H$_2$O-0.1% TFA): R$_t$=8.807 min. MS (ES): m/e (M+H+) 661 (M+Na+) 683.

Example 139

Preparation of 2-[2-(R,S)-1-(4-chloro-2,5-dimethyl-benzenesulfonyl)-3-oxo-1,2,3,4-tetrahydroquinoxalin-2-yl]-N-{4-[N-(furan-2-ylcarbonyl)-amino]pheneth-1-yl}acetamide The title compound was prepared using Method I' starting with 2-[2-(R,S)-1-(4-chloro-2,5-dimethylbenzenesulfonyl)-3-oxo-1,2,3,4-tetrahydroquinoxalin-2-yl]-N-[2-(4-aminophenyl)eth-1-yl]acetamide and furan-2-ylcarbonyl chloride.

HPLC (CH$_3$CN—H$_2$O-0.1% TFA): R$_t$=10.39 min. MS (ES): m/e (M+H+) 622 (M+Na+) 644.

Example 140

Preparation of 2-[2-(R,S)-1-(4-chloro-2,5-dimethyl-benzenesulfonyl)-3-oxo-1,2,3,4-tetrahydroquinoxalin-2-yl]-N-{4-[N-(isoxazol-5-ylcarbonyl)amino]pheneth-1-yl}acetamide The title compound was prepared using Method I' starting with 2-[2-(R,S)-1-(4-chloro-2,5-dimethylbenzenesulfonyl)-3-oxo-1,2,3,4-tetrahydroquinoxalin-2-yl]-N-[2-(4-aminophenyl)eth-1-yl]acetamide and isoxazol-5-ylcarbonyl chloride.

HPLC (CH$_3$CN—H$_2$O-0.1% TFA): R$_t$=10.738 min. MS (ES): m/e (M+H+) 623 (M+Na+) 645.

Example 141

Preparation of 2-[2-(R,S)-1-(4-chloro-2,5-dimethyl-benzenesulfonyl)-3-oxo-1,2,3,4-tetrahydroquinoxalin-2-yl]-N-{4-[N-(3-methylpyrazol-5-yl-carbonyl)amino]pheneth-1-yl}acetamide The title compound was prepared using Method I' starting with 2-[2-(R,S)-1-(4-chloro-2,5-dimethylbenzenesulfonyl)-3-oxo-1,2,3,4-tetrahydroquinoxalin-2-yl]-N-[2-(4-aminophenyl)eth-1-yl]acetamide and 3-methylpyrazol-5-ylcarbonyl chloride.

HPLC (CH$_3$CN—H$_2$O-0.1% TFA): R$_t$=10.466 min. MS (ES): m/e (M+H+) 636 (M+Na+) 658.

Example 142

Preparation of 2-[2-(R,S)-1-(4-chloro-2,5-dimethyl-benzenesulfonyl)-3-oxo-1,2,3,4-tetrahydroquinoxalin-2-yl]-N-{4-[N-(1-methyl-3-t-butylpyrazol-5-ylcarbonyl)amino]pheneth-1-yl}acetamide The title compound was prepared using Method I' starting with 2-[2-(R,S)-1-(4-chloro-2,5-dimethylbenzene-sulfonyl)-3-oxo-1,2,3,4-tetrahydroquinoxalin-2-yl]-N-[2-(4-aminophenyl)eth-1-yl]acetamide and 1-methyl-3-t-butylpyrazol-5-ylcarbonyl chloride.

HPLC (CH$_3$CN—H$_2$O-0.1% TFA): R$_t$=12.15 min. MS (ES): m/e (M+H+) 692 (M+Na+) 714.

Example 143

Preparation of 2-[2-(R,S)-1-(4-chloro-2,5-dimethyl-benzenesulfonyl)-3-oxo-1,2,3,4-tetrahydroquinoxalin-2-yl]-N-{4-[N-(4-methyl-1,2,3-thiadiazol-5-yl-carbonyl)amino]pheneth-1-yl}acetamide The title compound was prepared using Method I' starting with 2-[2-(R,S)-1-(4-chloro-2,5-dimethylbenzenesulfonyl)-3-oxo-1,2,3,4-tetrahydroquinoxalin-2-yl]-N-[2-(4-aminophenyl)eth-1-yl]acetamide and 4-methyl-1,2,3-thiadiazole-5-carbonyl chloride.

HPLC (CH$_3$CN—H$_2$O-0.1% TFA): R$_t$=10.454 min. MS (ES): m/e (M+H+) 654 (M+Na+) 676.

Example 144

Preparation of 2-[2-(R,S)-1-(4-chloro-2,5-dimethylbenzenesulfonyl)-3-oxo-1,2,3,4-tetrahydroquinoxalin-2-yl]-N-{4-[N-(chloromethylenecarbonyl)amino]pheneth-1-yl}acetamide The title compound was prepared using Method I' starting with 2-[2-(R,S)-1-(4-chloro-2,5-dimethylbenzene-sulfonyl)-3-oxo-1,2,3,4-tetrahydroquinoxalin-2-yl]-N-[2-(4-aminophenyl)eth-1-yl]acetamide and chloroacetyl chloride.

HPLC (CH$_3$CN—H$_2$O-0.1% TFA): R$_t$=10.755 min. MS (ES): m/e (M+H+) 604 (M+Na+) 626.

Example 145

Preparation of 2-[2-(R,S)-1-(4-chloro-2,5-dimethylbenzenesulfonyl)-3-oxo-1,2,3,4-tetrahydroquinoxalin-2-yl]-N-{4-[N-(chlorophen-2-ylcarbonyl)amino]pheneth-1-yl}acetamide The title compound was prepared by Method I' starting with 2-[2-(R,S)-1-(4-chloro-2,5-dimethylbenzene-sulfonyl)-3-oxo-1,2,3,4-tetrahydroquinoxalin-2-yl]-N-[2-(4-aminophenyl)eth-1-yl]acetamide and 2-chlorobenzoyl chloride.

HPLC (CH$_3$CN—H$_2$O-0.1% TFA): R$_t$=11.549 min. MS (ES): m/e (M+H+) 666 (M+Na+) 688.

Example 146

Preparation of 2-[2-(R,S)-1-(4-chloro-2,5-dimethylbenzenesulfonyl)-3-oxo-1,2,3,4-tetrahydroquinoxalin-2-yl]-N-{4-[N-(phenylcarbonyl)amino]pheneth-1-yl}acetamide The title compound was prepared by Method I' starting with 2-[2-(R,S)-1-(4-chloro-2,5-dimethylbenzene-sulfonyl)-3-oxo-1,2,3,4-tetrahydroquinoxalin-2-yl]-N-[2-(4-aminophenyl)eth-1-yl]acetamide and benzoyl chloride.

HPLC (CH$_3$CN—H$_2$O-0.1% TFA): R$_t$=11.405 min. MS (ES): m/e (M+H+) 632 (M+Na+) 654.

Example 147

Preparation of 2-[2-(R,S)-1-(4-chloro-2,5-dimethylbenzenesulfonyl)-3-oxo-1,2,3,4-tetrahydroquinoxalin-2-yl]-N-{4-[N-(isopropylcarbonyl)amino]pheneth-1-yl}acetamide The title compound was prepared by Method I' starting with 2-[2-(R,S)-1-(4-chloro-2,5-dimethylbenzene-sulfonyl)-3-oxo-1,2,3,4-tetrahydroquinoxalin-2-yl]-N-[2-(4-aminophenyl)eth-1-yl]acetamide and isobutyryl chloride.

HPLC (CH$_3$CN—H$_2$O-0.1% TFA): R$_t$=10.927 min. MS (ES): m/e (M+H+) 598 (M+Na+) 620

Example 148

Preparation of 2-[2-(R,S)-1-(4-chloro-2,5-dimethylbenzenesulfonyl)-3-oxo-1,2,3,4-tetrahydroquinoxalin-2-yl]-N-{4-[N-(pyrid-2-ylcarbonyl)amino]pheneth-1-yl}acetamide The title compound was prepared by Method I' starting with 2-[2-(R,S)-1-(4-chloro-2,5-dimethylbenzene-sulfonyl)-3-oxo-1,2,3,4-tetrahydroquinoxalin-2-yl]-N-[2-(4-aminophenyl)eth-1-yl]acetamide and pyrid-2-yl carbonyl chloride.

HPLC (CH$_3$CN—H$_2$O-0.1% TFA): R$_t$=11.392 min. MS (ES): m/e (M+H+) 633 (M+Na+) 655

Example 149

Preparation of 2-[2-(R,S)-1-(4-chloro-2,5-dimethylbenzenesulfonyl)-3-oxo-1,2,3,4-tetrahydroquinoxalin-2-yl]-N-{4-[N-(pyrid-4-ylcarbonyl)amino]pheneth-1-yl}acetamide The title compound was prepared using Method I' starting with 2-[2-(R,S)-1-(4-chloro-2,5-dimethylbenzene-sulfonyl)-3-oxo-1,2,3,4-tetrahydroquinoxalin-2-yl]-N-[2-(4-aminophenyl)eth-1-yl]acetamide and pyrid-4-ylcarbonyl chloride.

HPLC (CH$_3$CN—H$_2$O-0.1% TFA): R$_t$=9.53 min. MS (ES): m/e (M+H+) 633 (M+Na+) 655.

Example 150

Preparation of 2-[2-(R,S) 1-(4-chloro-2,5-dimethylbenzenesulfonyl)-3-oxo-1,2,3,4mixture was stirred at room temperature overnight. The solid was removed acetamide The title compound was prepared using Method I' starting with 2-[2-(R,S)-1-(4-chloro-2,5-dimethylbenzene-sulfonyl)-3-oxo-1,2,3,4-tetrahydroquinoxalin-2-yl]-N-[2-(4-aminophenyl)eth-1-yl]acetamide and pentanoyl chloride.

HPLC (CH$_3$CN—H$_2$O-0.1% TFA): R$_t$=11.4 min. MS (ES): m/e (M+H+) 612 (M+Na+) 634.

Example 151

Preparation of 2-[2-(R,S)-1-(4-chloro-2,5-dimethylbenzenesulfonyl)-3-oxo-1,2,3,4-tetrahydroquinoxalin-2-yl]-N-{4-[N-(t-butylmethylenecarbonyl)amino]pheneth-1-yl}acetamide The title compound was prepared using Method I' starting with 2-[2-(R,S)-1-(4-chloro-2,5-dimethylbenzene-sulfonyl)-3-oxo-1,2,3,4-tetrahydroquinoxalin-2-yl]-N-[2-(4-aminophenyl)eth-1-yl]acetamide and t-butylacetyl chloride.

HPLC (CH$_3$CN—H$_2$O-0.1% TFA): R$_t$=11.655 min. MS (ES): m/e (M+H+) 626 (M+Na) 648

Example 152

Preparation of 2-[2-(R,S)-1-(4-chloro-2,5-dimethylbenzenesulfonyl)-3-oxo-1,2,3,4-tetrahydroquinoxalin-2-yl]-N-{4-[N-(2-phenylethenylcarbonyl)amino]pheneth-1-yl}acetamide The title compound was prepared using Method I' starting with 2-[2-(R,S)-1-(4-chloro-2,5-dimethylbenzene-sulfonyl)-3-oxo-1,2,3,4-tetrahydroquinoxalin-2-yl]-N-[2-(4-aminophenyl)eth-1-yl]acetamide and cinnamoyl chloride.

HPLC (CH$_3$CN—H$_2$O-0.1% TFA): R$_t$=11.918 min. MS (ES): m/e (M+H+) 658 (M+Na+) 680.

Example 153

Preparation of 2-[2-(R,S)-1-(4-chloro-2,5-dimethyl-benzenesulfonyl)-3-oxo-1,2,3,4-tetrahydroquinoxalin-2-yl]-N-{4-[N-(fluorophen-2-ylcarbonyl)amino]pheneth-1-yl}acetamide The title compound was prepared using Method I' starting with 2-[2-(R,S)-1-(4-chloro-2,5-dimethylbenzene-sulfonyl)-3-oxo-1,2,3,4-tetrahydroquinoxalin-2-yl]-N-[2-(4-aminophenyl)eth-1-yl]acetamide and 2-fluorobenzoyl chloride.

HPLC (CH$_3$CN—H$_2$O-0.1% TFA): R$_t$=11.537 min. MS (ES): m/e (M+H+) 650 (M+Na+) 672.

Example 154

Preparation of 2-[2-(R,S)-1-(4-chloro-2,5-dimethyl-benzenesulfonyl)-3-oxo-1,2,3,4-tetrahydroquinoxalin-2-yl]-N-{4-[N-(methoxymethylenecarbonyl)amino]pheneth-1-yl}acetamide The title compound was prepared using Method I' starting with 2-[2-(R,S)-1-(4-chloro-2,5-dimethylbenzenesulfonyl)-3-oxo-1,2,3,4-tetrahydroquinoxalin-2-yl]-N-[2-(4-aminophenyl)eth-1-yl]acetamide and methoxyacetyl chloride.

HPLC (CH$_3$CN—H$_2$O-0.1% TFA): R$_t$=10.432 min. MS (ES): m/e (M+H+) 600 (M+Na+) 622.

Example 155

Preparation of 2-[2-(R,S)-1-(4-chloro-2,5-dimethyl-benzenesulfonyl)-3-oxo-1,2,3,4-tetrahydroquinoxalin-2-yl]-N-{4-[N-(ethylcarbonyl)amino]pheneth-1-yl}acetamide The title compound was prepared using Method I' starting with 2-[2-(R,S)-1-(4-chloro-2,5-dimethylbenzenesulfonyl)-3-oxo-1,2,3,4-tetrahydroquinoxalin-2-yl]-N-[2-(4-aminophenyl)eth-1-yl]acetamide and propionyl chloride.

HPLC (CH$_3$CN—H$_2$O-0.1% TFA): R$_t$=10.58 min. MS (ES): m/e (M+H+) 584 (M+Na+) 606.

Example 156

Preparation of 2-[2-(R,S)-1-(4-chloro-2,5-dimethyl-benzenesulfonyl)-3-oxo-1,2,3,4-tetrahydroquinoxalin-2-yl]-N-{4-[N-(propylcarbonyl)amino]pheneth-1-yl}acetamide The title compound was prepared using Method I' starting with 2-[2-(R,S)-1-(4-chloro-2,5-dimethylbenzenesulfonyl)-3-oxo-1,2,3,4-tetrahydroquinoxalin-2-yl]-N-[2-(4-aminophenyl)eth-1-yl]acetamide and butyryl chloride.

HPLC (CH$_3$CN—H$_2$O-0.1% TFA): R$_t$=10.931 min. MS (ES): m/e (M+H+) 598 (M+Na+) 620.

Example 157

Preparation of 2-[2-(R,S)-1-(4-chloro-2,5-dimethyl-benzenesulfonyl)-3-oxo-1,2,3,4-tetrahydroquinoxalin-2-yl]-N-{4-[N-(dichloromethylenecarbonyl)amino]pheneth-1-yl}acetamide The title compound was prepared using Method I' starting with 2-[2-(R,S)-1-(4-chloro-2,5-dimethylbenzenesulfonyl)-3-oxo-1,2,3,4-tetrahydroquinoxalin-2-yl]-N-[2-(4-aminophenyl)eth-1-yl]acetamide and dichloroacetyl chloride.

HPLC (CH$_3$CN—H$_2$O-0.1% TFA): R$_t$=11.307 min. MS (ES): m/e (M+H+) 638 (M+Na+) 660.

Example 158

Preparation of 2-[2-(R,S)-1-(4-chloro-2,5-dimethyl-benzenesulfonyl)-3-oxo-1,2,3,4-tetrahydroquinoxalin-2-yl]-N-{4-[N-(methylenedioxyphen-4-ylcarbonyl)amino]pheneth-1-yl}acetamide The title compound was prepared using Method I' starting with 2-[2-(R,S)-1-(4-chloro-2,5-dimethylbenzenesulfonyl)-3-oxo-1,2,3,4-tetrahydroquinoxalin-2-yl]-N-[2-(4-aminophenyl)eth-1-yl]acetamide and 3,4-methylenedioxybenzoyl chloride.

HPLC (CH$_3$CN—H$_2$O-0.1% TFA): R$_t$=11.48 min. MS (ES): m/e (M+H+) 676 (M+Na+) 698.

Example 159

Preparation of 2-[2-(R,S)-1-(4-chloro-2,5-dimethyl-benzenesulfonyl)-3-oxo-1,2,3,4-tetrahydroquinoxalin-2-yl]-N-(2-hydroxyeth-1-yl)acetamide The title compound was synthesized from 2-[(R,S)-1-(4-chloro-2,5-dimethylbenzenesulfonyl)-3-oxo-1,2,3,4-tetrahydroquinoxalin-2-yl]acetic acid and 2-aminoethanol using Method I.

$^1$H NMR (d$_6$-DMSO) δ=10.47 (s, 1H), 7.91 (t, J=7.8 Hz, 1H), 7.48 (s, 1H), 7.43 (s, 1H), 7.40 (d, J=7.8 Hz, 1H), 7.28 (t, J=7.8 Hz, 1H), 7.09 (t, J=7.8 Hz, 1H), 6.82 (d, J=7.8 Hz, 1H), 4.85 (dd, J=5.5, 8.8 Hz, 1H), 3.34–3.30 (m, 2H), 3.07–3.03 (m, 2H), 2.29–2.13 (m, 5H), 2.01 (s, 3H).

Example 160

Preparation of 2-[2-(R,S)-1-(4-chloro-2,5-dimethyl-benzenesulfonyl)-3-oxo-1,2,3,4-tetrahydroquinoxalin-2-yl]-N-(2-bromoeth-1-yl)acetamide The title compound was synthesized from 2-[2-(R,S)-1-(4-chloro-2,5-dimethylbenzenesulfonyl)-3-oxo-1,2,3,4-tetrahydroquinoxalin-2-yl]acetic acid and 2-bromoethylamine using Method I.

$^1$H NMR (CDCl$_3$) δ=8.09 (s, 1H), 7.70 (d, J=8.2 Hz, 1H), 7.57 (s, 1H), 7.31–7.14 (m, 4H), 6.75 (d, J=8.2 Hz, 1H), 6.32 (bs, 1H), 5.09 (dd, J=4.4, 9.9 Hz, 1H), 3.63–3.34 (m, 4H), 2.56 (dd, J=4.4, 14.8 Hz, 1H), 2.40 (dd, J=4.4, 14.8 Hz, 1H), 2.26 (s, 3H), 2.06 (s, 3H).

Example 161

Preparation of 2-[2-(R,S)-1-(4-chloro-2,5-dimethyl-benzenesulfonyl)-3-oxo-1,2,3,4-tetrahydroquinoxalin-2-yl]-N-[2-(imidazol-4-yl)eth-1-yl]acetamide The title compound was synthesized from 2-[2-(R,S)-1-(4-chloro-2,5-dimethylbenzenesulfonyl)-3-oxo-1,2,3,4-tetrahydroquinoxalin-2-yl]acetic acid and histamine using Method I.

$^1$H NMR (d$_6$-DMSO) δ=10.51 (s, 1H), 9.03 (s, 1H), 8.17 (t, J=7.5 Hz, 1H), 7.45–7.41 (m, 3H), 7.34 (d, J=7.5 Hz, 1H), 7.28 (t, J=7.5 Hz, 1H), 7.10 (t, J=7.5 Hz, 1H), 6.83 (d, J=7.5 Hz, 1H), 4.85 (dd, J=5.1, 9.9 Hz, 1H), 3.33–3.25 (m, 2H), 2.73 (t, J=6.6 Hz, 2H), 2.29–2.08 (m, 5H), 1.98 (s, 3H).

Example 162

Preparation of 2-[2-(R,S)-1-(4-chloro-2,5-dimethyl-benzenesulfonyl)-3-oxo-1,2,3,4-tetrahydroquinoxalin-2-yl]-N-[2-(indol-3-yl)eth-1-yl]acetamide The title compound was synthesized from 2-[2-(R,S)-1-(4-chloro-2,5-dimethylbenzenesulfonyl)-3-oxo-1,2,3,4-tetrahydroquinoxalin-2-yl]acetic acid and tryptamine using Method I and tryptamine.

$^1$H NMR (d$_6$-DMSO) δ=10.82 (s, 1H), 10.49 (s, 1H), 8.02 (t, J=5.6 Hz, 1H), 7.50–7.25 (m, 6H), 7.14–6.95 (m, 4H), 6.83 (d, J=7.8 Hz, 1H), 4.89 (dd, J=5.1, 9.3 Hz), 3.33–3.21 (m, 3H), 2.75 (t, J=7.8 Hz, 2H), 2.29–2.13 (m, 5H), 2.02 (s, 3H).

Example 163

Preparation of 2-[2-(R,S)-1-(4-chloro-2,5-dimethyl-benzenesulfonyl)-3-oxo-1,2,3,4-tetrahydroquinoxalin-2-yl]-N-[(2-dimethylamino)eth-1-yl]acetamide The title compound was synthesized from 2-[2-(R,S)-1-(4-chloro-2,5-dimethylbenzenesulfonyl)-3-oxo-1,2,3,4-tetrahydroquinoxalin-2-yl]acetic acid and N,N-dimethylethylenediamine using Method I.

$^1$H NMR (d$_6$-DMSO) δ=10.41 (s, 1H), 7.81 (t, J=7.8 Hz, 1H), 7.48–7.38 (m, 2H), 7.27 (t, J=7.8 Hz, 1H), 7.09 (t, J=7.8 Hz, 1H), 6.82 (d, J=7.8 Hz, 1H), 4.85 (dd, J=5.1, 8.7 Hz, 1H), 3.10–3.00 (m, 2H), 2.23–2.15 (m, 7H), 2.11 (s, 6H), 2.02 (s, 3H).

Example 164

Preparation of 2-[2-(R,S)-1-(4-chloro-2,5-dimethyl-benzenesulfonyl)-3-oxo-1,2,3,4-tetrahydroquinoxalin-2-yl]-N-[(4-methoxycarbonylphenyl)methyl) acetamide The title compound was synthesized from 2-[2-(R,S)-1-(4-chloro-2,5-dimethylbenzenesulfonyl)-3-oxo-1,2,3,4-tetrahydroquinoxalin-2-yl]acetic acid and methyl (4-aminomethyl)benzoate using Method I.

Example 165

Preparation of 2-[2-(R,S)-1-(4-chloro-2,5-dimethyl-benzenesulfonyl)-3-oxo-1,2,3,4-tetrahydroquinoxalin-2-yl]-N-(4-nitrobenzyl)acetamide The title compound was synthesized from 2-[2-(R,S)-1-(4-chloro-2,5-dimethylbenzenesulfonyl)-3-oxo-1,2,3,4-tetrahydroquinoxalin-2-yl]acetic acid and 4-nitrobenzylamine using Method I.

$^1$H NMR (d$_6$-DMSO) δ=10.52 (s, 1H), 8.61 (t, J=7.8 Hz, 1H), 8.19 (d, J=8.7 Hz, 2H), 7.54 (d, J=8.7 Hz, 2H), 7.46–7.42 (m, 3H), 7.29 (t, J=7.8 Hz, 1H), 7.12 (t, J=7.8 Hz, 1H), 6.83 (d, J=7.8 Hz, 1H), 4.94 (dd, J=3.9, 9.3 Hz, 1H), 4.50–4.42 (m, 1H), 4.33–4.25 (m, 1H), 2.43–2.26 (m, 2H), 2.22 (s, 3H), 1.99 (s, 3H).

Example 166

Preparation of 2-[2-(R,S)-1-(4-chloro-2,5-dimethyl-benzenesulfonyl)-3-oxo-1,2,3,4-tetrahydroquinoxalin-2-yl]-N-[2-(N-morpholino)eth-1-yl]acetamide The title compound was synthesized from 2-[2-(R,S)-1-(4-chloro-2,5-dimethylbenzenesulfonyl)-3-oxo-1,2,3,4-tetrahydroquinoxalin-2-yl]acetic acid and 4-(2-aminoethyl) morpholine using Method I.

$^1$H NMR (d$_6$-DMSO) δ=10.45 (s, 1H0, 7.83 (t, J=7.8 Hz, 1H), 7.46–7.40 (m, 3H), 7.28 (t, J=7.8 Hz, 1H0, 7.10 (t, J=7.8 Hz, 1H), 6.82 (d, J=7.8 Hz, 1H), 4.85 (dd, J=4.8, 8.7 Hz, 1H), 3.56 (m, 4H), 3.18–3.00 (m, 2H), 2.34–2.1 1(m, 11H), 2.01 (s, 3H).

Example 167

Preparation of 2-[2-(R,S)-1-(4-chloro-2,5-dimethyl-benzenesulfonyl)-3-oxo-1,2,3,4-tetrahydroquinoxalin-2-yl]-N-[2-(pyrid-2-yl)eth-1-yl]acetamide The title compound was synthesized from 2-[2-(R,S)-1-(4-chloro-2,5-dimethylbenzenesulfonyl)-3-oxo-1,2,3,4-tetrahydroquinoxalin-2-yl]acetic acid and 2-aminoethylpyridine using Method I.

$^1$H NMR (d$_6$-DMSO) δ=10.48 (s, 1H), 8.78 (d, J=5.4 Hz, 1H), 8.45 (t, J=8.1 Hz, 1H), 8.13 (t, J=7.8 Hz, 1H), 7.87 (t, J=8.1 Hz, 2H), 7.42 (d, J=5.4 Hz, 2H), 7.34 (d, J=7.8 Hz, 1H), 7.27 (t, J=7.8 Hz, 1H), 7.09 (t, J=7.8 Hz, 1H), 6.82 (d, J=7.8 Hz, 1H), 4.82 (dd, J=4.2, 8.7 Hz, 1H), 3.43–3.41 (m, 2H), 3.13–3.08 (m, 2H), 2.26–2.06 (m, 5H), 1.97 (s, 3H).

Example 168

Preparation of 2-[2-(R,S)-1-(4-chloro-2,5-dimethyl-benzenesulfonyl)-3-oxo-1,2,3 4-tetrahydroquinoxalin-2-yl]-N-(pyrid-2-ylmethyl)acetamide The title compound was synthesized from 2-[2-(R,S)-1-(4-chloro-2,5-dimethylbenzenesulfonyl)-3-oxo-1,2,3,4-tetrahydroquinoxalin-2-yl]acetic acid and 2-aminomethylpyridine using Method I.

$^1$H NMR (d$_6$-DMSO) δ=10.56 (s, 1H), 8.97 (t, J=5.4 Hz, 1H), 8.77 (d, J=5.4 Hz, 1H), 8.40 (t, J=7.8 Hz, 1H), 7.82 (t, J=7.8 Hz, 2H), 7.45–7.42 (m, 3H), 7.30 (t, J=7.8 Hz, 1H), 7.11 (t, J=7.8 Hz, 1H), 6.84 (d, J=7.8 Hz, 1H), 4.91 (dd, J=4.8, 9.9 Hz, 1H), 4.63–4.51 (m, 2H), 2.48–2.44 (m, 1H), 2.34–2.26 (m, 1H), 2.22 (s, 3H), 1.97 (s, 3H).

Example 169

Preparation of 2-[2-(R,S)-1-(napth-1-ylsulfonyl)-3-oxo-1,2,3,4-tetrahydroquinoxalin-2-yl]-N-benzylacetamide The title compound was synthesized from 2-[2-(R,S)-3-oxo-1,2,3,4-tetrahydroquinoxalin-2-yl]-N-benzylacetamide condensed with 1-naphthalene-sulfonyl chloride using Method G.

$^1$H NMR (d$_6$-DMSO) δ=10.88 (s, 1H), 8.37 (t, J=6.0 Hz, 1H), 8.24 (d, J=8.1 Hz, 1H), 8.06 (d, J=8.1 Hz, 1H), 8.01 (d, J=8.4 Hz, 1H), 7.89 (d, J=8.4 Hz, 1H), 7.60 (t, J=7.8 Hz, 1H), 7.53 (t, J=7.8 Hz, 1H), 7.45 (d, J=8.4 Hz, 1H), 7.34–7.07 (m, 8H), 6.53 (d, J=7.8 Hz, 1H), 5.03 (dd, J=4.8, 8.7 Hz, 1H), 4.33–4.26 (m, 1H), 4.16–4.09 (m, 1H), 2.44–2.21 (m, 2H).

Example 170

Preparation of 2-[2-(R,S)-1-(4-chloro-2,5-dimethyl-benzenesulfonyl)-3-oxo-1,2,3,4-tetrahydroquinoxalin-2-yl]-N-(4-aminobenzyl)acetamide The title compound was synthesized from 2-[2-(R,S)-1-(4-chloro-2,5-dimethylbenzenesulfonyl)-3-oxo-1,2,3,4-tetrahydroquinoxalin-2-yl]-N-(4-nitrobenzyl)acetamide using Method K.

$^1$H NMR (d$_6$-DMSO) δ=10.51 (s, 1H), 8.50 (t, J=5.7 Hz, 1H), 7.46–7.26 (m, 7H), 7.10 (t, J=7.8 Hz, 1H), 4.94 (dd, J=4.8, 9.3 Hz, 1H), 4.33 (dd, J=5.4, 15.3 Hz, 1H), 4.15 (dd, J=5.4, 15.3 Hz, 1H), 3.56 (bs, 2H), 2.36 (dd, 1H, J=5.3, 15.3 Hz), 2.28–2.20 (m, 4H), 1.97 (s, 3H).

Example 171

Preparation of 2-[2-(R,S)-1-(4-chloro-2,5-dimethyl-benzenesulfonyl)-3-oxo-1,2,3,4-tetrahydroquinoxalin-2-yl]-N-[1-methoxy]-N-methylacetamide The title compound was synthesized from 2-[2-(R,S)-1-(4-chloro-2,5-dimethylbenzenesulfonyl)-3-oxo-1,2,3,4-tetrahydroquinoxalin-2-yl]acetic acid and N,O-dimethylhydroxylamine using Method I.

$^1$H NMR (d$_6$-DMSO) δ=10.56 (s, 1H), 7.49–7.40 (m, 3H), 7.28 (t, J=7.8 Hz, 1H), 7.09 (t, J=7.8 Hz, 1H), 6.84 (d, J=7.8, 1H), 4.90 (dd, J=5.4, 8.1 Hz, 1H), 3.45 (s, 3H), 3.04 (s, 3H), 2.55–2.44 (m, 2H), 2.23 (s, 3H), 2.02 (s, 3H).

Example 172

Preparation of 2-[2-(R,S)-1-(4-chloro-2,5-dimethyl-benzenesulfonyl)-3-oxo-1,2,3,4-tetrahydroquinoxalin-2-yl]-N-(4-carboxybenzyl)acetamide The title compound was synthesized from 2-[2-(R,S)-1-(4-chloro-2,5-dimethylbenzenesulfonyl)-3-oxo-1,2,3,4-tetrahydroquinoxalin-2-yl]acetic acid and methyl 4-(aminomethyl)benzoate using Method I. The resulting product was then hydrolyzed using Method C.

$^1$H NMR (d$_6$-DMSO) δ=10.51 (s, 1H), 8.55 (t, J=5.8 Hz, 2H), 7.93 (d, J=8.4 Hz, 1H), 7.46–7.40 (m, 5H), 7.34 (t, J=8.4 Hz, 1H), 7.11 (t, J=8.4 Hz, 1H), 6.82 (d, J=8.4, 1H), 4.94 (dd, J=4.2, 9.9 Hz, 1H), 4.44 (dd, J=6.0, 16.5 Hz, 1H), 2.40 (dd, J=6.0, 16.5 Hz, 1H), 2.30–2.22 (m, 4H), 1.99 (s, 3H).

Example 173

Preparation of 2-[2-(R,S)-1-(2-chlorobenzenesulfonyl)-3-oxo-1,2,3,4-tetrahydroquinoxalin-2-yl]-N-benzylacetamide The title compound was synthesized from 2-[2-(R,S)-3-oxo-1,2,3,4-tetrahydroquinoxalin-2-yl]-N-benzylacetamide condensed to 2-chlorophenylsulfonyl chloride using Method G.

$^1$H NMR (d$_6$-DMSO) δ=10.54 (s, 1H), 8.34 (t, J=6.0 Hz, 1H), 7.83 (dd, J=2.2, 7.9 Hz, 1H), 7.43–7.49 (m, 2H), 7.15–7.33 (m, 6H), 7.01 (dt, J=1.5, 7.9 Hz, 1H), 6.84 (d, J=1.5, 7.9 Hz, 1H), 5.08 (dd, J=5.8, 9.0 Hz, 1H), 4.28 (dd, J=6.0, 15.0 Hz, 1H), 4.16 (dd, J=6.0, 15.0 Hz, 1H), 2.41 (dd, J=5.8, 15.0 Hz, 1H), 2.33 (dd, J=9.0, 15.0 Hz, 1H).

Example 174

Preparation of 2-[2-(R,S)-1-(3-chlorobenzenesulfonyl)-3-oxo-1,2,3,4-tetrahydroquinoxalin-2-yl]-N-benzylacetamide The title compound was synthesized from 2-[2-(R,S)-3-oxo-1,2,3,4-tetrahydroquinoxalin-2-yl]-N-benzylacetamide condensed with 3-chlorophenyl-sulfonyl chloride using Method G.

$^1$H NMR (d$_6$-DMSO) δ=10.36 (s, 1H), 8.35 (t, J=5.7 Hz, 1H), 7.76 (dd, J=2.2, 7.9 Hz, 1H), 7.52 (t, J=8.3 Hz, 1H), 7.46 (dd, J=1.4, 7.9 Hz, 1H), 7.20-7.34 (m, 8H), 7.12 (dt, J=1.4, 7.9 Hz, 1H), 6.80 (dd, J=2.2, 7.9 Hz, 1H), 5.01 (dd, J=5.8, 9.0 Hz, 1H), 4.34 (dd, J=6.0, 15.0 Hz, 1H), 4.16 (dd, J=6.0, 15.0 Hz, 1H), 2.38 (dd, J=5.8, 15.0 Hz, 1H), 2.26 (dd, J=9.0, 15.0 Hz, 1H).

Example 175

Preparation of 2-[2-(R,S)-1-(3,4-dichlorobenzenesulfonyl)-3-oxo-1,2,3,4-tetrahydroquinoxalin-2-yl]-N-benzylacetamide The title compound was synthesized from 2-[2-(R,S)-3-oxo-1,2,3,4-tetrahydroquinoxalin-2-yl]-N-benzylacetamide condensed with 3,4-dichlorophenylsulfonyl chloride using Method G.

$^1$H NMR (d$_6$-DMSO) δ=10.42 (s, 1H), 8.36 (t, J=5.8 Hz, 1H), 7.78 (d, J=7.9 Hz, 1H), 7.45 (d, J=7.9 Hz, 1H), 7.24–7.37 (m, 8H), 7.13 (d, J=7.9 Hz, 1H), 6.82 (d, J=7.9 Hz, 1H), 5.00 (dd, J=5.8, 9.0 Hz, 1H), 4.34 (dd, J=6.0, 15.0 Hz, 1H), 4.15 (dd, J=6.0, 15.0 Hz, 1H), 2.39 (dd, J=5.8, 14.9 Hz, 1H), 2.26 (dd, J=9.0, 14.9 Hz, 1H).

Example 176

Preparation of 2-[2-(R,S)-1-(2,4,6-trichlorobenzenesulfonyl)-3-oxo-1,2,3,4-tetrahydroquinoxalin-2-yl]-N-benzylacetamide The title compound was from 2-[2-(R,S)-3-oxo-1,2,3,4-tetrahydroquinoxalin-2-yl]-N-benzylacetamide condensed to 2,4,6-trichlorophenylsulfonyl chloride using Method G.

$^1$H NMR (d$_6$-DMSO) δ=10.72 (s, 1H), 8.38 (t, J=5.8 Hz, 1H), 7.86 (s, 2H), 7.51 (d, J=7.9 Hz, 1H), 7.20–7.31 (m, 6H), 7.04 (t, J=7.9 Hz, 1H), 6.90 (d, J=7.9 Hz, 1H), 5.07 (dd, J=5.8, 9.0 Hz, 1H), 4.24 (dd, J=6.0, 15.0 Hz, 1H), 4.15 (dd, J=6.0, 15.0 Hz, 1H), 2.30–2.49 (m, 2H).

Example 177

Preparation of 2-[2-(R,S)-1-(2,3-dichlorobenzenesulfonyl)-3-oxo-1,2,3,4-tetrahydroquinoxalin-2-yl]-N-phenethylacetamide The title compound was synthesized from 2-[2-(R,S)-3-oxo-1,2,3,4-tetrahydroquinoxalin-2-yl]acetic acid and phenethyl amine using Method D followed by condensation with 2,3-dichlorophenylsulfonyl chloride using Method G.

MS (ES): m/e 541 (M$^+$+Na); HPLC (CH$_3$CN—H$_2$O-0.1% TFA) (long column): R$_t$=28.11 min.

Example 178

Preparation of 2-[2-(R,S)-1-(2,4,5-trichlorobenzene-sulfonyl)-3-oxo-1,2,3,4-tetrahydroquinoxalin-2-yl]-N-benzylacetamide The title compound was synthesized from 2-[2-(R,S)-3-oxo-1,2,3,4-tetrahydroquinoxalin-2-yl]-N-benzylacetamide condensed to 2,4,5-trichlorophenylsulfonyl chloride using Method G.

$^1$H NMR (d$_6$-DMSO) δ=10.74 (s, 1H), 8.46 (t, J=5.4 Hz, 1H), 8.15 (s, 3H), 7.89 (s, 3H), 7.53 (d, J=7.8 Hz, 1H), 7.39–7.27 (m, 6H), 7.13 (dt, J=1.2, 7.8 Hz, 1H), 6.91 (dd, J=1.2, 7.8, 1H), 5.05 (dd, J=4.2, 9.3 Hz, 1H), 4.35 (dd, J=6.0, 15.0 Hz, 1H), 4.19 (dd, J=6.0, 15.0 Hz, 1H), 2.46 (dd, J=4.2, 14.7 Hz, 1H), 2.35 (dd, J=9.3, 14.7 Hz, 1H).

Example 179

Preparation of 2-[2-(R,S)-1-(3,5-bis(trifluoromethyl)benzenesulfonyl)-3-oxo-1,2,3,4-tetrahydroquinoxalin-2-yl]-N-benzylacetamide

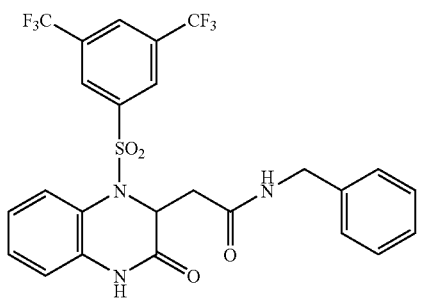

The title compound was synthesized from 2-[2-(R,S)-3-oxo-1,2,3,4-tetrahydroquinoxalin-2-yl]-N-benzylacetamide condensed to 3,5-di(trifluoromethyl) phenylsulfonyl chloride using Method G.

$^1$H NMR (d$_6$-DMSO) δ=10.37 (s, 1H), 8.59 (s, 1H), 8.42 (t, J=5.8 Hz, 1H), 7.67 (s, 2H), 7.49 (d, J=8.7 Hz, 1H), 7.15–7.35 (m, 8H), 5.02 (dd, J=5.4, 11.9 Hz, 1H), 4.33 (dd, J=6.0, 15.0 Hz, 1H), 4.15 (dd, J=6.0, 15.0 Hz, 1H), 2.25–2.44 (m, 2H).

Example 180

Preparation of 2-[2-(R,S)-1-(4-chloro-2,5-dimethyl-benzenesulfonyl)-3-oxo-1,2,3,4-tetrahydroquinoxalin-2-yl]-N-(4-phenylbut-1-yl)acetamide The title compound was synthesized from 2-[2-(R,S)-3-oxo-1,2,3,4-tetrahydroquinoxalin-2-yl]acetic acid and phenylbutylamine using Method D followed by reaction with 2,5-dimethyl-4-chlorophenylsulfonyl chloride using Method G.

$^1$H NMR (d$_6$-DMSO) δ=10.41 (s, 1H), 7.81 (t, J=5.8 Hz, 1H), 7.46 (s, 1H), 7.40 (s, 1H), 7.35 (d, J=7.9 Hz, 1H), 7.24–7.29 (m, 3H), 7.14–7.20 (m, 3H), 7.04 (t, J=7.9 Hz, 1H), 6.83 (d, J=7.9 Hz, 1H), 4.86 (dd, J=5.4, 10.0 Hz, 1H), 2.92–3.07 (m, 2H), 2.56 (t, J=7.2 Hz, 2H), 2.10–2.77 (m, 4H), 2.04 (s, 3H), 1.50–1.1.58 (m, 2H), 1.32–1.39 (m, 2H).

Example 181

Preparation of 2-[2-(R,S)-1-(4-chloro-2,5-dimethyl-benzenesulfonyl)-3-oxo-1,2,3,4-tetrahydroquinoxalin-2-yl]-N-[2-(piperidin-N-yl)eth-1-yl]acetamide The title compound was synthesized from 2-[2-(R,S)-3-oxo-1,2,3,4-tetrahydro-quinoxalin-2-yl]acetic acid and 1-aminoethylpiperidine using Method D followed by reaction with 2,5-dimethyl-4-chlorophenylsulfonyl chloride using Method G.

$^1$H NMR (d$_6$-DMSO) δ=10.48 (s, 1H), 9.90 (bs, 1H), 8.34 (t, J=5.7 Hz, 1H), 7.42–7.47 (m, 3H), 7.29 (t, J=7.6 Hz, 1H), 7.11 (t, J=7.6 Hz, 1H), 6.84 (d, J=7.6 Hz, 1H), 4.91 (dd, J=5.1, 9.0 Hz, 1H), 3.41–3.44 (m, 4H), 2.87–3.04 (m, 3H), 2.18–2.36 (m, 5H), 2.01 (s, 3H), 1.68–1.1.78 (m, 4H), 1.03–1.07 (m, 3H).

Example 182

Preparation of 2-[2-(R,S)-1-(2,3-dichlorobenzene-sulfonyl)-3-oxo-1,2,3,4-tetrahydroquinoxalin-2-yl]-N-isopropylacetamide The title compound was synthesized from 2-[2-(R,S)-3-oxo-1,2,3,4-tetrahydroquinoxalin-2-yl]acetic acid and isopropylamine using Method D; this was then reacted with 2,3-dichlorophenylsulfonyl chloride using Method G.

$^1$H NMR (d$_6$-DMSO) δ=10.60 (s, 1H), 7.93 (dd, J=1.4, 7.9 Hz, 1H), 7.86 (d, J=1.4, 7.9 Hz, 1H), 7.71 (d, J=7.6 Hz, 1H), 7.47–7.52 (m, 2H), 7.20 (t, J=7.6 Hz, 1H), 7.04 (t, J=7.6 Hz, 1H), 6.87 (d, J=7.6 Hz, 1H), 4.99 (dd, J=5.8, 9.0 Hz, 1H), 3.74 (m, 1H), 2.15–2.29 (m, 2H), 1.04 (d, J=6.5 Hz, 3H), 0.94 (d, J=6.5 Hz, 3H).

Example 183

Preparation of 2-[2-(R,S)-1-(2-methyl-5-nitrobenzenesulfonyl)-3-oxo-1,2,3,4-tetrahydroquinoxalin-2-yl]-N-benzylacetamide The title compound was synthesized from 2-[2-(R,S)-3-oxo-1,2,3,4-tetrahydroquinoxalin-2-yl]-N-benzylacetamide condensed to 2-methyl-5-nitrophenyl-sulfonyl chloride using Method G.

MS (ES): m/e 495 (M+H); HPLC (H$_2$O—CH$_3$CN-0.1% TFA) (long column): R$_t$=28.08 min.

Example 184

Preparation of 2-[2-(R,S)-1-(2,3-dichlorobenzene-sulfonyl)-3-oxo-1,2,3,4-tetrahydroquinoxalin-2-yl]-N,N-diisopropylacetamide The title compound was synthesized from 2-[2-(R,S)-3-oxo-1,2,3,4-tetrahydroquinoxalin-2-yl]acetic acid and diisopropylamine using Method D followed by reaction with 2,3-dichlorophenylsulfonyl chloride using Method G.

$^1$H NMR (d$_6$-DMSO) δ=10.65 (s, 1H), 7.93 (dd, J=1.4, 8.3 Hz, 1H), 7.86 (d, J=1.4, 8.3 Hz, 1H), 7.48–7.53 (m, 2H), 7.20 (dt, J=1.4, 7.6 Hz, 1H), 7.02 (dt, J=1.4, 7.6 Hz, 1H), 6.88 (dd, J=1.4, 7.6 Hz, 1H), 5.01 (dd, J=4.7, 7.9 Hz, 1H), 3.67–3.73 (m, 1H), 3.46–3.5 (m, 1H), 2.39–2.47 (m, 2H), 0.95–1.28 (m, 12H).(25)

Example 185

Preparation of 2-[2-(R,S)-1-(2,3-dichlorobenzenesulfonyl)-3-oxo-1,2,3,4-tetrahydroquinoxalin-2-yl]-N-[2-(pyrid-2-yl)eth-1-yl]acetamide The title compound was synthesized from 2-[2-(R,S)-3-oxo-1,2,3,4-tetrahydroquinoxalin-2-yl]acetic acid and 2-aminoethylpyridine using Method D followed by reaction with 2,3-dichlorophenylsulfonyl chloride using Method G.

$^1$H NMR (d$_6$-DMSO) δ=10.64 (s, 1H), 8.73 (d, J=5.0 Hz, 1H), 8.36 (t, J=7.2 Hz, 1H), 8.08 (t, J=5.8 Hz, 1H), 7.94 (dd, J=7.9, 1.4 Hz, 1H, 7.85–7.77 (m, 3H), 7.50 (t, J=7.9 Hz, 1H), 7.43 (d, J=7.9 Hz, 1H), 7.21 (dt, J=7.8, 1.4 Hz, 1H), 7.03 (dt, J=7.8, 1.4 Hz, 1H), 6.87 (dd, J=7.8, 1.4 Hz, 1H); MS (ES): m/e 520 (M+H).

Example 186

Preparation of 2-[2-(R,S)-1-(4-chloro-2,5-dimethyl-benzenesulfonyl)-3-oxo-1,2,3,4-tetrahydroquinoxalin-2-yl]-N-benzyl-N-methylacetamide The title compound was synthesized from 2-[2-(R,S)-3-oxo-1,2,3,4-tetrahydroquinoxalin-2-yl]acetic acid and N-methylbenzylamine using Method D followed by reaction with 2,5-dimethyl-4-chlorophenylsulfonyl chloride using Method G.

$^1$H NMR (d$_6$-DMSO) δ=10.49 (s, 0.67H),10.43 (s, 0.33H), 7.48–7.19 (m, 8H), 7.09–7.00 (m, 2H), 6.85 (d, J=7.6 Hz, 0.67H), 6.77 (d, J=7.6 Hz, 0.33H), 5.04–4.99 (m, 1H), 4.64 (d, J=14.4 Hz, 0.67H), 4.46 (d, J=17.0 Hz, 0.33H), 4.33 (d, J=14.4 Hz, 0.67H), 4.22 (d, J=17.0 Hz, 0.33H), 2.77 (s, 1H), 2.67 (s, 2H), 2.62–2.48 (m, 2H), 2.23 (s, 3H), 2.05–2.04 (m, 3H); MS (ES): m/e 513 (M+H); HPLC (CH$_3$CN—H$_2$O-0.1% TFA) (long column): R$_t$=31.08 min.

Example 187 (Intermediate Compound)

Preparation of 2-[2-(R,S)-1-(4-Chloro-2,5-dimethyl-benzenesulfonyl)-3-oxo-1,2,3,4-tetrahydroquinoxalin-2-yl]acetic acid The title compound was synthesized through multi-step procedures: first starting from 1,2-phenylenediamine and maleimide using Methods F then E; then reacting with 2,5-dimethyl-4-chlorophenylsulfonyl chloride using Method G to lead to the title compound.

$^1$H NMR (d$_6$-DMSO) δ=10.46 (s, 0.67H), 7.52 (s, 1H), 7.30 (dt, J=1.2, 7.5 Hz, 1H), 7.11 (dt, J=1.2, 7.5 Hz, 1H), 6.85 (dd, J=1.2, 7.5 Hz, 1H), 4.96 (dd, J=4.8, 9.3 Hz, 1H), 2.26 (s, 3H), 2.19 (dd, J=4.8, 15.6 Hz, 1H), 2.08–2.00 (m, 4H); $^{13}$C NMR (d$_6$-DMSO) δ=172.31, 167.69, 138.93, 137.32, 134.53, 134.58, 134.25, 133.20, 132.71, 129.04, 128.72, 123.30, 122.08, 116.42, 45.76, 37.99, 19.50, 19.32; MS (ES): m/e 409 (M+H); HPLC (CH$_3$CN—H$_2$O-0.1% TFA) (short column): R$_t$=4.94 min.

Example 188 (Intermediate Compound)

Preparation of 2-[2-(R,S)-1-(4-dichloro-2,5-dimethylbenzenesulfonyl)-3-oxo-1,2,3,4-tetrahydroquinoxalin-2-yl]methoxy acetic acid 2-[2-(R,S)-1-(4-Chloro-2,5-dimethylbenzenesulfonyl)-3-oxo-1,2,3,4-tetrahydroquinoxalin-2-yl]acetic acid (483 mg, 1.18 mmol) was dissolved in methanol (30 ml). The solution was heated under reflux with catalytic amount of conc. H$_2$SO$_4$ overnight. The solvent was concentrated to almost dryness and the solid was washed with water. After drying in the desicator, a white solid was obtained as the title compound.

$^1$H NMR (d$_6$-DMSO) δ=10.61 (s, 1H), 7.52–7.40 (m, 3H), 7.29 (t, J=7.5 Hz, 1H), 7.11 (t, J=7.5 Hz, 1H), 6.83 (d, J=7.5 Hz, 1H), 4.79 (dd, J=4.5, 9.6 Hz, 1H), 3.56 (s, 3H), 2.63 (dd, J=4.5, 14.7 Hz, 1H), 2.33–2.49 (m, 4H), 1.99 (s, 3H); MS (ES): m/e 446 (M$^+$+Na); HPLC (CH$_3$CN—H$_2$O-0.1% TFA) (long column): R$_t$=28.65 min.

Example 189

Preparation of 2-[2-(R,S)-1-(2,4,6-trimethylbenzenesulfonyl)-3-oxo-1,2,3,4-tetrahydroquinoxalin-2-yl]-N-cyclohexylmethylacetamide A mixture of 2-[2-(R,S)-1-(2,4,6,trimethylbenzenesulfonyl)-3-oxo-1,2,3,4-tetrahydroquinoxalin-2-yl]-N-benzylacetamide (100 mg, 0.21 mmol), PtO$_2$ (20 mg) in ethanol (25 mL) and glacial acetic acid (1.5 mL) was hydrogenated under a hydrogen balloon overnight. The reaction mixture was filtered through celite and rinsed with ethanol. The solvent was then evaporated under reduced pressure and the solid was washed with water several times. The title compound was obtained as a white solid after drying in the desicator.

$^1$H NMR (d$_6$-DMSO) δ=10.61 (s, 1H), 7.72 (t, J=4.7 Hz, 1H), 7.26–7.22 (m, 1H), 7.03–6.93 (m, 5H), 4.77 (dd, J=4.3, 9.0 Hz, 1H), 2.86 (q, J=6.5, 12.6 Hz, 1H), 2.70 (q, J=6.5, 12.6 Hz, 1H), 2.33 (s, 6H), 2.27 (m, 4H), 2.13 (dd, J=9.0, 14.1 Hz, 1H), 1.62–0.75 (m, 11H); MS (ES): m/e 506 (M$^+$+Na); HPLC (CH$_3$CN—H$_2$O-0.1% TFA) (long column): R$_t$=31.22 min.

Example 190 (Intermediate Compound)

Preparation of 2-[2-(R,S)-3-Oxo-1-(2,4,6-trimethyl-benzenesulfonyl)-1,2,3,4-tetrahydroquinoxalin-2-yl]-acetic acid Preparation of the title material followed the general procedure described in Method G with 2-[2-(R,S)-3-oxo-1,2,3,4-tetrahydroquinoxalin-2-yl]acetic acid and 2,4,6-trimethylbenzenesulfonyl chloride.

$^1$H NMR (d$_6$-DMSO) δ=12.55 (s, 1H), 10.68 (s, 1H), 7.28 (dt, J=1.6, 8.4 Hz, 1H), 7.10–7.07 (m, 3H), 7.01 (dt, J=1.6, 8.4 Hz, 1H), 6.95 (dd, J=1.6, 8.4 Hz, 1H), 4.66 (dd, J=4.4, 10.4 Hz, 1H), 2.50–2.45 (m, 1H), 2.36 (s, 6H), 2.28 (s, 3H), 2.13 (dd, J=10.4, 15.2 Hz, 1H); HPLC (CH$_3$CN—H$_2$O-0.1% TFA) (long column): R$_t$=23.22 min.

Example 191

Preparation of 2-[2-(R,S)-1-(4-chloro-2,5-dimethyl-benzenesulfonyl)-3-oxo-1,2,3,4-tetrahydroquinoxalin-2-yl]-N-[2-(piperidin-2-yl)eth-1-yl]acetamide The title compound was synthesized from 2-[2-(R,S)-1-(4-chloro-2,5-dimethylbenzenesulfonyl)-3-oxo-1,2,3,4-tetrahydroquinoxalin-2-yl]-N-[2-(pyrid-2-yl)eth-1-yl]acetamide using Method L (Step A).

$^1$H NMR (d$_6$-DMSO HCl salt) δ=10.49 (s, 1H), 8.26–8.20 (m, 1H), 7.46–7.40 (m, 3H), 7.30 (t, J=7.5 Hz, 1H), 7.12 (t, J=7.5 Hz, 1H), 6.82 (d, J=7.5 Hz, 1H), 4.90–4.87 (m, 1H), 3.29–3.25 (m, 2H), 3.06–2.88 (m, 3H), 2.38–2.10 (m, 5H), 111.95 (s, 3H), 1.90–1.35 (m, 8H); HPLC (CH₃CN—H₂O-0.1% TFA) (short column): $R_f$=3.62, 3.74 min. (provides a pair of diastereomers).

Example 192

Preparation of 2-[2-(R,S)-1-(4-chloro-2,5-dimethyl-benzenesulfonyl)-3-oxo-1,2,3,4-tetrahydroquinoxalin-2-yl]-N-(piperidin-2-ylmethyl)acetamide The title compound was synthesized from 2-[2-(R,S)-1-(4-chloro-2,5-dimethylbenzenesulfonyl)-3-oxo-1,2,3,4-tetrahydroquinoxalin-2-yl]-N-(pyrid-2-ylmethyl)acetamide using Method L (Step A).

¹H NMR (d₆-DMSO HCl salt) δ=10.55 (s, 1H), 8.30–8.26 (m, 1H), 7.48–7.41 (m, 3H), 7.30 (t, J=7.5 Hz, 1H), 7.12 (t, J=7.5 Hz, 1H), 6.84 (d, J=7.5 Hz, 1H), 4.92 (dd, J=5.4, 9.3 Hz, 1H), 3.29–3.11 (m, 3H), 3.08–2.91 (m, 1H), 2.88–2.72 (m, 1H), 2.36 (dd, J=5.4, 14.4 Hz, 1H), 2.25–2.18 (m, 4H), 1.99 (s, 3H), 1.83–1.31 (m, 6H); HPLC (CH₃CN—H₂O-0.1% TFA) (short column): $R_f$=3.88 (broad) min.

Example 193

Preparation of 2-[2-(R,S)-1-(4-chloro-2,5-dimethyl-benzenesulfonyl)-3-oxo-1,2,3,4-tetrahydroquinoxalin-2-yl]-N-(2-pyrid-3-yleth-1-yl)acetamide The title compound was synthesized from 2-[2-(R,S)-1-(4-chloro-2,5-dimethylbenzenesulfonyl)-3-oxo-1,2,3,4-tetrahydroquinoxalin-2-yl]acetic acid and 3-aminoethylpyridine using Method I.

¹H NMR (d₆-DMSO) δ=10.47 (s, 1H), 8.42–8.41 (m, 2H), 8.00 (t, J=4.8 Hz, 1H), 7.61 (d, J=7.5 Hz, 1H), 7.47–7.24 (m, 5H), 7.08 (t, J=7.5 Hz, 1H), 6.81 (d, J=7.5 Hz, 1H), 4.86 (dd, J=4.8, 9.3 Hz, 1H), 3.32–3.12 (m, 2H), 2.71–2.64 (m, 2H), 2.25–2.09 (m, 5H), 1.99 (s, 3H); ¹³C NMR (d₆-DMSO) d 167.62, 166.95, 150.54, 148.08, 139.14, 137.42, 136.88, 135.57, 134.61, 134.33, 134.09, 133.30, 132.75, 129.12, 128.87, 124.05, 123.45, 121.71, 116.45, 56.34, 36.67, 32.37, 19.40, 19.34.

Example 194

Preparation of 2-[2-(R,S)-1-(4-chloro-2,5-dimethyl-benzenesulfonyl)-3-oxo-1,2,3,4-tetrahydroquinoxalin-2-yl]-N-{2-[(N-methyl)pyrrolidin-2-yl]eth-1-yl}acetamide The title compound was synthesized from 2-[2-(R,S)-1-(4-chloro-2,5-dimethylbenzenesulfonyl)-3-oxo-1,2,3,4-tetrahydroquinoxalin-2-yl]acetic acid and 2-(1-methyl-pyrrolidin-2-yl)-ethylamine using Method I.

¹H NMR (d₆-DMSO) δ=10.46 (s, 1H), 7.88–7.85 (m, 1H), 7.47–7.38 (m, 3H), 7.28 (t, J=7.8 Hz, 1H), 7.10 (t, J=7.8 Hz, 1H), 6.82 (d, J=7.8 Hz, 1H), 4.86 (dd, J=4.8, 9.3 Hz, 1H), 3.11–3.01 (m, 1H), 2.99–2.88 (m, 2H), 2.22–2.2.12 (m, 8H), 2.09–1.98 (m, 5H), 1.91–1.80 (m, 1H), 1.71–1.55 (m, 3H), 1.38–1.15 (m, 2H); HPLC (CH₃CN—H₂O-0.1% TFA) (short column): $R_f$=3.43 min. (broad).

Example 195

Preparation of 2-[2-(R,S)-1-(4-chloro-2,5-dimethyl-benzenesulfonyl)-3-oxo-1,2,3,4-tetrahydroquinoxalin-2-yl]-N-[2-(piperidin-3-yl)eth-1-yl]acetamide The title compound was synthesized from 2-[2-(R,S)-1-(4-chloro-2,5-dimethylbenzenesulfonyl)-3-oxo-1,2,3,4-tet rahydroquinoxalin-2-yl]-N-(2-pyrid-3-yleth-1-yl)acetamide using Method L (Step A).

¹H NMR (d₆-DMSO HCl salt) δ=10.50 (d, J=7.2 Hz, 1H), 7.98–7.90 (m, 1H), 7.46–7.40 (m, 3H), 7.28 (t, J=7.8 Hz, 1H), 7.11 (t, J=7.8 Hz, 1H), 6.85 (d, J=7.8 Hz, 1H), 4.86 (dd, J=5.7, 9.3 Hz, 1H), 3.20–3.11 (m, 2H), 3.06–2.92 (m, 2H), 2.78–2.68 (m, 1H), 2.31–2.01 (m, 5H), 2.00 (s, 3H), 1.78–1.08 (m, 8H); HPLC (CH₃CN—H₂O-0.1% TFA) (short column): $R_f$=3.43 min.

Example 196

Preparation of 2-[2-(R,S)-1-(4-chloro-2,5-dimethyl-benzenesulfonyl)-3-oxo-1,2,3,4-tetrahydroquinoxalin-2-yl]-N-[3-(dimethylamino)prop-1-yl]acetamide The title compound was synthesized from 2-[2-(R,S)-1-(4-chloro-2,5-dimethylbenzenesulfonyl)-3-oxo-1,2,3,4-tetrahydroquinoxalin-2-yl]acetic acid and N,N-dimethylethylenediamine using Method I.

¹H NMR (d₆-DMSO) δ=10.46 (s, 1H), 7.87 (t, J=5.4 Hz, 1H), 7.46–7.39 (m, 3H), 7.28(t, J=7.8 Hz, 1H), 7.10 (t, J=7.8 Hz, 1H), 6.82 (d, J=7.8 Hz, 1H), 4.86 (dd, J=5.1, 9.3 Hz, 1H), 3.08–2.88 (m, 2H), 2.30–2.09 (m, 11H), 2.01 (s, 3H), 1.51–1.44 (m, 2H); HPLC (CH₃CN—H₂O-0.1% TFA) (short column): $R_f$=3.29 min.

Example 197

Preparation of 2-[2-(R,S)-1-(4-chloro-2,5-dimethyl-benzenesulfonyl)-3-oxo-1,2,3,4-tetrahydroquinoxalin-2-yl]-N-[2-(N-methylpiperidin-2-yl)]acetamide The title compound was synthesized from 2-[2-(R,S)-1-(4-chloro-2,5-dimethylbenzenesulfonyl)-3-oxo-1,2,3,4-tetrahydroquinoxalin-2-yl]-N-[2-(pyrid-2-yl)eth-1-yl]acetamide by Method J and Method K.

¹H NMR (d₆-DMSO) δ=10.46 (s, 1H), 7.86–7.80 (m, 1H), 7.47–7.39 (m, 3H), 7.28 (t, J=7.5 Hz, 1H), 7.10 (t, J=7.5 Hz, 1H), 6.82 (d, J=7.5 Hz, 1H), 4.88–4.83 (m, 1H), 3.11–2.89 (m, 2H), 2.73–2.69 (m, 1H), 2.26–2.20 (m, 4H), 2.15–2.08 (m, 4H), 2.02 (s, 3H), 1.96–1.83 (m, 2H), 1.65–1.15 (m, 8H); MS (ES): m/e 534 (M+H).

Example 198

Preparation of 2-[2-(R,S)-1-(4-chloro-2,5-dimethyl-benzenesulfonyl)-3-oxo-1,2,3,4-tetrahydroquinoxalin-2-yl]-N-[2-(N-methylpiperidin-3-yl)eth-1-yl]acetamide The title compound was synthesized from 2-[2-(R,S)-1-(4-chloro-2,5-dimethylbenzenesulfonyl)-3-oxo-1,2,3,4-tetrahydroquinoxalin-2-yl]-N-(2-pyrid-3-yleth-1-yl)acetamide by Method J and Method K.

¹H NMR (d₆-DMSO) δ=10.46 (s, 1H), 7.84 (t, J=5.4 Hz, 1H), 7.47–7.39 (m, 3H), 7.27 (t, J=7.5 Hz, 1H), 7.08 (t, J=7.5 Hz, 1H), 6.82 (d, J=7.5 Hz, 1H), 4.84 (dd, J=6.0, 9.0 Hz, 1H), 3.05–2.88 (m, 2H), 2.64–2.61 (m, 2H), 2.28–2.21 (m, 4H), 2.17–2.10 (m, 4H), 2.02 (s, 3H), 1.79–0.75 (m, 8H); MS (ES): m/e: 534 (M+H).

Example 199

Preparation of 2-[2-(R,S)-1-(4-chloro-2,5-dimethylbenzenesulfonyl)-3-oxo-1,2,3,4-tetrahydroquinoxalin-2-yl]-N-[(N-methylpiperidin-2-yl)methyl]acetamide The title compound was synthesized from 2-[2-(R,S)-1-(4-chloro-2,5-dimethylbenzenesulfonyl)-3-oxo-1,2,3,4-tetrahydroquinoxalin-2-yl]-N-(pyrid-2-ylmethyl)acetamide by Method J and Method K.

$^1$H NMR (d$_6$-DMSO) δ=10.46 (s, 1H), 7.74–7.68 (m, 1H), 7.45–7.36 (m, 3H), 7.28 (t, J=7.5 Hz, 1H), 7.12 (t, J=7.5 Hz, 1H), 6.82 (d, J=7.5 Hz, 1H), 4.86 (dd, J=5.7, 8.4 Hz, 1H), 3.32–3.29 (m, 1H), 3.04–2.79 (m, 2H), 2.72–2.68 (m, 1H), 2.42–1.91 (m, 13H), 1.81–1.15 (m, 8H).

Example 200

Preparation of 2-[2-(R,S)-1-(4-chloro-2,5-dimethylbenzenesulfonyl)-3-oxo-1,2,3,4-tetrahydroquinoxalin-2-yl]-N-cyanomethylacetamide The title compound was synthesized from 2-[2-(R,S)-1-(4-chloro-2,5-dimethylbenzenesulfonyl)-3-oxo-1,2,3,4-tetrahydroquinoxalin-2-yl]acetic acid and aminoacetonitrile using Method I.

$^1$H NMR (d$_6$-DMSO) δ=10.52 (s, 1H), 8.66 (t, J=5.4 Hz, 2H), 7.48–7.39 (m, 3H), 7.29 (t, J=7.5 Hz, 1H), 7.11 (t, J=7.5 Hz, 1H), 6.84 (d, J=7.5 Hz, 1H), 4.85 (dd, J=4.8, 9.3 Hz, 1H), 4.11–4.09 (m, 2H), 2.28 (dd, J=4.8, 14.7 Hz, 1H), 2.27–2.19 (m, 4H), 2.00 (s, 3H); $^{13}$C NMR (d$_6$-DMSO) δ 168.42, 166.57, 139.23, 137.43, 134.67, 134.19, 134.02, 133.34, 132.75, 129.26, 128.80, 123.58, 121.54, 117.99, 116.54, 56.07, 36.19, 27.45, 19.40, 19.34;); HPLC (CH$_3$CN—H$_2$O-0.1% TFA) (short column): R$_t$=4.11 min.

Example 201

Preparation of 2-[2-(R,S)-1-(4-chloro-2,5-dimethylbenzenesulfonyl)-3-oxo-1,2,3,4-tetrahydroquinoxalin-2-yl]-N-aminoacetamide To the solution of 2-[2-(R,S)-1-(4-chloro-2,5-dimethylbenzenesulfonyl)-3-oxo-1,2,3,4-tetrahydro-quinoxalin-2-yl]acetic acid (460 mg, 1.1 mmol) in methanol (20 ml) was added hydrazine hydrate (0.16 ml, 3.3 mmol). The resulting solution was stirred at room temperature overnight. Most of the solvent was removed under reduced pressure and the final small volume solution was place into a refrigerator overnight. The solid was isolated through filtration and washed with small amount of water to give the title compound.

$^1$H NMR (d$_6$-DMSO) δ=8.96 (s, 1H), 7.45–7.39 (m, 3H), 7.28 (t, J=7.5 Hz, 1H), 7.11 (t, J=7.5 Hz, 1H), 6.81 (d, J=7.5 Hz, 1H), 4.87 (dd, J=5.7, 9.0 Hz, 1H), 2.23–2.10 (m, 5H), 1.99 (s, 3H); MS (ES): m/e 423 (M+H).

Example 202

Preparation of 2-[2-(R,S)-1-(4-chloro-2,5-dimethylbenzenesulfonyl)-3-oxo-1,2,3,4-tetrahydroquinoxalin-2-yl]-N-methylcarboxamideacetamide 2-[2-(R,S)-1-(4-chloro-2,5-dimethylbenzenesulfonyl)-3-oxo-1,2,3,4-tetrahydroquinoxalin-2-yl]-N-cyanomethylacetamide (500 mg, 1.12 mmol) was suspended in conc. HCl (10 mL) and was stirred at room temperature for 24 hours. The solid was then isolated through filtration and washed with water a few times to give a white solid as the title compound.

$^1$H NMR (d$_6$-DMSO) δ=10.50 (s, 1H), 8.18 (t, J=5.4 Hz, 2H), 7.48–7.39 (m, 3H), 7.28 (dt, J=1.3, 7.7 Hz, 1H), 7.16–7.06 (m, 2H), 6.83 (dd, J=1.3, 7.7 Hz, 1H), 4.87 (dd, J=5.9, 8.4 Hz, 1H), 3.57–3.55 (m, 2H), 2.38–2.26 (m, 2H), 2.23 (s, 3H), 2.01 (s, 3H); MS (ES): m/e 487 (M$^+$+Na); HPLC (CH$_3$CN—H$_2$O-0.1% TFA) (short column): R$_t$=3.37 min.

Example 203

Preparation of 2-[2-(R,S)-1-(4-chloro-2,5-dimethylbenzenesulfonyl)-3-oxo-1,2,3,4-tetrahydroquinoxalin-2-yl]-N-[1-(R)-phenyleth-1-yl]acetamide The title compound was synthesized from 2-[2-(R,S)-1-(4-chloro-2,5-dimethylbenzenesulfonyl)-3-oxo-1,2,3,4-tetrahydroquinoxalin-2-yl]acetic acid and (R)-1-phenylethylamine using Method I.

$^1$H NMR (d$_6$-DMSO) δ=10.52 (s, 1H), 8.39–8.35 (m, 1H), 7.51–6.98 (m, 10H), 6.88 (d, J=7.8 Hz, 1H), 4.96–4.93 (m, 2H), 2.48–2.20 (m, 5H), 2.07 (s, 1.5H), 1.99 (s, 1.5H), 1.35 (d, J=7.4 HZ, 1.5H), 1.31 (d, J=7.4 Hz, 1.5H); MS: m/z (EI$^+$) 533 (M$^+$+Na); HPLC (CH$_3$CN—H$_2$O-0.1% TFA) (short column): R$_t$=5.31, 5.36 min (provided a pair of diasteromers).

Example 204

Preparation of 2-[2-(R,S)-1-(4-chloro-2,5-dimethylbenzenesulfonyl)-3-oxo-1,2,3,4-tetrahydroquinoxalin-2-yl]-N-[1-(S)-phenyleth-1-yl]acetamide The title compound was synthesized from 2-[2-(R,S)-1-(4-chloro-2,5-dimethylbenzenesulfonyl)-3-oxo-1,2,3,4-tetrahydroquinoxalin-2-yl]acetic acid and (S)-1-phenylethylamine using Method I.

$^1$H NMR (d$_6$-DMSO) δ=10.52 (s, 1H), 8.39–8.35 (m, 1H), 7.51–6.98 (m, 10H), 6.88 (d, J=7.8 Hz, 1H), 4.96–4.93 (m, 2H), 2.48–2.20 (m, 5H), 2.07 (s, 1.5H), 1.99 (s, 1.5H), 1.35 (d, J=7.4 HZ, 1.5H), 1.31 (d, J=7.4 Hz, 1.5H); MS: m/z (EI$^+$) 535 (M$^+$+Na); HPLC (CH$_3$CN—H$_2$O-0.1% TFA) (short column): R$_t$=5.31, 5.36 min.

Example 205

Preparation of 2-[2-(S)-1-(4-chloro-2,5-dimethylbenzenesulfonyl)-3-oxo-1,2,3,4-tetrahydroquinoxalin-2-yl]-N-[2-(pyrid-4-yl)eth-1-yl]acetamide The title compound was synthesized from 1,2-fluoronitrobenzene and L-aspartic acid using Methods A, B, and C; the resulting product was reacted with 2,5-dimethyl-4-chlorophenylsulfonyl chloride using Method H; reaction with 2-aminoethylpyridine using Method I led to the title compound.

$^1$H NMR (d$_6$-DMSO, TFA salt) δ=10.52 (s, 1H), 8.82 (d, J=6.6 Hz, 2H), 8.09 (t, J=5.4 Hz, 1H), 7.85 (d, J=6.6 Hz, 2H), 7.48 (s, 1H), 7.47 (s, 1H), 7.39–7.30 (m, 2H), 7.14 (dt, J=1.2, 7.5 Hz, 1H), 6.86 (dd, J=1.2, 7.5 Hz, 1H), 4.88 (dd, J=4.8, 9.3 Hz, 1H), 3.49–3.38 (m, 2H), 3.00–2.91 (m, 2H), 2.30–2.24 (m, 4H), 2.15 (dd, J=9.6, 14.4 Hz, 1H), 2.01 (s, 3H); MS (ES): m/e: 514 (M+H); HPLC (CH$_3$CN—H$_2$O-0.1% TFA) (short column): R$_t$=3.45 min.

Example 206

Preparation of 2-[2-(R)-1-(4-chloro-2,5-dimethyl-benzenesulfonyl)-3-oxo-1,2,3,4-tetrahydroquinoxalin-2-yl]-N-[2-(pyrid-4-yl)eth-1-yl]acetamide The title compound was synthesized from 1,2-fluoronitrobenzene and D-aspartic acid using Methods A, B, and C; reaction with 2,5-dimethyl-4-chlorophenylsulfonyl chloride using Method H followed by reaction with 2-aminoethylpyridine using Method I led to the title compound.

$^1$H NMR ($d_6$-DMSO HCl salt) δ=10.48 (s, 1H), 8.82 (d, J=6.6 Hz, 2H), 8.06 (t, J=5.4 Hz, 1H), 7.90 (d, J=6.6 Hz, 2H), 7.42 (s, 1H), 7.41 (s, 1H), 7.34–7.25 (m, 2H), 7.09 (t, J=7.5 Hz, 1H), 6.82 (d, J=7.5 Hz, 1H), 4.83 (dd, J=5.1, 9.0 Hz, 1H), 3.67–3.60 (m, 2H), 3.02–2.91 (m, 2H), 2.25–2.19 (m, 4H), 2.10 (dd, J=9.0, 14.1 Hz, 1H), 1.97 (s, 3H); MS (ES): m/e: 514 (M+H); HPLC ($CH_3CN$—$H_2O$-0.1% TFA) (short column): $R_t$=3.34 min.

Example 207

Preparation of 2-[2-(R)-1-(4-chloro-2,5-dimethyl-benzenesulfonyl)-3-oxo-1,2,3,4-tetrahydroquinoxalin-2-yl]-N-[2-(N-methylpiperidin-4-yl)eth-1-yl]acetamide The title compound was synthesized from 2-[2-(R)-1-(4-chloro-2,5-dimethylbenzenesulfonyl)-3-oxo-1,2,3,4-tetrahydroquinoxalin-2-yl]-N-[2-(pyrid-4-yl)eth-1-yl]acetamide using Methods J and K.

MS (ES): m/e 534 (M+H), 556 (M+Na).

Example 208

Preparation of 2-[2-(S)-1-(4-chloro-2,5-dimethyl-benzenesulfonyl)-3-oxo-1,2,3,4-tetrahydroquinoxalin-2-yl]-N-[2-(N-methylpiperidin-4-yl)eth-1-yl]acetamide The title compound was synthesized from 2-[2-(S)-1-(4-chloro-2,5-dimethylbenzenesulfonyl)-3-oxo-1,2,3,4-tetrahydroquinoxalin-2-yl]-N-[2-(pyrid-4-yl)eth-1-yl]acetamide using Methods J and K.

MS (ES): m/e 534 (M+H), 556 (M+Na); HPLC (acetonitrile-water-0.1% TFA) $R_t$=4.39 min

Example 209

Preparation of N-[2-(4-Amino-phenyl)-ethyl]-2-[1-(4-chloro-2,5-dimethylbenzenesulfonyl)-3-oxo-1,2,3,4-tetrahydroquinoxalin-2-yl]-acetamide The title compound was synthesized from 2-[2-(R,S)-1-(4-chloro-2,5-dimethylbenzenesulfonyl)-3-oxo-1,2,3,4-tetrahydroquinoxalin-2-yl]acetic acid and 4-aminoethylaniline using Method I.

$^1$H NMR ($d_6$-DMSO) δ=10.46 (s, 1H), 7.90 (t, J=5.4 Hz, 1H), 7.48–7.35 (m, 3H), 7.27 (dt, J=1.8, 7.8 Hz, 1H), 7.20–7.17 (m, 1H), 7.09 (dt, J=1.8, 7.8 Hz, 1H), 6.83–6.76 (m, 3H), 6.48 (d, J=9.3 Hz, 2H), 4.89–4.84 (m, 2H), 3.16–2.90 (m, 2H), 2.49–2.42 (m, 2H), 2.25–2.15 (m, 5H), 2.02 (s, 3H); MS (ES): m/e: 527 (M+H); HPLC ($CH_3CN$—$H_2O$-0.1% TFA) (short column): $R_t$=3.56 min.

Example 210

Preparation of 2-[2-(R,S)-1-(4-chloro-2,5-dimethyl-benzenesulfonyl)-3-oxo-1,2,3,4-tetrahydroquinoxalin-2-yl]-N-(pyrid-4-ylmethyl)acetamide The title compound was synthesized from 2-[2-(R,S)-1-(4-chloro-2,5-dimethylbenzenesulfonyl)-3-oxo-1,2,3,4-tetrahydroquinoxalin-2-yl]acetic acid and 4-aminomethylpyridine using Method I.

$^1$H NMR ($d_6$-DMSO) δ=10.56 (s, 1H), 8.59–8.53 (m, 3H), 7.51–7.47 (m, 3H), 7.37–7.30 (m, 3H), 7.17 (t, J=7.8 Hz, 1H), 6.88 (d, J=7.8 Hz, 1H), 4.98 (dd, J=5.0, 9.9 Hz, 1H), 4.38 (dd, J=6.0, 16.5 Hz, 1H), 4.23 (dd, J=5.4, 16.5 Hz, 1H), 2.46 (dd, J=5.0, 14.1 Hz, 1H), 2.36–2.27 (m, 4H), 2.04 (s, 3H).

Example 211

Preparation of 2-[2-(R,S)-1-(4-chloro-2,5-dimethyl-benzenesulfonyl)-3-oxo-1,2,3,4-tetrahydroquinoxalin-2-yl]-N-[2-(4-cyanophenyl)eth-1-yl]acetamide The title compound was synthesized from 2-[2-(R,S)-1-(4-chloro-2,5-dimethylbenzenesulfonyl)-3-oxo-1,2,3,4-tetrahydroquinoxalin-2-yl]acetic acid and 4-aminoethylbenzonitrile using Method I.

$^1$H NMR ($CD_3OD$) δ=8.11 (bs, 1H), 7.68 (d, J=8.1 Hz, 2H), 7.51–7.43 (m, 4H), 7.30–7.24 (m, 2H), 7.11 (dt, J=1.2, 8.1 Hz, 1H), 6.79 (dd, J=1.2, 8.1 Hz, 1H), 5.09 (dd, J=5.1, 9.9 Hz, 1H), 3.51–3.44 (m, 1H), 3.39–3.31 (m, 1H), 2.92–2.82 (m, 2H), 2.37 (dd, J=4.8, 14.1 Hz, 1H), 2.27–2.19 (m, 4H), 2.04 (s, 3H); MS (ES): m/e 537 (M+H); HPLC ($CH_3CN$—$H_2O$-0.1% TFA) (short column): $R_t$=5.73 min.

Example 212

Preparation of 2-[2-(R,S)-1-(4-chloro-2,5-dimethyl-benzenesulfonyl)-3-oxo-1,2,3,4-tetrahydroquinoxalin-2-yl]-N-[(pyrid-3-yl)methyl]acetamide The title compound was synthesized from 2-[2-(R,S)-1-(4-chloro-2,5-dimethylbenzenesulfonyl)-3-oxo-1,2,3,4-tetrahydroquinoxalin-2-yl]acetic acid and 3-aminomethylpyridine using Method I.

$^1$H NMR ($d_6$-DMSO) δ=10.49 (s, 1H), 8.49–8.44 (m, 3H), 7.66–7.64 (m, 1H), 7.66–7.25 (m, 5H), 7.10 (t, J=8.1 Hz, 1H), 6.82 (d, J=8.1 Hz, 1H), 4.91 (dd, J=5.1, 9.6 Hz, 1H), 4.32 (dd, J=5.7, 15.6 Hz, 1H), 4.19 (dd, J=5.1, 14.1 Hz, 1H), 2.38 (dd, J=5.1, 14.1 Hz, 1H), 2.34–2.20 (m, 4H), 1.99 (s, 3H).

Example 213

Preparation of 2-[2-(R,S)-1-(4-chloro-2,5-dimethyl-benzenesulfonyl)-3-oxo-4-t-butoxy-carbonylmethyl-1,2,3,4-tetrahydroquinoxalin-2-yl]-N-{2-[N-(t-butoxycarbonylmethyl)piperidin-4-yl]eth-1-yl}acetamide To a solution of 2-[2-(R,S)-1-(4-chloro-2,5-dimethylbenzenesulfonyl)-3-oxo-1,2,3,4-tetrahydroquinoxalin-2-yl]-N-[2-(piperidin-4-yl)eth-1-yl]acetamide (383 mg, 0.69 mmol) in DMF (10 ml) was added potassium carbonate (286.1 mg, 2.1 mmol) and t-butyl bromoacetate (161.5 mg, 0.83 mmol). The resulting mixture was stirred at room temperature overnight. The solid was removed through filtration and the filtrate was concentrated under reduced pressure. Column chromatography in silica gel afforded a white solid as the title compound.

$^1$H NMR (CDCl$_3$) δ=7.64 (dd, J=1.8, 8.4 Hz, 1H), 7.49 (s, 1H), 7.31 (dt, J=1.8, 8.4 Hz, 1H), 7.18 (dt, J=1.8, 8.4 Hz, 1H), 7.11 (s, 1H), 6.55 (d, J=8.1 Hz, 1H), 6.04 (t, J=5.4 Hz, 1H), 5.08 (t, J=5.4 Hz, 1H), 4.44 (d, J=17.0 Hz, 1H), 3.38 (d, J=17.0 Hz, 1H), 3.28–3.14 (m, 2H), 3.07 (s, 2H), 2.93–2.85 (m, 2H), 2.39–2.33 (m, 2H), 2.26 (s, 3H), 2.15–2.07 (m, 2H), 2.02 (s, 3H), 1.68–1.28 (m, 25H); $^{13}$C NMR (CDCl$_3$) d 164.83, 161.98, 161.76, 160.59, 134.53, 131.70, 129.60, 129.06, 128.32, 127.62, 127.27, 124.32, 123.80, 119.14, 117.96, 109.51, 78.10, 75.67, 55.21, 50.87, 48.26, 38.50, 32.20, 32.04, 30.61, 27.64, 26.72, 22.86, 22.67, 14.57, 13.99; MS (ES): m/e: 747 (M+H); HPLC (CH$_3$CN—H$_2$O-0.1% TFA) (short column): R$_t$=5.40 min.

Example 214

Preparation of 2-[2-(R,S)-1-(4-chloro-2,5-dimethyl-benzenesulfonyl)-3-oxo-1,2,3,4-tetrahydroquinoxa-lin-2-yl]-N-{2-[1-(t-butoxycarbonylmethyl)piperi-din-4-yl]eth-1-yl}acetamide To a solution of 2-[2-(R,S)-1-(4-chloro-2,5-dimethylben-zenesulfonyl)-3-oxo-1,2,3,4-tetrahydroquinoxalin-2-yl]-N-[2-(piperidin-4-yl)eth-1-yl]acetamide (383 mg, 0.69 mmol) in DMF (10 ml) was added potassium carbonate (286.1 mg, 2.1 mmol) and t-butyl bromoacetate (161.5 mg, 0.83 mmol). The resulting mixture was stirred at room temperature overnight. The solid was removed through filtration and the filtrate was concentrated under reduced pressure. Column chromatography in silica gel afforded a white solid as the title compound.

$^1$H NMR (CDCl$_3$) δ=8.64 (S, 1H), 7.63 (dd, J=1.4, 8.3 Hz, 1H), 7.53 (s, 1H), 7.28–7.23 (m, 1H), 7.15–7.10 (m, 2H), 6.78 (dd, J=1.3, 8.1 Hz, 1H), 6.10 (t, J=5.4 Hz, 1H), 5.02 (dd, J=4.4, 10.4 Hz, 1H), 3.30–3.21 (m, 2H), 3.10 (s, 2H), 2.95–2.92 (m, 2H), 2.51 (dd, J=4.6, 15.3 Hz, 1H), 2.34 (dd, J=10.0, 15.3 Hz, 1H), 2.24 (s, 3H), 2.16–2.01 (m, 2H), 1.98 (s, 3H), 1.70–1.30 (m, 16H); $^{13}$C NMR (CDCl$_3$) d 169.75, 167.05, 166.89, 139.65, 136.60, 134.54, 133.34, 132.87, 132.21, 131.87, 128.59, 128.25, 124.03, 121.46, 115.94, 80.77, 60.26, 55.88, 53.31, 37.31, 36.86, 35.76, 32.66, 31.86, 31.80, 28.01, 19.64, 19.18; MS (ES): m/e: 633 (M+H); HPLC (CH$_3$CN—H$_2$O-0.1% TFA) (short column): R$_t$=4.23 min.

Example 215

Preparation of 2-[2-(R)-1-(4-chloro-2,5-dimethyl-benzenesulfonyl)-3-oxo-1,2,3,4-tetrahydroquinoxa-lin-2-yl]-N-(2-piperidin-4-yleth-1-yl)acetamide The title compound was synthesized from 2-[2-(R)-1-(4-chloro-2,5-dimethylbenzenesulfonyl)-3-oxo-1,2,3,4-tet-rahydroquinoxalin-2-yl]-N-[2-(pyrid-4-yl)eth-1-yl]aceta-mide using Method K.

$^1$H NMR (d$_6$-DMSO HCl salt) δ=10.53 (s, 1H), 7.96 (t, J=5.4 Hz, 1H), 7.48–7.43 (m, 3H), 7.34 (t, J=7.5 Hz, 1H), 7.17 (t, J=7.5 Hz, 1H), 6.87 (d, J=7.5 Hz, 1H), 4.92 (dd, J=4.5, 9.9 Hz, 1H), 3.31–3.18 (m, 3H), 3.02–2.85 (m, 3H), 2.33–2.11 (m, 5H), 2.01 (s, 3H), 1.67–1.27 (m, 7H); MS (ES): mi/e 519 (M+H); HPLC (CH$_3$CN—H$_2$O-0.1% TFA) (short column): R$_t$=3.31 min.

Example 216

Preparation of 2-[2-(R,S)-1-(4-chloro-2,5-dimethyl-benzenesulfonyl)-3-oxo-1,2,3,4-tetrahydroquinoxa-lin-2-yl]-N-(pyrazin-2-ylmethyl)acetamide

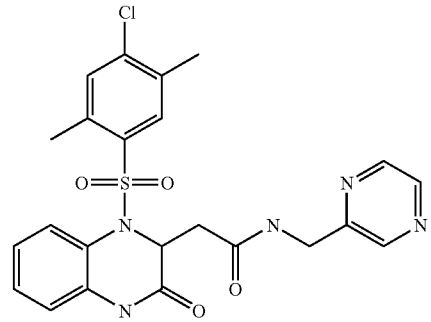

The title compound was synthesized from 2-[2-(R,S)-1-(4-chloro-2,5-dimethylbenzenesulfonyl)-3-oxo-1,2,3,4-tet-rahydroquinoxalin-2-yl]acetic acid and 3-aminomethylpyra-zine using Method I.

$^1$H NMR (d$_6$-DMSO) δ=10.50 (s, 1H), 8.62 (t, J=5.4 Hz, 1H), 8.60–8.53 (m, 3H), 7.47–7.39 (m, 3H), 7.26 (t, J=7.8 Hz, 1H), 7.09 (t, J=7.8 Hz, 1H), 6.83 (d, J=7.8 Hz, 1H), 4.90 (dd, J=5.3, 8.9 Hz, 1H), 4.40–4.32 (m, 2H), 2.38 (dd, J=5.3, 13.9 Hz, 1H), 2.29–2.22 (m, 4H), 1.99 (s, 3H); $^{13}$C NMR (d$_6$-DMSO) d 167.74, 166.45, 166.36, 154.15, 144.09, 143.52, 138.82, 137.06, 134.30, 133.94, 133.74, 133.60, 132.97, 132.40, 128.87, 128.45, 123.20, 121.36, 116.21, 116.15, 56.16, 42.81, 36.52, 19.26, 19.22; MS: m/z (EI$^+$) 500 (M+H); HPLC (CH$_3$CN—H$_2$O-0.1% TFA) (short column): R$_t$=4.40 min.

Example 217

Preparation of 2-[2-(R,S)-1-(4-chloro-2,5-dimethyl-benzenesulfonyl)-3-oxo-1,2,3,4-tetrahydroquinoxa-lin-2-yl]-N-[(2-aminopyrid-4-yl)methyl]acetamide The title compound was synthesized from 2-[2-(R,S)-1-(4-chloro-2,5-dimethylbenzenesulfonyl)-3-oxo-1,2,3,4-tet-rahydroquinoxalin-2-yl]acetic acid and 2-amino-5-aminom-ethylpyridine (D. Feng, J. Med. Chem., 40(23):3726–3733 (1997)) using Method I.

$^1$H NMR (d$_6$-DMSO) δ=10.54 (s, 1H), 8.47 (t, J=5.4 Hz, 1H), 7.82 (d, J=2.4 Hz, 1H), 7.70 (dd, J=2.1, 9.0 Hz, 1H), 7.50–7.40 (m, 3H), 7.32 (dt, J=1.5, 7.8 Hz, 1H), 7.14 (dt, J=1.2, 7.8 Hz, 1H), 6.88–6.84 (m, 2H), 4.94 (dd, J=4.8, 9.3 Hz, 1H), 4.19 (dd, J=6.0, 15.0 Hz, 1H), 4.08 (dd, J=6.0, 15.0 Hz, 1H), 2.39 (dd, J=4.8, 14.4 Hz, 1H), 2.27–2.20 (m, 4H), 2.03 (s, 3H); MS (ES): m/e 514 (M+H); HPLC (CH$_3$CN—H$_2$O-0.1% TFA) (short column): R$_t$=3.28 min.

Example 218

Preparation of 2-[2-(R,S)-1-(4-chloro-2,5-dimethyl-benzenesulfonyl)-3-oxo-1,2,3,4-tetrahydroquinoxa-lin-2-yl]-N-{2-[4-(aminoethyleneamidino)phenyl]eth-1-yl}acetamide The title compound was synthesized from 2-[2-(R,S)-1-(4-chloro-2,5-dimethylbenzenesulfonyl)-3-oxo-1,2,3,4-tet-rahydroquinoxalin-2-yl]-N-[2-(4-cyanophenyl)eth-1-yl]ac-etamide and ethylenediamine using Method T.

¹H NMR (d₆-DMSO) δ=10.54 (s, 1H), 9.67 (bs, 1H), 8.15 (t, J=5.4 Hz, 1H), 8.03 (bs, 1H), 7.80 (d, J=8.1 Hz, 2H), 7.54–7.44 (m, 5H), 7.34 (t, J=7.8 Hz, 1H), 7.16 (t, J=7.8 Hz, 1H), 6.87 (d, J=7.8 Hz, 1H), 5.09 (dd, J=5.1, 9.9 Hz, 1H), 3.51–3.44 (m, 1H), 3.39–3.31 (m, 1H), 2.92–2.82 (m, 2H), 2.37 (dd, J=4.8, 14.1 Hz, 1H), 2.27–2.19 (m, 4H), 2.04 (s, 3H); ¹³C NMR (d₆-DMSO) d 167.18, 166.49, 163.93, 158.45, 158.03, 146.08, 138.81, 137.00, 134.30, 133.95, 133.72, 132.99, 132.33, 129.40, 128.89, 128.68, 128.47, 123.21, 121.38, 116.21, 56.17, 37.14, 36.60, 35.20, 19.28, 19.24; MS (ES): m/e: 597 (M+H); HPLC (CH₃CN—H₂O-0.1% TFA) (short column) R$_t$=2.99 min.

Example 219

Preparation of 2-[2-(R,S)-1-(4-chloro-2,5-dimethylbenzenesulfonyl)-3-oxo-1,2,3,4-tetrahydroquinoxalin-2-yl]-N-{2-[4-(imidazolin-2-yl)phenyl]eth-1-yl}acetamide The title compound was synthesized from 2-[2-(R,S)-1-(4-chloro-2,5-dimethylbenzenesulfonyl)-3-oxo-1,2,3,4-tetrahydroquinoxalin-2-yl]-N-[2-(4-cyanophenyl)eth-1-yl]acetamide and ethylenediamine using Method T.

¹H NMR (d₆-DMSO) δ=10.47 (s, 1H), 10.43 (d, J=3.1 Hz, 1H), 8.04 (t, J=5.4 Hz, 1H), 7.86 (d, J=8.3 Hz, 2H), 7.51 (s, 1H), 7.48 (s, 1H), 7.44 (d, J=8.3 Hz, 2H), 7.36 (dd, J=1.4, 9.0 Hz, 1H), 7.28 (dt, J=1.4, 8.0 Hz, 1H), 7.08 (dt, J=1.5, 9.0 Hz, 1H), 6.82 (dd, J=1.5, 8.0 Hz, 1H), 5.09 (dd, J=5.1, 9.9 Hz, 1H), 3.51–3.44 (m, 1H), 3.39–3.31 (m, 1H), 2.92–2.82 (m, 2H), 2.37 (dd, J=4.8, 14.1 Hz, 1H), 2.27–2.19 (m, 4H), 2.04 (s, 3H); ¹³C NMR (d₆-DMSO) δ=167.63, 166.91, 165.57, 147.74, 139.16, 137.38, 134.63, 134.31, 134.07, 133.32, 132.70, 130.32, 129.19, 129.05, 128.81, 123.50, 121.68, 120.57, 116.50, 56.36, 44.82, 36.68, 35.40, 19.40, 19.37; MS (ES): m/e: 580 (M+H); HPLC (CH₃CN—H₂O-0.1% TFA) (short column): R$_t$=3.65 min.

Example 220

Preparation of 2-[2-(R,S)-1-(4-chloro-2,5-dimethylbenzenesulfonyl)-3-oxo-1,2,3,4-tetrahydroquinoxalin-2-yl]-N-(2-aminothiazol-5-ylmethylacetamide

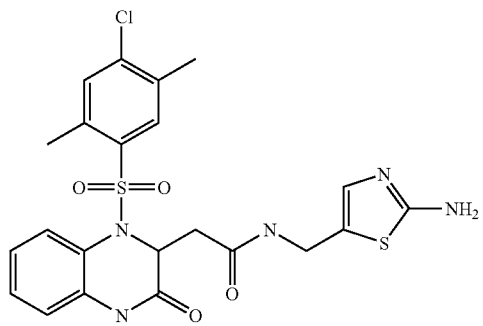

The title compound was synthesized from 2-[2-(R,S)-1-(4-chloro-2,5-dimethylbenzenesulfonyl)-3-oxo-1,2,3,4-tetrahydroquinoxalin-2-yl]acetic acid and 2-amino-5-aminomethylthiazole (P. Marshaw, J. Med. Chem. 38(6):994–1004 (1995); J. Heterocyclic Chem. 18(2):205 (1981)) using Method I.

¹H NMR (d₆-DMSO) δ=10.49 (s, 1H), 8.43 (t, J=5.4 Hz, 1H), 7.45–7.41 (m, 3H), 7.29 (dt, J=1.5, 7.7 Hz, 1H), 7.09 (dt, J=1.5, 7.7 Hz, 1H), 7.32 (d, J=7.7 Hz, 1H), 6.46 (s, 1H), 4.91 (dd, J=5.6, 9.4 Hz, 1H), 4.12–4.07 (m, 2H), 2.37 (dd, J=5.4, 15.1 Hz, 1H), 2.28–2.06 (m, 4H), 1.99 (s, 3H); MS: m/z (EI⁺) 520 (M+H); HPLC (CH₃CN—H₂O-0.1% TFA) (short column) R$_t$=3.49 min.

Example 221

Preparation of 2-[1-(4-chloro-2,5-dimethylbenzenesulfonyl)-3-oxo-1,2,3,4-tetrahydroquinoxalin-2-yl]-N-phenethylacetamide The title compound was synthesized from 2-[2-(R,S)-1-(4-chloro-2,5-dimethylbenzenesulfonyl)-3-oxo-1,2,3,4-tetrahydroquinoxalin-2-yl]acetic acid and 3-phenylethylamine using Method I.

¹H NMR (d₆-DMSO) δ=10.47 (s, 1H), 7.94 (t, J=5.4 Hz, 1H), 7.48–7.408 (m, 10H), 6.82 (d, J=7.5 Hz, 1H), 4.92 (dd, J=5.3, 9.2 Hz, 1H), 3.26–3.12 (m, 2H), 2.67 (t, J=7.1 Hz, 2H), 2.23–2.11 (m, 5H), 2.02 (s, 3H); ¹³C NMR (d₆-DMSO) d 167.01, 166.74, 139.76, 138.79, 137.09, 134.27, 134.00, 132.97, 132.41, 128.96, 128.79, 128.63, 128.51, 126.38, 123.13, 121.40, 119.92, 116.15, 56.15, 53.52, 36.72, 35.24, 19.29, 19.23; MS (ES): m/e: 513 (M+H); HPLC (CH₃CN—H₂O-0.1% TFA) (short column): R$_t$=6.11 min.

Example 222

Preparation of 2-[2-(R,S)-1-(4-chloro-2,5-dimethylbenzenesulfonyl)-3-oxo-1,2,3,4-tetrahydroquinoxalin-2-yl]-N-(3-phenylprop-1-yl)acetamide The title compound was synthesized from 2-[2-(R,S)-1-(4-chloro-2,5-dimethylbenzenesulfonyl)-3-oxo-1,2,3,4-tetrahydroquinoxalin-2-yl]acetic acid and 3-phenylpropylamine using Method I.

¹H NMR (d₆-DMSO) δ=10.49 (s, 1H), 7.98 (t, J=5.4 Hz, 1H), 7.52 (s, 1H), 7.46–7.44 (m, 2H), 7.35–7.19 (m, 6H), 7.13 (t, J=7.5 Hz, 1H), 6.88 (d, J=7.5 Hz, 1H), 4.92 (dd, J=5.1, 9.3 Hz, 1H), 3.11–2.94 (m, 2H), 2.60 (t, J=6.9 Hz, 2H), 2.35–2.19 (m, 5H), 2.05 (s, 3H), 1.67 (p, J=6.6 HZ, 2H); ¹³C NMR (d₆-DMSO) d 167.01, 166.53, 142.10, 138.78, 137.04, 134.27, 134.01, 132.81, 132.39, 130.11, 128.69, 128.57, 128.48, 126.02, 123.14, 121.41, 119.92, 116.15, 56.27, 38.54, 36.73, 32.72, 31.13, 19.29, 19.22; MS (ES): m/e: 527 (M+H); HPLC (CH₃CN—H₂O-0.1% TFA) (short column): R$_t$=6.41 min.

Example 223

Preparation of 2-[2-(R,S)-1-(4-chloro-2,5-dimethylbenzenesulfonyl)-3-oxo-4-methyl-1,2,3,4-tetrahydroquinoxalin-2-yl]-N-[2-(pyrid-4-yl)eth-1-yl]acetamide The title compound was synthesized from N-methyl-1,2-phenylene diamine and oxalacetic acid diethyl ester using Method V.

¹H NMR (d₆-DMSO) δ=8.52–8.50 (m, 2H), 8.04 (t, J=5.4 Hz, 1H), 7.47–7.39 (m, 4H), 7.27–7.22 (m, 3H), 7.16 (d, J=8.1 Hz, 1H), 5.03 (dd, J=4.8, 8.7 Hz, 1H), 3.32–3.21 (m, 2H), 2.77 (s, 3H), 2.70 (dt, J=4.5,7.2 Hz, 2H), 2.27–2.11 (m, 5H), 2.00 (s, 3H); ¹³C NMR (d₆-DMSO) δ=167.60, 165.95, 150.10, 149.03, 139.13, 137.38, 136.05, 134.72, 133.79, 133.13, 132.47, 129.65, 129.33, 124.86, 124.20, 123.65, 116.37, 56.80, 36.52, 34.45, 28.74, 19.43, 19.32; MS (ES): m/e 528 (M+H); HPLC (CH₃CN—H₂O-0.1% TFA) (short column): R$_t$=3.74 min.

Example 224

Preparation of 2-[2-(R,S)-1-(4-chloro-2,5-dimethyl-benzenesulfonyl)-3-oxo-4-methyl-1,2,3,4-tetrahydroquinoxalin-2-yl]-N-[2-(piperidin-4-yl)eth-1-yl] acetamide The title compound was synthesized from 2-[2-(R,S)-1-(4-chloro-2,5-dimethylbenzenesulfonyl)-3-oxo-4-methyl-1,2,3,4-tetrahydroquinoxalin-2-yl]-N-[2-(pyrid-4-yl)eth-1-yl] acetamide using Method L (Step A).

$^1$H NMR (d$_6$-DMSO HCl salt) δ=7.91 (t, J=5.4 Hz, 1H), 7.46–7.40 (m, 3H), 7.34 (s, 1H), 7.24 (t, J=7.8 Hz, 1H), 7.12 (d, J=7.8 Hz, 1H), 4.99 (dd, J=4.5, 9.9 Hz, 1H), 3.35–3.12 (m, 3H), 2.95–2.83 (m, 3H), 2.69 (s, 3H), 2.26–2.22 (m, 4H), 2.10–2.06 (m, 1H), 1.92 (s, 3H), 1.87–1.21 (m, 7H); MS (ES): m/e: 534 (M+H); HPLC (CH$_3$CN—H$_2$O-0.1% TFA) (short column): R$_t$=3.76 min.

Example 225

Preparation of 2-[2-(R,S)-1-(4-chloro-2,5-dimethyl-benzenesulfonyl)-3-oxo-4-methyl-1,2,3,4-tetrahydro-quinoxalin-2-yl]-N-[2-(N-methyl-1,2,5,6-tetrahydropyid-4-yl)eth-1-yl]acetamide The title compound was synthesized from 2-[2-(R,S)-1-(4-chloro-2,5-dimethylbenzenesulfonyl)-3-oxo-4-methyl-1,2,3,4-tetrahydroquinoxalin-2-yl]-N-[2-(pyrid-4-yl)eth-1-yl] acetamide by Method J.

$^1$H NMR (d$_6$-DMSO HCl salt) δ=8.02–7.99 (m, 1H), 7.47–7.41 (m, 4H), 7.30–7.25 (m, 1H), 7.16 (d, J=8.1 Hz, 1H), 5.43–5.38 (m, 1H), 5.05–4.99 (m, 1H), 3.70–3.47 (m, 3H), 3.22–2.97 (m, 3H), 2.77–2.74 (m, 6H), 2.60–2.47 (m, 1H), 2.33–2.16 (m, 6H), 2.13–2.07 (m, 2H), 1.98–1.97 (s, 3H); MS (ES): m/e 545 (M+H); HPLC (CH$_3$CN—H$_2$O-0.1% TFA) (short column): R$_t$=3.85 min.

Example 226

Preparation of 2-[2-(R,S)-1-(4-chloro-2,5-dimethyl-benzenesulfonyl)-3-oxo-1,2,3,4-tetrahydro-6,7-dichloroquinoxalin-2-yl]-N-benzylacetamide 4,5-Dichlorobenzene-1,2-diamine was reacted with N-benzylmaleimide using Method F, followed by condensation with 4-chloro-2,5-dimethylbenzenesulfonyl chloride using Method G.

$^1$H NMR (DMSO-d$_6$) δ=2.09 (s, 3H), 2.24(s, 3H), 2.32(m, 2H), 4.00 (dd, J=6 Hz, 1H), 4.32 (dd, J=6 Hz, 1H), 4.83(dd, J=6 Hz, 1H),7.01–7.54 (m, Ar—H, 9H), 8.37(t, J=5.7 Hz, 1H), 10.76 (s, 1H); MS (ES): m/e 568.1 (M+H), 590.1 (M+Na).

Example 227

Preparation of 2-[2-(R,S)-1-(2,4,6-trimethylbenzenesulfonyl)-3-oxo-1,2,3,4-tetrahydro-6,7-dichloroquinoxalin-2-yl]-N-benzylacetamide 4,5-Dichlorobenzene-1,2-diamine was reacted with N-benzylmaleimide using Method F, followed by condensation with 2,4,6-trimethyl-benzenesulfonyl chloride using Method G to afford the title compound.

$^1$H NMR (DMSO-d$_6$) δ=15–2.50 (dd, and s, 11H), 4.05 (dd, J=5.4 Hz, 1H), 4.25 (dd, J=5.4 Hz, 1H), 4.68 (dd, J=5.4 Hz, 1H), 7.02–7.31 (m, Ar—H, 7H), 8.34 (t, 1H), 10.93(s, 1H); MS (ES): m/e 547 (M+H), 569 (M+Na).

Example 228

Preparation of 2-[2-(R,S)-1-(2.4.6-trimethylbenzenesulfonyl)-3-oxo-1,2,3,4-tetrahydro-6,7-dimethylquinoxalin-2-yl]-N-benzylacetamide 4,5-Dimethylbenzene-1,2-diamine reacted with N-benzylmaleimide using Method F. The resulting product reacted with 2,4,6-trimethyl-benzenesulfonyl chloride using Method G to afford the desired material.

$^1$H NMR (DMSO-d$_6$): δ=2.04–2.30(m, 17H), 3.29 (d, 1H), 4.10 (dd, 2H), 4.71 (dd, 1H), 6.68–7.30(m, 4H), 8.28(t, 1H, NH), 10.48(s, NH); MS (ES): m/e 506.3, (M+H), 528.3 (M+Na); HPLC (CH$_3$CN—H$_2$O-0.1% TFA) (short column): R$_t$=4.11 min.

Example 229

2-[2-(R,S)-1-(4-chloro-2,5-dimethylbenzenesulfonyl)-3-oxo-1,2,3,4-tetrahydro-6,7-dimethylquinoxalin-2-yl]-N-benzylacetamide The title compound was prepared from 4,5-dimethyl 1,2-phenylene-diamine using Method F, followed by Method G using 2,5-dimethyl 4-chloro-benzenesulfonyl chloride.

$^1$H NMR (DMSO-d$_6$) δ=2.0–2.5 (dd, m, s 14H), 4.15(dd, J=14.5 Hz, 1H), 4.3 (dd, J=14.5 Hz, 1H), 4.89 (dd, J=4.5 Hz, 1H), 7.14–7.49 (m, ArH, 8H), 8.36(t, 1H, NH), 10.35 (s, 1H, NH); MS (ES): m/e 527 (M+H), 549 (M+Na).

Example 230

Preparation of 2-[2-(R,S)-1-(2,4,6-trimethylbenzenesulfonyl)-3-oxo-4-methyl-1,2,3,4-tetrahydroquinoxalin-2-yl]N-benzylacetamide N-Methyl-benzene-1,2-diamine reacted with N-benzylmaleimide using Method F. The resulting product reacted with 2,4,6-trimethylbenzenesulfonyl chloride using Method G to afford the title material.

$^1$H NMR (DMSO-d$_6$) δ=2.14–2.30 (m, 2H), 2.24 (s, 9H), 2.98 (s, 3H), 3.72–4.53 (m, 2H), 4.92 (dd, 1H), 7.06–7.41 (m, 11H), 8.34 (t, 1H, NH); MS (ES): m/e 492 (M+H), 541 (M+Na); HPLC (CH$_3$CN—H$_2$O-0.1% TFA) (short column): R$_t$=5.64 min.

Example 231

Preparation of 2-[2-(R,S)-1-(4-chloro-2,5-dimethyl-benzenesulfonyl)-3-oxo-1,2,3,4-tetrahydroquinoxalin-2-yl]-N-[2-(pyrid-4-yl)eth-1-yl]acetamide 2-[2-(R,S)-1-(4-Chloro-2,5-dimethylbenzenesulfonyl)-3-oxo-1,2,3,4-tetrahydroquinoxalin-2-yl]acetic acid reacted with 2-pyridin-4-ylethylamine using Method I to afford the title material.

$^1$H NMR (DMSO-d$_6$) δ=1.90–2.20 (m, s, 8H), 2.64 (t, 2H), 3.19–3.51 (m, 2H), 4.85 (dd, 1H), 6.79–7.46 (m, Ar—H, 8H), 7.98 (t, 1H), 8.44 (d, 2H), 10.45 (s, 1H); MS (ES): m/e 514 (M+H), 536 (M+Na); HPLC (CH$_3$CN—H$_2$O-0.1% TFA) (short column): R$_t$=3.28 min.

Example 232

Preparation of 2-[2-(R,S)-1-(4-chloro-2,5-dimethylbenzenesulfonyl)-3-oxo-1,2,3,4-tetrahydroquinoxalin-2-yl]-N-[2-(N-methylpiperidin-4-yl)eth-1-yl]acetamide 2-[2-(R,S)-1-(4-chloro-2,5-dimethylbenzenesulfonyl)-3-oxo-1,2,3,4-tetrahydroquinoxalin-2-yl]-N-[2-(pyrid-4-yl)eth-1-yl]acetamide was subjected to Method J and Method K to afford the title material as an HCl salt.

$^1$H NMR (DMSO-d$_6$) δ=1.0–1.15 (m, 2H), 1.65 (bd, 2H), 1.80(t, 2H), 1.95–2.20(m, 2H), 2.0(s, 3H), 2.09(s,3H), 2.21 (s, 3H), 2.70(bd, 2H), 2.90(m, 2H), 3.10 (m, 2H), 4.83 (dd, 1H), 6.80–7.44(m, ArH, 6H), 7.81(t, 1H, NH); MS (ES): m/e 534 (M+H), 556 (M+Na).

Example 233

Preparation of 2-[2-(R,S)-1-(4-chloro-2,5-dimethylbenzenesulfonyl)-3-oxo-1,2,3,4-tetrahydroquinoxalin-2-yl]-N-[2-(piperidin-4-yl)eth-1-yl]acetamide 2-[2-(R,S)-1-(4-chloro-2,5-dimethylbenzenesulfonyl)-3-oxo-1,2,3,4-tetrahydroquinoxalin-2-yl]-N-[2-(pyrid-4-yl)eth-1-yl]acetamide was subjected to Method L (Step A) to afford the title material as an HCl salt.

$^1$H NMR (DMSO-d$_6$) δ=1.28 (m, 2H), 1.83 (t, 2H), 2.0–2.10(m, 2H), 1.96 (s, 3H), 2.20 (s, 3H), 2.75–2.90(br m, 4H), 3.05–3.40 (bm, 4H), 4.85 (dd, 1H), 6.81 (s, 1H, Ar), 6.83 (s, 1H, Ar), 7.11–7.40 (m, 5H, ArH), 7.95 (t, NH), 8.82 (br t, NH), 8.95 (b t, NH), 10.41 (s, NH); MS (ES): m/e 520 (M+H).

Example 234

Preparation of 2-[2-(R,S)-1-(4-chloro-2,5-dimethylbenzenesulfonyl)-3-oxo-1,2,3,4-tetrahydroquinoxalin-2-yl]-N-[2-(pyrid-4-yl-N-oxide)eth-1-yl]acetamide 2-[2-(R,S)-1-(4-chloro-2,5-dimethylbenzenesulfonyl)-3-oxo-1,2,3,4-tetrahydroquinoxalin-2-yl]-N-[2-(pyrid-4-yl)eth-1-yl]acetamide reacted with m-chloroperbenzoic acid (1.0 eq) in dioxane to afford the title material.

$^1$H NMR (DMSO-d$_6$) δ=1.99(s, 3H), 2.10–2.15(m, 2H), 2.10 (s, 3H), 2.65 (m, 2H) 3.20(m, 2H), 4.84 (dd, J=4.8 Hz, 1H), 6.80–7.36 (m, 8H, ArH), 7.40 (s, 1H), 7.95(t, 1H, NH), 8.05(d, 2H), 10.46 (s, 1H, NH); MS (ES): m/e 530 (M+H), 552 (M+Na); HPLC (CH$_3$CN—H$_2$O-0.1% TFA) (short column): R$_t$=3.21 min.

Example 235

2-[2-(R,S)-1-(2,6-dichlorobenzenesulfonyl)-3-oxo-1,2,3,4-tetrahydroquinoxalin-2-yl]-N-benzylacetamide Benzene-1,2-diamine reacted with N-methylmaleimide using Method F. The resulting product reacted with 2,6-dichlorobenzenesulfonyl using Method G to afford the title material.

$^1$H NMR (DMSO-d$_6$) δ=2.32–2.45(m, 2H), 4.18(m, 2H), 5.14(dd, J=5.7 Hz, 1H), 6.80–7.60(m, Ar—H, 1H), 8.34(t, J=3.6 Hz, 1H), 10.63 (s, 1H); MS (ES): m/e 504 (M+H); HPLC (CH$_3$CN—H$_2$O-0.1% TFA) (short column): R$_t$=26.5 min.

Example 236

Preparation of 2-[2-(R,S)-1-(4-chloro-2,5-dimethylbenzenesulfonyl)-3-oxo-1,2,3,4-tetrahydroquinoxalin-2-yl]-methylenecarbonyl-(4-methylpiperazin-1-yl)

2-[2-(R,S)-3-Oxo-1,2,3,4-tetrahydroquinoxalin-2-yl]acetic acid was reacted with N-methylpiperazine using Method D. The resulting product was then reacted with 4-chloro-2,5-dimethylbenzenesulfonyl chloride using Method G to afford the title product.

$^1$H NMR (DMSO-d$_6$) δ=1.98(s,1.5H), 2.0(1.5H), 2.26(s, 3H), 2.40–3.05(m, 11H), 3.2–3.8(m, 4H), 4.9(bd, 1H), 6.82–7.47(m, 6H), 10.55(s, 0.5H), 10.57(s, 0.5H); MS (ES): m/e 492 (M+H).

Example 237

Preparation of 2-[2-(R,S)-1-(4-chloro-2,5-dimethylbenzenesulfonyl)-3-oxo-1,2,3,4-tetrahydroquinoxalin-2-yl]-N-[2-(4-methylpiperazin-1-yl)eth-1-yl]acetamide 2-Chloroethylamine hydrochloride was reacted with 1-methylpiperazine in water. After evaporation of the water, the resulting amine was reacted with 2-[2-(R,S)-1-(4-chloro-2,5-dimethylbenzenesulfonyl)-3-oxo-1,2,3,4-tetrahydroquinoxalin-2-yl]acetic acid using Method I. The product was isolated from preparative HPLC as a TFA salt.

$^1$H NMR (DMSO-d$_6$) δ=2.04 (s, 3H), 2.10–2.40(m, 2H), 2.27(s, 3H), 2.80(s, 3H), 2.6–3.5 (bm, 6H), 4.93 (dd, J=3.9 Hz), 6.86–7.50(m, Ar—H, 6H), 8.15(bt, 1H), 10.53(s, 1H); MS (ES): m/e 535 (M+H).

Example 238

Preparation of 2-[2-(R,S)-1-(4-chloro-2,5-dimethylbenzenesulfonyl)-3-oxo-1,2,3,4-tetrahydroquinoxalin-2-yl]-N-(2-chloroeth-1-yl)acetamide The title compound was prepared using 2-[2-(R,S)-1-(4-chloro-2,5-dimethylbenzenesulfonyl)-3-oxo-1,2,3,4-tetrahydroquinoxalin-2-yl]acetic acid was treated with chloroethyl amine using Method I.

$^1$H NMR (DMSO-d$_6$) δ=2.00(s, 3H), 2.22(s, 3H), 2.10–2.30(m, 2H), 3.30(bt, 2H), 3.51(bt, 2H), 4.85(dd, J=4.8 Hz), 6.90–7.60(m, Ar—H, 6H), 8.21(bt, 1), 10.50(s, 1H); MS (ES): m/e 470.0 (M+H), 492.0 (M+Na); HPLC (CH$_3$CN—H$_2$O-0.1% TFA) (short column): R$_t$=5.33 min.

Example 239

Preparation of 2-[2-(R,S)-1-(4-chloro-2,5-dimethylbenzenesulfonyl)-3-oxo-1,2,3,4-tetrahydroquinoxalin-2-yl]-N-[2-(N-methyl-1,2,5,6-tetrahydropyrid-4-yl)eth-1-yl]acetamide 2-[2-(R,S)-1-(4-chloro-2,5-dimethylbenzenesulfonyl)-3-oxo-1,2,3,4-tetrahydroquinoxalin-2-yl]-N-[2-(pyrid-4-yl)eth-1-yl]acetamide was subjected to Method J to afford the title material.

$^1$H NMR (DMSO-d$_6$) δ=1.97–2.19 (m, 2H), 2.07(s, 3H), 2.19(s, 3H), 2.35(s, 3H), 2.38(bt, 2H), 2.85–3.13(m, 6H), 4.84(dd, J=Hz, 1H), 5.31(s, 1H), 6.79–7.41(m, Ar—H, 6H), 7.81 (t, J=Hz, 1H), 10.44 (s, 1H); MS (ES): m/e 532 (M+H).

Example 240

Preparation of 2-[2-(R,S)-1-(4-chloro-2,5-dimethyl-benzenesulfonyl)-3-oxo-1,2,3,4-tetrahydroquinoxalin-2-yl]-N-[2-(N-cyclopropylpiperidin-4-yl)eth-1-yl]acetamide Reaction of 2-[2-(R,S)-1-(4-chloro-2,5-dimethylbenzenesulfonyl)-3-oxo-1,2,3,4-tetrahydroquinoxalin-2-yl]-N-[2-(piperidin-4-yl)eth-1-yl]acetamide with 1-ethoxy-1-trimethysiloxy cyclopropane using Method L gave the title material.

$^1$H NMR (DMSO-d$_6$) δ=0.21 (bd, 2H), 0.34(bd, 2H), 0.90–1.85(m, 5H), 1.9–2.4(m, 2H), 2.20(s, 3H), 2.45(s, 3H), 3.00(m, 2H), 3.30(m, 6H), 4.81(dd, J=4.5 Hz, 1H), 6.77–7.41(m, Ar—H, 6H), 7.76(bt, 1H), 10.40(s, 1H); MS (ES): m/e 560 (M+H); HPLC (CH$_3$CN—H$_2$O-0.1% TFA) (short column): R$_t$=3.60 min.

Example 241

Preparation of 2-[2-(R,S)-1-(4-chloro-2,5-dimethyl-benzenesulfonyl)-3-oxo-1,2,3,4-tetrahydroquinoxalin-2-yl]-N-[1-(R)-methoxycarbonyl-2-pyrid-4-yl)eth-1-yl]acetamide 2-t-Butoxycarbonylamino-3-(R)-pyridin-4-yl-propionic acid was converted to its methyl ester using Method P. The resulting ester reacted with 2-[2-(R,S)-1-(4-chloro-2,5-dimethylbenzenesulfonyl)-3-oxo-1,2,3,4-tetrahydro-quinoxalin-2-yl]acetic acid using Method I to afford the title product.

$^1$H NMR (DMSO-d$_6$) δ=1.92 (s, 3H), 1.96(s, 3H), 2.22 (bm, 5H), 2.80–3.40(m, 2H), 3.58(s, 3H), 3.61(s, 3H), 4.48(m, 1H), 4.80(bd, 1H), 6.77–7.41(m, Ar—H, 8H), 8.43 (brd, 1H), 8.49(d, 2H), 10.44(s, 1H); MS (ES): m/e 571.0 (M+H), 592.6 (M+Na); HPLC (CH$_3$CN—H$_2$O-0.1% TFA) (short column): R$_t$=3.19, 4.21 min. (provided a pair of diastereomers).

Example 242

Preparation of 2-[2-(R,S)-1-(4-chloro-2,5-dimethyl-benzenesulfonyl)-3-oxo-1,2,3,4-tetrahydroquinoxalin-2-yl]-N-[1-(R)-(methoxycarbonyl)-2-(N-methyl-1,2,3,6-tetrahydropyrid-4-yl)eth-1-yl]acetamide 2-[2-(R,S)-1-(4-chloro-2,5-dimethylbenzenesulfonyl)-3-oxo-1,2,3,4-tetrahydroquinoxalin-2-yl]-N-[1-(R)-methoxycarbonyl-2-pyrid-4-yl)eth-1-yl]acetamide was subjected to Method J to afford the title compound.

$^1$H NMR (DMSO-d$_6$) δ=1.98 (s, 3H), 2.20 and 2.24 (s, 3H), 2.24 (m, 2H), 2.33 (m, 4H), 2.70 (bd, 2H), 3.29(bm, 2H), 3.60 and 3.56 (s, 3H), 4.28 (m, 1H), 4.82(m, 1H), 5.32(bd, 1H), 6.78–7.43(m, Ar—H, 6H), 8.24(t, 1H), 10.43 (bs, 1H); MS (ES): m/e 590 (M+H), 611.8 (M+Na).

Example 243

Preparation of 2-[2-(R,S)-1-(4-chloro-2,5-dimethyl-benzenesulfonyl)-3-oxo-1,2,3,4-tetrahydroquinoxalin-2-yl]-N-[1-(R)-(methoxycarbonyl)-2-(N-methylpiperidin-4-yl)eth-1-yl]acetamide 2-[2-(R,S)-1-(4-chloro-2,5-dimethylbenzenesulfonyl)-3-oxo-1,2,3,4-tetrahydroquinoxalin-2-yl]-N-[1-(R)-(methoxycarbonyl)-2-(N-methyl-1,2,3,6-tetrahydropyrid-4-yl)eth-1-yl]acetamide subjected to Method K to afford the title compound as a diastereomeric mixture.

$^1$H NMR (DMSO-d$_6$) δ=0.9–1.40(m, 9H), 1.97(s, 3H), 2.16, 2.21(s, 3H), 2.24(s, 3H), 2.74(bt, 2H), 3.58 and 3.61(s, 3H), 4.22, 4.32 (m, 1H), 4.86 (m, 1H), 6.80–7.47(m Ar—H, 6H), 8.31(t, 1H), 10.43 (bt, 1H); MS (ES): m/e 592 (M+H), 614 (M+Na); ); HPLC (CH$_3$CN—H$_2$O-0.1% TFA) (short column): R$_t$=3.40 min.

Example 244

Preparation of 2-[2-(R,S)-1-(4-chloro-2,5-dimethyl-benzenesulfonyl)-3-oxo-1,2,3,4-tetrahydroquinoxalin-2-yl]-N-{2-[N-(α,α-dimethylglycine)piperidin-4-yl]eth-1-yl}acetamide 2-t-Butoxycarbonylamino-2-methyl-propionic acid reacted with 2-[2-(R,S)-1-(4-chloro-2,5-dimethylbenzenesulfonyl)-3-oxo-1,2,3,4-tetrahydroquinoxalin-2-yl]-N-[2-(piperidin-4-yl)eth-1-yl]acetamide using Method I followed by cleavage of the tert-butoxycarbonyl group using neat TFA at room temperature for a few hours. The title compound was isolated in good yields.

$^1$H NMR (DMSO-d$_6$) δ=0.94–1.85(bm, 4H), 1.51 (s, 6H), 1.90 (s, 3H), 2.1 (s, 3H), 2.10–2.47 (m, 2H), 2.70–3.1 1(m, 4H), 4.35(bt, 4H), 4.84(dd, 1H), 7.41–7.79(m, 6H, ArH), 7.86(bt, NH), 8.06, (bt, NH2), 10.43(s, NH);

LCMS 605 (M+H).

Example 245

Preparation of 2-[2-(R,S)-1-(4-chloro-2,5-dimethyl-benzenesulfonyl)-3-oxo-1,2,3,4-tetrahydroquinoxalin-2-yl]-N-{2-[N-(α-aminoacetyl)piperidin-4-yl]eth-1-yl}acetamide t-Butoxycarbonylamino-acetic acid reacted with 2-[2-(R,S)-1-(4-chloro-2,5-dimethylbenzenesulfonyl)-3-oxo-1,2,3,4-tetrahydroquinoxalin-2-yl]-N-[2-(piperidin-4-yl)eth-1-yl]acetamide using Method I followed by cleavage of the tert-butoxycarbonyl group using TFA at room temperature for a few hours. The title compound was isolated in good yields.

$^1$H NMR (DMSO-d$_6$) δ=0.9–1.30(m, 4H), 1.30(m, 2H), 1.75(m, 2H), 1.98(s, 3H), 2.07–2.27 (m, 2H), 2.15 (s, 3H), 2.67(bt, 2H), 3.69(bd, 2H), 3.69(bt, 2H), 3.85(bt, 2H), 4.40(bt, 2H), 4.87(dd, J=3.9 Hz), 6.81–7.43(m, Ar—H, 6H), 7.88(br. t, 1H), 7.98(bt, NH2), 10.45(s, 1H); MS (ES): m/e 577 (M+H); HPLC (CH$_3$CN—H$_2$O-0.1% TFA) (short column): R$_t$=5.20 min.

Example 246

Preparation of 2-[2-(R,S)-1-(4-chloro-2,5-dimethyl-benzenesulfonyl)-3-oxo-1,2,3,4-tetrahydroquinoxalin-2-yl]-N-[(piperidin-1-yl)carbonylmethyl]acetamide t-Butoxy carbonyl glycine was condensed with piperidine using Method S. The resulting amide was treated with neat TFA at room temperature for a few hours. TFA was evaporated under reduced pressure, and the resulting amine was condensed with 2[2-(R,S)-(4-chloro-2,5-dimethylbenzenesulfonyl)-3-oxo-1,2,3,4-tetrahydroquinoxalin-2-yl]acetic acid using Method S, to provide the desired material in good yield.

¹H NMR (DMSO-d₆) δ=9.63 (s, 1H), 7.20 (m, 1H), 6.63 (s, 1H), 6.55 (m, 2H), 6.29 (m, 1H), 5.99 (m, 1H), 4.05 (m, 1H), 3.02 (m, 2H), 2.55 (m, 2H), 2.47 (s, 2H), 1.65 (m, 2H), 1.40 (s, 3H), 1.18 (s, 3H), 0.58 (m, 6H). MS (ES): m/e 533.1 (M+H), 555.1 (M+Na).

Example 247

Preparation of 2-[2-(R or S)-1-(4-chloro-2,5-dimethylbenzenesulfonyl)-3-oxo-1,2,3,4-tetrahydroquinoxalin-2-yl]-N-[1-(R)-2-phenyl-1-(methoxycarbonyl)eth-1-yl]acetamide D-phenylalanine methyl ester hydrochloride salt was condensed to 2[2-(R,S)-1-(4-chloro-2,5-dimethylbenzenesulfonyl)-3-oxo-1,2,3,4-tetrahydroquinoxalin-2-yl]acetic acid using Method S to provide the desired material in good yields.
¹H NMR (CDCl₃) δ=8.78 (s, 1H), 7.59 (m, 2H), 7.31 (m, 5H), 7.19 (m, 4H), 6.85 (m, 1H), 6.58 (m, 1H), 5.15 (m, 1H), 4.90 (m, 1H), 3.79 (s, 3H), 2.93 (m, 2H), 2.52 (m, 2H), 2.31 (s, 3H), 2.01 (s, 3H); MS (ES): m/e 571 (M+H), 593 (M+Na).

Example 248

Preparation of 2-[2-(R or S)-1-(4-chloro-2,5-dimethylbenzenesulfonyl)-3-oxo-1,2,3,4-tetrahydroquinoxalin-2-yl]-N-[1-(R)-1-pyrrolidin-N-ylcarbonyl-2-phenyleth-1-yl]acetamide t-Butoxy carbonyl D-phenylalanine was condensed with pyrrolidine using Method S. The resulting amide was treated with neat TFA at room temperature for a few hours. TFA was evaporated under reduced pressure, and the resulting amine was condensed with 2-[2-(R,S)-1-(4-chloro-2,5-dimethyl-benzenesulfonyl)-3-oxo-1,2,3,4-tetrahydroquinoxalin-2-yl]acetic acid using Method S, to provide the desired material in good yield.
¹H NMR (CDCl₃) δ=9.09 (s, 1H), 7.71 (m, 3H), 7.26 (m, 9H), 6.87 (m, 1H), 5.20 (m, 1H), 5.01 (m, 1H), 3.41 (m, 1H), 3.04 (m, 1H), 2.98 (m, 2H), 2.72 (m, 1H), 2.61 (m, 2H), 2.47 (m, 1H), 2.31 (s, 3H), 2.18 (s, 3H), 1.70 (m, 4H); MS (ES): m/e 610 (M+H), 632 (M+Na).

Example 249

Preparation of 2-[2-(R,S)-1-(4-chloro-2,5-dimethylbenzenesulfonyl)-3-oxo-1,2,3,4-tetrahydroquinoxalin-2-yl]-N-[2-(4-hydroxyphenyl)-1-(S)-(methoxycarbonyl)eth-1-yl]acetamide L-tyrosine methyl ester hydrochloride salt was condensed to 2[2-(R,S)-1-(4-chloro-2,5-dimethylbenzenesulfonyl)-3-oxo-1,2,3,4-tetrahydroquinoxalin-2-yl]acetic acid using Method S.
HPLC (acetonitrile/water): R_f=4.80, 4.99 min.

Example 250

Preparation of 2-[2-(R,S)-1-(4-chloro-2,5-dimethylbenzenesulfonyl)-3-oxo-1,2,3,4-tetrahydroquinoxalin-2-yl]-N-[2-phenyl-1-(S)-(methoxycarbonyl)eth-1-yl]acetamide L-phenylalanine methyl ester hydrochloride salt was condensed to 2-[2-(R,S)-1-(4-chloro-2,5-dimethylbenzenesulfonyl)-3-oxo-1,2,3,4-tetrahydroquinoxalin-2-yl]acetic acid using Method S.
HPLC (acetonitrile/water 6:3) R_f=14.91, 15.26 min.

Example 251

Preparation of 2-[2-(R,S)-1-(4-chloro-2,5-dimethylbenzenesulfonyl)-3-oxo-1,2,3,4-tetrahydroquinoxalin-2-yl]-N-[2-(4-cyanophenyl)-1-(R)-(pyrrolidin-N-ylcarbonyl)eth-1-yl]acetamide

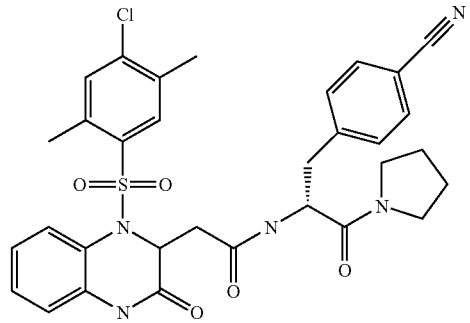

t-Butoxycarbonyl-D-p-cyanophenylalanine was condensed with pyrrolidine using Method S. The resulting amide was treated with neat TFA at room temperature for a few hours. TFA was evaporated under reduced pressure, and the resulting amine was condensed with 2-[2-(R,S)-1-(4-chloro-2,5-dimethyl-benzenesulfonyl)-3-oxo-1,2,3,4-tetrahydroquinoxalin-2-yl]acetic acid using Method S, to provide the desired material in good yield.
MS (ES): m/e 635 (M+H), 658 (M+Na).

Example 252

Preparation of 2-[2-(R,S)-1-(4-chloro-2,5-dimethylbenzenesulfonyl)-3-oxo-1,2,3,4-tetrahydroquinoxalin-2-yl]-N-[2-(phenyl)-1-(S)-(pyrrolidin-N-ylcarbonyl)eth-1-yl]-N-methylacetamide t-Butoxycarbonyl-L-phenylalanine was condensed with pyrrolidine using Method S. The resulting amide was treated with neat TFA at room temperature for a few hours. TFA was evaporated under reduced pressure, and the resulting amine was condensed with 2-[2-(R,S)-1-(4-chloro-2,5-dimethylbenzenesulfonyl)-3-oxo-1,2,3,4-tetrahydroquinoxalin-2-yl]acetic acid using Method S, to provide the desired material in good yield.
¹H NMR (CDCl₃) δ=9.85 (s, 1H), 9.25 (s, 1H), 7.63 (m, 11H), 5.12 (m, 1H), 4.90 (m, 1H), 3.24 (m, 8H), 2.18 (d, 3H), 2.09 (d, 3H), 1.45 (m, 4H).

Example 253

Preparation of 2-[2-(R,S)-1-(4-chloro-2,5-dimethylbenzenesulfonyl)-3-oxo-1,2,3,4-tetrahydroquinoxalin-2-yl]-N-(2-phenyl-1-(R)-carboxy-eth-1-yl)acetamide This compound was obtained from 2-[2-(R,S)-1-(4-chloro-2,5-dimethylbenzenesulfonyl)-3-oxo-1,2,3,4-tetrahydroquinoxalin-2-yl]-N-[1-(R)-2-phenyl-1-(methoxycarbonyl)eth-1-yl]acetamide using Method C.
HPLC (CH₃CN—H₂O-0.1% TFA): R_f=10.37, 11.54 min.

Example 254

2-[2-(R,S)-1-(4-chloro-2,5-dimethylbenzenesulfonyl)-3-oxo-1,2,3,4-tetrahydroquinoxalin-2-yl]-N-[2-(4-hydroxyphenyl)-1-(R)-(methoxycarbonyl)eth-1-yl]acetamide D-tyrosine methyl ester hydrochloride salt was condensed to 2-[2-(R,S)-1-(4-chloro-2,5-dimethylbenzenesulfonyl)-3-oxo-1,2,3,4-tetrahydroquinoxalin-2-yl]acetic acid using Method S to provide the desired material in good yields.
MS (ES): m/e 587 (M+H), 609 (M+Na).

Example 255

Preparation of 2-[2-(R,S)-1-(4-chloro-2,5-dimethyl-benzenesulfonyl)-3-oxo-1,2,3,4-tetrahydroquinoxalin-2-yl]-N-methylacetamide Methylamine hydrochloride salt was condensed to 2-[2-(R,S)-1-(4-chloro-2,5-dimethylbenzenesulfonyl)-3-oxo-1,2,3,4-tetrahydroquinoxalin-2-yl]acetic acid using Method S.
$^1$H NMR (CDCl$_3$) δ=7.67 (m, 2H), 7.56 (s, 1H), 7.24 (m, 1H), 7.16 (m), 6.74 (m, 1H), 6.00 (m, 1H), 5.04 (m, 1H), 2.78 (s, 3H), 2.58 (m, 2H), 2.26 (s, 3H), 2.04 (s, 3H); MS (ES): m/e 423 (M+H), 444 (M+Na).

Example 256

Preparation of 2-[2-(R,S)-1-(4-chloro-2,5-dimethyl-benzenesulfonyl)-3-oxo-1,2,3,4-tetrahydroquinoxalin-2-yl]-N-[2-(4-cyanophenyl)-1-(S)-(pyrrolidin-N-ylcarbonyl)eth-1-yl]acetamide

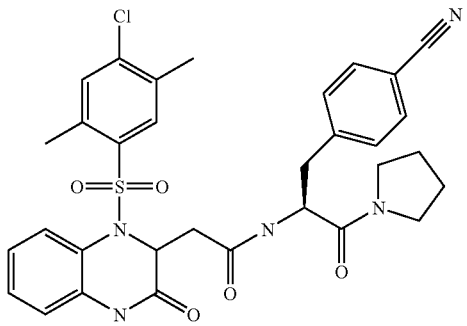

t-Butoxycarbonyl-L-p-cyanophenylalanine was condensed with pyrrolidine using Method S. The resulting amide was treated with neat TFA at room temperature for a few hours. TFA was evaporated under reduced pressure, and the resulting amine was condensed with 2-[2-(R,S)-1-(4-chloro-2,5-dimethylbenzenesulfonyl)-3-oxo-1,2,3,4-tetrahydroquinoxalin-2-yl]acetic acid using Method S, to provide the desired material in good yield.
HPLC ((CH$_3$CN—H$_2$O-0.1% TFA) R$_t$=11.66, 12.03 min.

Example 257

Preparation of 2-[2-(R,S)-1-(4-chloro-2,5-dimethyl-benzenesulfonyl)-3-oxo-1,2,3,4-tetrahydroquinoxalin-2-yl]-N-[1-(R)-(t-butoxycarbonyl)-2-(phenyl)eth-1-yl]acetamide D-phenylalanine t-butyl ester hydrochloride salt was condensed to 2-[2-(R,S)-1-(4-chloro-2,5-dimethylbenzenesulfonyl)-3-oxo-1,2,3,4-tetrahydroquinoxalin-2-yl]acetic acid using Method S to provide the desired material in good yields.
$^1$H NMR (CDCl$_3$) δ=9.08 (s, 1H), 9.02 (s, 1H), 7.53 (m, 2H), 7.30 (m, 8H), 6.80 (m, 2H), 6.50 (d, 1H), 6.40 (d, 1H), 5.12 (m, 1H), 4.75 (m, 1H), 3.10 (m, 2H), 2.50 (m, 1H), 2.33 (m, 1H), 2.19 (d, 3H), 2.04 (d, 3H), 1.38 (s, 9H), 1.39 (s, 9H).

Example 258

Preparation of 2-[2-(R,S)-1-(4-chloro-2,5-dimethyl-benzenesulfonyl)-3-oxo-1,2,3,4-tetrahydroquinoxalin-2-yl]-N-[1-(R)-(isopropoxycarbonyl)-2-(phenyl)eth-1-yl]acetamide D-phenylalanine iso-propyl ester hydrochloride salt was condensed to 2-[2-(R,S)-1-(4-chloro-2,5-dimethylbenzenesulfonyl)-3-oxo-1,2,3,4-tetrahydroquinoxalin-2-yl]acetic acid using Method S to provide the desired material in good yield.
$^1$H NMR (CDCl$_3$) δ=9.23 (s, 1H), 9.05 (s, 1H), 7.51 (m, 2H), 7.20 (m, 8H), 6.77 (m, 2H), 6.55 (m, 1H), 5.11 (m, 1H), 5.05 (m, 1H), 4.81 (m, 1H), 3.10 (m, 2H), 2.50 (m, 1H), 2.32 (m, 1H), 2.19 (s, 3H), 2.04 (s, 3H), 1.23 (d, 2H), 1.12 (d, 2H).

Example 259

Preparation of 2-[2-(R,S)-1-(4-chloro-2,5-dimethyl-benzenesulfonyl)-3-oxo-1,2,3,4-tetrahydroquinoxalin-2-yl]-N-{1-(S)-[pyrrolidin-N-ylcarbonyl]-2-[4-(2-imidazolin-2-yl)phenyl]eth-1-yl}acetamide 2-[2-(R,S)-1-(4-chloro-2,5-dimethylbenzenesulfonyl)-3-oxo-1,2,3,4-tetrahydroquinoxalin-2-yl]-N-[2-(4-cyanophenyl)-1-(S)-(pyrrolidin-N-ylcarbonyl)eth-1-yl]acetamide and ethylenediamine were submitted to Method T, and the desired material isolated as a TFA salt upon HPLC purification.
HPLC (acetonitrile/water-0.1% TFA 3:6): R$_t$=5.49 nm.

Example 260

Preparation of 2-[2-(R,S)-1-(4-chloro-2,5-dimethyl-benzenesulfonyl)-3-oxo-1,2,3,4-tetrahydroquinoxalin-2-yl]-N,N-diisopropylacetamide N,N-diisopropyl amine was condensed to 2-[2-(R,S)-1-(4-chloro-2,5-dimethylbenzenesulfonyl)-3-oxo-1,2,3,4-tetrahydroquinoxalin-2-yl]acetic acid using Method S.
$^1$H NMR (CDCl$_3$) δ=8.11 (s, 1H), 7.63 (d, 1H), 7.55 (s, 1H), 7.20 (t, 1H), 7.05 (t, 1H), 6.75 (d, 1H), 5.10 (t, 1H), 3.83 (m, 1H), 3.4 (m, 1H), 2.61 (d, 2H), 2.24 (s, 3H), 2.11 (s, 3H), 1.30 (d, 3H), 1.22 (d, 3H), 1.18 (d, 6H).

Example 261

Preparation of 2-[2-(R or S)-1-(4-chloro-2,5-dimethylbenzenesulfonyl)-3-oxo-1,2,3,4-tetrahydroquinoxalin-2-yl]-N-{2-[(4-imidazolin-2-yl)phenyl]-1-(R)-(pyrrolidin-N-ylcarbonyl)eth-1-yl}acetamide 2-[2-(R,S)-1-(4-chloro-2,5-dimethylbenzenesulfonyl)-3-oxo-1,2,3,4-tetrahydroquinoxalin-2-yl]-N-[2-(4-cyanophenyl)-1-(R)-(pyrrolidin-N-ylcarbonyl)eth-1-yl]acetamide and

Example 262

Preparation of 2-[2-(R or S)-1-(4-chloro-2,5-dimethylbenzenesulfonyl)-3-oxo-1,2,3,4-tetrahydroquinoxalin-2-yl]-N-{2-[4-(imidazolin-2-yl)phenyl]-1-(R)-(pyrrolidin-1-ylcarbonyl)eth-1-yl}acetamide 2-[2-(R,S)-1-(4-chloro-2,5-dimethylbenzenesulfonyl)-3-oxo-1,2,3,4-tetrahydroquinoxalin-2-yl]-N-[2-(4-cyanophenyl)-1-(R)-(pyrrolidin-N-ylcarbonyl)eth-1-yl]acetamide and ethylenediamine were submitted to Method T, and the desired material isolated as one diastereomer, upon prep HPLC purification.

HPLC (acetonitrile/water-0.1% TFA): $R_t$=3.89 min; MS (ES): m/e 678 (M+H).

Example 263

Preparation of 2-[2-(R,S)-1-(4-chloro-2,5-dimethylbenzenesulfonyl)-3-oxo-1,2,3,4-tetrahydroquinoxalin-2-yl]-methylenecarbonyl-(2-(R,S)-methylpiperidin-N-yl)

The title compound was obtained using Method W starting with 2-(R,S)-methylpiperidine and 2-[2-(R,S)-1-(4-chloro-2,5-dimethylphenylsulfonyl)-3-oxo-1,2,3,4-tetrahydroquinoxalin-2-yl]acetic acid.

MS (ES): m/e 491 (M+H).

Example 264

Preparation of 2-[2-(R,S)-1-(4-chloro-2,5-dimethylbenzenesulfonyl)-3-oxo-1,2,3,4-tetrahydroquinoxalin-2-yl]-methylenecarbonyl-[4-acetylpiperazin-1-yl]

The title compound was obtained using Method W, starting with 4-acetylpiperazine and 2-[2-(R,S)-1-(4-chloro-2,5-dimethylphenylsulfonyl)-3-oxo-1,2,3,4-tetrahydroquinoxalin-2-yl]acetic acid.

MS (ES): m/e 520 (M+H).

Example 265

Preparation of 2-[2-(R,S)-1-(4-chloro-2,5-dimethylbenzenesulfonyl)-3-oxo-1,2,3,4-tetrahydroquinoxalin-2-yl]-N,N-di(2-methoxyeth-1-yl)acetamide The title compound was obtained using Method W, starting with 2-methoxyethylamine and 2-[2-(R,S)-1-(4-chloro-2,5-dimethylphenylsulfonyl)-3-oxo-1,2,3,4-tetrahydroquinoxalin-2-yl]acetic acid.

MS (ES): m/e 525 (M+H).

Example 266

Preparation of 2-[2-(R,S)-1-(4-chloro-2,5-dimethylbenzenesulfonyl)-3-oxo-1,2,3,4-tetrahydroquinoxalin-2-yl]-N-cyclohexyl-N-ethylacetamide The title compound was obtained using Method W, starting with N-cyclohexyl-N-ethylamine and 2-[2-(R,S)-1-(4-chloro-2,5-dimethylphenyl-sulfonyl)-3-oxo-1,2,3,4-tetrahydroquinoxalin-2-yl]acetic acid.

MS (ES): m/e 519 (M+H).

Example 267

Preparation of 2-[2-(R,S)-1-(4-chloro-2,5-dimethylbenzenesulfonyl)-3-oxo-1,2,3,4-tetrahydroquinoxalin-2-yl]-methylenecarbonyl-[4-(R,S)-hydroxypiperidin-N-yl]

The title compound was obtained using Method W, starting with 2-[2-(R,S)-1-(4-chloro-2,5-dimethylphenylsulfonyl)-3-oxo-1,2,3,4-tetrahydroquinoxalin-2-yl]acetic acid and hydroxypiperidine.

MS (ES): m/e 493 (M+H).

Example 268

Preparation of 2-[2-(R,S)-1-(4-chloro-2,5-dimethylbenzenesulfonyl)-3-oxo-1,2,3,4-tetrahydroquinoxalin-2-yl]-N,N-diethylacetamide The title compound was obtained using Method W, starting with 2-[2-(R,S)-1-(4-chloro-2,5-dimethylphenylsulfonyl)-3-oxo-1,2,3,4-tetrahydroquinoxalin-2-yl]acetic acid and N,N-diethylamine.

MS (ES): m/e 465 (M+H).

Example 269

Preparation of 2-[2-(R,S)-1-(4-chloro-2,5-dimethylbenzenesulfonyl)-3-oxo-1,2,3,4-tetrahydroquinoxalin-2-yl]-N-phenethyl-N-methylacetamide The title compound was obtained using Method W, starting with 2-[2-(R,S)-1-(4-chloro-2,5-dimethylphenylsulfonyl)-3-oxo-1,2,3,4-tetrahydroquinoxalin-2-yl]acetic acid and N-phenethyl-N-methylamine.

MS (ES): m/e 527 (M+H).

Example 270

Preparation of 2-[2-(R,S)-1-(4-chloro-2,5-dimethylbenzenesulfonyl)-3-oxo-1,2,3,4-tetrahydroquinoxalin-2-yl]-methylenecarbonyl-[3-(R,S)-carboxamide-piperidin-N-yl]

The title compound was obtained using Method, starting with 2-[2-(R,S)-1-(4-chloro-2,5-dimethylphenylsulfonyl)-3-oxo-1,2,3,4-tetrahydroquinoxalin-2-yl]acetic acid and 3-(R,S)-carboxamide-piperidine.

MS (ES): m/e 520 (M+H).

Example 271

Preparation of 2-[2-(R,S)-1-(4-chloro-2,5-dimethylbenzenesulfonyl)-3-oxo-1,2,3,4-tetrahydroquinoxalin-2-yl]-methylenecarbonyl-[2-(S)-hydroxymethylpyrrolidin-N-yl]

The title compound was obtained using Method W, starting with 2-[2-(R,S)-1-(4-chloro-2,5-dimethylphenylsulfonyl)-3-oxo-1,2,3,4-tetrahydroquinoxalin-2-yl]acetic acid and 2-(S)-hydroxymethylpyrrolidine.

MS (ES): m/e 493 (M+H).

Example 272

Preparation of 2-[2-(R,S)-1-(4-chloro-2,5-dimethyl-benzenesulfonyl)-3-oxo-1,2,3,4-tetrahydroquinoxalin-2-yl]-methylenecarbonyl-[2-(S)-methoxymethylpyrrolidin-1-yl]

The title compound was obtained using Method W, starting with 2-[2-(R,S)-1-(4-chloro-2,5-dimethylphenylsulfonyl)-3-oxo-1,2,3,4-tetrahydroquinoxalin-2-yl]acetic acid and [2-(S)-methoxymethylpyrrolidine.
MS (ES): m/e 507 (M+H).

Example 273

Preparation of 2-[2-(R,S)-1-(4-chloro-2,5-dimethyl-benzenesulfonyl)-3-oxo-1,2,3,4-tetrahydroquinoxalin-2-yl]-N-(n-hexyl)-N-methylacetamide The title compound was obtained using Method W, starting with 2-[2-(R,S)-1-(4-chloro-2,5-dimethylphenylsulfonyl)-3-oxo-1,2,3,4-tetrahydroquinoxalin-2-yl]acetic acid and N-methyl hexylamine.
MS (ES): m/e 513 (M+H).

Example 274

Preparation of 2-[2-(R,S)-1-(4-chloro-2,5-dimethyl-benzenesulfonyl)-3-oxo-1,2,3,4-tetrahydroquinoxalin-2-yl]-N-[2-(4-hydroxyphenyl)-1-(S)-(t-butoxyoxycarbonyl)eth-1-yl]acetamide The title compound was prepared from 2-[2-(R,S)-1-(4-chloro-2,5-dimethylphenylsulfonyl)-3-oxo-1,2,3,4-tetrahydro-quinoxalin-2-yl]acetic acid and L-tyrosine t-butyl ester hydrochloride salt using Method Y.
HPLC (acetonitrile/water-0.1% TFA): $R_t$=30.0, 31.1 min.

Example 275

Preparation of 2-[2-(R,S)-1-(4-chloro-2,5-dimethyl-benzenesulfonyl)-3-oxo-1,2,3,4-tetrahydroquinoxalin-2-yl]-methylenecarbonyl-[2-(S)-methoxycarbonylpyrrolidin-N-yl]

The title compound was prepared using Method X, starting with 2-[2-(R,S)-1-(4-chloro-2,5-dimethylphenylsulfonyl)-3-oxo-1,2,3,4-tetrahydroquinoxalin-2-yl]acetic acid and 2-(S)-methoxycarbonylpyrrolidine.
HPLC (acetonitrile/water-0.1% TFA): $R_t$=27.41,27.5 min.

Example 276

Preparation of 2-[2-(R,S)-1-(4-chloro-2,5-dimethyl-benzenesulfonyl)-3-oxo-1,2,3,4-tetrahydroquinoxalin-2-yl]-N-[1-(S)-carboxamide-2-(S)-methylbut-1-yl]acetamide The title compound was prepared using Method X, starting with 2-[2-(R,S)-1-(4-chloro-2,5-dimethylphenylsulfonyl)-3-oxo-1,2,3,4-tetrahydroquinoxalin-2-yl]acetic acid and 1-(S)-carboxamide-2-(S)-methylbut-1-ylamine.
HPLC (acetonitrile/water-0.1% TFA): $R_t$=25.7, 26.27 min.

Example 277

Preparation of 2-[2-(R,S)-1-(4-chloro-2,5-dimethyl-benzenesulfonyl)-3-oxo-1,2,3,4-tetrahydroquinoxalin-2-yl]-N-methoxycarbonylmethylacetamide The title compound was prepared using Method X, starting with 2-[2-(R,S)-1-(4-chloro-2,5-dimethylphenylsulfonyl)-3-oxo-1,2,3,4-tetrahydroquinoxalin-2-yl]acetic acid and N-methoxycarbonylmethylamine.
HPLC (acetonitrile/water-0.1% TFA): $R_t$=25.12; 25.2 min.

Example 278

Preparation of 2-[2-(R,S)-1-(4-chloro-2,5-dimethyl-benzenesulfonyl)-3-oxo-1,2,3,4-tetrahydroquinoxalin-2-yl]-N-[1-(R)-carboxamide-2-(phenyl)eth-1-yl]acetamide The title compound was prepared from 2-[2-(R,S)-1-(4-chloro-2,5-dimethylphenylsulfonyl)-3-oxo-1,2,3,4-tetrahydroquinoxalin-2-yl]acetic acid and 2-phenylalanine carboxamide hydrochloride salt using Method Z.
HPLC (acetonitrile/water-0.1% TFA): $R_t$=3.29; 3.37 min.

Example 279

Preparation of 2-[2-(R,S)-1-(4-chloro-2,5-dimethyl-benzenesulfonyl)-3-oxo-1,2,3,4-tetrahydroquinoxalin-2-yl]-methylenecarbonyl-[2-(R)-hydroxy-5-(S)-methoxycarbonylpyrrolidin-N-yl]

The title compound was prepared from 2-[2-(R,S)-1-(4-chloro-2,5-dimethylphenylsulfonyl)-3-oxo-1,2,3,4-tetrahydroquinoxalin-2-yl]acetic acid and 2-(R)-hydroxy-5-(S)-methoxycarbonylpyrrolidine using Method Z.
HPLC (acetonitrile/water-0.1% TFA): $R_t$=2.64 min.

Example 280

Preparation of 2-[2-(R,S)-1-(4-chloro-2,5-dimethyl-benzenesulfonyl)-3-oxo-1,2,3,4-tetrahydroquinoxalin-2-yl]-N-[1-(R)-(methoxycarbonyl)eth-1-yl]acetamide The title compound was prepared from 2-[2-(R,S)-1-(4-chloro-2,5-dimethylphenylsulfonyl)-3-oxo-1,2,3,4-tetrahydroquinoxalin-2-yl]acetic acid and D-alanine methyl ester hydrochloride salt using Method Z.
HPLC (acetonitrile/water-0.1% TFA): $R_t$=3.17, 3.23 min.

Example 281

Preparation of 2-[2-(R,S)-1-(4-chloro-2,5-dimethyl-benzenesulfonyl)-3-oxo-1,2,3,4-tetrahydroquinoxalin-2-yl]-N-[1-(S)-(t-butoxycarbonyl)-3-methylbut-1-yl]acetamide The title compound was prepared from 2-[2-(R,S)-1-(4-chloro-2,5-dimethylphenylsulfonyl)-3-oxo-1,2,3,4-tetrahydroquinoxalin-2-yl]acetic acid and L-leucine t-butyl ester hydrochloride salt using Method Z.
HPLC (acetonitrile/water-0.1% TFA): $R_t$=5.50 min.

Example 282

Preparation of 2-[2-(R,S)-1-(4-chloro-2,5-dimethyl-benzenesulfonyl)-3-oxo-1,2,3,4-tetrahydroquinoxalin-2-yl]-N-[1-(S)-1,3-dicarboxamideprop-1-yl]acetamide The title compound was prepared from 2-[2-(R,S)-1-(4-chloro-2,5-dimethylphenylsulfonyl)-3-oxo-1,2,3,4-tetrahydroquinoxalin-2-yl]acetic acid and L-asparagine carboxamide hydrochloride salt using Method Z.

HPLC (acetonitrile/water-0.1% TFA) $R_t$=2.29 nm.

Example 283

Preparation of 2-[2-(R,S)-1-(4-chloro-2,5-dimethyl-benzenesulfonyl)-3-oxo-1,2,3,4-tetrahydroquinoxalin-2-yl]-N-[1-(R)-1.3-di(benzyloxy-carbonyl)prop-1-yl]acetamide The title compound was prepared from 2-[2-(R,S)-1-(4-chloro-2,5-dimethylphenylsulfonyl)-3-oxo-1,2,3,4-tetrahydroquinoxalin-2-yl]acetic acid and D-glutamic acid dibenzyl ester hydrochloride salt using Method Z.

HPLC (acetonitrile/water-0.1% TFA): $R_t$=5.65 min.

Example 284

Preparation of 2-[2-(R,S)-1-(4-chloro-2,5-dimethyl-benzenesulfonyl)-3-oxo-1,2,3,4-tetrahydroquinoxalin-2-yl]-N-(3-t-butoxycarbonyl-1-methoxycarbonliprop-1-yl)acetamide The title compound was prepared from 2-[2-(R,S)-1-(4-chloro-2,5-dimethylphenylsulfonyl)-3-oxo-1,2,3,4-tetrahydroquinoxalin-2-yl]acetic acid and L-glutamic acid methyl ester β-t-butyl ester hydrochloride salt using Method Z.

HPLC (acetonitrile/water-0.1% TFA): $R_t$=4.58 min.

Example 285

Preparation of 2-[2-(R,S)-1-(4-chloro-2,5-dimethyl-benzenesulfonyl)-3-oxo-1,2,3,4-tetrahydroquinoxalin-2-yl]-N-[1-(S-ethoxycarbonyleth-1-yl]acetamide The title compound was prepared from 2-[2-(R,S)-1-(4-chloro-2,5-dimethylphenylsulfonyl)-3-oxo-1,2,3,4-tetrahydroquinoxalin-2-yl]acetic acid and L-alanine ethyl ester hydrochloride salt using Method Z.

HPLC (acetonitrile/water-0.1% TFA): $R_t$=3.65 min.

Example 286

Preparation of 2-[2-(R,S)-1-(4-chloro-2,5-dimethyl-benzenesulfonyl)-3-oxo-1,2,3,4-tetrahydroquinoxalin-2-yl]-N-[1-(S)-carboxamide-2-(indol-3-yl)eth-1-yl]acetamide The title compound was prepared from 2-[2-(R,S)-1-(4-chloro-2,5-dimethylphenylsulfonyl)-3-oxo-1,2,3,4-tetrahydroquinoxalin-2-yl]acetic acid and tryptophan carboxamide hydrochloride salt using Method Z.

HPLC (acetonitrile/water-0.1% TFA): $R_t$=3.28 min.

Example 287

Preparation of 2-[2-(R,S)-1-(4-chloro-2,5-dimethyl-benzenesulfonyl)-3-oxo-1,2,3,4-tetrahydroquinoxalin-2-yl]-N-[1-(R)-methoxycarbonylphenylmethyl)]acetamide The title compound was prepared from 2-[2-(R,S)-1-(4-chloro-2,5-dimethylphenylsulfonyl)-3-oxo-1,2,3,4-tetrahydroquinoxalin-2-yl]acetic acid and D-phenylglycine methyl ester using Method Z.

HPLC (acetonitrile/water-0.1% TFA): $R_t$=4.21 min.

Example 288

Preparation of 2-[2-(R,S)-1-(4-chloro-2,5-dimethyl-benzenesulfonyl)-3-oxo-1,2,3,4-tetrahydroquinoxalin-2-yl]-methylenecarbonyl-[2-(R)-methoxycarbonylpyrrolidin-N-yl The title compound was prepared from 2-[2-(R,S)-1-(4-chloro-2,5-dimethylphenylsulfonyl)-3-oxo-1,2,3,4-tetrahydroquinoxalin-2-yl]acetic acid and D-proline methyl ester hydrochloride salt using Method Z.

HPLC (acetonitrile/water-0.1% TFA): $R_t$=3.49 min.

Example 289

Preparation of 2-[2-(R,S)-1-(4-chloro-2,5-dimethyl-benzenesulfonyl)-3-oxo-1,2,3,4-tetrahydroquinoxalin-2-yl]-N-[2-(indol-3-yl)-1-(R)-(methoxycarbonyl)eth-1-yl]acetamide The title compound was prepared from 2-[2-(R,S)-1-(4-chloro-2,5-dimethylphenylsulfonyl)-3-oxo-1,2,3,4-tetrahydroquinoxalin-2-yl]acetic acid and D-tryptophan methyl ester hydrochloride salt using Method Y.

HPLC (acetonitrile/water-0.1% TFA): $R_t$=30.3, 30.43 min.

Example 290

Preparation of 2-[2-(R,S)-1-(4-chloro-2,5-dimethyl-benzenesulfonyl)-3-oxo-1,2,3,4-tetrahydroquinoxalin-2-yl]-N-[1-(S)-carboxamide-2-(phenyl)eth-1-yl]acetamide The title compound was prepared from 2-[2-(R,S)-1-(4-chloro-2,5-dimethylphenylsulfonyl)-3-oxo-1,2,3,4-tetrahydroquinoxalin-2-yl]acetic acid and L-phenylalanine carboxamide hydrochloride salt using Method X.

HPLC (acetonitrile/water-0.1% TFA): $R_t$=3.29, 3.37 min.

Example 291

Preparation of 2-[2-(R,S)-1-(4-chloro-2,5-dimethyl-benzenesulfonyl)-3-oxo-1,2,3,4-tetrahydroquinoxalin-2-yl]-N-[1-(S)-(t-butoxycarbonyl)-2-(4-hydroxyphenyl)eth-1-yl]acetamide The title compound was prepared from 2-[2-(R,S)-1-(4-chloro-2,5-dimethylphenylsulfonyl)-3-oxo-1,2,3,4-tetrahydroquinoxalin-2-yl]acetic acid and L-tyrosine t-butyl ester hydrochloride salt using Method X.

Example 292

Preparation of 2-[2-(R,S)-1-(4-chloro-2,5-dimethyl-benzenesulfonyl)-3-oxo-1,2,3,4-tetrahydroquinoxalin-2-yl]-N-[2-(N-methyl-1,2,5,6-tetrahydropyrid-4-yl)-1-(R)-(pyrrolidin-N-ylcarbonyl)eth-1-yl]acetamide 2-[2-(R,S)-1-(4-chloro-2,5-dimethylbenzenesulfonyl)-3-oxo-1,2,3,4-tetrahydro-quinoxalin-2-yl]-N-[2-(pyrid-4-yl)-1-(R)-(pyrrolidin-N-ylcarbonyl)eth-1-yl]acetamide was converted to the title compound by Method J.

$^1$H NMR (DMSO-$d_6$) δ=1.8–2.2 (m, 6H), 2.89 (bd, 2H), 3.10–3.60(m, 8H), 4.6(m, 1H), 4.83(m, 1H), 5.26(bd, 1H), 5.34(bd), 6.78–7.40(m, Ar—H, 6H), 8.14(d, J=7.5 Hz, 1H), 10.42(s, 1H), 10.44(s, 1H); MS (ES): m/e 629 (M+H); HPLC (CH$_3$CN—H$_2$O-0.1% TFA) (short column): R$_t$=4.39 min.

Example 293

Preparation of 2-[2-(R,S)-1-(4-chloro-2,5-dimethyl-benzenesulfonyl)-3-oxo-1,2,3,4-tetrahydroquinoxalin-2-yl]-N-[2-(N-methylpiperidin-4-yl)eth-1-yl]-N-isopropylacetamide 2-[2-(R,S)-1-(4-chloro-2,5-dimethylbenzenesulfonyl)-3-oxo-1,2,3,4-tetrahydro-quinoxalin-2-yl]-N-[2-(pyrid-4-yl)eth-1-yl]-N-isopropylacetamide was subjected to Methods J and K to afford the title material.

$^1$H NMR (DMSO-$d_6$) δ=0.81–1.28(m, 12H), 1.66–1.78 (m, 1H), 2.04(s, 3H), 2.15(s, 3H), 2.20(s,3H), 2.10–2.45(m, 2H), 2.50–3.13(m, 6H), 3.70(m, 1H), 4.41(m, 1H), 4.90(m, 1H), 6.80–7.46(m, 6H), 10.51(s, 1H), 10.54(s, 1H); MS (ES): m/e 576 (M+H); HPLC (CH$_3$CN—H$_2$O-0.1% TFA) (short column) R$_t$=4.01 min.

Example 294

Preparation of 2-[2-(R,S)-1-(4-chloro-2,5-dimethyl-benzenesulfonyl)-3-oxo-1,2,3,4-tetrahydroquinoxalin-2-yl]-N-[2-(N-phenylpiperidin-4-yl)eth-1-yl]acetamide 2-[2-(R,S)-1-(4-chloro-2,5-dimethylbenzenesulfonyl)-3-oxo-1,2,3,4-tetrahydroquinoxalin-2-yl]-N-[2-(piperidin-4-yl)eth-1-yl]acetamide reacted with triphenylbismuth diacetate using Method M which led to the title material.

$^1$H NMR (DMSO-$d_6$) δ=1.75–1.13(m,7H), 2.02(s,3H), 2.24(s,3H), 2.00–2.28(m, 2H), 2.69(bt, 2H), 3.18(m,2H), 3.70(bd, 2H), 4.81(dd, J=6 Hz, 1H), 6.71–7.47(m, Ar—H, 11H), 7.89(t, J=3.0 Hz, 1H), 10.47(s, 1H); MS (ES): m/e 596 (M+H); HPLC (CH$_3$CN—H$_2$O-0.1% TFA) (short column): R$_t$=5.59 min.

Example 295

Preparation of 2-[2-(R,S)-1-(4-chloro-2,5-dimethyl-benzenesulfonyl)-3-oxo-1,2,3,4-tetrahydroquinoxalin-2-yl]-N-[2-(N-methylpiperidin-4-yl)eth-1-yl]-N-methylacetamide 2-[2-(R,S)-1-(4-chloro-2,5-dimethylbenzenesulfonyl)-3-oxo-1,2,3,4-tetrahydroquinoxalin-2-yl]-N-[2-(pyrid-4-yl)eth-1-yl]-N-methylacetamide was subjected to Methods J and K to afford the title material.

$^1$H NMR (DMSO-$d_6$) δ=1.34–1.95(m, 7H), 1.96(s, 3H), 2.23(s, 3H), 2.0–2.47(m, 2H), 2.95–3.50(m, 6H), 3.00(s, 3H), 3.05(s, 3H), 4.86(m, 1H), 6.79–7.40(m, Ar—H, 6H), 7.91(bt, 1H), 10.44(s, 1H); MS (ES): m/e 548 (M+H); HPLC (CH$_3$CN—H$_2$O-0.1% TFA) (short column): R$_t$=3.70 min.

Example 296

Preparation of 2-[2-(R,S)-1-(4-chloro-2,5-dimethyl-benzenesulfonyl)-3-oxo-1,2,3,4-tetrahydroquinoxalin-2-yl]-N-[2-(pyrid-4-yl)eth-1-yl]-N-methylacetamide The title compound was obtained by reacting methyl-(2-pyridin-4-yl-ethyl)-amine with 2-[2-(R,S)-1-(4-chloro-2,5-dimethylbenzenesulfonyl)-3-oxo-1,2,3,4-tetrahydroquinoxalin-2-yl] acetic acid using Method I.

$^1$H NMR (DMSO-$d_6$) δ=1.97(s, 3H), 2.20(s, 3H), 2.38–2.47(m, s, 2.67(s, 3H), 2.60–2.74(m, 5H), 3.25–3.47 (m, 4H), 4.88(m, 1H), 6.78–7.44(m, Ar—H, 8H), 8.31–8.43 (dd, 2H), 10.48, 10.50(s, 1H); MS (ES): m/e 528 (M+H); HPLC (CH$_3$CN—H$_2$O-0.1% TFA) (short column): R$_t$=3.53 min.

Example 297

Preparation of 2-[2-(R,S)-1-(4-chloro-2,5-dimethyl-benzenesulfonyl)-3-oxo-1,2,3,4-tetrahydroquinoxalin-2-yl]-N-[2-(pyrid-4-yl)-1-(R)-(pyrrolidin-N-ylcarbonyl)eth-1-yl]acetamide (R)-2-t-Butoxycarbonylamino-3-pyridin-4-yl-propionic acid reacted with pyrrolidine using Method I. Deprotection of BOC group with HCl gas using Method O followed by reaction with 2-[2-(R,S)-1-(4-chloro-2,5-dimethylbenzenesulfonyl)-3-oxo-1,2,3,4-tetrahydroquinoxalin-2-yl]acetic acid using Method I led to the title compound.

$^1$H NMR (DMSO-$d_6$) δ=1.65–2.10(m, 4H), 1.99(s, 3H), 2.20(s, 3H), 2.60(m, 2H), 2.91(m, 2H), 3.21(m, 4H), 4.67(q, 1H), 4.77(dd, J=5.1 Hz, 1H), 6.76–7.39(m, Ar—H, 8H), 8.38(d, J=4.8 z, 1H), 8.42(d, 2H), 10.40(bs, 1H); MS (ES): m/e 611 (M+H); HPLC (CH$_3$CN—H$_2$O-0.1% TFA) (short column): R$_t$=4.10 and 4.34 min.

Example 298

Preparation of 2-[2-(R,S)-1-(4-chloro-2,5-dimethyl-benzenesulfonyl)-3-oxo-1,2,3,4-tetrahydroquinoxalin-2-yl]-N-{2-[N-(pyrid-4-yl)piperidin-4-yl]eth-1-yl}acetamide 2-[2-(R,S)-1-(4-chloro-2,5-dimethylbenzenesulfonyl)-3-oxo-1,2,3,4-tetrahydroquinoxalin-2-yl]-N-[2-(piperidin-4-yl)eth-1-yl]acetamide reacted with 4-chloropyridine using Method N to afford the title compound.

$^1$H NMR (DMSO-$d_6$) δ=1.04–1.22 (m, 4H), 1.90–2.20(m, 4H),1.95(s, 3H), 2.19(s, 3H), 2.90(m, 2H), 3.14(br. t, 2H), 4.22(bd, 2H), 4.86(dd, J=4.5 Hz), 6.79–7.45(m, Ar—H, 8H), 7.89(t, J=5.4 Hz, 1H), 8.16(d, 2H), 10.44(s, 1H); MS (ES): m/e 597 (M+H); HPLC (CH$_3$CN—H$_2$O-0.1% TFA) (short column): R$_t$=4.59 min.

Example 299

Preparation of 2-[2-(R,S)-1-(4-chloro-2,5-dimethyl-benzenesulfonyl)-3-oxo-1,2,3,4-tetrahydroquinoxalin-2-yl]-N-[2-(N-methylpiperidin-4-yl-1-(R)-(pyrrolidin-N-ylcarbonyl)eth-1-yl]acetamide 2-[2-(R,S)-1-(4-chloro-2,5-dimethylbenzenesulfonyl)-3-oxo-1,2,3,4-tetrahydroquinoxalin-2-yl]-N-[2-(pyrid-4-yl)-1-(R)-(pyrrolidin-N-ylcarbonyl)eth-1-yl]acetamide was converted to the title compound using Methods J and K.

$^1$H NMR (DMSO-d$_6$) δ=1.10–1.85(m, 10H), 1.86 (s, 3H), 2.16(s, 3H), 2.0–2.50(m, 2H), 2.61(s, 3H) 3.0–3.43(m, 10H), 4.57(m, 1H), 4.81(br.dd, 1H), 6.74–7.36(m, Ar—H, 6H), 8.20(br t, 1H), 10.39(s, 1H); MS (ES): m/e 631 (M+H); HPLC (CH$_3$CN—H$_2$O-0.1% TFA) (short column): R$_t$=4.19 and 4.53 min.

Example 300

Preparation of 2-[2-(R,S)-1-(4-chloro-2,5-dimethyl-benzenesulfonyl)-3-oxo-1,2,3,4-tetrahydroquinoxalin-2-yl]-N-[2-(4-methylpiperazin-1-yl)eth-1-yl]acetamide 2-Chloro-ethylamine-hydrochloride reacted with 1-methylpiperazine in water. After evaporation of water, the resulting amine was reacted with 2-[2-(R,S)-1-(4-chloro-2,5-dimethylbenzenesulfonyl)-3-oxo-1,2,3,4-tetrahydroquinoxalin-2-yl]acetic acid using Method I.

$^1$H NMR (DMSO-d$_6$) δ=2.04 (s, 3H), 2.10–2.40 (m, 2H), 2.27 (s, 3H), 2.80 (s, 3H), 2.6–3.5 (bm, 6H), 4.93 (dd, J=3.9 Hz), 6.86–7.50 (m, Ar—H, 6H), 8.15 (bt, 1H), 10.53 (s, 1H). MS (ES): m/e 535 (M+H).

Example 301

Preparation of 2-[2-(R,S)-1-(4-chloro-2,5-dimethyl-benzenesulfonyl)-3-oxo-1,2,3,4-tetrahydroquinoxalin-2-yl]-N-[2-(N-cyclopropylpiperidin-4-yl)-1-(R)-(pyrrolidin-N-ylcarbonyl)eth-1-yl]acetamide 2-[2-(R,S)-1-(4-chloro-2,5-dimethylbenzenesulfonyl)-3-oxo-1,2,3,4-tetrahydroquinoxalin-2-yl]-N-[2-(pyrid-4-yl)-1-(R)-(pyrrolidin-N-ylcarbonyl)eth-1-yl]acetamide was hydrogenated with PtO$_2$ using Method L to afford the title compound.

$^1$H NMR (DMSO-d$_6$) δ=0.20 (bd, 2H), 0.40 (bd, 2H), 1.0–2.0 (m, 12H), 1.90 (s, 3H), 2.18 (s, 3H), 2.0–2.50 (m, 4H), 2.84 (m, 4H), 3.0–3.5 (m, 4H), 4.55 (m, 1H), 6.76 (m, Ar—H, 6H), 8.12 (bdd, 1H), 10.39 (s, 1H); MS (ES): m/e 657 (M+H).

Example 302

Preparation of 2-[2-(R,S)-1-(2-chloro-4-fluorobenzenesulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and 2-chloro-4-fluorobenzenesulfonylchloride using Method H'.

MS (ES): m/e 503.3 (M+H). HPLC (CH$_3$CN—H$_2$O-0.1% TFA): R$_t$=2.29 min.

Example 303

Preparation of 2-[2-(R,S)-1-(2,4,6-triisopropylbenzenesulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and 2,4,6-tri-iso-propylbenzenesulfonyl chloride using Method H'.

MS (ES): m/e 577.3 (M+H). HPLC (CH$_3$CN—H$_2$O-0.1% TFA): R$_t$=3.00 min.

Example 304

Preparation of 2-[2-(R,S)-1-(5-dimethylamino-napthalenesulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and 5-dimethylamino-naphthalenesulfonyl chloride using Method H'.

MS (ES): m/e 544.4 (M+H). HPLC (CH$_3$CN—H$_2$O-0.1% TFA): R$_t$=2.41 min.

Example 305

Preparation of 2-[2-(R,S)-1-(2-methoxy-5-methyl-benzenesulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and 2-methoxy-5-methylbenzene-sulfonyl chloride using Method H'.

MS (ES): m/e 495.3 (M+H). HPLC (CH$_3$CN—H$_2$O-0.1% TFA): R$_t$=2.28 min.

Example 306

Preparation of 2-[2-(R,S)-1-(2-cyanobenzenesulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and 2-cyanobenzenesulfonyl chloride using Method H'.

MS (ES): m/e 476.3 (M+H); HPLC (CH$_3$CN—H$_2$O-0.1% TFA): R$_t$=2.07 min.

Example 307

Preparation of 2-[2-(R,S)-1-(2-fluorobenzenesulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and 2-fluorobenzenesulfonyl chloride using Method H'.

MS (ES): m/e 469.3 (M+H); HPLC (CH$_3$CN—H$_2$O-0.1% TFA): R$_t$=2.13 min.

Example 308

Preparation of 2-[2-(R,S)-1-(2-methoxy-4-methyl-benzenesulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and 2-methoxy-4-methylbenzene-sulfonyl chloride using Method H'.
MS (ES): m/e 495.3 (M+H); HPLC (CH$_3$CN—H$_2$O-0.1% TFA): R$_t$=2.31 min.

Example 309

Preparation of 2-[2-(R,S)-1-(2.5-dimethoxybenzene-sulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and 2,5-dimethoxybenzene-sulfonyl chloride using Method H'.
MS (ES): m/e 511.3 (M+H); HPLC (CH$_3$CN—H$_2$O-0.1% TFA): R$_t$=2.20 min.

Example 310

Preparation of 2-[2-(R,S)-1-(2,4-difluorobenzene-sulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and 2,4-difluorobenzenesulfonyl chloride using Method H'.
MS (ES): m/e 487.3 (M+H). HPLC (CH$_3$CN—H$_2$O-0.1% TFA): R$_t$=2.20 min.

Example 311

Preparation of 2-[2-(R,S)-1-(2-methoxy-5-bromobenzenesulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and 2-methoxy-5-bromobenzene-sulfonyl chloride using Method H'.
MS (ES): m/e 560.3 (M+H). HPLC (CH$_3$CN—H$_2$O-0.1% TFA): R$_t$=2.35 min.

Example 312

Preparation of 2-[2-(R,S)-1-(2,3-dimethyl-imidazole-5-ylsulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and 2,3-dimethyl-imidazole-5-ylsulfonyl chloride using Method H'.
MS (ES): m/e 469.3 (M+H); HPLC (CH$_3$CN—H$_2$O-0.1% TFA): R$_t$=1.61 min.

Example 313

Preparation of 2-[2-(R,S)-1-(2-acetamido-4-methyl-thiazol-5-ylsulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and 2-acetamido-4-methylthiazol-5-ylsulfonyl chloride using Method H'.
MS (ES): m/e 529.3 (M+H); HPLC (CH$_3$CN—H$_2$O-0.1% TFA): R$_t$=2.11 min.

Example 314

Preparation of 2-[2-(R,S)-1-(quinolin-8-ylsulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and quinolin-8-ylsulfonyl chloride using Method H'.
MS (ES): m/e 502.2 (M+H); HPLC (CH$_3$CN—H$_2$O-0.1% TFA): R$_t$=2.17 min.

Example 315

Preparation of 2-[2-(R,S)-1-(thiophen-2-ylsulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and thiophen-2-ylsulfonyl chloride using Method H'.
MS (ES): m/e 457.2 (M+H); HPLC (CH$_3$CN—H$_2$O-0.1% TFA): R$_t$=2.08 min.

Example 316

Preparation of 2-[2-(R,S)-1-(2-methoxycarbonyl-thiophen-3-ylsulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and 2-methoxycarbonyl-thiophen-3-ylsulfonyl chloride using method H'.
MS (ES): m/e 515.3 (M+H); HPLC (CH$_3$CN—H$_2$O-0.1% TFA): R$_t$=2.08 min.

Example 317

Preparation of 2-[2-(R,S)-1-(2,5-dichlorobenzene-sulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and 2,5-dichlorobenzenesulfonyl chloride using method H'.
MS (ES): m/e 520.2 (M+H); HPLC (CH$_3$CN—H$_2$O-0.1% TFA): R$_t$=2.40 min.

Example 318

Preparation of 2-[2-(R,S)-1-(4-bromo-2-ethyl-benzenesulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and 4-bromo-2-ethylbenzene-sulfonyl chloride using method H'.
MS (ES): m/e 558.3 (M+H); HPLC (CH$_3$CN—H$_2$O-0.1% TFA): R$_t$=2.55 min.

Example 319

Preparation of 2-[2-(R,S)-1-(5-chloro-2-methoxybenzenesulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and 5-chloro-2-methoxybenzene-sulfonyl chloride using method H'.
MS (ES): m/e 515.3 (M+H); HPLC (CH$_3$CN—H$_2$O-0.1% TFA): R$_t$=2.33 min.

Example 320

Preparation of 2-[2-(R,S)-1-(2-chloro-4-trifluoromethylbenzenesulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and 2-chloro-4-trifluoromethyl-benzenesulfonyl chloride using method H'.
MS (ES): m/e 553.3 (M+H); HPLC (CH$_3$CN—H$_2$O-0.1% TFA): R$_t$=2.51 min.

Example 321

Preparation of 2-[2-(R,S)-1-(2,4-dichloro-5-methylbenzenesulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and 2,4-dichloro-5-methylbenzenesulfonyl chloride using method H'.
MS (ES): m/e 534.3 (M+H); HPLC (CH$_3$CN—H$_2$O-0.1% TFA): R$_t$=2.52 min.

Example 322

Preparation of 2-[2-(R,S)-1-(4-bromo-2-trifluoromethoxybenzenesulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and 4-bromo-2-trifluoromethoxy-benzenesulfonyl chloride using method H'.
MS (ES): m/e 614.2 (M+H); HPLC (CH$_3$CN—H$_2$O-0.1% TFA): R$_t$=2.56 min.

Example 323

Preparation of 2-[2-(R,S)-1-(2-chloro-4-cyanobenzenesulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and 2-chloro-4-cyanobenzene-sulfonyl chloride using method H'.
MS (ES): m/e 510.3 (M+H); HPLC (CH$_3$CN—H$_2$O-0.1% TFA): R$_t$=2.35 min.

Example 324

Preparation of 2-[2-(R,S)-1-(5-fluoro-2-methylbenzenesulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and 5-fluoro-2-methylbenzenesulfonyl chloride using method H'.
MS (ES): m/e 483.3 (M+H); HPLC (CH$_3$CN—H$_2$O-0.1% TFA): R$_t$=2.31 min.

Example 325

Preparation of 2-[2-(R,S)-1-(2-nitrobenzenesulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and 2-nitrobenzenesulfonyl chloride using Method H'.
MS (ES): m/e 496.3 (M+H); HPLC (CH$_3$CN—H$_2$O-0.1% TFA): R$_t$=2.19 min.

Example 326

Preparation of 2-[2-(R,S)-1-(2-trifluoromethylbenzenesulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and 2-trifluoro-methylbenzenesulfonyl chloride using Method H'.
MS (ES): m/e 519.1 (M+H); HPLC (CH$_3$CN—H$_2$O-0.1% TFA): R$_t$=2.40 min.

Example 327

Preparation of 2-[2-(R,S)-1-(3-N-methylimidazol-5-ylsulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and 3-N-methylimidazol-5-ylsulfonyl chloride using Method H'.
MS (ES): m/e 455.3 (M+H); HPLC (CH$_3$CN—H$_2$O-0.1% TFA): R$_t$=2.20 min.

Example 328

Preparation of 2-[2-(R,S)-1-(3,5-dimethyl-isooxazol-4-ylsulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and 3,5-dimethyl-isooxazol-4-ylsulfonyl chloride using Method H'.
MS (ES): m/e 470.2 (M+H); HPLC (CH$_3$CN—H$_2$O-0.1% TFA): R$_t$=2.12 min.

Example 329

Preparation of 2-[2-(R,S)-1-(N-morpholinosulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and N-morpholinosulfonyl chloride using Method H'.
MS (ES): m/e 460.2 (M+H); HPLC (CH$_3$CN—H$_2$O-0.1% TFA): R$_t$=2.10 min.

Example 330

Preparation of 2-[2-(R,S)-1-(2,5-dibromobenzenesulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and 2,5-dibromobenzenesulfonyl chloride using method H'.
MS (ES): m/e 609.1 (M+H); HPLC (CH$_3$CN—H$_2$O-0.1% TFA): R$_t$=2.45 min.

Example 331

Preparation of 2-[2-(R,S)-1-(2,3,4,5,6-pentamethylbenzenesulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and 2,3,4,5,6-pentamethylbenzenesulfonyl chloride using method H'.
MS (ES): m/e 521.3 (M+H); HPLC (CH$_3$CN—H$_2$O-0.1% TFA): R$_t$=2.61 min.

Example 332

Preparation of 2-[2-(R,S)-1-(4-bromo-2,5-difluorobenzenesulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and 4-bromo-2,5-difluorobenzene-sulfonyl chloride using method H'.
MS (ES): m/e 566.2 (M+H); HPLC (CH$_3$CN—H$_2$O-0.1% TFA): R$_t$=2.49 min.

Example 333

Preparation of 2-[2-(R,S)-1-(2,3,5,6-tetramethylbenzenesulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and 2,3,5,6-tetramethylbenzenesulfonyl chloride using method H'.
MS (ES): m/e 507.3 (M+H); HPLC (CH$_3$CN—H$_2$O-0.1% TFA): R$_t$=2.52 min.

Example 334

Preparation of 2-[2-(R,S)-1-(2-chloro-6-methylbenzenesulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and 2-chloro-6-methylbenzenesulfonyl chloride using method H'.
MS (ES): m/e 499.3 (M+H); HPLC (CH$_3$CN—H$_2$O-0.1% TFA): R$_t$=2.32 min.

Example 335

Preparation of 2-[2-(R,S)-1-(2-chlorobenzenesulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and 2-chlorobenzenesulfonyl chloride using method H'.
MS (ES): m/e 485.3 (M+H); HPLC (CH$_3$CN—H$_2$O-0.1% TFA): R$_t$=2.21 min.

Example 336

Preparation of 2-[2-(R,S)-1-(2,4,5-trichlorobenzenesulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and 2,4,5-trichlorobenzenesulfonyl chloride using method H'.
MS (ES): m/e 554.3 (M+H); HPLC (CH$_3$CN—H$_2$O-0.1% TFA): R$_t$=2.55 min.

Example 337

Preparation of 2-[2-(R,S)-1-(2-methyl-5-nitrobenzenesulfonyl)-3-oxo-1,2,3,4-tetrahydroquinoxalin-2-yl]-N-[2-(pyrid-4-yl)eth-1-yl]acetamide The title compound was synthesized from 2-[2-(R,S)-3-oxo-1,2,3,4-tetrahydroquinoxalin-2-yl]-N-(pyrid-4-yl)ethylacetamide and 2-methyl-5-nitrobenzene-sulfonyl chloride using method H'.
MS (ES): m/e 510.3 (M+H); HPLC (CH$_3$CN—H$_2$O-0.1% TFA): R$_t$=2.35 min.

Example 338

Preparation of 2-[2-(R)-1-(2.3-dichlorobenzene-sulfonyl)-3-oxo-1,2,3,4-tetra-hydroquinoxalin-2-yl]-N-[2-(N-(1-pyridin-2-yl)piperidin-4-yl)eth-1-yl]acetamide The title compound was synthesized from (R)-1-[(2,3-dichloro-benzene sulfonyl)-3-oxo-1,2,3,4-tetrahydroquinoxalin-2-yl] acetic acid and 2-[1-(pyrid-2-yl) piperidin-4-yl] ethylamine (described in Method K') using Method S'.

MS (ES) m/e 602 (M+H); HPLC (CH$_3$CN—H$_2$O-0.1% TFA) (short column) R$_t$=2.732 min.

Example 339

Preparation of 2-[2-(R)-1-(4-chloro-2,5-dimethyl-benzenesulfonyl)-3-oxo-1,2,3,4-tetrahydroquinoxalin-2-yl]-N-[2-(1-aminophen-4-yl)eth-1-yl]acetamide The title compound was synthesized from (R)-1-[(4-chloro-2,3-dimethyl-benzenesulfonyl)-3-oxo-1,2,3,4-tetrahydroquinoxalin-2-yl] acetic acid and 4-amino phenethylamine (Aldrich) using Method S'.

MS (ES) m/e 527 (M+H); HPLC (CH$_3$CN—H$_2$O-0.1% TFA) (short column) R$_t$=2.956 min.

Example 340

Preparation of 2-[2-(R)-1-(2,3-dichlorobenzene-sulfonyl)-3-oxo-1,2,3,4-tetrahydroquinoxalin-2-yl]-N-[2-(N-(4-methylpyridin-2-yl) piperidin-4-yl)eth-1-yl]acetamide The title compound was synthesized using (R)-1-[(2,3-dichlorobenzene-sulfonyl)-3-oxo-1,2,3,4-tetrahydro-quinoxalin-2-yl] acetic acid and 2-[1-(4-methyl-pyrid-2-yl)piperidin-4-yl] ethylamine hydrochloride salt using Method S'. The amine was synthesized from N-t-butoxycarbonyl 2-(piperidin-2-yl) ethylamine and 4-methyl-2-fluoro pyridine (Aldrich), using Method K'.

MS (ES) m/e 616 (M+H); HPLC (CH$_3$CN—H$_2$O-0.1% TFA) (short column) R$_t$=2.920 min.

Example 341

Preparation of 2-[2-(R)-1-(2,3-dichlorobenzene-sulfonyl)-3-oxo-1,2,3,4-tetrahydroquinoxalin-2-yl]-N-[2-(N-(3-methylpyridin-2-yl)piperidin-4-yl)eth-1-yl]acetamide The title compound was synthesized using (R)-1-[(2,3-dichloro-benzene sulfonyl)-3-oxo-1,2,3,4-tetrahydroquinoxalin-2-yl] acetic acid and 2-[1-(3-methyl-pyrid-2-yl)piperidin-4-yl] ethylamine hydrochloride salt using Method S'. The amine was synthesized from N-t-butoxycarbonyl 2-(piperidin-2-yl) ethylamine and 3-methyl-2-fluoro pyridine (Aldrich), using Method K'.

MS: (ES) m/e 616 (M+H); HPLC (CH$_3$CN—H$_2$O-0.1% TFA) (short column) R$_t$=2.907 min.

Example 342

Preparation of 2-[2-(R)-1-(2,3-dichlorobenzene-sulfonyl)-3-oxo-1,2,3,4-tetrahydroquinoxalin-2-yl]-N-[2-(N-(6-methylpyridin-2-yl)piperidin-4-yl)eth-1-yl]acetamide The title compound was synthesized using (R)-1-[(2,3-dichloro-benzene sulfonyl)-3-oxo-1,2,3,4-tetrahydro-quinoxalin-2-yl] acetic acid and 2-[1-(6-methyl-pyrid-2-yl)piperidin-4-yl] ethylamine hydrochloride salt using Method S'. The amine was synthesized from N-t-butoxycarbonyl 2-(piperidin-2-yl) ethylamine and 6-methyl-2-fluoro pyridine (Aldrich), using Method K'.

MS (ES) m/e 616 (M+H); HPLC (CH$_3$CN—H$_2$O-0.1% TFA) (short column) R$_t$=2.872 min.

Example 343

Preparation of 2-[2-(R)-1-(2,3-dichlorobenzene-sulfonyl)-3-oxo-1,2,3,4-tetrahydroquinoxalin-2-yl]-N-ethyl-N-[2-(N-(6-methylpyridin-2-yl)piperidin-4-yl)eth-1-yl]acetamide The title compound was synthesized using (R)-1-[(2,3-dichloro-benzene sulfonyl)-3-oxo-1,2,3,4-tetrahydro-quinoxalin-2-yl] acetic acid and 2-(N-ethyl)-[1-(6-methyl-pyrid-2-yl)piperidin-4-yl] ethylamine hydrochloride salt using Method S'. The amine was synthesized from 2-(N-ethyl)-eth-1-yl-pyridine using Method T', followed by Method K', using N-ethyl-t-butoxycarbonyl 2-(piperidin-2-yl)ethyl amine, instead of N-t-butoxycarbonyl 2-(piperidin-2-yl) ethyl amine and 6-methyl-2-fluoro pyridine (Aldrich).

MS (ES) m/e 644 (M+H); HPLC (CH$_3$CN—H$_2$O-0.1% TFA) (short column) R$_t$=3.139 min.

Example 344

Preparation of 2-[2-(R) 1-(2,3-dichlorobenzene-sulfonyl)-3-oxo-1,2,3,4-tetrahydroquinoxalin-2-yl]-N-ethyl-N-[2-(N-(1-pyridin-2-yl) piperidin-4-yl)eth-1-yl]acetamide The title compound was synthesized using (R)-1-[(2,3-dichloro-benzene sulfonyl)-3-oxo-1,2,3,4-tetrahydro-quinoxalin-2-yl] acetic acid and 2-(N-ethyl)-[1-(pyrid-2-yl)piperidin-4-yl] ethylamine hydrochloride salt using Method S'. The amine was synthesized from 2-(N-ethyl)-eth-1-yl-pyridine using Method T', followed by Method K', using N-ethyl-t-butoxycarbonyl 2-(piperidin-2-yl)ethyl amine, instead of N-t-butoxycarbonyl 2-(piperidin-2-yl) ethyl amine and 2-fluoro pyridine (Aldrich).

MS (ES) m/e 630 (M+H); HPLC (CH$_3$CN—H$_2$O-0.1% TFA) (short column) R$_t$=3.014 min.

Example 345

Preparation of 2-[2-(R,S)-1-(4-chloro-2,5-dimethyl-benzenesulfonyl)-3-oxo-1,2,3,4-tetrahydroquinoxalin-2-yl]-N-[2-(2-methylpyridin-4-yl)eth-1-yl]acetamide A solution of R-[1-(4-chloro-2,5-dimethyl-benzenesulfonyl)-3-oxo-1,2,3,4-tetrahydro-quinoxalin-2-yl]-acetic acid (150 mg, 0.37 mmol), 2-(2-methyl-pyridin-4-yl)-ethylamine (described in Method V') (87.4 mg, 0.64 mmol) and triethyl amine (230 µL, 1.65 mmol) in 3 mL of acetonitrile was treated with HATU (153 mg, 0.4 mmol). The resulting solution was stirred several hours at room temperature, concentrated and chromatographed to give pure title compound.

MS(ES): m/e (EI*) 527.1 [M+H]

Example 346

Preparation of 2-[2-(R,S)-1-(4-chloro-2,5-dimethyl-benzenesulfonyl)-3-oxo-1,2,3,4-tetrahydroquinoxalin-2-yl]-N-(benzoimidazol-2-ylamino)eth-1-ylacetamide A mixture of N1-(1H-benzoimidazol-2-yl)-ethane-1,2-diamine (113 mg), described in Method W', R-[1-(4-chloro-2,5-dimethylbenzenesulfonyl)-3-oxo-1,2,3,4-tetrahydroquinoxalin-2-yl]-acetic acid, and triethyl amine (230 µL) in 5 mL of acetonitrile, with a small amount of DMF added for solubility, was treated with HATU (153 mg). The resulting homogeneous solution was stirred at room temperature for 2 hours then concentrated and diluted with a mixture of choroform and isopropanol (3:1). The organic layer was washed with saturated aqueous odium bicarbonate solution and brine, dried in vacuo, and concentrated. The residue was purified by HPLC.

MS(ES): m/e (EI*) 566.2 [M+H]

Example 347

Preparation of 2-[2-(R)-1-(4-chloro-2,5-dimethyl-benzenesulfonyl)-3-oxo-1,2,3,4-tetrahydroquinoxalin-2-yl]-N-[3-(benzoimidazol-2-ylamino)prop-1-yl]acetamide The title compound was prepared in the same manner as that described for Example 362 after HPLC purification, from N1-(1H-benzoimidazol-2-yl)-ethane-1,3-diamine and R-[1-(4-chloro-2,5-dimethyl-benzenesulfonyl)-3-oxo-1,2,3,4-tetrahydro-quinoxalin-2-yl]-acetic acid. N1-(1H-benzoimidazol-2-yl)-ethane-1,3-diamine was obtained from 1,3-diamine using Method W'.

MS(ES): m/e (EI*) 580.2 [M+H]

Example 348

Preparation of 2-[2-(R)-1-(4-chloro-2,5-dimethyl-benzenesulfonyl)-3-oxo-1,2,3,4-tetrahydroquinoxalin-2-yl]-N-[2-(1-(pyrid-2-yl)phen-4-yl)eth-1-yl]acetamide R-[1-(4-Chloro-2,5-dimethyl-benzenesulfonyl)-3-oxo-1,2,3,4-tetrahydroqinox alin-2-yl]acetic acid and 2-(4-Pyridin-2-yl-phenyl)-ethylamine were reacted using Method U' to give the title compound. This was then purified by column chromatography over silica gel with EtOAc (100%) as eluent.

HPLC (CH$_3$CN—H$_2$O-0.1% TFA) (short column): R$_t$=3.09 min.

Example 349

Preparation of 2-[2-(R)-1-(2,3-dichlorobenzene-sulfonyl)-3-oxo-1,2,3,4-tetrahydroquinoxalin-2-yl]-N-methyl-N-[2-(pyridin-4-yl)eth-1-yl]acetamide R-[1-(2,3-Dichloro-benzenesulfonyl)-3-oxo-1,2,3,4-tetrahydro-qinoxalin-2-yl]-acetic acid and N-methyl-(2-pyridin-4-yl-ethyl)-amine (Array) were reacted using Method U' to give the title compound. The solvent was removed under vacuum and the crude residue dissolved in CH$_2$Cl$_2$ (25 mL). The organic layer was washed with brine (4×20 mL) and dried over Na$_2$SO$_4$. The solvent was removed under vacuum and the crude mixture purified by column chromatography over silica gel with 0.5%–2% MeOH/CH$_2$Cl$_2$ as eluent.

HPLC (CH$_3$CN—H2O-0.1% TFA) (short column): R$_t$=2.49 min.

Example 350

Preparation of 2-[2-(R)-1-(2,3-dichlorobenzene-sulfonyl)-3-oxo-1,2,3,4-tetrahydroquinoxalin-2-yl]-N-isopropyl-N-[2-(pyridin-4-yl)eth-1-yl]acetamide R-[1-(2,3-Dichloro-benzenesulfonyl)-3-oxo-1,2,3,4-tetrahydro-qinoxalin-2-yl]acetic acid and N-isopropyl-(2-pyridin-4-yl-ethyl)-amine, obtained as described in Method U, were reacted using Method U' to give the title compound. The solvent was removed under vacuum and the crude residue dissolved in CH$_2$Cl$_2$ (25 mL). The organic layer was washed with brine (4×20 mL) and dried over Na$_2$SO$_4$. The solvent was removed under vacuum and then purified by column chromatography over silica gel EtOAc (100%) as eluent.

HPLC (CH$_3$CN—H$_2$O-0.1% TFA) (short column): R$_t$=3.06 min.

Example 351

Preparation of 2-[2-(R)-1-(2,3-dichlorobenzene-sulfonyl)-3-oxo-1,2,3,4-tetrahydroquinoxalin-2-yl]-N-ethyl-N-[2-(pyridin-4-yl)eth-1-yl]acetamide R-[1-(2,3-Dichloro-benzenesulfonyl)-3-oxo-1,2,3,4-tetrahydro-qinoxalin-2-yl]-acetic acid and N-ethyl-(2-pyridin-4-yl-ethyl)-amine trifluoroacetate salt (Method X'), obtained from vinyl pyridine using Method T', were reacted using Method S' to give the title compound. Brine (50 mL) was added at −20° C., extracted with CH$_2$Cl$_2$ (50 mL) and dried over Na$_2$SO$_4$. The solvent was removed under vacuum and then purified by column chromatography over silica gel with 0.5%–3% MeOH/CH$_2$Cl$_2$ as eluent.

HPLC (CH$_3$CN—H$_2$O-0.1% TFA) (short column): R$_t$=2.62 min.

Example 352

Preparation of 2-[2-(R)-1-(2,3-dichlorobenzene-sulfonyl)-3-oxo-1,2,3,4-tetrahydroquinoxalin-2-yl]-N-ethyl-N-[2-(N-methyl-piperidin-4-yl) eth-1-yl]acetamide The pyridinium salt of 2-[2-(R)-1-(2,3-dichlorobenzene-sulfonyl)-3-oxo-1,2,3,4-tetrahydroquinoxalin-2-yl]-N-ethyl-N-[2-(pyridin-4-yl)eth-1-yl]acetamide was formed using Method J and taken on without purification to the next step. Reduction of the methyl iodide salt with excess PtO$_2$ in MeOH was performed under 54 psi at room temperature overnight. The crude mixture was filtered over celite. Upon evaporation of the solvent under reduced pressure, the residue was dissolved in EtOH and cooled to 0° C. HCl was then added dropwise to a pH=3. The solvent was then removed under vacuum without heat to give the title compound as the HCL salt.

HPLC (CH$_3$CN—H$_2$O-0.1% TFA) (short column): R$_t$=2.71 min.

Example 353

Preparation of 2-[2-(R)-1-(4-chloro-2,5-dimethyl-benzenesulfonyl)-3-oxo-1,2,3,4-tetrahydroquinoxalin-2-yl]-N-[2-[N-(3-methylpyridin-2-yl)piperidin-4-yl]eth-1-yl]acetamide The title compound was synthesized using (R)-1-[(4-chloro-2,5-dimethyl-benzene sulfonyl)-3-oxo-1,2,3,4-tetrahydro-quinoxalin-2-yl] acetic acid and 2-[1-(3-methyl-pyrid-2-yl)piperidin-4-yl] ethylamine hydrochloride salt using Method U'. The amine was synthesized from N-t-butoxycarbonyl 2-(piperidin-2-yl) ethylamine and 3-methyl-2-fluoro pyridine (Aldrich), using Method K'.

MS (ES): m/e 611 (M+H).

Example 354

Preparation of 2-[2-(R)-1-(4-chloro-2,5-dimethyl-benzenesulfonyl)-3-oxo-1,2,3,4-tetrahydroquinoxalin-2-yl]-N-[2-[N-(4-methylpyridin-2-yl)piperidin-4-yl]eth-1-yl]acetamide The title compound was synthesized using (R)-1-[(4-chloro-2,5-dimethylbenzene sulfonyl)-3-oxo-1,2,3,4-tetrahydroquinoxalin-2-yl] acetic acid and 2-[1-(4-methyl-pyrid-2-yl)piperidin-4-yl] ethylamine hydrochloride salt using Method U'. The amine was synthesized from N-t-butoxycarbonyl 2-(piperidin-2-yl) ethylamine and 4-methyl-2-fluoro pyridine (Aldrich), using Method K'.

MS (ES): m/e 611 (M+H). HPLC (CH$_3$CN—H$_2$O-0.1% TFA) (short column): R$_t$=3.19 min

Example 355

Preparation of 2-[2-(R)-1-(2,3-dichlorobenzenesulfonyl)-3-oxo-1,2,3,4-tetrahydroquinoxalin-2-yl]-N-methyl-N-[2-(N-methyl-piperidin-4-yl)eth-1-yl]acetamide The title compound was synthesized using (R,S)-1-[(4-chloro-2,5-dimethyl-benzene sulfonyl)-3-oxo-1,2,3,4-tetrahydroquinoxalin-2-yl] acetic acid and 2-N-methyl-[1-(N-methyl)piperidin-4-yl]ethylamine hydrochloride salt using Method I. The amine was synthesized from N-methyl-(2-pyridin-4-yl-ethyl)amine (Array) using Method J. The crude material was purified on prep HPLC.

MS (ES): m/e 554 (M+H).

Example 356

Preparation of 2-[2-(R)-1-(4-chloro-2,5-dimethyl-benzenesulfonyl)-3-oxo-1,2,3,4-tetrahydroquinoxalin-2-yl]-N-[4-(pyrid-2-yl)but-3-yn-1-yl]acetamide The title compound was synthesized using (R,S)-1-[(4-chloro-2,5-dimethyl-benzenesulfonyl)-3-oxo-1,2,3,4-tetrahydro-quinoxalin-2-yl] acetic acid and 4-(pyridin-2-yl)but-3-lylamine hydrochloride salt using Method U'. The amine was obtained from pent-4-ynoic acid using Method Y'. MS (ES): m/e 537 (M+H).

HPLC (CH$_3$CN—H$_2$O-0.1% TFA) (short column): R$_t$=2.85 min

Example 357

Preparation of 2-[2-(R)-1-(4-chloro-2,5-dimethyl-benzenesulfonyl)-3-oxo-1,2,3,4-tetrahydroquinoxalin-2-yl]-N-[4-(pyrid-2-yl)but-3-yn-1-yl] acetamide The title compound was synthesized using (R,S)-1-[(4-chloro-2,5-dimethyl-benzene sulfonyl)-3-oxo-1,2,3,4-tetrahydro-quinoxalin-2-yl] acetic acid and 4-(pyridin-2-yl)but-3-yn-lylamine hydrochloride salt using Method U'. The amine was obtained from pent-4-ynoic acid using Method Y', replacing 4-bromopyridine with 2-bromo pyridine (Aldrich).

MS (ES): m/e 537 (M+H). HPLC (CH$_3$CN—H$_2$O-0.1% TFA) (short column): R$_t$=2.86 min

Biological Example

The potency and efficacy to inhibit the bradykinin B1 receptor was determined for the compounds of this invention in a cell-based fluorescent calcium-mobilization assay. The assay measures the ability of test compounds to inhibit B1 agonist-induced increase of intracellular free Ca$^{+2}$ in a native human B1 receptor-expressing cell line.

In this example, the following additional abbreviations have the meanings set forth below. Abbreviations heretofore defined are as defined previously. Undefined abbreviations have there art recognized meanings.

| | |
|---|---|
| BSA = | bovine serum albumin |
| DMSO = | dimethylsulfoxide |
| FBS = | fetal bovine serum |
| MEM = | minimum essential medium |
| mM = | millimolar |
| ng = | nanogram |
| μg = | micrograms |
| μM = | micromolar |

Specifically, calcium indicator-loaded cells are pre-incubated in the absence or presence of different concentrations of test compounds followed by stimulation with selective B1 agonist peptide while Ca-dependent fluorescence is monitored.

IMR-90 human lung fibroblast cells (CCL 186, American Type Tissue Collection) are grown in MEM supplemented with 10% FBS as recommended by ATCC. Confluent cells are harvested by trypsinization and seeded into black wall/clear bottom 96-well plates (Costar #3904) at approx. 13,000 cells/well. The following day, cells are treated with 0.35 ng/mL interleukin-1β in 10% FBS/MEM for 2 hours to up-regulate B1 receptors. Induced cells are loaded with fluorescent calcium indicator by incubation with 2.3 μM Fluo-4/AM (Molecular Probes) at 37° C. for 1.5 hrs in the presence of an anion transport inhibitor (2.5 mM probenecid in 1% FBS/MEM). Extracellular dye is removed by washing with assay buffer (2.5 mM probenecid, 0.1% BSA, 20 mM HEPES in Hank's Balanced Salt Solution without bicarbonate or phenol red, pH 7.5) and cell plates are kept in dark until used. Test compounds are assayed at 7 concentrations in triplicate wells. Serial dilutions are made in half log-steps at 100-times final concentration in DMSO and then diluted in assay buffer. Compound addition plates contain 2.5-times final concentrations of test compounds or controls in 2.5% DMSO/assay buffer. Agonist plates contain 5-times the final concentration of 2.5 nM (3×EC50) B1 agonist peptide des-Arg$^{10}$-kallidin (DAKD, Bachem) in assay buffer. Addition of test compounds to cell plate, incubation for 5 min at 35° C., followed by the addition of B1 agonist DAKD is carried out in the Fluorometric Imaging Plate Reader (FLIPR, Molecular Devices) while continuously monitoring Ca-dependent fluorescence. Peak height of DAKD-induced fluorescence is plotted as function of concentration of test compounds. $IC_{50}$ values are calculated by fitting a 4-parameter logistic function to the concentration-response data using non-linear regression (Xlfit, IDBS).

Typical potencies observed for B1 receptor agonist peptides are $EC_{50}$=approx. 0.8 nM and approx. 100 nM for des-Arg$^{10}$-kallidin and des-Arg$^{9}$-bradykinin, respectively, while for B1 antagonist peptide des-Arg$^{10}$, Leu$^{9}$-kallidin $IC_{50}$ is approx. 1 nM.

The compounds of this invention, including those of Formula I, as well as the commercially available compounds of Examples 79 and 80 exhibited $IC_{50}$ values of 0.1 to 10,000 nM in this assay.

In view of the above, all of these compounds exhibit B1 antagonistic properties and, accordingly, are useful in treating disease conditions mediated at least in part by B1.

What is claimed is:

1. A compound of Formula I:

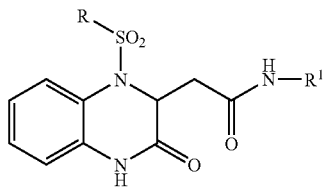

R is selected from the group consisting of naphthyl, substituted aryl, heteroaryl, substituted heteroaryl, heterocyclic and substituted heterocyclic; and $R^1$ is selected from the group consisting of alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic and substituted heterocyclic;

or pharmaceutically acceptable salts thereof;

with the proviso that $R^1$ is selected from the group consisting of:

I alkylene-C(=O)$R^a$, wherein alkylene is optionally substituted and $R^a$ is selected from the group consisting of hydroxyl, —$NR^bR^b$, —$OR^b$, alkyl, substituted alkyl, alkenyl, substituted alkenyl, alkynyl, substituted alkynyl, aryl, substituted aryl, cycloalkyl, substituted cycloalkyl, heteroaryl, substituted heterocyclyl, substituted heterocyclyl wherein each $R^b$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic and substituted heterocyclic;

II alkylene-$X^a$, wherein alkylene is optionally substituted and $X^a$ is selected from the group consisting of —OH, cyano, and —$NR^bR^b$ wherein each $R^b$ is independently as defined above;

III alkylene-het$^a$—C(=O)—CH($R^b$)$NR^bR^b$, wherein alkylene is optionally substituted and het$^a$ is a nitrogen containing heterocycyl attached to the —C(O)— group through a ring nitrogen atom of the het$^a$ group and each $R^b$ is as defined above;

IV alkylene-het$^a$—C(=O)-het$^b$, wherein alkylene is optionally substituted and het$^a$ is as defined above and het$^b$ is a heterocyclyl;

V alkylene-$R^c$—$NR^b$C(=$NR^b$)$NR^bR^b$, wherein alkylene is optionally substituted, each $R^b$ is as defined above and $R^c$ is selected from the group consisting of aryl, substituted aryl, cycloalkyl, substituted cycloalkyl, heteroaryl, substituted heteroaryl, heterocyclic and substituted heterocyclic;

VI alkylene-$R^c$—$NR^b$C(=O)—$NR^bR^b$, wherein alkylene is optionally substituted, each $R^b$ is as defined above and $R^c$ is as defined above;

VII alkylene-$R^c$—alkylene-C(=O)$R^b$, wherein alkylene is optionally substituted and $R^b$ and $R^c$ are as defined above;

VIII alkylene-$R^c$—C(=O)-alkylene-$(X^b)_n$, wherein alkylene is optionally substituted, $X^b$ is selected from the group consisting of —OH, halo, cyano, and —$NR^bR^b$, n is one except when $X^b$ is halo then n can be 1–3; and further wherein each $R^b$ is independently as defined above and $R^c$ is as defined above;

IX alkylene-$R^c$—C(=O)—$R^d$, wherein alkylene is optionally substituted and $R^c$ is selected from the group consisting of aryl, substituted aryl, cycloalkyl, substituted cycloalkyl, heteroaryl, substituted heteroaryl, heterocyclic and substituted heterocyclic and $R^d$ is selected from the group consisting of substituted alkyl, aryl, heteroaryl, heterocyclic and cycloalkyl;

X alkylene-$R^c$—$NR^b$C(=O)$R^e$ wherein alkylene is optionally substituted, $R^b$ and $R^c$ are as defined above, and where $R^e$ is substituted alkyl, alkenyl, substituted alkenyl, aryl, substituted aryl, cycloalkyl, substituted heteroaryl;

XI alkynylene-$R^d$ where $R^d$ is as defined above;

XII alkenylene-$R^d$ where $R^d$ is as defined above; and

XIII alkylene-$R^c$—$NR^b$—C(=$NR^b$)$R^b$, wherein alkylene is optionally substituted, and each of $R^b$ and $R^c$ are as defined above;

with the further provisos that:

A. when $R^1$ is 2-(pyrid-4-yl)eth-1-yl, then R is not 1-methylpyrazol-4-yl;

B. when $R^1$ is benzyl, then R is not 2,4-difluorophenyl;

C. when $R^1$ is benzyl, then R is not phenyl;

D. when $R^1$ is phenyl, then R is not quinolin-8-yl; and

E. when $R^1$ is benzyl, then R is not thien-2-yl;

and with the further proviso excluding the following known compounds:

F. when $R^1$ is 2-methoxyphenyl, then R is not 4-methylphenyl; and

G. when $R^1$ is 2-ethoxyphenyl, then R is not 4-methylphenyl.

2. The compound according to claim 1 wherein R is selected from the group consisting of phenyl; naphth-1-yl; 5-dimethylamino-naphth-1-yl; 2-fluorophenyl; 2-chlorophenyl; 2-cyanophenyl; 2-methylphenyl; 2-nitrophenyl; 2-trifluoromethylphenyl; 3-chlorophenyl; 4-methylphenyl (tolyl); 2,5-dibromo-phenyl; 4-bromo-2-ethylphenyl; 4-bromo-2-trifluoromethoxyphenyl; 2,3-dichlorophenyl; 2,4-dichlorophenyl; 3,4-dichlorophenyl; 2,5-dichlorophenyl; 3,5-dichlorophenyl; 2,6-dichlorophenyl; 2-chloro-4-4cyanophenyl; 2-chloro-4-fluorophenyl; 3-chloro-2-methylphenyl; 2-chloro-6-methylphenyl; 5-chloro-2- methoxyphenyl; 2-chloro-4-trifluoromethylphenyl; 2,4-difluorophenyl; 5-fluoro-2-methylphenyl; 2,5-dimethoxyphenyl; 2-methoxy-4-methylphenyl; 2-methoxy-5-bromophenyl; 2-methoxy-5-methylphenyl; 2,5-dimethylphenyl; 2-methyl-5-nitrophenyl; 3,5-di(trifluoromethyl)phenyl; 4-bromo-2,5-difluorophenyl; 2,3,4-trichlorophenyl; 2,4,5-trichlorophenyl; 2,4,6-trichlorophenyl; 2,4-dichloro-5-methylphenyl; 4-chloro-2,5-dimethylphenyl; 2,4,6-tri(iso)propylphenyl; 2,4,6-trimethylphenyl; 2,3,5-trimethyl-4-chlorophenyl; 2,3,6-trimethyl-4-methoxyphenyl; 2,3,4,5,6-pentamethylphenyl; 5-chloro-1,3-dimethylpyrazol-4-yl; 2-methoxycarbonyl-thiophen-3-yl; 2,3-dimethylimidazol-5yl; 2-methylcarbonylamino-4-methyl-thiazol-5-yl; quinolin-8-yl; thiophen-2-yl; 1-methylimidiazol-4-yl; 3,5-dimethylisoxazol-4-yl; and N-morpholino.

3. The compound of claim 2, wherein R is 4-chloro-2,5-dimethylphenyl.

4. The compound according to claim 3 wherein $R^1$ is selected from the group consisting of:
- 2-[(4-amidino)phenyl]-1-(R)-(pyrrolidin-N-ylcarbonyl)eth-1-yl,
- 2-[N-(α-aminoacetyl)piperid-4-yl]eth-1-yl,
- 2-[4-(aminoethyleneamidino)phenyl]eth-1-yl, 2-[N-(1-amino-1-methylethylcarbonyl)piperid-4-yl]eth-1-yl,
- 1-(S)-carboxamide-2-(indol-3-yl)eth-1-yl,
- carboxamidemethyl,
- 1-carboxamide-2-(S)-methyl-but-1-yl,
- 1-(S)-carboxamide-2-(phenyl)eth-1-yl,
- 1-(R)-carboxamide-2-(phenyl)eth-1-yl,
- cyanomethyl,
- 2-(4-cyanophenyl)-1-(R)-(pyrrolidin-N-ylcarbonyl)eth-1-yl,
- 2-(4-cyanophenyl)-1-(S)-(pyrrolidin-N-ylcarbonyl)eth-1-yl,
- 2-(N-cyclopropylpiperidin-4-yl)-1-(R)-(pyrrolidin-N-ylcarbonyl)eth-1-yl,
- 1-(R)-1,3-di(benzyloxycarbonyl)prop-1-yl,
- 1-(S)-1,3-dicarboxamideprop-1-yl,
- (2-dimethylamino)eth-1-yl,
- 3-(dimethylamino)prop-1-yl,
- 1-(S)-ethoxycarbonyleth-1-yl,
- 1-(R)-(1-N-ethylamino-carbonyl)-4-amino-n-butyl,
- 1-(S)-(1-N-ethylamino-carbonyl)-4-amino-n-butyl,
- 1-(R)-(1-N-ethylaminocarbonyl)-5-(t-butoxycarbonylamino)-pent-5-yl,
- 1-(S)-(1-N-ethylaminocarbonyl)-5-(t-butoxycarbonylamino)-pent-5-yl,
- 1-(R)-(1-N-ethylaminocarbonyl)-4-(N'-t-butoxycarbonylamino)-n-but-1-yl,
- 1-(S)-(1-N-ethylaminocarbonyl)-4-(N'-t-butoxycarbonylamino)-n-but-1-yl,
- 1-(R)-(1-N-ethylaminocarbonyl)-5-guanadino-n-pent-5-yl,
- 1-(S)-(1-N-ethylaminocarbonyl)-5-guanadino-n-pent-5-yl,
- 1-R,S-(1-N-ethylaminocarbonyl)-4-(N'-t-butoxycarbonyl)-guanadino-n-but-1-yl,
- 1-(R)-(1-N-ethylaminocarbonyl)-5-(N'-t-butoxycarbonylamino)-n-pent-5-yl,
- 1-(S)-(1-N-ethylaminocarbonyl)-5-(N'-t-butoxycarbonylamino)-n-pent-5-yl,
- 2-hydroxyeth-1-yl,
- 2-(4-hydroxyphenyl)-1-(S)-(methoxycarbonyl)eth-1-yl,
- 2-(4-hydroxyphenyl)-1-(S)-(isopropoxycarbonyl)eth-1-yl,
- 2-(4-hydroxyphenyl)-1-(R)-(methoxycarbonyl)eth-1-yl,
- 2-(N-hydroxypyrid-4-yl)eth-1-yl,
- 2-(imidazol-4-yl)eth-1-yl,
- 2-[4-(imidazolin-2-yl)phenyl]-1-(R)-(pyrrolidin-1-ylcarbonyl)eth-1-yl,
- 2-(indol-3-yl)eth-1-yl,
- 2-(indol-3-yl)-1-(S)-(methoxycarbonyl)eth-1-yl,
- 2-(indol-3-yl)-1-(R)-(methoxycarbonyl)eth-1-yl,
- 1-(R)-(isopropoxycarbonyl)-2-(phenyl)eth-1-yl,
- 1-(R)-(methoxycarbonyl)eth-1-yl,
- methoxycarbonylmethyl,
- methoxycarbonylphenylmethyl,
- 2-methoxyeth-1-yl,
- 1-(R)-(methoxycarbonyl)-2-(N-methylpiperidin-4-yl)eth-1-yl,
- 1-(R)-(methoxycarbonyl)-2-(N-methyl-1,2,3,6-tetrahydropyrid-4-yl)eth-1-yl,
- 1-(R)-(methoxycarbonyl)-2-pyrid-4-yl)eth-1-yl,
- 1-(R)-(N-methyl-N-ethylcarbamoyl)-3-(guanadino)prop-1-yl,
- 2-(N-methylpiperidin-4-yl)-1-(R)-(pyrrolidin-N-ylcarbonyl)eth-1-yl,
- 2-(N-methyl-1,2,5,6-tetrahydropyrid-4-yl)-1-(R)-(pyrrolidin-N-ylcarbonyl) eth-1-yl,
- 3-(2-methylthiazol-4-yl)-pyrazol-5-yl,
- 1-(R)-2-phenyl-1-(methoxycarbonyl)eth-1-yl,
- 1-(S)-2-phenyl-1-(methoxycarbonyl)eth-1-yl,
- 2-(phenyl)-1-(S)-(pyrrolidin-N-ylcarbonyl)eth-1-yl,
- (piperidin-1-yl)carbonylmethyl,
- 1-(R)-(pyrrolidin-N-ylcarbonyl)-2-(4-amidino)phenyl-eth-1-yl,
- 1-(S)-(pyrrolidin-N-ylcarbonyl)-2-(4-amidino)phenyl-eth-1-yl,
- 1-(R)-(pyrrolidin-N-ylcarbonyl)-5-amino-n-pent-1-yl,
- 1-(S)-(pyrrolidin-N-ylcarbonyl)-5-amino-n-pent-1-yl,
- 1-(R)-(pyrrolidin-N-ylcarbonyl)-2-(4-biphenyl)eth-1-yl,
- 1-(S)-(pyrrolidin-N-ylcarbonyl)-2-(4-biphenyl)eth-1-yl,
- 1-(R)-(pyrrolidin-N-ylcarbonyl-2-(4-iodophenyl)eth-1-yl,
- 1-(S)-(pyrrolidin-N-ylcarbonyl-2-(4-iodophenyl)eth-1-yl,
- 1-(R)-(pyrrolidin-N-carbonyl)-4-(t-butoxycarbonylamino)-n-but-1-yl,
- 1-(S)-(pyrrolidin-N-carbonyl)-4-(t-butoxycarbonylamino)-n-but-1-yl,
- 1-(S)-(pyrrolidin-N-ylcarbonyl)-2-[4-(2-imidazolin-2-yl)phenyl]eth-1-yl,
- 2-(R)-(pyrrolidin-N-ylcarbonyl-3-phenylprop-2-yl,
- 1-(R)-(pyrrolidin-N-ylcarbonyl)-2-[4-(N-methylpiperidin-2-yl)eth-1-yl,
- 1-(S)-(pyrrolidin-N-ylcarbonyl)-2-[4-(N-methylpiperidin-2-yl)phenyl)]eth-1-yl,
- 1-(R)-(pyrrolidin-N-ylcarbonyl)-2-[N-methyl-1,2,5,6-tetrahydropyridin-4-yl)-phen-4-yl)]eth-1-yl,
- 1-(S)-(pyrrolidin-N-ylcarbonyl)-2-[N-methyl-1,2,5,6-tetrahydropyridin-4-yl)-phen-4-yl)]eth-1-yl,
- 1-(R)-(pyrrolidin-N-ylcarbonyl)-2-[4-(piperidin-2-yl)cyclohexyl)]eth-1-yl,
- 1-(S)-(pyrrolidin-N-ylcarbonyl)-2-[4-(piperidin-2-yl)cyclohexyl)]eth-1-yl,
- 1-(R)-(pyrrolidin-N-ylcarbonyl)-2-[N-(phenyl)-piperidin-4-yl)]eth-1-yl,
- 1-(S)-(pyrrolidin-N-ylcarbonyl)-2-[N-(phenyl)-piperidin-4-yl)]eth-1-yl,
- 1-(R)-(pyrrolidin-N-ylcarbonyl)-2-[N-(pyridin-4-yl)-piperidin-4-yl)]eth-1-yl,
- 1-(S)-(pyrrolidin-N-ylcarbonyl)-2-[N-(pyridin-4-yl)-piperidin-4-yl)]eth-1-yl, 1-(R)-(pyrrolidin-N-ylcarbonyl)-2-[4-(pyridin-4-yl)phenyl)]eth-1-yl,
1-(S)-(pyrrolidin-N-ylcarbonyl)-2-[4-(pyridin-4-yl)phenyl)]eth-1-yl,
1-(R)-(pyrrolidin-N-ylcarbonyl)-2-[4-(pyrid-2-yl)phenyl]eth-1-yl,
1-(S)-(pyrrolidin-N-ylcarbonyl)-2-[4-(pyrid-2-yl)phenyl]eth-1-yl,
1-(R)-(pyrrolidin-N-ylcarbonyl)-2-[4-(pyrimidin-2-yl)phenyl]eth-1-yl,
1-(S)-(pyrrolidin-N-ylcarbonyl)-2-[4-(pyrimidin-2-yl)phenyl]eth-1-yl,
1-(R)-(pyrrolidin-N-ylcarbonyl)-2-[4-(N-t-butoxycarbonylpyrrol-2-yl)phenyl]eth-1-yl,
1-(S)-(pyrrolidin-N-ylcarbonyl)-2-[4-(N-t-butoxycarbonylpyrrol-2-yl)phenyl]eth-1-yl,
1-(S)-(t-butoxycarbonyl)-2-(4-hydroxyphenyl)eth-1-yl,
3-t-butoxycarbonyl-1-methoxycarbonylprop-1-yl,
1-(S)-(t-butoxycarbonyl)-3-methylprop-1-yl,
1-(R)-(t-butoxycarbonyl)-3-methylprop-1-yl,
1-(R)-(t-butoxycarbonyl)-2-(phenyl)eth-1-yl,
1-(R)-1-pyrrolidin-N-ylcarbonyl-2-phenyleth-1-yl,
2-phenyl-1-(R)-carboxy-eth-1-yl,
2-[N-(α,α dimethylglycine)piperidin-4-yl]eth-1-yl,
2-{4-(ethylamino-amidino)phenyl]eth-1-yl,
1-(R)-(pyrrolidin-N-ylcarbonyl)-3-(guanadino)but-1-yl,
1-(R)-(pyrrolidin-N-ylcarbonyl)-4-(N'-t-butoxycarbonyl)-guanadino-n-but-1-yl,
1-(R)-(pyrrolidin-N-ylcarbonyl)-5-(N'-t-butoxycarbonylamino)-n-pent-5-yl,
1-(R)-(pyrrolidin-N-ylcarbonyl)-4-amino-n-butyl,
1-(R)-(pyrrolidin-N-ylcarbonyl)-4-guanadino-but-4-yl,
1-(R)-(pyrrolidin-N-ylcarbonyl)-2-[4-(N-methyl-1,2,3,6-tetrahydropyridin-6-yl)phenyl)]eth-1-yl,
1-(R)-(pyrrolidin-N-ylcarbonyl)-2-[4-(N-t-butoxycarbonylpyrrol-2-yl)phenyl]eth-1-yl,
4-N-[(N',N'-dimethylaminocarbonyl)amino-phen-4-yl]eth-1-yl,
2-[N-(N'-morpholino-carbonyl)piperidin-4-yl]eth-1-yl,
2-{N-[(2-(thiophen-2-yl)methylenecarbonyl]-piperidin-4-yl}eth-1-yl,
2-[N-(3,5-dimethyloxazol-4-ylcarbonyl)piperidin-4-yl]eth-1-yl,
2-[N-(furan-2-ylcarbonyl)-piperidin-4-yl]eth-1-yl,
2-[N-(oxazol-5-yl-carbonyl)piperidin-4-yl]eth-1-yl,
2-[N-(5-methylpyrazol-3-ylcarbonyl)piperidin-4-yl]eth-1-yl,
2-[N-(1-methyl-3-t-butylpyrazol-5-ylcarbonyl)piperidin-4-yl]eth-1-yl,
2-[N-(4-methylthiadiazol-5-ylcarbonyl)piperidin-4-yl]eth-1-yl,
2-[N-(chloromethylene-carbonyl)piperidin-4-yl]eth-1-yl,
2-[N-(benzylcarbonyl)-piperidin-4-yl]eth-1-yl,
2-[N-(2-phenylethenyl-carbonyl)piperidin-4-yl]eth-1-yl,
2-[N-(methoxymethylene-carbonyl)piperidin-4-yl]eth-1-yl,
2-[N-(pyrazin-2-ylcarbonyl)piperidin-4-yl]eth-1-yl,
2-[N-(isoquinolin-3-ylcarbonyl)piperidin-4-yl]eth-1-yl,
2-[N-(pyrrolidin-5-one-2-ylcarbonyl)piperidin-4-yl]eth-1-yl,
2-[N-(N'-acetylpyrrolidin-2-ylcarbonyl)piperidin-4-yl]eth-1-yl,
2-[N-(dichloromethylenecarbonyl)piperidin-4-yl]eth-1-yl,
4-[N-(pyrazin-2-ylcarbonyl)amino]pheneth-1-yl,
4-[N-(isoquinolin-2-ylcarbonyl)amino]pheneth-1-yl,
4-[N-(N'-acetylpyrrolidin-2-ylcarbonyl)amino]-pheneth-1-yl,
4-[N-(1,2-benzothiadiazol-5-ylcarbonyl)amino]-pheneth-1-yl,
4-[N-(benzofuran-5-ylcarbonyl)amino]pheneth-1-yl,
4-[N-(3-methylisoxazol-5-ylcarbonyl)amino]-pheneth-1-yl,
4-[N-(methoxyphen-3-ylcarbonyl)amino]pheneth-1-yl,
4-[N-(thiophen-2-ylmethylenecarbonyl)amino]pheneth-1-yl,
4-[N-(3,5-dimethyl-isoxazol-4-ylcarbonyl)-amino]pheneth-1-yl,
4-[N-(2-(pyrid-3-yl)ethylcarbonyl)amino]pheneth-1-yl,
4-[N-(furan-2-ylcarbon-yl)amino]pheneth-1-yl,
4-[N-(isoxazol-5-ylcar-bonyl)amino]pheneth-1-yl,
4-[N-(3-methylpyrazol-5-yl-5-ylcarbonyl)amino]-pheneth-1-yl,
4-[N-(1-methyl-3-t-butyl-pyrazol-5-ylcarbonyl)-amino]pheneth-1-yl,
4-[N-(4-methyl-1,2,3-thiadiazol-5-ylcarbonyl)-amino]-pheneth-1-yl,
4-[N-(chloromethylene-carbonyl)amino]pheneth-1-yl,
4-[N-(chlorophen-2-ylcarbonyl)amino]pheneth-1-yl,
4-[N-(phenylcarbonyl)amino]pheneth-1-yl,
4-[N-(pyrid-2-ylcarbonyl)-aminopheneth-1-yl,
4-[N-(2-phenylethenyl-carbonyl)amino]pheneth-1-yl,
4-[N-(2-phenylethenyl-carbonyl)amino]pheneth-1-yl,
4-[N-(fluorophen-2-ylcarbonyl)amino]pheneth-1-yl,
4-[N-(methoxymethylenecarbonyl)amino]pheneth-1-yl,
4-[N-(dichloromethylene-carbonyl)amino]pheneth-1-yl,
4-[N-(methylenedioxy-phen-4-ylcarbonyl)amino]-pheneth-1-yl,
1-[(R)-(pyrrolidin-N-ylcarbonyl)]-2-[N-methylpyrid-2-yl)phen-4-yl]eth-1-yl,
1-[(R)-(pyrrolidin-N-ylcarbonyl)]-2-[(N-methylpyrid-4-yl)phen-4-yl]eth-1-yl,
1-[(R)-(pyrrolidin-N-ylcarbonyl)]-2-[(N-methylpyrid-4-yl)phen-4-yl]eth-1-yl,
1-[(R)-(pyrrolidin-N-ylcarbonyl)]-2-[1-(piperidin-2-yl)phen-4-yl]eth-1-yl,
1-(R)-(pyrrolidin-N-ylcarbonyl)-2-[4-(N-methylpyrid-4-yl)phen-1-yl]eth-1-yl,
4-(pyridin-2-yl)but-3-yn-1-yl and
(benzoimidazol-2-ylamino)eth-1-yl.

5. A compound selected from the group consisting of:
2-[2-(R,S)-1-(4-chloro-2,5-dimethylbenzenesulfonyl)-3-oxo-1,2,3,4-tetrahydroquinoxalin-2-yl]-N-[1-(R)-1-pyrrolidin-N-ylcarbonyl-2-phenyleth-1-yl]acetamide
2-[2-(R,S)-1-(4-chloro-2,5-dimethylbenzenesulfonyl)-3-oxo-1,2,3,4-tetrahydroquinoxalin-2-yl]-N-[(piperidin-1-yl)carbonylmethyl]acetamide
2-[2-(R,S)-1-(4-chloro-2,5-dimethylbenzenesulfonyl)-3-oxo-1,2,3,4-tetrahydroquinoxalin-2-yl]-N-(2-hydroxyeth-1-yl)acetamide
2-[2-(R or S)-1-(4-chloro-2,5-dimethylbenzenesulfonyl)-3-oxo-1,2,3,4-tetrahydroquinoxalin-2-yl]-N-[1-(R)-2-phenyl-1-(methoxycarbonyl)eth-1-yl]acetamide
2-[2-(S or R)-1-(4-chloro-2,5-dimethylbenzenesulfonyl)-3-oxo-1,2,3,4-tetrahydroquinoxalin-2-yl]-N-[1-(R)-2-phenyl-1-(methoxycarbonyl)eth-1-yl]acetamide
2-[2-(R,S)-1-(4-chloro-2,5-dimethylbenzenesulfonyl)-3-oxo-1,2,3,4-tetrahydroquinoxalin-2-yl]-N-[(2-dimethylamino)eth-1-yl]acetamide
2-[2-(R,S)-1-(4-chloro-2,5-dimethylbenzenesulfonyl)-3-oxo-1,2,3,4-tetrahydroquinoxalin-2-yl]-N-[1-(R)-(methoxycarbonyl)-2-(N-methylpiperidin-4-yl)eth-1-yl]acetamide 2-[2-(R,S)-1-(4-chloro-2,5-dimethylbenzenesulfonyl)-3-oxo-1,2,3,4-tetrahydroquinoxalin-2-yl]-N-[1-(R)-1,3-di(benzyloxycarbonyl)prop-1-yl]acetamide
2-[2-(R,S)-1-(4-chloro-2,5-dimethylbenzenesulfonyl)-3-oxo-1,2,3,4-tetrahydroquinoxalin-2-yl]-N-[1-(R)-(iso-propoxycarbonyl)-2-(phenyl)eth-1-yl]acetamide
2-[2-(R,S)-1-(4-chloro-2,5-dimethylbenzenesulfonyl)-3-oxo-1,2,3,4-tetrahydroquinoxalin-2-yl]-N-[1-(R)-(methoxycarbonyl)eth-1-yl]acetamide
2-[2-(R,S)-1-(4-chloro-2,5-dimethylbenzenesulfonyl)-3-oxo-1,2,3,4-tetrahydroquinoxalin-2-yl]-N-[1-(R)-methoxycarbonyl-2-pyrid-4-yl)eth-1-yl]acetamide
2-[2-(R,S)-1-(4-chloro-2,5-dimethylbenzenesulfonyl)-3-oxo-1,2,3,4-tetrahydroquinoxalin-2-yl]-N-[1-(R)-(methoxycarbonyl)-2-(N-methyl-1,2,3,6-tetrahydropyrid-4-yl)eth-1-yl]acetamide
2-[2-(R or S)-1-(4-chloro-2,5-dimethylbenzenesulfonyl)-3-oxo-1,2,3,4-tetrahydroquinoxalin-2-yl]-N-[1-(R)-(methoxycarbonyl)-2-(N-methylpiperidin-4-yl)eth-1-yl]acetamide
2-[2-(S or R)-1-(4-chloro-2,5-dimethylbenzenesulfonyl)-3-oxo-1,2,3,4-tetrahydroquinoxalin-2-yl]-N-[1-(R)-(methoxycarbonyl)-2-(N-methylpiperidin-4-yl)eth-1-yl]acetamide
2-[2-(R,S)-1-(4-chloro-2,5-dimethylbenzenesulfonyl)-3-oxo-1,2,3,4-tetrahydroquinoxalin-2-yl]-N-{1-(S)-[pyrrolidin-N-ylcarbonyl]-2-[4-(2-imidazolin-2-yl)phenyl]eth-1-yl}acetamide
2-[2-(R,S)-1-(4-chloro-2,5-dimethylbenzenesulfonyl)-3-oxo-1,2,3,4-tetrahydroquinoxalin-2-yl]-N-[1-(S)-(t-butoxycarbonyl)-3-methylbut-1-yl]acetamide
2-[2-(R,S)-1-(4-chloro-2,5-dimethylbenzenesulfonyl)-3-oxo-1,2,3,4-tetrahydroquinoxalin-2-yl]-N-[1-(R)-(t-butoxycarbonyl)-3-methylprop-1-yl]acetamide
2-[2-(R,S)-1-(4-chloro-2,5-dimethylbenzenesulfonyl)-3-oxo-1,2,3,4-tetrahydroquinoxalin-2-yl]-N-[1-(S)-(t-butoxycarbonyl)-2-(4-hydroxyphenyl)eth-1-yl]acetamide
2-[2-(R,S)-1-(4-chloro-2,5-dimethylbenzenesulfonyl)-3-oxo-1,2,3,4-tetrahydroquinoxalin-2-yl]-N-[1-(R)-(t-butoxycarbonyl)-2-(phenyl)eth-1-yl]acetamide
2-[2-(R,S)-1-(4-chloro-2,5-dimethylbenzenesulfonyl)-3-oxo-1,2,3,4-tetrahydroquinoxalin-2-yl]-N-[1-(S)-carboxamide-2-(indol-3-yl)eth-1-yl]acetamide
2-[2-(R,S)-1-(4-chloro-2,5-dimethylbenzenesulfonyl)-3-oxo-1,2,3,4-tetrahydroquinoxalin-2-yl]-N-[1-(R)-carboxamide-2-(phenyl)eth-1-yl]acetamide
2-[2-(R,S)-1-(4-chloro-2,5-dimethylbenzenesulfonyl)-3-oxo-1,2,3,4-tetrahydroquinoxalin-2-yl]-N-[1-(S)-carboxamide-2-(S)-methylbut-1-yl]acetamide
2-[2-(R,S)-1-(4-chloro-2,5-dimethylbenzenesulfonyl)-3-oxo-1,2,3,4-tetrahydroquinoxalin-2-yl]-N-[1-(S)-carboxamide-2-(phenyl)eth-1-yl]acetamide
2-[2-(R,S)-1-(4-chloro-2,5-dimethylbenzenesulfonyl)-3-oxo-1,2,3,4-tetrahydroquinoxalin-2-yl]-N-[1-(S)-ethoxycarbonyleth-1-yl]acetamide
2-[2-(R,S)-1-(4-chloro-2,5-dimethylbenzenesulfonyl)-3-oxo-1,2,3,4-tetrahydroquinoxalin-2-yl]-N-[1-(S)-1,3-dicarboxamideprop-1-yl]acetamide
2-[2-(R,S)-1-(4-chloro-2,5-dimethylbenzenesulfonyl)-3-oxo-1,2,3,4-tetrahydroquinoxalin-2-yl]-N-[2-(N-cyclopropylpiperidin-4-yl)-1-(R)-(pyrrolidin-N-ylcarbonyl)eth-1-yl]acetamide
2-[2-(R,S)-1-(4-chloro-2,5-dimethylbenzenesulfonyl)-3-oxo-1,2,3,4-tetrahydroquinoxalin-2-yl]-N-[2-(N-methyl-1,2,5,6-tetrahydropyrid-4-yl)-1-(R)-(pyrrolidin-N-ylcarbonyl)eth-1-yl]acetamide
2-[2-(R,S)-1-(4-chloro-2,5-dimethylbenzenesulfonyl)-3-oxo-1,2,3,4-tetrahydroquinoxalin-2-yl]-N-[2-(N-methylpiperidin-4-yl)-1-(R)-(pyrrolidin-N-ylcarbonyl)eth-1-yl]acetamide
2-[2-(R,S)-1-(4-chloro-2,5-dimethylbenzenesulfonyl)-3-oxo-1,2,3,4-tetrahydroquinoxalin-2-yl]-N-[2-(4-cyanophenyl)-1-(R)-(pyrrolidin-N-ylcarbonyl)eth-1-yl]acetamide
2-[2-(R,S)-1-(4-chloro-2,5-dimethylbenzenesulfonyl)-3-oxo-1,2,3,4-tetrahydroquinoxalin-2-yl]-N-[2-(4-cyanophenyl)-1-(S)-(pyrrolidin-N-ylcarbonyl)eth-1-yl]acetamide
2-[2-(R,S)-1-(4-chloro-2,5-dimethylbenzenesulfonyl)-3-oxo-1,2,3,4-tetrahydroquinoxalin-2-yl]-N-[2-(4-hydroxyphenyl)-1-(S)-(methoxycarbonyl)eth-1-yl]acetamide
2-[2-(R,S)-1-(4-chloro-2,5-dimethylbenzenesulfonyl)-3-oxo-1,2,3,4-tetrahydroquinoxalin-2-yl]-N-[2-(4-hydroxyphenyl)-1-(S)-(t-butoxycarbonyl)eth-1-yl]acetamide
2-[2-(R,S)-1-(4-chloro-2,5-dimethylbenzenesulfonyl)-3-oxo-1,2,3,4-tetrahydroquinoxalin-2-yl]-N-[2-(4-hydroxyphenyl)-1-(R)-(methoxycarbonyl)eth-1-yl]acetamide
2-[2-(R,S)-1-(4-chloro-2,5-dimethylbenzenesulfonyl)-3-oxo-1,2,3,4-tetrahydroquinoxalin-2-yl]-N-[2-(indol-3-yl)-1-(S)-(methoxycarbonyl)eth-1-yl]acetamide
2-[2-(R,S)-1-(4-chloro-2,5-dimethylbenzenesulfonyl)-3-oxo-1,2,3,4-tetrahydroquinoxalin-2-yl]-N-[2-(indol-3-yl)-1-(R)-(methoxycarbonyl)eth-1-yl]acetamide
2-[2-(R,S)-1-(4-chloro-2,5-dimethylbenzenesulfonyl)-3-oxo-1,2,3,4-tetrahydroquinoxalin-2-yl]-N-[2-(phenyl)-1-(S)-(pyrrolidin-N-ylcarbonyl)eth-1-yl]-N-methylacetamide
2-[2-(R,S)-1-(4-chloro-2,5-dimethylbenzenesulfonyl)-3-oxo-1,2,3,4-tetrahydroquinoxalin-2-yl]-N-[2-(pyrid-4-yl)-1-(R)-(pyrrolidin-N-ylcarbonyl)eth-1-yl]acetamide
2-[2-(R,S)-1-(4-chloro-2,5-dimethylbenzenesulfonyl)-3-oxo-1,2,3,4-tetrahydroquinoxalin-2-yl]-N-[2-phenyl-1-(S)-(methoxycarbonyl)eth-1-yl]acetamide
2-[2-(R,S)-1-(4-chloro-2,5-dimethylbenzenesulfonyl)-3-oxo-1,2,3,4-tetrahydroquinoxalin-2-yl]-N-(2-phenyl-1-(R)-carboxy-eth-1-yl)acetamide
2-[2-(R,S)-1-(4-chloro-2,5-dimethylbenzenesulfonyl)-3-oxo-1,2,3,4-tetrahydroquinoxalin-2-yl]-N-{2-[N-(α,α-dimethylglycine)piperidin-4-yl]eth-1-yl}acetamide
2-[2-(R,S)-1-(4-chloro-2,5-dimethylbenzenesulfonyl)-3-oxo-1,2,3,4-tetrahydroquinoxalin-2-yl]-N-{2-[N-(α-aminoacetyl)piperidin-4-yl]eth-1-yl}acetamide
2-[2-(R or S)-1-(4-chloro-2,5-dimethylbenzenesulfonyl)-3-oxo-1,2,3,4-tetrahydroquinoxalin-2-yl]-N-{2-[4-(imidazolin-2-yl)phenyl]-1-(R)-(pyrrolidin-1-ylcarbonyl)eth-1-yl}acetamide
2-[2-(S or R)-1-(4-chloro-2,5-dimethylbenzenesulfonyl)-3-oxo-1,2,3,4-tetrahydroquinoxalin-2-yl]-N-{2-[4-(imidazolin-2-yl)phenyl]-1-(R)-(pyrrolidin-1-ylcarbonyl)eth-1-yl}acetamide
2-[2-(R,S)-1-(4-chloro-2,5-dimethylbenzenesulfonyl)-3-oxo-1,2,3,4-tetrahydroquinoxalin-2-yl]-N-[3-(dimethylamino)prop-1-yl]acetamide
2-[2-(R,S)-1-(4-chloro-2,5-dimethylbenzenesulfonyl)-3-oxo-1,2,3,4-tetrahydroquinoxalin-2-yl]-N-(3-t-butoxycarbonyl-1-methoxycarbonylprop-1-yl)acetamide
2-[2-(R,S)-1-(4-chloro-2,5-dimethylbenzenesulfonyl)-3-oxo-1,2,3,4-tetrahydroquinoxalin-2-yl]-N-{2-[4-ethylaminoamidino)phenyl]eth-1-yl}acetamide 2-[2-(R,S)-1-(4-chloro-2,5-dimethylbenzenesulfonyl)-3-oxo-1,2,3,4-tetrahydroquinoxalin-2-yl]-N-methylcarboxamideacetamide 2-[2-(R,S)-1-(4-chloro-2,5-dimethylbenzenesulfonyl)-3-oxo-1,2,3,4-tetrahydroquinoxalin-2-yl]-N-cyanomethylacetamide 2-[2-(R or S)-1-(4-chloro-2,5-dimethylbenzenesulfonyl)-3-oxo-1,2,3,4-tetrahydroquinoxalin-2-yl]-N-{2-[(4-imidazolin-2-yl)phenyl]-1-(R)-(pyrrolidin-N-ylcarbonyl)eth-1-yl}acetamide 2-[2-(S or R)-1-(4-chloro-2,5-dimethylbenzenesulfonyl)-3-oxo-1,2,3,4-tetrahydroquinoxalin-2-yl]-N-{2-[(4-imidazolin-2-yl)phenyl]-1-(R)-(pyrrolidin-N-ylcarbonyl)eth-1-yl}acetamide 2-[2-(R,S)-1-(4-chloro-2,5-dimethylbenzenesulfonyl)-3-oxo-1,2,3,4-tetrahydroquinoxalin-2-yl]-N-[1-(S)-methoxy]-N-methylacetamide 2-[2-(R,S)-1-(4-chloro-2,5-dimethylbenzenesulfonyl)-3-oxo-1,2,3,4-tetrahydroquinoxalin-2-yl]-N-[1-(R)-methoxycarbonylphenylmethyl)]acetamide 2-[2-(R,S)-1-(4-chloro-2,5-dimethylbenzenesulfonyl)-3-oxo-1,2,3,4-tetrahydroquinoxalin-2-yl]-N-methoxycarbonylmethylacetamide 2-[2-(R or S)-1-(4-chloro-2,5-dimethylbenzenesulfonyl)-3-oxo-1,2,3,4-tetrahydroquinoxalin-2-yl]-N-{2-[(4-amidinophenyl]-1-(R)-(pyrrolidin-N-ylcarbonyl)eth-1-yl}acetamide 2-[2-(S or R)-1-(4-chloro-2,5-dimethylbenzenesulfonyl)-3-oxo-1,2,3,4-tetrahydroquinoxalin-2-yl]-N-{2-[(4-amidinophenyl]-1-(R)-(pyrrolidin-N-ylcarbonyl)eth-1-yl}acetamide 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-3-(guanadino)but-1-yl]acetamide 2-[2-(S or R)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-3-(guanadino)but-1-yl]acetamide 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-5-amino-n-pent-1-yl]acetamide 2-[2-(S or R)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-5-amino-n-pent-1-yl]acetamide 2-[2-(R,S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-4-(N'-t-butoxy-carbonyl)-guanadino-n-but-1-yl]acetamide 2-[2-(R or S)-1-(4-chloro-2,5-dimethylbenzenesulfonyl)-3-oxo-1,2,3,4-tetrahydroquinoxalin-2-yl]-N-[1-(R)-pyrrolidin-N-ylcarbonyl-5-(N'-t-butoxy-carbonylamino)-n-pent-5-yl]acetamide 2-[2-(S or R)-1-(4-chloro-2,5-dimethylbenzenesulfonyl)-3-oxo-1,2,3,4-tetrahydroquinoxalin-2-yl]-N-[1-(R)-pyrrolidin-N-ylcarbonyl-5-(N'-t-butoxy-carbonylamino)-n-pent-5-yl]acetamide 2-[2-(S or R)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-4-amino-n-butyl]acetamide 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-4-(N'-t-butoxy-carbonylamino)-n-but-1-yl]acetamide 2-[2-(S or R)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-4-(N'-t-butoxy-carbonylamino)-n-but-1-yl]acetamide 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-2-(4-amidino)phenyleth-1-yl]acetamide 2-[2-(S or R)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-2-(4-amidino)phenyleth-1-yl]acetamide 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-4-guanidino-but-1-yl]acetamide 2-[2-(S or R)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-4-guanidino-but-1-yl]acetamide 2-[2-(S,R)-1-(4-chloro-2,5-dimethylbenzenesulfonyl)-3-oxo-1,2,3,4-tetrahydroquinoxalin-2-yl]-methylenecarbonyl-[4-(2-aminoethyl)]piperidin-1-yl]acetamide 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-2-(4-iodophenyl)eth-1-yl]acetamide 2-[2-(R,S)-1-(4-chloro-2,5-dimethylbenzenesulfonyl)-3-oxo-1,2,3,4-tetrahydroquinoxalin-2-yl]-methylenecarbonyl-{[4-(2-(N-t-butoxycarbonyl-amino)ethyl)piperidin-1-yl]}acetamide 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-4-amino-n-butyl]acetamide 2-[2-(S or R)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-4-amino-n-butyl]acetamide 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-5-(t-butoxy-carbonylamino)-pent-5-yl]acetamide 2-[2-(S or R)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-5-(t-butoxy-carbonylamino)-pent-5-yl]acetamide 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-5-amino-n-pent-1-yl]acetamide 2-[2-(S or R)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-5-amino-n-pent-1-yl]acetamide 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-4-(t-butoxy-carbonylamino)-n-but-1-yl]acetamide 2-[2-(S or R)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-4-(t-butoxy-carbonylamino)-n-but-1-yl]acetamide 2-[2-(R or S)-1-(4-chloro-2,5-dimethylbenzenesulfonyl)-3-oxo-1,2,3,4-tetrahydroquinoxalin-2-yl]-N-[1-(R)-(pyrrolidin-N-ylcarbonyl)-2-(4-iodophenyl)-eth-1-yl]acetamide 2-[2-(S or R)-1-(4-chloro-2,5-dimethylbenzenesulfonyl)-
3-oxo-1,2,3,4-tetrahydroquinoxalin-2-yl]-N-[1-(R)-
(pyrrolidin-N-ylcarbonyl)-2-(4-iodophenyl)-eth-1-yl]
acetamide
2-[2-(R or S)-1-(4-chloro-2,5-dimethylbenzenesulfonyl)-
3-oxo-1,2,3,4-tetrahydroquinoxalin-2-yl]-N-{1-(R)-
[pyrrolidin-N-ylcarbonyl]-2-[4-(pyrid-2-yl)phenyl]eth-
1-yl}acetamide
2-[2-(S or R)-1-(4-chloro-2,5-dimethylbenzenesulfonyl)-
3-oxo-1,2,3,4-tetrahydroquinoxalin-2-yl]-N-{1-(R)-
[pyrrolidin-N-ylcarbonyl]-2-[4-(pyrid-2-yl)phenyl]eth-
1-yl}acetamide
2-[2-(R or S)-1-(4-chloro-2,5-dimethylbenzenesulfonyl)-
3-oxo-1,2,3,4-tetrahydroquinoxalin-2-yl]-N-{1-(R)-
[pyrrolidin-N-ylcarbonyl]-2-[4-(pyrid-2-yl)phenyl]eth-
1-yl}acetamide
2-[2-(S or R)-1-(4-chloro-2,5-dimethylbenzenesulfonyl)-
3-oxo-1,2,3,4-tetrahydroquinoxalin-2-yl]-N-{1-(R)-
[pyrrolidin-N-ylcarbonyl]-2-[4-(pyrid-2-yl)phenyl]eth-
1-yl}acetamide
2-[2-(R or S)-1-(4-chloro-2,5-dimethylbenzenesulfonyl)-
3-oxo-1,2,3,4-tetrahydroquinoxalin-2-yl]-N-{1-(R)-
(pyrrolidin-N-ylcarbonyl)-2-[4-(pyrimidin-2-yl)phe-
nyl]eth-1-yl}acetamide
2-[2-(S or R)-1-(4-chloro-2,5-dimethylbenzenesulfonyl)-
3-oxo-1,2,3,4-tetrahydroquinoxalin-2-yl]-N-{1-(R)-
(pyrrolidin-N-ylcarbonyl)-2-[4-(pyrimidin-2-yl)phe-
nyl]eth-1-yl}acetamide
2-[2-(R or S)-1-(4-chloro-2,5-dimethylbenzenesulfonyl)-
3-oxo-1,2,3,4-tetrahydroquinoxalin-2-yl]-N-{1-(R)-
[pyrrolidin-N-ylcarbonyl]-2-[4-(piperidin-2-yl)cyclo-
hexyl]eth-1-yl}acetamide
2-[2-(S or R)-1-(4-chloro-2,5-dimethylbenzenesulfonyl)-
3-oxo-1,2,3,4-tetrahydroquinoxalin-2-yl]-N-{1-(R)-
[pyrrolidin-N-ylcarbonyl]-2-[4-(piperidin-2-yl)cyclo-
hexyl]eth-1-yl}acetamide
2-[2-(R or S)-1-(4-chloro-2,5-dimethylbenzenesulfonyl)-
3-oxo-1,2,3,4-tetrahydroquinoxalin-2-yl]-N-{1-(R)-
[pyrrolidin-N-ylcarbonyl]-2-[4-(N-methyl-1,2,3,6-tet-
rahydropyridin-6-yl)phenyl]eth-1-yl}acetamide
2-[2-(S or R)-1-(4-chloro-2,5-dimethylbenzenesulfonyl)-
3-oxo-1,2,3,4-tetrahydroquinoxalin-2-yl]-N-{1-(R)-
[pyrrolidin-N-ylcarbonyl]-2-[4-(N-methyl-1,2,3,6-tet-
rahydropyridin-6-yl)phenyl]eth-1-yl}acetamide
2-[2-(R or S)-1-(4-chloro-2,5-dimethylbenzenesulfonyl)-
3-oxo-1,2,3,4-tetrahydroquinoxalin-2-yl]-N-{1-(R)-
[pyrrolidin-N-ylcarbonyl]-2-[4-(pyridin-4-yl)phenyl]
eth-1-yl}acetamide
2-[2-(S or R)-1-(4-chloro-2,5-dimethylbenzenesulfonyl)-
3-oxo-1,2,3,4-tetrahydroquinoxalin-2-yl]-N-{1-(R)-
[pyrrolidin-N-ylcarbonyl]-2-[4-(pyridin-4-yl)phenyl]
eth-1-yl}acetamide
2-[2-(R or S)-1-(4-chloro-2,5-dimethylbenzenesulfonyl)-
3-oxo-1,2,3,4-tetrahydroquinoxalin-2-yl]-N-{1-(R)-
[pyrrolidin-N-ylcarbonyl]-2-[N-(phenyl)-piperidin-4-
yl)]eth-1-yl}acetamide
2-[2-(S or R)-1-(4-chloro-2,5-dimethylbenzenesulfonyl)-
3-oxo-1,2,3,4-tetrahydroquinoxalin-2-yl]-N-{1-(R)-
[pyrrolidin-N-ylcarbonyl]-2-[N-(phenyl)-piperidin-4-
yl)]eth-1-yl}acetamide
2-[2-(R or S)-1-(4-chloro-2,5-dimethylbenzenesulfonyl)-
3-oxo-1,2,3,4-tetrahydroquinoxalin-2-yl]-N-{1-(R)-
[pyrrolidin-N-ylcarbonyl]-2-[N-(pyridin-4-yl)-piperi-
din-4-yl]eth-1-yl}acetamide
2-[2-(S or R)-1-(4-chloro-2,5-dimethylbenzenesulfonyl)-
3-oxo-1,2,3,4-tetrahydroquinoxalin-2-yl]-N-{1-(R)-
[pyrrolidin-N-ylcarbonyl]-2-[N-(pyridin-4-yl)-piperi-
din-4-yl]eth-1-yl}acetamide
2-[2-(R or S)-1-(4-chloro-2,5-dimethylbenzenesulfonyl)-
3-oxo-1,2,3,4-tetrahydroquinoxalin-2-yl]-N-{1-(R)-
[pyrrolidin-N-ylcarbonyl]-2-[(N-methyl-1,2,5,6-tet-
rahydropyridin-4-yl)-phen-4-yl]eth-1-yl}acetamide
2-[2-(S or R)-1-(4-chloro-2,5-dimethylbenzenesulfonyl)-
3-oxo-1,2,3,4-tetrahydroquinoxalin-2-yl]-N-{1-(R)-
[pyrrolidin-N-ylcarbonyl]-2-[(N-methyl-1,2,5,6-tet-
rahydropyridin-4-yl)-phen-4-yl]eth-1-yl}acetamide
2-[2-(R or S)-1-(4-chloro-2,5-dimethylbenzenesulfonyl)-
3-oxo-1,2,3,4-tetrahydroquinoxalin-2-yl]-N-[1-(R)-
(pyrrolidin-N-ylcarbonyl)-2-(4-biphenyl)ethy-1-yl]ac-
etamide
2-[2-(S or R)-1-(4-chloro-2,5-dimethylbenzenesulfonyl)-
3-oxo-1,2,3,4-tetrahydroquinoxalin-2-yl]-N-[1-(R)-
(pyrrolidin-N-ylcarbonyl)-2-(4-biphenyl)eth-1-yl]ac-
etamide
2-[2-(S or R)-1-(4-chloro-2,5-dimethylbenzenesulfonyl)-
3-oxo-1,2,3,4-tetrahydroquinoxalin-2-yl]-N-{1-(R)-
[pyrrolidin-N-ylcarbonyl]-2-[4-(N-t-butoxycarbon-
ylpyrrol-2-yl)phenyl]eth-1-yl}acetamide
2-[2-(R or S)-1-(4-chloro-2,5-dimethylbenzenesulfonyl)-
3-oxo-1,2,3,4-tetrahydroquinoxalin-2-yl]-N-{1-(R)-
[pyrrolidin-N-ylcarbonyl]-2-[4-(N-t-butoxycarbon-
ylpyrrol-2-yl)phenyl]eth-1-yl}acetamide
2-[2-(R,S)-1-(4-chloro-2,5-dimethylbenzenesulfonyl)-3-
oxo-1,2,3,4-tetrahydroquinoxalin-2-yl]-N-{2-[N-(N',
N'-dimethylaminocarbonyl)aminophen-1-yl]eth-1-
yl}acetamide
2-[2-(R,S)-1-(4-chloro-2,5-dimethylbenzenesulfonyl)-3-
oxo-1,2,3,4-tetrahydroquinoxalin-2-yl]-N-{2-[N-(me-
thylcarbonylmethylene)piperidin-4-yl]eth-1-
yl}acetamide
2-[2-(R,S)-1-(2,3-dichlorobenzenesulfonyl)-3-oxo-1,2,3,
4-tetrahydroquinoxalin-2-yl]-N-[2-(N', N'-dimethy-
lamino)eth-1-yl]acetamide
2-[2-(R,S)-1-(4-chloro-2,5-dimethylbenzenesulfonyl)-3-
oxo-1,2,3,4-tetrahydroquinoxalin-2-yl]-N-{2-[N-(N'-
morpholinocarbonyl)piperidin-4-yl]eth-1-
yl}acetamide
2-[2-(R,S)-1-(4-chloro-2,5-dimethylbenzenesulfonyl)-3-
oxo-1,2,3,4-tetrahydroquinoxalin-2-yl]-N-{2-[N-
[(thiophen-2-yl)methylenecarbonyl]piperidin-4-yl]eth-
1-yl}acetamide
2-[2-(R,S)-1-(4-chloro-2,5-dimethylbenzenesulfonyl)]-3-
oxo-1,2,3,4-tetrahydroquinoxalin-2-yl]-N-{2-[N-(3,5-
dimethyloxazol-4-ylcarbonyl)piperidin-4-yl]eth-1-
yl}acetamide
2-[2-(R,S)-1-(4-chloro-2,5-dimethylbenzenesulfonyl)]-3-
oxo-1,2,3,4-tetrahydroquinoxalin-2-yl]-N-{2-[(N-fu-
ran-2-ylcarbonyl)piperidin-4-yl]-1-yl}acetamide
2-[2-(R,S)-1-(4-chloro-2,5-dimethylbenzenesulfonyl)]-3-
oxo-1,2,3,4-tetrahydroquinoxalin-2-yl]-N-{2-[N-(3,5-
dimethyloxazol-3-ylcarbonyl)piperidin-4-yl]eth-1-
yl}acetamide
2-[2-(R,S)-1-(4-chloro-2,5-dimethylbenzenesulfonyl)]-3-
oxo-1,2,3,4-tetrahydroquinoxalin-2-yl]-N-{2-[N-(5-
methylpyrazol-3-ylcarbonyl)piperidin-4-yl]eth-1-
yl}acetamide
2-[2-(R,S)-1-(4-chloro-2,5-dimethylbenzenesulfonyl)]-3-
oxo-1,2,3,4-tetrahydroquinoxalin-2-yl]-N-{2-[N-(1-
methyl-3-t-butylpyrazol-5-ylcarbonyl)piperidin-4-yl]
eth-1-yl}acetamide 2-[2-(R,S)-1-(4-chloro-2,5-dimethylbenzenesulfonyl)]-3-oxo-1,2,3,4-tetrahydroquinoxalin-2-yl]-N-{2-[N-(4-methylthiadiazol-5-ylcarbonyl)piperidin-4-yl]eth-1-yl}acetamide
2-[2-(R,S)-1-(4-chloro-2,5-dimethylbenzenesulfonyl)]-3-oxo-1,2,3,4-tetrahydroquinoxalin-2-yl]-N-{2-[N-(chloromethylenecarbonyl)piperidin-4-yl]-1-yl}-acetamide
2-[2-(R,S)-1-(4-chloro-2,5-dimethylbenzenesulfonyl)]-3-oxo-1,2,3,4-tetrahydroquinoxalin-2-yl]-N-{2-[N-(benzylcarbonyl)piperidin-4-yl]eth-1-yl}-acetamide
2-[2-(R,S)-1-(4-chloro-2,5-dimethylbenzenesulfonyl)]-3-oxo-1,2,3,4-tetrahydroquinoxalin-2-yl]-N-{2-[N-(2-phenylethenylcarbonyl)piperidin-4-yl]eth-1-yl}acetamide
2-[2-(R,S)-1-(4-chloro-2,5-dimethylbenzenesulfonyl)]-3-oxo-1,2,3,4-tetrahydroquinoxalin-2-yl]-N-{2-[N-(methoxymethylenecarbonyl)piperidin-4-yl]eth-1-yl}acetamide
2-[2-(R,S)-1-(4-chloro-2,5-dimethylbenzenesulfonyl)]-3-oxo-1,2,3,4-tetrahydroquinoxalin-2-yl]-N-{2-[N-(pyrazin-2-ylcarbonyl)piperidin-4-yl]eth-1-yl}acetamide
2-[2-(R,S)-1-(4-chloro-2,5-dimethylbenzenesulfonyl)]-3-oxo-1,2,3,4-tetrahydroquinoxalin-2-yl]-N-{2-[N-(isoquinolin-3-ylcarbonyl)piperidin-4-yl]eth-1-yl}acetamide
2-[2-(R,S)-1-(4-chloro-2,5-dimethylbenzenesulfonyl)]-3-oxo-1,2,3,4-tetrahydroquinoxalin-2-yl]-N-{2-[N-(pyrrolidin-5-one-2-ylcarbonyl)piperidin-4-yl]eth-1-yl}acetamide
2-[2-(R,S)-1-(4-chloro-2,5-dimethylbenzenesulfonyl)]-3-oxo-1,2,3,4-tetrahydroquinoxalin-2-yl]-N-{2-[N-(N'-acetylpyrrolidin-2-ylcarbonyl)piperidin-4-yl]eth-1-yl}acetamide
2-[2-(R,S)-1-(4-chloro-2,5-dimethylbenzenesulfonyl)]-3-oxo-1,2,3,4-tetrahydroquinoxalin-2-yl]-N-{2-[N-(dichloromethylenecarbonyl)piperidin-4-yl]eth-1-yl}acetamide
2-[2-(R,S)-1-(4-chloro-2,5-dimethylbenzenesulfonyl)]-3-oxo-1,2,3,4-tetrahydroquinoxalin-2-yl]-N-{4-[N-(pyrazin-2-ylcarbonyl)amino]pheneth-1-yl}-acetamide
2-[2-(R,S)-1-(4-chloro-2,5-dimethylbenzenesulfonyl)]-3-oxo-1,2,3,4-tetrahydroquinoxalin-2-yl]-N-{4-[N-(isoquinolin-2-ylcarbonyl)amino]pheneth-1-yl}acetamide
2-[2-(R,S)-1-(4-chloro-2,5-dimethylbenzenesulfonyl)]-3-oxo-1,2,3,4-tetrahydroquinoxalin-2-yl]-N-{4-[N-(N'-acetylpyrrolidin-2-ylcarbonyl)amino]pheneth-1-yl}acetamide
2-[2-(R,S)-1-(4-chloro-2,5-dimethylbenzenesulfonyl)]-3-oxo-1,2,3,4-tetrahydroquinoxalin-2-yl]-N-{4-[N-(1,2-benzothiadiazol-5-ylcarbonyl)amino]pheneth-1-yl}acetamide
2-[2-(R,S)-1-(4-chloro-2,5-dimethylbenzenesulfonyl)]-3-oxo-1,2,3,4-tetrahydroquinoxalin-2-yl]-N-{4-[N-(benzofuran-5-ylcarbonyl)amino]pheneth-1-yl}acetamide
2-[2-(R,S)-1-(4-chloro-2,5-dimethylbenzenesulfonyl)]-3-oxo-1,2,3,4-tetrahydroquinoxalin-2-yl]-N-{4-[N-(3-methylisoxazol-5-ylcarbonyl)amino]pheneth-1-yl}acetamide
2-[2-(R,S)-1-(4-chloro-2,5-dimethylbenzenesulfonyl)]-3-oxo-1,2,3,4-tetrahydroquinoxalin-2-yl]-N-{4-[N-(N-morpholinocarbonyl)amino]pheneth-1-yl}acetamide
2-[2-(R,S)-1-(4-chloro-2,5-dimethylbenzenesulfonyl)]-3-oxo-1,2,3,4-tetrahydroquinoxalin-2-yl]-N-{4-[N-(methoxyphen-3-ylcarbonyl)amino]pheneth-1-yl}acetamide
2-[2-(R,S)-1-(4-chloro-2,5-dimethylbenzenesulfonyl)]-3-oxo-1,2,3,4-tetrahydroquinoxalin-2-yl]-N-{4-[N-(thiophen-2-ylmethylenecarbonyl)amino]pheneth-1-yl}acetamide
2-[2-(R,S)-1-(4-chloro-2,5-dimethylbenzenesulfonyl)]-3-oxo-1,2,3,4-tetrahydroquinoxalin-2-yl]-N-{4-[N-(3,5-dimethylisoxazol-4-ylcarbonyl)amino]pheneth-1-yl}acetamide
2-[2-(R,S)-1-(4-chloro-2,5-dimethylbenzenesulfonyl)]-3-oxo-1,2,3,4-tetrahydroquinoxalin-2-yl]-N-{4-[N-(2-(pyrid-3-yl)ethylcarbonyl)amino]pheneth-1-yl}acetamide
2-[2-(R,S)-1-(4-chloro-2,5-dimethylbenzenesulfonyl)]-3-oxo-1,2,3,4-tetrahydroquinoxalin-2-yl]-N-{4-[N-(furan-2-ylcarbonyl)amino]pheneth-1-yl}acetamide
2-[2-(R,S)-1-(4-chloro-2,5-dimethylbenzenesulfonyl)]-3-oxo-1,2,3,4-tetrahydroquinoxalin-2-yl]-N-{4-[N-(isoxazol-5-ylcarbonyl)amino]pheneth-1-yl}acetamide
2-[2-(R,S)-1-(4-chloro-2,5-dimethylbenzenesulfonyl)]-3-oxo-1,2,3,4-tetrahydroquinoxalin-2-yl]-N-{4-[N-(3-methylpyrazol-5-ylcarbonyl)amino]pheneth-1-yl}acetamide
2-[2-(R,S)-1-(4-chloro-2,5-dimethylbenzenesulfonyl)]-3-oxo-1,2,3,4-tetrahydroquinoxalin-2-yl]-N-{4-[N-(1-methyl-3-t-butylpyrazol-5-ylcarbonyl) amino]pheneth-1-yl}acetamide
2-[2-(R,S)-1-(4-chloro-2,5-dimethylbenzenesulfonyl)]-3-oxo-1,2,3,4-tetrahydroquinoxalin-2-yl]-N-{4-[N-(4-methyl-1,2,3-thiadiazol-5-ylcarbonyl) amino]pheneth-1-yl}acetamide
2-[2-(R,S)-1-(4-chloro-2,5-dimethylbenzenesulfonyl)]-3-oxo-1,2,3,4-tetrahydroquinoxalin-2-yl]-N-{4-[N-(chloromethylenecarbonyl)amino]pheneth-1-yl}acetamide
2-[2-(R,S)-1-(4-chloro-2,5-dimethylbenzenesulfonyl)]-3-oxo-1,2,3,4-tetrahydroquinoxalin-2-yl]-N-{4-[N-(chlorophen-2-ylcarbonyl)amino]pheneth-1-yl}acetamide
2-[2-(R,S)-1-(4-chloro-2,5-dimethylbenzenesulfonyl)]-3-oxo-1,2,3,4-tetrahydroquinoxalin-2-yl]-N-{4-[N-(phenylcarbonyl)amino]pheneth-1-yl}acetamide
2-[2-(R,S)-1-(4-chloro-2,5-dimethylbenzenesulfonyl)]-3-oxo-1,2,3,4-tetrahydroquinoxalin-2-yl]-N-{4-[N-(pyrid-2-ylcarbonyl)amino]pheneth-1-yl}acetamide
2-[2-(R,S)-1-(4-chloro-2,5-dimethylbenzenesulfonyl)]-3-oxo-1,2,3,4-tetrahydroquinoxalin-2-yl]-N-{4-[N-(pyrid-4-ylcarbonyl)amino]pheneth-1-yl}acetamide
2-[2-(R,S)-1-(4-chloro-2,5-dimethylbenzenesulfonyl)]-3-oxo-1,2,3,4-tetrahydroquinoxalin-2-yl]-N-{4-[N-(2-phenylethenylcarbonyl)amino]pheneth-1-yl}acetamide
2-[2-(R,S)-1-(4-chloro-2,5-dimethylbenzenesulfonyl)]-3-oxo-1,2,3,4-tetrahydroquinoxalin-2-yl]-N-{4-[N-(fluorophen-2-ylcarbonyl)amino]pheneth-1-yl}acetamide
2-[2-(R,S)-1-(4-chloro-2,5-dimethylbenzenesulfonyl)]-3-oxo-1,2,3,4-tetrahydroquinoxalin-2-yl]-N-{4-[N-(methoxymethylenecarbonyl)amino]pheneth-1-yl}acetamide
2-[2-(R,S)-1-(4-chloro-2,5-dimethylbenzenesulfonyl)]-3-oxo-1,2,3,4-tetrahydroquinoxalin-2-yl]-N-{4-[N-(dichloromethylenecarbonyl)amino]pheneth-1-yl}acetamide
2-[2-(R,S)-1-(4-chloro-2,5-dimethylbenzenesulfonyl)]-3-oxo-1,2,3,4-tetrahydroquinoxalin-2-yl]-N-{$4$-[N-(methylenedioxyphen-4-ylcarbonyl) amino]pheneth-1-yl}acetamide
2-[2-(R or S)-1-(4-chloro-2,5-dimethylbenzenesulfonyl)]-3-oxo-1,2,3,4-tetrahydroquinoxalin-2-yl]-N-{1-

[(R)-(pyrrolidin-N-ylcarbonyl)]-2-[N-(methylpyrid-2-yl)phen-4-yl]eth-1-yl}acetamide 2-[2-(S or R)-1-(4-chloro-2,5-dimethylbenzenesulfonyl)]-3-oxo-1,2,3,4-tetrahydroquinoxalin-2-yl]-N-{1-[(R)-(pyrrolidin-N-ylcarbonyl)]-2-[N-(methylpyrid-2-yl)phen-4-yl]eth-1-yl}acetamide 2-[2-(R or S)-1-(4-chloro-2,5-dimethylbenzenesulfonyl)]-3-oxo-1,2,3,4-tetrahydroquinoxalin-2-yl]-N-{1-[(R)-(pyrrolidin-N-ylcarbonyl)]-2-[N-(methylpyrid-4-yl)phen-4-yl]eth-1-yl}acetamide 2-[2-(S or R)-1-(4-chloro-2,5-dimethylbenzenesulfonyl)]-3-oxo-1,2,3,4-tetrahydroquinoxalin-2-yl]-N-{1-[(R)-(pyrrolidin-N-ylcarbonyl)]-2-[N-(methylpyrid-4-yl)phen-4-yl]eth-1-yl}acetamide 2-[2-(R or S)-1-(4-chloro-2,5-dimethylbenzenesulfonyl)]-3-oxo-1,2,3,4-tetrahydroquinoxalin-2-yl]-N-{1-[(R)-(pyrrolidin-N-ylcarbonyl)]-2-[1-(piperidin-2-yl)phen-4-yl]eth-1-yl}acetamide 2-[2-(S or R)-1-(4-chloro-2,5-dimethylbenzenesulfonyl)]-3-oxo-1,2,3,4-tetrahydroquinoxalin-2-yl]-N-{1-[(R)-(pyrrolidin-N-ylcarbonyl)]-2-[1-(piperidin-2-yl)phen-4-yl]eth-1-yl}acetamide 2-[2-(R or S)-1-(4-chloro,2,5-dimethylbenzenesulfonyl)]-3-oxo-1,2,3,4-tetrahydroquinoxalin-2-yl]-N-methyl-N-{1-[(R)-pyrrolidin-N-ylcarbonyl)-2-[4-(N-methylpyrid-4-yl)phen-1-yl)eth-1-yl]}acetamide 2-[2-(S or R)-1-(4-chloro-2,5-dimethylbenzenesulfonyl)]-3-oxo-1,2,3,4-tetrahydroquinoxalin-2-yl]-N-methyl-N-{1-[(R)-pyrrolidin-N-ylcarbonyl)-2-[4-(N-methylpyrid-4-yl)phen-1-yl)eth-1-yl]}acetamide 2-[2-(R, S)-1-(2,5-dimethyl-4-chlorobenzenesulfonyl)-3-oxo-1,2,3,4-tetrahydroquinoxalin-2-yl]-N-[4-(pyridin-2-yl)-3-butyn-1-yl]acetamide 2-[2-(R,S)-1-(4-chloro-2,5-dimethylbenzenesulfonyl)-3-oxo-1,2,3,4-tetrahydroquinoxalin-2-yl]-N-[4-(pyrid-4-yl)but-3-yn-1-yl]acetamide 2-[2-(R,S)-1-(4-chloro-2,5-dimethylbenzenesulfonyl)-3-oxo-1,2,3,4-tetrahydroquinoxalin-2-yl]-N-[2-(benzoimidazol-2-ylamino)eth-1-yl]acetamide 2-[2-(R,S)-1-(4-chloro-2,5-dimethylbenzenesulfonyl)-3-oxo-1,2,3,4-tetrahydroquinoxalin-2-yl]-N-[3-(benzoimidazol-2-ylamino)prop-1-yl]acetamide and pharmaceutically acceptable salts thereof.

6. A pharmaceutical composition comprising a pharmaceutically acceptable diluent and an effective amount of a compound of claim 1.

7. A method for treating or palliating adverse symptoms in a mammal associated with the presence or secretion of bradykinin in the mammal which comprises administering thereto a pharmaceutical composition of claim 6 wherein adverse symptoms in the mammal associated with the release of bradykinin are selected from the group consisting of burns, perioperative pain, migraine, shock, central nervous system injury, asthma, rhinitis, premature labor, inflammatory arthritis, and inflammatory bowel disease.

8. A method for treating or ameliorating pain, hyperalgesia, hyperthermia and/or edema in a mammal which is associated with the release of bradykinin in the mammal which comprises administering to the mammal a pharmaceutical composition of claim 6.

* * * * *